(12) United States Patent
Berinstein et al.

(10) Patent No.: US 8,911,991 B2
(45) Date of Patent: Dec. 16, 2014

(54) MULTI-ANTIGEN VECTORS OF MELANOMA

(75) Inventors: Neil Berinstein, Toronto (CA); James Tartaglia, Aurora (CA); Mark Parrington, Bradford (CA); Dennis L. Panicali, Cambridge, MA (US); Linda Gritz, Somerville, MA (US)

(73) Assignee: Sanofi Pasteur Limited, Toronto, Ontario (CA)

( * ) Notice: Subject to any disclaimer, the term of this patent is extended or adjusted under 35 U.S.C. 154(b) by 1205 days.

(21) Appl. No.: 10/933,874

(22) Filed: Sep. 3, 2004

(65) Prior Publication Data

US 2006/0127360 A1 Jun. 15, 2006

Related U.S. Application Data

(60) Provisional application No. 60/500,572, filed on Sep. 5, 2003, provisional application No. 60/504,007, filed on Sep. 18, 2003.

(51) Int. Cl.
*C12N 15/63* (2006.01)
*G01N 33/574* (2006.01)
*A61K 39/00* (2006.01)

(52) U.S. Cl.
CPC ...... *G01N 33/5743* (2013.01); *C12N 2799/023* (2013.01); *A61K 2039/5256* (2013.01); *A61K 39/0011* (2013.01); *A61K 2039/53* (2013.01); *A61K 2039/5258* (2013.01)
USPC ...................................... 435/320.1

(58) Field of Classification Search
None
See application file for complete search history.

(56) References Cited

U.S. PATENT DOCUMENTS

| | | | |
|---|---|---|---|
| 2003/0113919 A1* | 6/2003 | Emtage et al. | 435/456 |
| 2004/0033234 A1* | 2/2004 | Berinstein et al. | 424/185.1 |
| 2004/0091995 A1* | 5/2004 | Schlom et al. | 435/235.1 |

* cited by examiner

*Primary Examiner* — Celine Qian
(74) *Attorney, Agent, or Firm* — Patrick J. Halloran; Reza Yacoob

(57) ABSTRACT

The present invention relates to peptides, polypeptides, and nucleic acids and the use of the peptide, polypeptide or nucleic acid in preventing and/or treating cancer. In particular, the invention relates to peptides and nucleic acid sequences encoding such peptides for use in diagnosing, treating, or preventing melanoma.

1 Claim, 53 Drawing Sheets

FIGURE 2A

DNA Sequence of pALVAC.Tricom(CD3) #33

```
  1  GGAAATTGTA AACGTTAATA TTTTGTTAAA ATTCGCGTTA AATTTTTGTT
     CCTTTAACAT TGCAATTAT  AAAACAATTT TAAGCGCAAT TTAAAAACAA
 51  AAATCAGCTC ATTTTTAAC  CAATAGGCCG AAATCGGCAA AATCCCTTAT
     TTTAGTCGAG TAAAAAATTG GTTATCCGGC TTTAGCCGTT TTAGGGAATA
101  AAATCAAAAG AATAGACCGA GATAGGGTTG AGTGTTGTTC CAGTTTGGAA
     TTTAGTTTTC TTATCTGGCT CTATCCCAAC TCACAACAAG GTCAAACCTT
151  CAAGAGTCCA CTATTAAAGA ACGTGGACTC CAACGTCAAA GGGCGAAAAA
     GTTCTCAGGT GATAATTTCT TGCACCTGAG GTTGCAGTTT CCCGCTTTTT
201  CCGTCTATCA GGGCGATGGC CCACTACGTG AACCATCACC CTAATCAAGT
     GGCAGATAGT CCCGCTACCG GGTGATGCAC TTGGTAGTGG GATTAGTTCA
251  TTTTTGGGGT CGAGGTGCCG TAAAGCACTA AATCGGAACC CTAAAGGGAG
     AAAAACCCCA GCTCCACGGC ATTTCGTGAT TTAGCCTTGG GATTTCCCTC
301  CCCCCGATTT AGAGCTTGAC GGGGAAAGCC GGCGAACGTG GCGAGAAAGG
     GGGGGCTAAA TCTCGAACTG CCCCTTTCGG CCGCTTGCAC CGCTCTTTCC
351  AAGGGAAGAA AGCGAAAGGA GCGGGCGCTA GGGCGCTGGC AAGTGTAGCG
     TTCCCTTCTT TCGCTTTCCT CGCCCGCGAT CCCGCGACCG TTCACATCGC
401  GTCACGCTGC GCGTAACCAC CACACCCGCC GCGCTTAATG CGCCGCTACA
     CAGTGCGACG CGCATTGGTG GTGTGGGCGG CGCGAATTAC GCGGCGATGT
451  GGGCGCGTCG CGCCATTCGC CATTCAGGCT GCGCAACTGT TGGGAAGGGC
     CCCGCGCAGC GCGGTAAGCG GTAAGTCCGA CGCGTTGACA ACCCTTCCCG
501  GATCGGTGCG GGCCTCTTCG CTATTACGCC AGCTGGCGAA AGGGGGATGT
     CTAGCCACGC CCGGAGAAGC GATAATGCGG TCGACCGCTT TCCCCCTACA
551  GCTGCAAGGC GATTAAGTTG GGTAACGCCA GGGTTTTCCC AGTCACGACG
     CGACGTTCCG CTAATTCAAC CCATTGCGGT CCCAAAAGGG TCAGTGCTGC
601  TTGTAAAACG ACGGCCAGTG AATTGTAATA CGACTCACTA TAGGGCGAAT
     AACATTTTGC TGCCGGTCAC TTAACATTAT GCTGAGTGAT ATCCCGCTTA
651  TGGGTACCGC GGCCGCGTCG ACATGCATTG TTAGTTCTGT AGATCAGTAA
     ACCCATGGCG CCGGCGCAGC TGTACGTAAC AATCAAGACA TCTAGTCATT
     ~~~~~~~~~~~~~~~~~~~~~~~~~~~~~~~~~~~~~~~~~~~~
                            Left Arm
701  CGTATAGCAT ACGAGTATAA TTATCGTAGG TAGTAGGTAT CCTAAAATAA
     GCATATCGTA TGCTCATATT AATAGCATCC ATCATCCATA GGATTTATT
     ~~~~~~~~~~~~~~~~~~~~~~~~~~~~~~~~~~~~~~~~~~~~
                            Left Arm
751  ATCTGATACA GATAATAACT TGTAAATCA  ATTCAGCAAT TTCTCTATTA
     TAGACTATGT CTATTATTGA ACATTTAGT  TAAGTCGTTA AAGAGATAAT
     ~~~~~~~~~~~~~~~~~~~~~~~~~~~~~~~~~~~~~~~~~~~~
                            Left Arm
801  TCATGATAAT GATTAATACA CAGCGTGTCG TTATTTTTTG TTACGATAGT
     AGTACTATTA CTAATTATGT GTCGCACAGC AATAAAAAAC AATGCTATCA
     ~~~~~~~~~~~~~~~~~~~~~~~~~~~~~~~~~~~~~~~~~~~~
                            Left Arm
851  ATTTCTAAAG TAAAGAGCAG GAATCCCTAG TATAATAGAA ATAATCCATA
     TAAAGATTTC ATTTCTCGTC CTTAGGGATC ATATTATCTT TATTAGGTAT
     ~~~~~~~~~~~~~~~~~~~~~~~~~~~~~~~~~~~~~~~~~~~~
                            Left Arm
901  TGAAAAATAT AGTAATGTAC ATATTTCTAA TGTTAACATA TTTATAGGTA
     ACTTTTTATA TCATTACATG TATAAAGATT ACAATTGTAT AAATATCCAT
     ~~~~~~~~~~~~~~~~~~~~~~~~~~~~~~~~~~~~~~~~~~~~
                            Left Arm
951  AATCCAGGAA GGGTAATTTT TACATATCTA TATACGCTTA TTACAGTTAT
     TTAGGTCCTT CCCATTAAAA ATGTATAGAT ATATGCGAAT AATGTCAATA
```

FIGURE 2B

```
                              Left Arm
1001    TAAAAATATA CTTGCAAACA TGTTAGAAGT AAAAAAGAAA GAACTAATTT
        ATTTTTATAT GAACGTTTGT ACAATCTTCA TTTTTTCTTT CTTGATTAAA
                              Left Arm
1051    TACAAAGTGC TTTACCAAAA TGCCAATGGA AATTACTTAG TATGTATATA
        ATGTTTCACG AAATGGTTTT ACGGTTACCT TTAATGAATC ATACATATAT
                              Left Arm
1101    ATGTATAAAG GTATGAATAT CACAAACAGC AAATCGGCTA TTCCCAAGTT
        TACATATTTC CATACTTATA GTGTTTGTCG TTTAGCCGAT AAGGGTTCAA
                              Left Arm 1151    GAGAAACGGT ATAATAGATA TATTTCTAGA TACCATTAAT AACCTTATAA
        CTCTTTGCCA TATTATCTAT ATAAAGATCT ATGGTAATTA TTGGAATATT
                              Left Arm
1201    GCTTGACGTT TCCTATAATG CCTACTAAGA AAACTAGAAG ATACATACAT
        CGAACTGCAA AGGATATTAC GGATGATTCT TTTGATCTTC TATGTATGTA
                              Left Arm
1251    ACTAACGCCA TACGAGAGTA ACTACTCATC GTATAACTAC TGTTGCTAAC
        TGATTGCGGT ATGCTCTCAT TGATGAGTAG CATATTGATG ACAACGATTG
                              Left Arm
1301    AGTGACACTG ATGTTATAAC TCATCTTTGA TGTGGTATAA ATGTATAATA
        TCACTGTGAC TACAATATTG AGTAGAAACT ACACCATATT TACATATTAT
                              Left Arm
1351    ACTATATTAC ACTGGTATTT TATTTCAGTT ATATACTATA TAGTATTAAA
        TGATATAATG TGACCATAAA ATAAAGTCAA TATATGATAT ATCATAATTT
                              Left Arm
1401    AATTATATTT GTATAATTAT ATTATTATAT TCAGTGTAGA AAGTAAAATA
        TTAATATAAA CATATTAATA TAATAATATA AGTCACATCT TCATTTTAT
                              Left Arm
1451    CTATAAATAT GTATCTCTTA TTTATAACTT ATTAGTAAAG TATGTACTAT
        GATATTTATA CATAGAGAAT AAAATATTGAA TAATCATTTC ATACATGATA
                              Left Arm
1501    TCAGTTATAT TGTTTTATAA AAGCTAAATG CTACTAGATT GATATAAATG
        AGTCAATATA ACAAAATATT TTCGATTTAC GATGATCTAA CTATATTTAC
                              Left Arm
1551    AATATGTAAT AAATTAGTAA TGTAGTATAC TAATATTAAC TCACATTTGA
        TTATACATTA TTTAATCATT ACATCATATG ATTATAATTG AGTGTAAACT
                              Left Arm
                                                              30K Pr.

1601    CTAATTAGCT ATAAAAACCC TAAGGTAGGC GGCCGCACTA GAGGATTCGA
        GATTAATCGA TATTTTTGGG ATTCCATCCG CCGGCGTGAT CTCCTAAGCT
```

FIGURE 2C

```
                                  30K Pr.
         ~~~~~~~~~~~~~~~~~~~~~~~~~~~~~~~~~~~~~~~~~~~~~~~~~~~~
 1651    CAAACACCAA TAATTCCCTT CTCTTCATTC CGGACATTAA ATTGGCTATA
         GTTTGTGGTT ATTAAGGGAA GAGAAGTAAG GCCTGTAATT TAACCGATAT
                                  30K Pr.
         ~~~~~~~~~~~~~~~~~~~~~~~~~~~~~~~~~~~~~~~~~~~~~~~~~~~~
 1701    GATAATAAAG ACATTGAGAT GTTACAGGCT CTGTTCAAAT ACGACATTAA
         CTATTATTTC TGTAACTCTA CAATGTCCGA GACAAGTTTA TGCTGTAATT
                                  30K Pr.
         ~~~~~~~~~~~~~~~~~~~~~~~~~~~~~~~~~~~~~~~~~~~~~~~~~~~~
 1751    TATCTATTCT GCTAATCTGG AAAATGTACT ATTGGATGAT GCCGAAATAG
         ATAGATAAGA CGATTAGACC TTTTACATGA TAACCTACTA CGGCTTTATC
                                  30K Pr.
         ~~~~~~~~~~~~~~~~~~~~~~~~~~~~~~~~~~~~~~~~~~~~~~~~~~~~
 1801    CTAAAATGAT TATAGAAAAG CATGTTGAAT ACAAGTCTGA CTCCTATACA
         GATTTTACTA ATATCTTTTC GTACAACTTA TGTTCAGACT GAGGATATGT
                                  30K Pr.
         ~~~~~~~~~~~~~~~~~~~~~~~~~~~~~~~~~~~~~~~~~~~~~~~~~~~~
 1851    AAAGATCTCG ATATAGTCAA GAATAATAAA TTGGATGAAA TAATTAGCAA
         TTTCTAGAGC TATATCAGTT CTTATTATTT AACCTACTTT ATTAATCGTT
                                  30K Pr.
         ~~~~~~~~~~~~~~~~~~~~~~~~~~~~~~~~~~~~~~~~~~~~~~~~~~~~
 1901    AAACAAGGAA CTCAGACTCA TGTACGTCAA TTGTGTAAAG AAAAACTAAT
         TTTGTTCCTT GAGTCTGAGT ACATGCAGTT AACACATTTC TTTTTGATTA
                                  30K Pr.
         ~~~~~~~~~~~~~~~~~~~~~~~~~~~~~~~~~~~~~~~~~~~~~~~~~~~~
 1951    TAGATTCTCC CACATTTTTG TTAACATTAC ACTAACTAAT TGGTAAAATT
         ATCTAAGAGG GTGTAAAAAC AATTGTAATG TGATTGATTA ACCATTTTAA
                                  30K Pr.
         ~~~~~~~~~~~~~~~~~~~~~~~~~~~~~~~~~~~~~~~~~~~~~~~~~~~~
 2001    GATAGAATAA TTATGTGTAT ATAAGATAGA TTTCCTATTG TCTTACTCAT
         CTATCTTATT AATACACATA TATTCTATCT AAAGGATAAC AGAATGAGTA
                     30K Pr.
         ~~~~~~~~~~~~~~~~~~~~~~~~~~~~~~~~~~~~
                                            hLFA-3
                                  ~~~~~~~~~~~~~~~~~~
 2051    TGCATCGTGG GAATTCAGAT CAGCTTCCGC GGCATGGTTG CTGGGAGCGA
         ACGTAGCACC CTTAAGTCTA GTCGAAGGCG CCGTACCAAC GACCCTCGCT
```

FIGURE 2D

```
                                hLFA-3
       ~~~~~~~~~~~~~~~~~~~~~~~~~~~~~~~~~~~~~~~~~~~~~~~~~~~
2101   CGCGGGGCGG GCCCTGGGGG TCCTCAGCGT GGTCTGCCTG CTGCACTGCT
       GCGCCCCGCC CGGGACCCCC AGGAGTCGCA CCAGACGGAC GACGTGACGA
                                hLFA-3
       ~~~~~~~~~~~~~~~~~~~~~~~~~~~~~~~~~~~~~~~~~~~~~~~~~~~
2151   TTGGTTTCAT CAGCTGTTTT TCCCAACAAA TATATGGTGT TGTGTATGGG
       AACCAAAGTA GTCGACAAAA AGGGTTGTTT ATATACCACA ACACATACCC
                                hLFA-3
       ~~~~~~~~~~~~~~~~~~~~~~~~~~~~~~~~~~~~~~~~~~~~~~~~~~~
2201   AATGTAACTT TCCATGTACC AAGCAATGTG CCTTTAAAAG AGGTCCTATG
       TTACATTGAA AGGTACATGG TTCGTTACAC GGAAATTTTC TCCAGGATAC
                                hLFA-3
       ~~~~~~~~~~~~~~~~~~~~~~~~~~~~~~~~~~~~~~~~~~~~~~~~~~~
2251   GAAAAAACAA AAGGATAAAG TTGCAGAACT GGAAAATTCT GAATTCAGAG
       CTTTTTTGTT TTCCTATTTC AACGTCTTGA CCTTTTAAGA CTTAAGTCTC
                                hLFA-3
       ~~~~~~~~~~~~~~~~~~~~~~~~~~~~~~~~~~~~~~~~~~~~~~~~~~~
2301   CTTTCTCATC TTTTAAAAAT AGGGTTTATT TAGACACTGT GTCAGGTAGC
       GAAAGAGTAG AAAATTTTTA TCCCAAATAA ATCTGTGACA CAGTCCATCG
                                hLFA-3
       ~~~~~~~~~~~~~~~~~~~~~~~~~~~~~~~~~~~~~~~~~~~~~~~~~~~
2351   CTCACTATCT ACAACTTAAC ATCATCAGAT GAAGATGAGT ATGAAATGGA
       GAGTGATAGA TGTTGAATTG TAGTAGTCTA CTTCTACTCA TACTTTACCT
                                hLFA-3
       ~~~~~~~~~~~~~~~~~~~~~~~~~~~~~~~~~~~~~~~~~~~~~~~~~~~
2401   ATCGCCAAAT ATTACTGATA CCATGAAGTT CTTTCTTTAT GTGCTTGAGT
       TAGCGGTTTA TAATGACTAT GGTACTTCAA GAAAGAAATA CACGAACTCA
                                hLFA-3
       ~~~~~~~~~~~~~~~~~~~~~~~~~~~~~~~~~~~~~~~~~~~~~~~~~~~
2451   CTCTTCCATC TCCCACACTA ACTTGTGCAT TGACTAATGG AAGCATTGAA
       GAGAAGGTAG AGGGTGTGAT TGAACACGTA ACTGATTACC TTCGTAACTT
                                hLFA-3
       ~~~~~~~~~~~~~~~~~~~~~~~~~~~~~~~~~~~~~~~~~~~~~~~~~~~
2501   GTCCAATGCA TGATACCAGA GCATTACAAC AGCCATCGAG GACTTATAAT
       CAGGTTACGT ACTATGGTCT CGTAATGTTG TCGGTAGCTC CTGAATATTA
                                hLFA-3
       ~~~~~~~~~~~~~~~~~~~~~~~~~~~~~~~~~~~~~~~~~~~~~~~~~~~
2551   GTACTCATGG GATTGTCCTA TGGAGCAATG TAAACGTAAC TCAACCAGTA
       CATGAGTACC CTAACAGGAT ACCTCGTTAC ATTTGCATTG AGTTGGTCAT
                                hLFA-3
       ~~~~~~~~~~~~~~~~~~~~~~~~~~~~~~~~~~~~~~~~~~~~~~~~~~~
2601   TATATTTTAA GATGGAAAAT GATCTTCCAC AAAAAATACA GTGTACTCTT
       ATATAAAATT CTACCTTTTA CTAGAAGGTG TTTTTATGT CACATGAGAA
                                hLFA-3
       ~~~~~~~~~~~~~~~~~~~~~~~~~~~~~~~~~~~~~~~~~~~~~~~~~~~
2651   AGCAATCCAT TATTTAATAC AACATCATCA ATCATTTGA CAACCTGTAT
       TCGTTAGGTA ATAAATTATG TTGTAGTAGT TAGTAAAACT GTTGGACATA
                                hLFA-3
       ~~~~~~~~~~~~~~~~~~~~~~~~~~~~~~~~~~~~~~~~~~~~~~~~~~~
2701   CCCAAGCAGC GGTCATTCAA GACACAGATA TGCACTTATA CCCATACCAT
       GGGTTCGTCG CCAGTAAGTT CTGTGTCTAT ACGTGAATAT GGGTATGGTA
                                hLFA-3
       ~~~~~~~~~~~~~~~~~~~~~~~~~~~~~~~~~~~~~~~~~~~~~~~~~~~
2751   TAGCAGTAAT TACAACATGT ATTGTGCTGT ATATGAATGG TATTCTGAAA
       ATCGTCATTA ATGTTGTACA TAACACGACA TATACTTACC ATAAGACTTT
```

FIGURE 2E

```
           hLFA-3                                     I3 Pr.
       ~~~~~~~~~~~~~~~~~~~~~~~~~~~~~~~~~~~~~~      ~~~~~~~~~~
2801   TGTGACAGAA AACCAGACAG AACCAACTCC AATTGATTGG CTCGACCGGG
       ACACTGTCTT TTGGTCTGTC TTGGTTGAGG TTAACTAACC GAGCTGGCCC
                             I3 Pr.
       ~~~~~~~~~~~~~~~~~~~~~~~~~~~~~~~~~~~~~~~~~~~~~~~~~~~~~
2851   AATGTACTAT CTACGTACGA AACCCGCATC CGCTCCCATT CAATTCACAT
       TTACATGATA GATGCATGCT TTGGGCGTAG GCGAGGGTAA GTTAAGTGTA
                             I3 Pr.
       ~~~~~~~~~~~~~~~~~~~~~~~~~~~~~~~~~~~~~~~~~~~~~~~~~~~~~
2901   TGGACAAGGA TAAAATAAAA CCACTGGTGG TTTGCGATTC CGAAATCTGT
       ACCTGTTCCT ATTTTATTTT GGTGACCACC AAACGCTAAG GCTTTAGACA
                             I3 Pr.
       ~~~~~~~~~~~~~~~~~~~~~~~~~~~~~~~~~~~~~~~~~~~~~~~~~~~~~
2951   ACATCATGCA GTGGTTAAAC AAAAACATTT TTATTCTCAA ATGAGATAAA
       TGTAGTACGT CACCAATTTG TTTTTGTAAA AATAAGAGTT TACTCTATTT
                             I3 Pr.
       ~~~~~~~~~~~~~~~~~~~~~~~~~~~~~~~~~~~~~~~~~~~~~~~~~~~~~
3001   GTGAAAATAT ATATCATTAT ATTACAAAGT ACAATTATTT AGGTTTAATC
       CACTTTTATA TATAGTAATA TAATGTTTCA TGTTAATAAA TCCAAATTAG
         I3 Pr.                        hICAM
       ~~~~~~~~~~  ~~~~~~~~~~~~~~~~~~~~~~~~~~~~~~~~~~~~~~~~~
3051   AATCCCGCGG GCTATGGCTC CCAGCAGCCC CCGGCCCGCG CTGCCCGCAC
       TTAGGGCGCC CGATACCGAG GGTCGTCGGG GGCCGGGCGC GACGGGCGTG
                             hICAM
       ~~~~~~~~~~~~~~~~~~~~~~~~~~~~~~~~~~~~~~~~~~~~~~~~~~~~~
3101   TCCTGGTCCT GCTCGGGGCT CTGTTCCCAG GACCTGGCAA TGCCCAGACA
       AGGACCAGGA CGAGCCCCGA GACAAGGGTC CTGGACCGTT ACGGGTCTGT
                             hICAM
       ~~~~~~~~~~~~~~~~~~~~~~~~~~~~~~~~~~~~~~~~~~~~~~~~~~~~~
3151   TCTGTGTCCC CCTCAAAAGT CATCCTGCCC CGGGGAGGCT CCGTGCTGGT
       AGACACAGGG GGAGTTTTCA GTAGGACGGG GCCCCTCCGA GGCACGACCA
                             hICAM
       ~~~~~~~~~~~~~~~~~~~~~~~~~~~~~~~~~~~~~~~~~~~~~~~~~~~~~
3201   GACATGCAGC ACCTCCTGTG ACCAGCCCAA GTTGTTGGGC ATAGAGACCC
       CTGTACGTCG TGGAGGACAC TGGTCGGGTT CAACAACCCG TATCTCTGGG
                             hICAM
       ~~~~~~~~~~~~~~~~~~~~~~~~~~~~~~~~~~~~~~~~~~~~~~~~~~~~~
3251   CGTTGCCTAA AAAGGAGTTG CTCCTGCCTG GAACAACCG GAAGGTGTAT
       GCAACGGATT TTTCCTCAAC GAGGACGGAC CCTTGTTGGC CTTCCACATA
                             hICAM
       ~~~~~~~~~~~~~~~~~~~~~~~~~~~~~~~~~~~~~~~~~~~~~~~~~~~~~
3301   GAACTGAGCA ATGTGCAAGA AGATAGCCAA CCAATGTGCT ATTCAAACTG
       CTTGACTCGT TACACGTTCT TCTATCGGTT GGTTACACGA TAAGTTTGAC
                             hICAM
       ~~~~~~~~~~~~~~~~~~~~~~~~~~~~~~~~~~~~~~~~~~~~~~~~~~~~~
3351   CCCTGATGGG CAGTCAACAG CTAAAACCTT CCTCACCGTG TACTGGACTC
       GGGACTACCC GTCAGTTGTC GATTTTGGAA GGAGTGGCAC ATGACCTGAG
                             hICAM
       ~~~~~~~~~~~~~~~~~~~~~~~~~~~~~~~~~~~~~~~~~~~~~~~~~~~~~
3401   CAGAACGGGT GGAACTGGCA CCCCTCCCCT CTTGGCAGCC AGTGGGCAAG
       GTCTTGCCCA CCTTGACCGT GGGGAGGGGA GAACCGTCGG TCACCCGTTC
                             hICAM
       ~~~~~~~~~~~~~~~~~~~~~~~~~~~~~~~~~~~~~~~~~~~~~~~~~~~~~
3451   AACCTTACCC TACGCTGCCA GGTGGAGGGT GGGGCACCCC GGGCCAACCT
       TTGGAATGGG ATGCGACGGT CCACCTCCCA CCCCGTGGGG CCCGGTTGGA
```

FIGURE 2F

```
              hICAM
     ~~~~~~~~~~~~~~~~~~~~~~~~~~~~~~~~~~~~~~~~~~~~~~~~~~
3501 CACCGTGGTG CTGCTCCGTG GGGAGAAGGA GCTGAAACGG GAGCCAGCTG
     GTGGCACCAC GACGAGGCAC CCCTCTTCCT CGACTTTGCC CTCGGTCGAC
              hICAM
     ~~~~~~~~~~~~~~~~~~~~~~~~~~~~~~~~~~~~~~~~~~~~~~~~~~
3551 TGGGGGAGCC CGCTGAGGTC ACGACCACGG TGCTGGTGAG GAGAGATCAC
     ACCCCCTCGG GCGACTCCAG TGCTGGTGCC ACGACCACTC CTCTCTAGTG
              hICAM
     ~~~~~~~~~~~~~~~~~~~~~~~~~~~~~~~~~~~~~~~~~~~~~~~~~~
3601 CATGGAGCCA ATTTCTCGTG CCGCACTGAA CTGGACCTGC GGCCCCAAGG
     GTACCTCGGT TAAAGAGCAC GGCGTGACTT GACCTGGACG CCGGGGTTCC
              hICAM
     ~~~~~~~~~~~~~~~~~~~~~~~~~~~~~~~~~~~~~~~~~~~~~~~~~~
3651 GCTGGAGCTG TTTGAGAACA CCTCGGCCCC CTACCAGCTC AGACCTTTG
     CGACCTCGAC AAACTCTTGT GGAGCCGGGG GATGGTCGAG GTCTGGAAAC
              hICAM
     ~~~~~~~~~~~~~~~~~~~~~~~~~~~~~~~~~~~~~~~~~~~~~~~~~~
3701 TCCTGCCAGC GACTCCCCCA CAACTTGTCA GCCCCCGGGT CCTAGAGGTG
     AGGACGGTCG CTGAGGGGGT GTTGAACAGT CGGGGGCCCA GGATCTCCAC
              hICAM
     ~~~~~~~~~~~~~~~~~~~~~~~~~~~~~~~~~~~~~~~~~~~~~~~~~~
3751 GACACGCAGG GGACCGTGGT CTGTTCCCTG ACGGGCTGT TCCCAGTCTC
     CTGTGCGTCC CCTGGCACCA GACAAGGGAC CTGCCCGACA AGGGTCAGAG
              hICAM
     ~~~~~~~~~~~~~~~~~~~~~~~~~~~~~~~~~~~~~~~~~~~~~~~~~~
3801 GGAGGCCCAG GTCCACCTGG CACTGGGGGA CCAGAGGTTG AACCCCACAG
     CCTCCGGGTC CAGGTGGACC GTGACCCCCT GGTCTCCAAC TTGGGGTGTC
              hICAM
     ~~~~~~~~~~~~~~~~~~~~~~~~~~~~~~~~~~~~~~~~~~~~~~~~~~
3851 TCACCTATGG CAACGACTCC TTCTCGGCCA AGGCCTCAGT CAGTGTGACC
     AGTGGATACC GTTGCTGAGG AAGAGCCGGT TCCGGAGTCA GTCACACTGG
              hICAM
     ~~~~~~~~~~~~~~~~~~~~~~~~~~~~~~~~~~~~~~~~~~~~~~~~~~
3901 GCAGAGGACG AGGGCACCCA GCGGCTGACG TGTGCAGTAA TACTGGGGAA
     CGTCTCCTGC TCCCGTGGGT CGCCGACTGC ACACGTCATT ATGACCCCTT
              hICAM
     ~~~~~~~~~~~~~~~~~~~~~~~~~~~~~~~~~~~~~~~~~~~~~~~~~~
3951 CCAGAGCCAG GAGACACTGC AGACAGTGAC CATCTACAGC TTTCCGGCGC
     GGTCTCGGTC CTCTGTGACG TCTGTCACTG GTAGATGTCG AAAGGCCGCG
              hICAM
     ~~~~~~~~~~~~~~~~~~~~~~~~~~~~~~~~~~~~~~~~~~~~~~~~~~
4001 CCAACGTGAT TCTGACGAAG CCAGAGGTCT CAGAAGGGAC CGAGGTGACA
     GGTTGCACTA AGACTGCTTC GGTCTCCAGA GTCTTCCCTG GCTCCACTGT
              hICAM
     ~~~~~~~~~~~~~~~~~~~~~~~~~~~~~~~~~~~~~~~~~~~~~~~~~~
4051 GTGAAGTGTG AGGCCCACCC TAGAGCCAAG GTGACGCTGA ATGGGGTTCC
     CACTTCACAC TCCGGGTGGG ATCTCGGTTC CACTGCGACT TACCCCAAGG
              hICAM
     ~~~~~~~~~~~~~~~~~~~~~~~~~~~~~~~~~~~~~~~~~~~~~~~~~~
4101 AGCCCAGCCA CTGGGCCCGA GGGCCCAGCT CCTGCTGAAG GCCACCCCAG
     TCGGGTCGGT GACCCGGGCT CCCGGGTCGA GGACGACTTC CGGTGGGGTC
              hICAM
     ~~~~~~~~~~~~~~~~~~~~~~~~~~~~~~~~~~~~~~~~~~~~~~~~~~
4151 AGGACAACGG GCGCAGCTTC TCCTGCTCTG CAACCCTGGA GGTGGCCGGC
     TCCTGTTGCC CGCGTCGAAG AGGACGAGAC GTTGGGACCT CCACCGGCCG
```

FIGURE 2G

```
                                       hICAM
         ~~~~~~~~~~~~~~~~~~~~~~~~~~~~~~~~~~~~~~~~~~~~~~~~~~~~
4201    CAGCTTATAC ACAAGAACCA GACCCGGGAG CTTCGTGTCC TGTATGGCCC
        GTCGAATATG TGTTCTTGGT CTGGGCCCTC GAAGCACAGG ACATACCGGG
                                       hICAM
         ~~~~~~~~~~~~~~~~~~~~~~~~~~~~~~~~~~~~~~~~~~~~~~~~~~~~
4251    CCGACTGGAC GAGAGGGATT GTCCGGGAAA CTGGACGTGG CCAGAAAATT
        GGCTGACCTG CTCTCCCTAA CAGGCCCTTT GACCTGCACC GGTCTTTTAA
                                       hICAM
         ~~~~~~~~~~~~~~~~~~~~~~~~~~~~~~~~~~~~~~~~~~~~~~~~~~~~
4301    CCCAGCAGAC TCCAATGTGC CAGGCTTGGG GGAACCCATT GCCCGAGCTC
        GGGTCGTCTG AGGTTACACG GTCCGAACCC CCTTGGGTAA CGGGCTCGAG
                                       hICAM
         ~~~~~~~~~~~~~~~~~~~~~~~~~~~~~~~~~~~~~~~~~~~~~~~~~~~~
4351    AAGTGTCTAA AGGATGGCAC TTTCCCACTG CCCATCGGGG AATCAGTGAC
        TTCACAGATT TCCTACCGTG AAAGGGTGAC GGGTAGCCCC TTAGTCACTG
                                       hICAM
         ~~~~~~~~~~~~~~~~~~~~~~~~~~~~~~~~~~~~~~~~~~~~~~~~~~~~
4401    TGTCACTCGA GATCTTGAGG GCACCTACCT CTGTCGGGCC AGGAGCACTC
        ACAGTGAGCT CTAGAACTCC CGTGGATGGA GACAGCCCGG TCCTCGTGAG
                                       hICAM
         ~~~~~~~~~~~~~~~~~~~~~~~~~~~~~~~~~~~~~~~~~~~~~~~~~~~~
4451    AAGGGGAGGT CACCCGCGAG GTGACCGTGA ATGTGCTCTC CCCCGGTAT
        TTCCCCTCCA GTGGGCGCTC CACTGGCACT TACACGAGAG GGGGGCCATA
                                       hICAM
         ~~~~~~~~~~~~~~~~~~~~~~~~~~~~~~~~~~~~~~~~~~~~~~~~~~~~
4501    GAGATTGTCA TCATCACTGT GGTAGCAGCC GCAGTCATAA TGGGCACTGC
        CTCTAACAGT AGTAGTGACA CCATCGTCGG CGTCAGTATT ACCCGTGACG
                                       hICAM
         ~~~~~~~~~~~~~~~~~~~~~~~~~~~~~~~~~~~~~~~~~~~~~~~~~~~~
4551    AGGCCTCAGC ACGTACCTCT ATAACCGCCA GCGGAAGATC AAGAAATACA
        TCCGGAGTCG TGCATGGAGA TATTGGCGGT CGCCTTCTAG TTCTTTATGT
                                       hICAM
         ~~~~~~~~~~~~~~~~~~~~~~~~~~~~~~~~~~~~~~~~~~~~~~~~~~~~
4601    GACTACAACA GGCCCAAAAA GGGACCCCCA TGAAACCGAA CACACAAGCC
        CTGATGTTGT CCGGGTTTTT CCCTGGGGGT ACTTTGGCTT GTGTGTTCGG
           hICAM                                      sE/L Pr.
         ~~~~~~~~~~~~~~~                       ~~~~~~~~~~~~~~~
4651    ACGCCTCCCT GAGCATGCAT GTAGCTTAAA AATTGAAATT TTATTTTTTT
        TGCGGAGGGA CTCGTACGTA CATCGAATTT TAACTTTAA AATAAAAAAA
           sE/L Pr.
         ~~~~~~~~~~~~~~~~~~
4701    TTTTTGGAAT ATAAATAAGC TCGAAGTCGA AATTCCTGCA GCCCGGGGCC
        AAAAACCTTA TATTTATTCG AGCTTCAGCT TTAAGGACGT CGGGCCCCGG
                                       hB7.1
         ~~~~~~~~~~~~~~~~~~~~~~~~~~~~~~~~~~~~~~~~~~~~~~~~~~~~
4751    ATGGGCCACA CACGGAGGCA GGGAACATCA CCATCCAAGT GTCCATACCT
        TACCCGGTGT GTGCCTCCGT CCCTTGTAGT GGTAGGTTCA CAGGTATGGA
                                       hB7.1
         ~~~~~~~~~~~~~~~~~~~~~~~~~~~~~~~~~~~~~~~~~~~~~~~~~~~~
4801    CAATTTCTTT CAGCTCTTGG TGCTGGCTGG TCTTTCTCAC TTCTGTTCAG
        GTTAAAGAAA GTCGAGAACC ACGACCGACC AGAAAGAGTG AAGACAAGTC
                                       hB7.1
         ~~~~~~~~~~~~~~~~~~~~~~~~~~~~~~~~~~~~~~~~~~~~~~~~~~~~
4851    GTGTTATCCA CGTGACCAAG GAAGTGAAAG AAGTGGCAAC GCTGTCCTGT
        CACAATAGGT GCACTGGTTC CTTCACTTTC TTCACCGTTG CGACAGGACA
```

FIGURE 2H
hB7.1

```
4901    GGTCACAATG TTTCTGTTGA AGAGCTGGCA CAAACTCGCA TCTACTGGCA
        CCAGTGTTAC AAAGACAACT TCTCGACCGT GTTTGAGCGT AGATGACCGT
                                 hB7.1
4951    AAAGGAGAAG AAAATGGTGC TGACTATGAT GTCTGGAGAC ATGAATATAT
        TTTCCTCTTC TTTTACCACG ACTGATACTA CAGACCTCTG TACTTATATA
                                 hB7.1
5001    GGCCCGAGTA CAAGAACCGG ACCATCTTTG ATATCACTAA TAACCTCTCC
        CCGGGCTCAT GTTCTTGGCC TGGTAGAAAC TATAGTGATT ATTGGAGAGG
                                 hB7.1
5051    ATTGTGATCC TGGCTCTGCG CCCATCTGAC GAGGGCACAT ACGAGTGTGT
        TAACACTAGG ACCGAGACGC GGGTAGACTG CTCCCGTGTA TGCTCACACA
                                 hB7.1
5101    TGTTCTGAAG TATGAAAAAG ACGCTTTCAA GCGGGAACAC CTGGCTGAAG
        ACAAGACTTC ATACTTTTTC TGCGAAAGTT CGCCCTTGTG GACCGACTTC
                                 hB7.1
5151    TGACGTTATC AGTCAAAGCT GACTTCCCTA CACCTAGTAT ATCTGACTTT
        ACTGCAATAG TCAGTTTCGA CTGAAGGGAT GTGGATCATA TAGACTGAAA
                                 hB7.1
5201    GAAATTCCAA CTTCTAATAT TAGAAGGATA ATTTGCTCAA CCTCTGGAGG
        CTTTAAGGTT GAAGATTATA ATCTTCCTAT TAAACGAGTT GGAGACCTCC
                                 hB7.1
5251    TTTTCCAGAG CCTCACCTCT CCTGGTTGGA AAATGGAGAA GAATTAAATG
        AAAAGGTCTC GGAGTGGAGA GGACCAACCT TTTACCTCTT CTTAATTTAC
                                 hB7.1
5301    CCATCAACAC AACAGTTTCC CAAGATCCTG AAACTGAGCT CTATGCTGTT
        GGTAGTTGTG TTGTCAAAGG GTTCTAGGAC TTTGACTCGA GATACGACAA
                                 hB7.1
5351    AGCAGCAAAC TGGATTTCAA TATGACAACC AACCACAGCT TCATGTGTCT
        TCGTCGTTTG ACCTAAAGTT ATACTGTTGG TTGGTGTCGA AGTACACAGA
                                 hB7.1
5401    CATCAAGTAT GGACATTTAA GAGTGAATCA GACCTTCAAC TGGAATACAA
        GTAGTTCATA CCTGTAAATT CTCACTTAGT CTGGAAGTTG ACCTTATGTT
                                 hB7.1
5451    CCAAGCAAGA GCATTTTCCT GATAACCTGC TCCCATCCTG GCCATTACC
        GGTTCGTTCT CGTAAAAGGA CTATTGGACG AGGGTAGGAC CCGGTAATGG
                                 hB7.1
5501    TTAATCTCAG TAAATGGAAT TTTCGTGATA TGCTGCCTGA CCTACTGCTT
        AATTAGAGTC ATTTACCTTA AAAGCACTAT ACGACGGACT GGATGACGAA
                                 hB7.1
5551    TGCCCCACGC TGCAGAGAGA GAAGGAGGAA TGAGAGATTG AGAAGGGAAA
        ACGGGGTGCG ACGTCTCTCT CTTCCTCCTT ACTCTCTAAC TCTTCCCTTT
```

FIGURE 2I hB7.1

```
5601 GTGTACGCCC TGTATAAAAG CTTTCTAGGT TTTTGTTTAG GGCTGCAGGA
     CACATGCGGG ACATATTTTC GAAAGATCCA AAAACAAATC CCGACGTCCT
5651 ATTCCTCGAG GGATCCCGAT TTTTATGACT AGTTAATCAA ATAAAAAGCA
     TAAGGAGCTC CCTAGGGCTA AAAATACTGA TCAATTAGTT TATTTTTCGT
                                                        Right Arm
5701 TACAAGCTAT TGCTTCGCTA TCGTTACAAA ATGGCAGGAA TTTTGTGTAA
     ATGTTCGATA ACGAAGCGAT AGCAATGTTT TACCGTCCTT AAAACACATT
                            Right Arm
5751 ACTAAGCCAC ATACTTGCCA ATGAAAAAAA TAGTAGAAAG GATACTATTT
     TGATTCGGTG TATGAACGGT TACTTTTTTT ATCATCTTTC CTATGATAAA
                            Right Arm
5801 TAATGGGATT AGATGTTAAG GTTCCTTGGG ATTATAGTAA CTGGGCATCT
     ATTACCCTAA TCTACAATTC CAAGGAACCC TAATATCATT GACCCGTAGA
                            Right Arm
5851 GTTAACTTTT ACGACGTTAG GTTAGATACT GATGTTACAG ATTATAATAA
     CAATTGAAAA TGCTGCAATC CAATCTATGA CTACAATGTC TAATATTATT
                            Right Arm
5901 TGTTACAATA AAATACATGA CAGGATGTGA TATTTTTCCT CATATAACTC
     ACAATGTTAT TTTATGTACT GTCCTACACT ATAAAAAGGA GTATATTGAG
                            Right Arm
5951 TTGGAATAGC AAATATGGAT CAATGTGATA GATTTGAAAA TTTCAAAAAG
     AACCTTATCG TTTATACCTA GTTACACTAT CTAAACTTTT AAAGTTTTTC
                            Right Arm
6001 CAAATAACTG ATCAAGATTT ACAGACTATT TCTATAGTCT GTAAAGAAGA
     GTTTATTGAC TAGTTCTAAA TGTCTGATAA AGATATCAGA CATTTCTTCT
                            Right Arm
6051 GATGTGTTTT CCTCAGAGTA ACGCCTCTAA ACAGTTGGGA GCGAAAGGAT
     CTACACAAAA GGAGTCTCAT TGCGGAGATT TGTCAACCCT CGCTTTCCTA
                            Right Arm
6101 GCGCTGTAGT TATGAAACTG GAGGTATCTG ATGAACTTAG AGCCCTAAGA
     CGCGACATCA ATACTTTGAC CTCCATAGAC TACTTGAATC TCGGGATTCT
                            Right Arm
6151 AATGTTCTGC TGAATGCGGT ACCCTGTTCG AAGGACGTGT TTGGTGATAT
     TTACAAGACG ACTTACGCCA TGGGACAAGC TTCCTGCACA AACCACTATA
                            Right Arm
6201 CACAGTAGAT AATCCGTGGA ATCCTCACAT AACAGTAGGA TATGTTAAGG
     GTGTCATCTA TTAGGCACCT TAGGAGTGTA TTGTCATCCT ATACAATTCC
                            Right Arm
6251 AGGACGATGT CGAAAACAAG AAACGCCTAA TGGAGTGCAT GTCCAAGTTT
     TCCTGCTACA GCTTTTGTTC TTTGCGGATT ACCTCACGTA CAGGTTCAAA
                            Right Arm
```

FIGURE 2J

```
6301    AGGGGGCAAG AAATACAAGT TCTAGGATGG TATTAATAAG TATCTAAGTA
        TCCCCCGTTC TTTATGTTCA AGATCCTACC ATAATTATTC ATAGATTCAT
        ~~~~~~~~~~~~~~~~~~~~~~~~~~~~~~~~~~~~~~~~~~~~~~~~~~~
                              Right Arm
6351    TTTGGTATAA TTTATTAAAT AGTATAATTA TAACAAATAA TAAATAACAT
        AAACCATATT AAATAATTTA TCATATTAAT ATTGTTTATT ATTTATTGTA
        ~~~~~~~~~~~~~~~~~~~~~~~~~~~~~~~~~~~~~~~~~~~~~~~~~~~
                              Right Arm
6401    GATAACGGTT TTTATTAGAA TAAAATAGAG ATAATATCAT AATGATATAT
        CTATTGCCAA AAATAATCTT ATTTTATCTC TATTATAGTA TTACTATATA
        ~~~~~~~~~~~~~~~~~~~~~~~~~~~~~~~~~~~~~~~~~~~~~~~~~~~
                              Right Arm
6451    AATACTTCAT TACCAGAAAT GAGTAATGGA AGACTTATAA ATGAACTGCA
        TTATGAAGTA ATGGTCTTTA CTCATTACCT TCTGAATATT TACTTGACGT
        ~~~~~~~~~~~~~~~~~~~~~~~~~~~~~~~~~~~~~~~~~~~~~~~~~~~
                              Right Arm
6501    TAAAGCTATA AGGTATAGAG ATATAAATTT AGTAAGGTAT ATACTTAAAA
        ATTTCGATAT TCCATATCTC TATATTAAA TCATTCCATA TATGAATTTT
        ~~~~~~~~~~~~~~~~~~~~~~~~~~~~~~~~~~~~~~~~~~~~~~~~~~~
                              Right Arm
6551    AATGCAAATA CAATAACGTA AATATACTAT CAACGTCTTT GTATTTAGCC
        TTACGTTTAT GTTATTGCAT TTATATGATA GTTGCAGAAA CATAAATCGG
        ~~~~~~~~~~~~~~~~~~~~~~~~~~~~~~~~~~~~~~~~~~~~~~~~~~~
                              Right Arm
6601    GTAAGTATTT CTGATATAGA AATGGTAAAA TTATTACTAG AACACGGTGC
        CATTCATAAA GACTATATCT TTACCATTTT AATAATGATC TTGTGCCACG
        ~~~~~~~~~~~~~~~~~~~~~~~~~~~~~~~~~~~~~~~~~~~~~~~~~~~
                              Right Arm
6651    CGATATTTTA AAATGTAAAA ATCCTCCTCT TCATAAAGCT GCTAGTTTAG
        GCTATAAAAT TTTACATTTT TAGGAGGAGA AGTATTTCGA CGATCAAATC
        ~~~~~~~~~~~~~~~~~~~~~~~~~~~~~~~~~~~~~~~~~~~~~~~~~~~
                              Right Arm
6701    ATAATACAGA AATTGCTAAA CTACTAATAG ATTCTGGCGC TGACATAGAA
        TATTATGTCT TTAACGATTT GATGATTATC TAAGACCGCG ACTGTATCTT
        ~~~~~~~~~~~~~~~~~~~~~~~~~~~~~~~~~~~~~~~~~~~~~~~~~~~
                              Right Arm
6751    CAGATACATT CTGGAAATAG TCCGTTATAT ATTTCTGTAT ATAGAAACAA
        GTCTATGTAA GACCTTTATC AGGCAATATA TAAAGACATA TATCTTTGTT
        ~~~~~~~~~~~~~~~~~~~~~~~~~~~~~~~~~~~~~~~~~~~~~~~~~~~
                              Right Arm
6801    TAAGTCATTA ACTAGATATT TATTAAAAAA AGGTGTTAAT TGTAATAGAT
        ATTCAGTAAT TGATCTATAA ATAATTTTTT TCCACAATTA ACATTATCTA
        ~~~~~~~~~~~~~~~~~~~~~~~~~~~~~~~~~~~~~~~~~~~~~~~~~~~
                              Right Arm
6851    TCTTTCTAAA TTATTACGAT GTACTGTATG ATAAGATATC TGATGATATG
        AGAAAGATTT AATAATGCTA CATGACATAC TATTCTATAG ACTACTATAC
        ~~~~~~~~~~~~~~~~~~~~~~~~~~~~~~~~~~~~~~~~~~~~~~~~~~~
                              Right Arm
6901    TATAAAATAT TTATAGATTT TAATATTGAT CTTAATATAC AAACTAGAAA
        ATATTTTATA AATATCTAAA ATTATAACTA GAATTATATG TTTGATCTTT
        ~~~~~~~~~~~~~~~~~~~~~~~~~~~~~~~~~~~~~~~~~~~~~~~~~~~
                              Right Arm
6951    TTTTGAAACT CCGTTACATT ACGCTATAAA GTATAAGAAT ATAGATTTAA
        AAAACTTTGA GGCAATGTAA TGCGATATTT CATATTCTTA TATCTAAATT
        ~~~~~~~~~~~~~~~~~~~~~~~~~~~~~~~~~~~~~~~~~~~~~~~~~~~
                              Right Arm
```

FIGURE 2K

```
7001   TTAGGATATT GTTAGATAAT AGTATTAAAA TAGATAAAAG TTTATTTTTG
       AATCCTATAA CAATCTATTA TCATAATTTT ATCTATTTTC AAATAAAAAC
       ~~~~~~~~~~~~~~~~~~~~~~~~~~~~~~~~~~~~~~~~~~~~~~~~~~~
                              Right Arm
7051   CATAAACAGT ATCTCATAAA GGCACTTAAA AATAATTGTA GTTACGATAT
       GTATTTGTCA TAGAGTATTT CCGTGAATTT TTATTAACAT CAATGCTATA
       ~~~~~~~~~~~~~~~~~~~~~~~~~~~~~~~~~~~~~~~~~~~~~~~~~~~
                              Right Arm
7101   AATAGCGTTA CTTATAAATC ACGGAGTGCC TATAAACGAA CAAGATGATT
       TTATCGCAAT GAATATTTAG TGCCTCACGG ATATTGCTT GTTCTACTAA
       ~~~~~~~~~~~~~~~~~~~~~~~~~~~~~~~~~~~~~~~~~~~~~~~~~~~
                              Right Arm
7151   TAGGTAAAAC CCCATTACAT CATTCGGTAA TTAATAGAAG AAAAGATGTA
       ATCCATTTTG GGGTAATGTA GTAAGCCATT AATTATCTTC TTTTCTACAT
       ~~~~~~~~~~~~~~~~~~~~~~~~~~~~~~~~~~~~~~~~~~~~~~~~~~~
                              Right Arm
7201   ACAGCACTTC TGTTAAATCT AGGAGCTGAT ATAAACGTAA TAGATGACTG
       TGTCGTGAAG ACAATTTAGA TCCTCGACTA TATTTGCATT ATCTACTGAC
       ~~~~~~~~~~~~~~~~~~~~~~~~~~~~~~~~~~~~~~~~~~~~~~~~~~~
                              Right Arm
7251   TATGGGCAGT CCCTTACATT ACGCTGTTTC ACGTAACGAT ATCGAAACAA
       ATACCCGTCA GGGAATGTAA TGCGACAAAG TGCATTGCTA TAGCTTTGTT
       ~~~~~~~~~~~~~~~~~~~~~~~~~~~~~~~~~~~~~~~~~~~~~~~~~~~
                              Right Arm
7301   CAAAGACACT TTTAGAAAGA GGATCTAATG TTAATGTGGT TAATAATCAT
       GTTTCTGTGA AAATCTTTCT CCTAGATTAC AATTACACCA ATTATTAGTA
       ~~~~~~~~~~~~~~~~~~~~~~~~~~~~~~~~~~~~~~~~~~~~~~~~~~~
                              Right Arm
7351   ATAGATACCG TTCTAAATAT AGCTGTTGCA TCTAAAAACA AAACTATAGT
       TATCTATGGC AAGATTTATA TCGACAACGT AGATTTTGT TTTGATATCA
       ~~~~~~~~~~~~~~~~~~~~~~~~~~~~~~~~~~~~~~~~~~~~~~~~~~~
                              Right Arm
7401   AAACTTATTA CTGAAGTACG GTACTGATAC AAAGTTGGTA GGATTAGATA
       TTTGAATAAT GACTTCATGC CATGACTATG TTTCAACCAT CCTAATCTAT
       ~~~~~~~~~~~~~~~~~~~~~~~~~~~~~~~~~~~~~~~~~~~~~~~~~~~
                              Right Arm
7451   AACATGTTAT TCACATAGCT ATAGAAATGA AAGATATTAA TATACTGAAT
       TTGTACAATA AGTGTATCGA TATCTTTACT TTCTATAATT ATATGACTTA
       ~~~~~~~~~~~~~~~~~~~~~~~~~~~~~~~~~~~~~~~~~~~~~~~~~~~
                              Right Arm
7501   GCGATCTTAT TATATGGTTG CTATGTAAAC GTCTATAATC ATAAAGGTTT
       CGCTAGAATA ATATACCAAC GATACATTTG CAGATATTAG TATTTCCAAA
       ~~~~~~~~~~~~~~~~~~~~~~~~~~~~~~~~~~~~~~~~~~~~~~~~~~~
                              Right Arm
7551   CACTCCTCTA TACATGGCAG TTAGTTCTAT GAAAACAGAA TTTGTTAAAC
       GTGAGGAGAT ATGTACCGTC AATCAAGATA CTTTTGTCTT AAACAATTTG
       ~~~~~~~~~~~~~~~~~~~~~~~~~~~~~~~~~~~~~~~~~~~~~~~~~~~
                              Right Arm
7601   TCTTACTTGA CCACGGTGCT TACGTAAATG CTAAAGCTAA GTTATCTGGA
       AGAATGAACT GGTGCCACGA ATGCATTTAC GATTTCGATT CAATAGACCT
       ~~~~~~~~~~~~~~~~~~~~~~~~~~~~~~~~~~~~~~~~~~~~~~~~~~~
                              Right Arm
7651   AATACTCCTT TACATAAAGC TATGTTATCT AATAGTTTTA ATAATATAAA
       TTATGAGGAA ATGTATTTCG ATACAATAGA TTATCAAAAT TATTATATTT
       ~~~~~~~~~~~~~~~~~~~~~~~~~~~~~~~~~~~~~~~~~~~~~~~~~~~
```

FIGURE 2L

```
            Right Arm
7701   ATTACTTTTA TCTTATAACG CCGACTATAA TTCTCTAAAT AATCACGGTA
       TAATGAAAAT AGAATATTGC GGCTGATATT AAGAGATTTA TTAGTGCCAT
       ~~~~~~~~~~~~~~~~~~~~~~~~~~~~~~~~~~~~~~~~~~~~~~~~~~
            Right Arm
7751   ATACGCCTCT AACTTGTGTT AGCTTTTTAG ATGACAAGAT AGCTATTATG
       TATGCGGAGA TTGAACACAA TCGAAAAATC TACTGTTCTA TCGATAATAC
       ~~~~~~~~~~~~~~~~~~~~~~~~~~~~~~~~~~~~~~~~~~~~~~~~~~
            Right Arm
7801   ATAATATCTA AAATGATGTT AGAAATATCT AAAAATCCTG AAATAGCTAA
       TATTATAGAT TTTACTACAA TCTTTATAGA TTTTTAGGAC TTTATCGATT
       ~~~~~~~~~~~~~~~~~~~~~~~~~~~~~~~~~~~~~~~~~~~~~~~~~~
            Right Arm
7851   TTCAGAAGGT TTTATAGTAA ACATGGAACA TATAAACAGT AATAAAAGAC
       AAGTCTTCCA AAATATCATT TGTACCTTGT ATATTGTCA TTATTTTCTG
       ~~~~~~~~~~~~~~~~~~~~~~~~~~~~~~~~~~~~~~~~~~~~~~~~~~
            Right Arm
7901   TACTATCTAT AAAAGAATCA TGCGAAAAAG AACTAGATGT TATAACACAT
       ATGATAGATA TTTTCTTAGT ACGCTTTTTC TTGATCTACA ATATTGTGTA
       ~~~~~~~~~~~~~~~~~~~~~~~~~~~~~~~~~~~~~~~~~~~~~~~~~~
            Right Arm
7951   ATAAAGTTAA ATTCTATATA TTCTTTTAAT ATCTTTCTTG ACAATAACAT
       TATTTCAATT TAAGATATAT AAGAAAATTA TAGAAAGAAC TGTTATTGTA
       ~~~~~~~~~~~~~~~~~~~~~~~~~~~~~~~~~~~~~~~~~~~~~~~~~~
            Right Arm
8001   AGATCTTATG GTAAAGTTCG TAACTAATCC TAGAGTTAAT AAGATACCTG
       TCTAGAATAC CATTTCAAGC ATTGATTAGG ATCTCAATTA TTCTATGGAC
       ~~~~~~~~~~~~~~~~~~~~~~~~~~~~~~~~~~~~~~~~~~~~~~~~~~
            Right Arm
8051   CATGTATACG TATATATAGG GAATTAATAC GGAAAAATAA ATCATTAGCT
       GTACATATGC ATATATATCC CTTAATTATG CCTTTTTATT TAGTAATCGA
       ~~~~~~~~~~~~~~~~~~~~~~~~~~~~~~~~~~~~~~~~~~~~~~~~~~
            Right Arm
8101   TTTCATAGAC ATCAGCTAAT AGTTAAAGCT GTAAAAGAGA GTAAGAATCT
       AAAGTATCTG TAGTCGATTA TCAATTTCGA CATTTTCTCT CATTCTTAGA
       ~~~~~~~~~~~~~~~~~~~~~~~~~~~~~~~~~~~~~~~~~~~~~~~~~~
            Right Arm
8151   AGGAATAATA GGTAGGTTAC CTATAGATAT CAAACATATA ATAATGGAAC
       TCCTTATTAT CCATCCAATG GATATCTATA GTTTGTATAT TATTACCTTG
       ~~~~~~~~~~~~~~~~~~~~~~~~~~~~~~~~~~~~~~~~~~~~~~~~~~
            Right Arm
8201   TATTAAGTAA TAATGATTTA CATTCTGTTA TCACCAGCTG TTGTAACCCA
       ATAATTCATT ATTACTAAAT GTAAGACAAT AGTGGTCGAC AACATTGGGT
       ~~~~~~~~~~~~~~~~~~~~~~~~~~~~~~~~~~~~~~~~~~~~~~~~~~
            Right Arm
8251   GTAGTATAAA GAGCTCCAGC TTTTGTTCCC TTTAGTGAGG GTTAATTCCG
       CATCATATTT CTCGAGGTCG AAAACAAGGG AAATCACTCC CAATTAAGGC
       ~~~~~~~~~~~~~~~~~
         Right Arm
8301   AGCTTGGCGT AATCATGGTC ATAGCTGTTT CCTGTGTGAA ATTGTTATCC
       TCGAACCGCA TTAGTACCAG TATCGACAAA GGACACACTT TAACAATAGG
8351   GCTCACAATT CCACACAACA TACGAGCCGG AAGCATAAAG TGTAAAGCCT
       CGAGTGTTAA GGTGTGTTGT ATGCTCGGCC TTCGTATTTC ACATTTCGGA
8401   GGGGTGCCTA ATGAGTGAGC TAACTCACAT TAATTGCGTT GCGCTCACTG
       CCCCACGGAT TACTCACTCG ATTGAGTGTA ATTAACGCAA CGCGAGTGAC
8451   CCCGCTTTCC AGTCGGGAAA CCTGTCGTGC CAGCTGCATT AATGAATCGG
```

FIGURE 2M

```
      GGGCGAAAGG TCAGCCCTTT GGACAGCACG GTCGACGTAA TTACTTAGCC
8501  CCAACGCGCG GGGAGAGGCG GTTTGCGTAT TGGGCGCTCT TCCGCTTCCT
      GGTTGCGCGC CCCTCTCCGC CAAACGCATA ACCCGCGAGA AGGCGAAGGA
8551  CGCTCACTGA CTCGCTGCGC TCGGTCGTTC GGCTGCGGCG AGCGGTATCA
      GCGAGTGACT GAGCGACGCG AGCCAGCAAG CCGACGCCGC TCGCCATAGT
8601  GCTCACTCAA AGGCGGTAAT ACGGTTATCC ACAGAATCAG GGGATAACGC
      CGAGTGAGTT TCCGCCATTA TGCCAATAGG TGTCTTAGTC CCCTATTGCG
8651  AGGAAAGAAC ATGTGAGCAA AAGGCCAGCA AAAGGCCAGG AACCGTAAAA
      TCCTTTCTTG TACACTCGTT TTCCGGTCGT TTTCCGGTCC TTGGCATTTT
8701  AGGCCGCGTT GCTGGCGTTT TTCCATAGGC TCCGCCCCCC TGACGAGCAT
      TCCGGCGCAA CGACCGCAAA AAGGTATCCG AGGCGGGGGG ACTGCTCGTA
8751  CACAAAAATC GACGCTCAAG TCAGAGGTGG CGAAACCCGA CAGGACTATA
      GTGTTTTTAG CTGCGAGTTC AGTCTCCACC GCTTTGGGCT GTCCTGATAT
8801  AAGATACCAG GCGTTTCCCC CTGGAAGCTC CCTCGTGCGC TCTCCTGTTC
      TTCTATGGTC CGCAAAGGGG GACCTTCGAG GGAGCACGCG AGAGGACAAG
8851  CGACCCTGCC GCTTACCGGA TACCTGTCCG CCTTTCTCCC TTCGGGAAGC
      GCTGGGACGG CGAATGGCCT ATGGACAGGC GGAAAGAGGG AAGCCCTTCG
8901  GTGGCGCTTT CTCATAGCTC ACGCTGTAGG TATCTCAGTT CGGTGTAGGT
      CACCGCGAAA GAGTATCGAG TGCGACATCC ATAGAGTCAA GCCACATCCA
8951  CGTTCGCTCC AAGCTGGGCT GTGTGCACGA ACCCCCCGTT CAGCCCGACC
      GCAAGCGAGG TTCGACCCGA CACACGTGCT TGGGGGGCAA GTCGGGCTGG
9001  GCTGCGCCTT ATCCGGTAAC TATCGTCTTG AGTCCAACCC GGTAAGACAC
      CGACGCGGAA TAGGCCATTG ATAGCAGAAC TCAGGTTGGG CCATTCTGTG
9051  GACTTATCGC CACTGGCAGC AGCCACTGGT AACAGGATTA GCAGAGCGAG
      CTGAATAGCG GTGACCGTCG TCGGTGACCA TTGTCCTAAT CGTCTCGCTC
9101  GTATGTAGGC GGTGCTACAG AGTTCTTGAA GTGGTGGCCT AACTACGGCT
      CATACATCCG CCACGATGTC TCAAGAACTT CACCACCGGA TTGATGCCGA
9151  ACACTAGAAG GACAGTATTT GGTATCTGCG CTCTGCTGAA GCCAGTTACC
      TGTGATCTTC CTGTCATAAA CCATAGACGC GAGACGACTT CGGTCAATGG
9201  TTCGGAAAAA GAGTTGGTAG CTCTTGATCC GGCAAACAAA CCACCGCTGG
      AAGCCTTTTT CTCAACCATC GAGAACTAGG CCGTTTGTTT GGTGGCGACC
9251  TAGCGGTGGT TTTTTGTTT GCAAGCAGCA GATTACGCGC AGAAAAAAAG
      ATCGCCACCA AAAAACAAA CGTTCGTCGT CTAATGCGCG TCTTTTTTTC
9301  GATCTCAAGA AGATCCTTTG ATCTTTTCTA CGGGGTCTGA CGCTCAGTGG
      CTAGAGTTCT TCTAGGAAAC TAGAAAAGAT GCCCCAGACT GCGAGTCACC
9351  AACGAAAACT CACGTTAAGG GATTTTGGTC ATGAGATTAT CAAAAAGGAT
      TTGCTTTTGA GTGCAATTCC CTAAAACCAG TACTCTAATA GTTTTTCCTA
9401  CTTCACCTAG ATCCTTTTAA ATTAAAAATG AAGTTTTAAA TCAATCTAAA
      GAAGTGGATC TAGGAAAATT TAATTTTTAC TTCAAAATTT AGTTAGATTT
9451  GTATATATGA GTAAACTTGG TCTGACAGTT ACCAATGCTT AATCAGTGAG
      CATATATACT CATTTGAACC AGACTGTCAA TGGTTACGAA TTAGTCACTC
9501  GCACCTATCT CAGCGATCTG TCTATTTCGT TCATCCATAG TTGCCTGACT
      CGTGGATAGA GTCGCTAGAC AGATAAAGCA AGTAGGTATC AACGGACTGA
9551  CCCCGTCGTG TAGATAACTA CGATACGGGA GGGCTTACCA TCTGGCCCCA
      GGGGCAGCAC ATCTATTGAT GCTATGCCCT CCCGAATGGT AGACCGGGGT
9601  GTGCTGCAAT GATACCGCGA GACCCACGCT CACCGGCTCC AGATTTATCA
      CACGACGTTA CTATGGCGCT CTGGGTGCGA GTGGCCGAGG TCTAAATAGT
9651  GCAATAAACC AGCCAGCCGG AAGGGCCGAG CGCAGAAGTG GTCCTGCAAC
      CGTTATTTGG TCGGTCGGCC TTCCCGGCTC GCGTCTTCAC CAGGACGTTG
9701  TTTATCCGCC TCCATCCAGT CTATTAATTG TTGCCGGGAA GCTAGAGTAA
      AAATAGGCGG AGGTAGGTCA GATAATTAAC AACGGCCCTT CGATCTCATT
9751  GTAGTTCGCC AGTTAATAGT TTGCGCAACG TTGTTGCCAT TGCTACAGGC
      CATCAAGCGG TCAATTATCA AACGCGTTGC AACAACGGTA ACGATGTCCG
9801  ATCGTGGTGT CACGCTCGTC GTTTGGTATG GCTTCATTCA GCTCCGGTTC
      TAGCACCACA GTGCGAGCAG CAAACCATAC CGAAGTAAGT CGAGGCCAAG
```

FIGURE 2N

```
 9851   CCAACGATCA AGGCGAGTTA CATGATCCCC CATGTTGTGC AAAAAAGCGG
        GGTTGCTAGT TCCGCTCAAT GTACTAGGGG GTACAACACG TTTTTTCGCC
 9901   TTAGCTCCTT CGGTCCTCCG ATCGTTGTCA GAAGTAAGTT GGCCGCAGTG
        AATCGAGGAA GCCAGGAGGC TAGCAACAGT CTTCATTCAA CCGGCGTCAC
 9951   TTATCACTCA TGGTTATGGC AGCACTGCAT AATTCTCTTA CTGTCATGCC
        AATAGTGAGT ACCAATACCG TCGTGACGTA TTAAGAGAAT GACAGTACGG
10001   ATCCGTAAGA TGCTTTTCTG TGACTGGTGA GTACTCAACC AAGTCATTCT
        TAGGCATTCT ACGAAAAGAC ACTGACCACT CATGAGTTGG TTCAGTAAGA
10051   GAGAATAGTG TATGCGGCGA CCGAGTTGCT CTTGCCCGGC GTCAATACGG
        CTCTTATCAC ATACGCCGCT GGCTCAACGA GAACGGGCCG CAGTTATGCC
10101   GATAATACCG CGCCACATAG CAGAACTTTA AAAGTGCTCA TCATTGGAAA
        CTATTATGGC GCGGTGTATC GTCTTGAAAT TTTCACGAGT AGTAACCTTT
10151   ACGTTCTTCG GGGCGAAAAC TCTCAAGGAT CTTACCGCTG TTGAGATCCA
        TGCAAGAAGC CCCGCTTTTG AGAGTTCCTA GAATGGCGAC AACTCTAGGT
10201   GTTCGATGTA ACCCACTCGT GCACCCAACT GATCTTCAGC ATCTTTTACT
        CAAGCTACAT TGGGTGAGCA CGTGGGTTGA CTAGAAGTCG TAGAAAATGA
10251   TTCACCAGCG TTTCTGGGTG AGCAAAAACA GGAAGGCAAA ATGCCGCAAA
        AAGTGGTCGC AAAGACCCAC TCGTTTTTGT CCTTCCGTTT TACGGCGTTT
10301   AAAGGGAATA AGGGCGACAC GGAAATGTTG AATACTCATA CTCTTCCTTT
        TTTCCCTTAT TCCCGCTGTG CCTTTACAAC TTATGAGTAT GAGAAGGAAA
10351   TTCAATATTA TTGAAGCATT TATCAGGGTT ATTGTCTCAT GAGCGGATAC
        AAGTTATAAT AACTTCGTAA ATAGTCCCAA TAACAGAGTA CTCGCCTATG
10401   ATATTTGAAT GTATTTAGAA AAATAAACAA ATAGGGGTTC CGCGCACATT
        TATAAACTTA CATAAATCTT TTTATTTGTT TATCCCCAAG GCGCGTGTAA
10451   TCCCCGAAAA GTGCCACCTG
        AGGGGCTTTT CACGGTGGAC
```

FIGURE 3A: Donor plasmid p1132

```
                          C5 Right Arm
         ~~~~~~~~~~~~~~~~~~~~~~~~~~~~~~~~~~~~~~~~~~~~~~~~~~~
   1     TGAATGTTAA ATGTTATACT TTGGATGAAG CTATAAATAT GCATTGGAAA
         ACTTACAATT TACAATATGA AACCTACTTC GATATTTATA CGTAACCTTT
                          C5 Right Arm
         ~~~~~~~~~~~~~~~~~~~~~~~~~~~~~~~~~~~~~~~~~~~~~~~~~~~
  51     AATAATCCAT TTAAAGAAAG GATTCAAATA CTACAAAACC TAAGCGATAA
         TTATTAGGTA AATTTCTTTC CTAAGTTTAT GATGTTTTGG ATTCGCTATT
                          C5 Right Arm
         ~~~~~~~~~~~~~~~~~~~~~~~~~~~~~~~~~~~~~~~~~~~~~~~~~~~
 101     TATGTTAACT AAGCTTATTC TTAACGACGC TTTAAATATA CACAAATAAA
         ATACAATTGA TTCGAATAAG AATTGCTGCG AAATTTATAT GTGTTTATTT
                          C5 Right Arm
         ~~~~~~~~~~~~~~~~~~~~~~~~~~~~~~~~~~~~~~~~~~~~~~~~~~~
 151     CATAATTTTT GTATAACCTA ACAAATAACT AAAACATAAA AATAATAAAA
         GTATTAAAAA CATATTGGAT TGTTTATTGA TTTTGTATTT TTATTATTTT
                          C5 Right Arm
         ~~~~~~~~~~~~~~~~~~~~~~~~~~~~~~~~~~~~~~~~~~~~~~~~~~~
 201     GGAAATGTAA TATCGTAATT ATTTTACTCA GGAATGGGGT TAAATATTTA
         CCTTTACATT ATAGCATTAA TAAAATGAGT CCTTACCCCA ATTTATAAAT
                          C5 Right Arm
         ~~~~~~~~~~~~~~~~~~~~~~~~~~~~~~~~~~~~~~~~~~~~~~~~~~~
 251     TATCACGTGT ATATCTATAC TGTTATCGTA TACTCTTTAC AATTACTATT
         ATAGTGCACA TATAGATATG ACAATAGCAT ATGAGAAATG TTAATGATAA
                          C5 Right Arm
         ~~~~~~~~~~~~~~~~~~~~~~~~~~~~~~~~~~~~~~~~~~~~~~~~~~~
 301     ACGAATATGC AAGAGATAAT AAGATTACGT ATTTAAGAGA ATCTTGTCAT
         TGCTTATACG TTCTCTATTA TTCTAATGCA TAAATTCTCT TAGAACAGTA
                          C5 Right Arm
         ~~~~~~~~~~~~~~~~~~~~~~~~~~~~~~~~~~~~~~~~~~~~~~~~~~~
 351     GATAATTGGG TACGACATAG TGATAAATGC TATTTCGCAT CGTTACATAA
         CTATTAACCC ATGCTGTATC ACTATTTACG ATAAAGCGTA GCAATGTATT
                          C5 Right Arm
         ~~~~~~~~~~~~~~~~~~~~~~~~~~~~~~~~~~~~~~~~~~~~~~~~~~~
 401     AGTCAGTTGG AAAGATGGAT TTGACAGATG TAACTTAATA GGTGCAAAAA
         TCAGTCAACC TTTCTACCTA AACTGTCTAC ATTGAATTAT CCACGTTTTT
                          C5 Right Arm
         ~~~~~~~~~~~~~~~~~~~~~~~~~~~~~~~~~~~~~~~~~~~~~~~~~~~
 451     TGTTAAATAA CAGCATTCTA TCGGAAGATA GGATACCAGT TATATTATAC
         ACAATTTATT GTCGTAAGAT AGCCTTCTAT CCTATGGTCA ATATAATATG
                          C5 Right Arm
         ~~~~~~~~~~~~~~~~~~~~~~~~~~~~~~~~~~~~~~~~~~~~~~~~~~~
 501     AAAAATCACT GGTTGGATAA AACAGATTCT GCAATATTCG TAAAAGATGA
         TTTTTAGTGA CCAACCTATT TTGTCTAAGA CGTTATAAGC ATTTTCTACT
                          C5 Right Arm
         ~~~~~~~~~~~~~~~~~~~~~~~~~~~~~~~~~~~~~~~~~~~~~~~~~~~
 551     AGATTACTGC GAATTGTAA ACTATGACAA TAAAAGCCA TTTATCTCAA
         TCTAATGACG CTTAAACATT TGATACTGTT ATTTTTCGGT AAATAGAGTT
                          C5 Right Arm
         ~~~~~~~~~~~~~~~~~~~~~~~~~~~~~~~~~~~~~~~~~~~~~~~~~~~
 601     CGACATCGTG TAATTCTTCC ATGTTTTATG TATGTGTTTC AGATATTATG
         GCTGTAGCAC ATTAAGAAGG TACAAAATAC ATACACAAAG TCTATAATAC
```

FIGURE 3B
C5 Right Arm

```
 651   AGATTACTAT AAACTTTTTG TATACTTATA TTCCGTAAAC TATATTAATC
       TCTAATGATA TTTGAAAAAC ATATGAATAT AAGGCATTTG ATATAATTAG
                         C5 Right Arm 701   ATGAAGAAAA TGAAAAAGTA TAGAAGCTGT TCACGAGCGG TTGTTGAAAA
       TACTTCTTTT ACTTTTTCAT ATCTTCGACA AGTGCTCGCC AACAACTTTT
                         C5 Right Arm 751   CAACAAAATT ATACATTCAA GATGGCTTAC ATATACGTCT GTGAGGCTAT
       GTTGTTTTAA TATGTAAGTT CTACCGAATG TATATGCAGA CACTCCGATA
                         C5 Right Arm 801   CATGGATAAT GACAATGCAT CTCTAAATAG GTTTTTGGAC AATGGATTCG
       GTACCTATTA CTGTTACGTA GAGATTTATC CAAAAACCTG TTACCTAAGC
                         C5 Right Arm 851   ACCCTAACAC GGAATATGGT ACTCTACAAT CTCCTCTTGA AATGGCTGTA
       TGGGATTGTG CCTTATACCA TGAGATGTTA GAGGAGAACT TTACCGACAT
                         C5 Right Arm 901   ATGTTCAAGA ATACCGAGGC TATAAAAATC TTGATGAGGT ATGGAGCTAA
       TACAAGTTCT TATGGCTCCG ATATTTTTAG AACTACTCCA TACCTCGATT
                         C5 Right Arm 951   ACCTGTAGTT ACTGAATGCA CAACTTCTTG TCTGCATGAT GCGGTGTTGA
       TGGACATCAA TGACTTACGT GTTGAAGAAC AGACGTACTA CGCCACAACT
                         C5 Right Arm 1001   GAGACGACTA CAAAATAGTG AAAGATCTGT TGAAGAATAA CTATGTAAAC
       CTCTGCTGAT GTTTTATCAC TTTCTAGACA ACTTCTTATT GATACATTTG
                         C5 Right Arm 1051   AATGTTCTTT ACAGCGGAGG CTTTACTCCT TTGTGTTTGG CAGCTTACCT
       TTACAAGAAA TGTCGCCTCC GAAATGAGGA AACACAAACC GTCGAATGGA
                         C5 Right Arm 1101   TAACAAAGTT AATTTGGTTA AACTTCTATT GGCTCATTCG GCGGATGTAG
       ATTGTTTCAA TTAAACCAAT TTGAAGATAA CCGAGTAAGC CGCCTACATC
                         C5 Right Arm 1151   ATATTTCAAA CACGGATCGG TTAACTCCTC TACATATAGC CGTATCAAAT
       TATAAAGTTT GTGCCTAGCC AATTGAGGAG ATGTATATCG GCATAGTTTA
                         C5 Right Arm 1201   AAAAATTTAA CAATGGTTAA ACTTCTATTG AACAAAGGTG CTGATACTGA
       TTTTTAAATT GTTACCAATT TGAAGATAAC TTGTTTCCAC GACTATGACT
                         C5 Right Arm 1251   CTTGCTGGAT AACATGGGAT GTACTCCTTT AATGATCGCT GTACAATCTG
       GAACGACCTA TTGTACCCTA CATGAGGAAA TTACTAGCGA CATGTTAGAC
```

FIGURE 3C

```
                           C5 Right Arm
      ~~~~~~~~~~~~~~~~~~~~~~~~~~~~~~~~~~~~~~~~~~~~~~~~~~~~~
1301  GAAATATTGA AATATGTAGC ACACTACTTA AAAAAAATAA AATGTCCAGA
      CTTTATAACT TTATACATCG TGTGATGAAT TTTTTTTATT TTACAGGTCT
                           C5 Right Arm
      ~~~~~~~~~~~~~~~~~~~~~~~~~~~~~~~~~~~~~~~~~~~~~~~~~~~~
1351  ACTGGGAAAA ATTGATCTTG CCAGCTGTAA TTCATGGTAG AAAAGAAGTG
      TGACCCTTTT TAACTAGAAC GGTCGACATT AAGTACCATC TTTTCTTCAC
                           C5 Right Arm
      ~~~~~~~~~~~~~~~~~~~~~~~~~~~~~~~~~~~~~~~~~~~~~~~~~~~~
1401  CTCAGGCTAC TTTTCAACAA AGGAGCAGAT GTAAACTACA TCTTTGAAAG
      GAGTCCGATG AAAAGTTGTT TCCTCGTCTA CATTTGATGT AGAAACTTTC
                           C5 Right Arm
      ~~~~~~~~~~~~~~~~~~~~~~~~~~~~~~~~~~~~~~~~~~~~~~~~~~~~
1451  AAATGGAAAA TCATATACTG TTTTGGAATT GATTAAAGAA AGTTACTCTG
      TTTACCTTTT AGTATATGAC AAAACCTTAA CTAATTTCTT TCAATGAGAC
                      C5 Right Arm
      ~~~~~~~~~~~~~~~~~~~~~~~~~~~~~~~~~~~~~~~~~
1501  AGACACAAAA GAGGTAGCTG AAGTGGTACT CTCAAAGGTA CGTGACTAAT
      TCTGTGTTTT CTCCATCGAC TTCACCATGA GAGTTTCCAT GCACTGATTA
                                                    Repeat Region
                                                    ~~~~~~~~~~
1551  TAGCTATAAA AAGGATCGGC CGCTCTAGAA CTAGTGGATC GGGTTCTTTA
      ATCGATATTT TTCCTAGCCG GCGAGATCTT GATCACCTAG CCCAAGAAAT
                          Repeat Region
      ~~~~~~~~~~~~~~~~~~~~~~~~~~~~~~~~~~~~~~~~~~~~~~~~~~~~
1601  TTCTATACTT AAAAAGTGAA AATAAATACA AAGGTTCTTG AGGGTTGTGT
      AAGATATGAA TTTTTCACTT TTATTTATGT TTCCAAGAAC TCCCAACACA
                          Repeat Region
      ~~~~~~~~~~~~~~~~~~~~~~~~~~~~~~~~~~~~~~~~~~~~~~~~~~~~
1651  TAAATTGAAA GCGAGAAATA ATCATAAATT ATTTCATTAT CGCGATATCC
      ATTTAACTTT CGCTCTTTAT TAGTATTTAA TAAAGTAATA GCGCTATAGG
                          Repeat Region
      ~~~~~~~~~~~~~~~~~~~~~~~~~~~~~~~~~~~~~~~~~~~~~~~~~~~~
1701  GTTAAGTTTG TATCGTACCC CGATCCCCCG AGCCATGCAG GCCGAAGGCC
      CAATTCAAAC ATAGCATGGG GCTAGGGGGC TCGGTACGTC CGGCTTCCGG
                          Repeat Region
      ~~~~~~~~~~~~~~~~~~~~~~~~~~~~~~~~~~~~~~~~~~~~~~~~~~~~
1751  GGGGCACAGG GGGTTCGACG GGCGATGCTG ATGGCCCAGG AGGCCCTGGC
      CCCCGTGTCC CCCAAGCTGC CCGCTACGAC TACCGGGTCC TCCGGGACCG
                          Repeat Region
      ~~~~~~~~~~~~~~~~~~~~~~~~~~~~~~~~~~~~~~~~~~~~~~~~~~~~
1801  ATTCCTGATG GCCCAGGGGG CAATGCTGGC GGCCCAGGAG AGGCGGGTGC
      TAAGGACTAC CGGGTCCCCC GTTACGACCG CCGGGTCCTC TCCGCCCACG
                          Repeat Region
      ~~~~~~~~~~~~~~~~~~~~~~~~~~~~~~~~~~~~~~~~~~~~~~~~~~~~
1851  CACGGGCGGC AGAGGTCCCC GGGGCGCAGG GGCAGCAAGG GCCTCGGGGC
      GTGCCCGCCG TCTCCAGGGG CCCCGCGTCC CCGTCGTTCC GGAGCCCCG
                          Repeat Region
      ~~~~~~~~~~~~~~~~~~~~~~~~~~~~~~~~~~~~~~~~~~~~~~~~~~~~
1901  CGGGAGGAGG CGCCCCGCGG GGTCCGCATG GCGGCGCGGC TTCAGGGCTG
      GCCCTCCTCC GCGGGGCGCC CCAGGCGTAC CGCCGCGCCG AAGTCCCGAC
                          Repeat Region
      ~~~~~~~~~~~~~~~~~~~~~~~~~~~~~~~~~~~~~~~~~~~~~~~~~~~~
1951  AATGGATGCT GCAGATGCGG GGCCAGGGGG CCGGAGAGCC GCCTGCTTGA
      TTACCTACGA CGTCTACGCC CCGGTCCCCC GGCCTCTCGG CGGACGAACT
```

FIGURE 3D

```
        Repeat Region
        ~~~~~~~~~~~~~~~~~~~~~~~~~~~~~~~~~~~~~~~~
2001    GTTCTACCTC GCCATGCCTT TCGCGACACC CATAGCTTGA TATCGAATTC
        CAAGATGGAG CGGTACGGAA AGCGCTGTGG GTATCGAACT ATAGCTTAAG
                                   C1B promoter
                                   ~~~~~~~~~~~~~~~~~~~~~~~~~~~~
2051    TAGGGGGATC CACTAGTTCT AGAGGATCAT TATTTAACGT AAACTAAATG
        ATCCCCCTAG GTGATCAAGA TCTCCTAGTA ATAAATTGCA TTTGATTTAC
                     C1B promoter
        ~~~~~~~~~~~~~~~~~~~~~~~~~~~~~~~~~~~~~~~~~~~~~~~~~~
2101    GAAAAGCTAT TTACAGGTAC ATACGGTGTT TTTCTGGAAT CAAATGATTC
        CTTTTCGATA AATGTCCATG TATGCCACAA AAAGACCTTA GTTTACTAAG
                     C1B promoter
        ~~~~~~~~~~~~~~~~~~~~~~~~~~~~~~~~~~~~~~~~~~~~~~~~~~
2151    TGATTTTGAG GATTTTATCA ATACAATAAT GACAGTGCTA ACTGGTAAAA
        ACTAAAACTC CTAAAATAGT TATGTTATTA CTGTCACGAT TGACCATTTT
                     C1B promoter
        ~~~~~~~~~~~~~~~~~~~~~~~~~~~~~~~~~~~~~~~~~~~~~~~~~~
2201    AAGAAAGCAA ACAATTATCA TGGCTAACAA TTTTTATTAT ATTTGTAGTA
        TTCTTTCGTT TGTTAATAGT ACCGATTGTT AAAAATAATA TAAACATCAT
                     C1B promoter
        ~~~~~~~~~~~~~~~~~~~~~~~~~~~~~~~~~~~~~~~~~~~~~~~~~~
2251    TGCATAGTGG TCTTTACGTT TCTTTATTTA AAGTTAATGT GTTAAGATTA
        ACGTATCACC AGAAATGCAA AGAAATAAAT TTCAATTACA CAATTCTAAT
           C1B promoter                              LacZ
        ~~~~~~~~~~~~~~~~~~                    ~~~~~~~~~~~~~~~~~~~
2301    AATGGAGTAA TTGGATCCCC CATCGATGGG GAATTCACTG GCCGTCGTTT
        TTACCTCATT AACCTAGGGG GTAGCTACCC CTTAAGTGAC CGGCAGCAAA
                                   LacZ
        ~~~~~~~~~~~~~~~~~~~~~~~~~~~~~~~~~~~~~~~~~~~~~~~~~~
2351    TACAACGTCG TGACTGGGAA AACCCTGGCG TTACCCAACT TAATCGCCTT
        ATGTTGCAGC ACTGACCCTT TTGGGACCGC AATGGGTTGA ATTAGCGGAA
                                   LacZ
        ~~~~~~~~~~~~~~~~~~~~~~~~~~~~~~~~~~~~~~~~~~~~~~~~~~
2401    GCAGCACATC CCCCTTTCGC CAGCTGGCGT AATAGCGAAG AGGCCCGCAC
        CGTCGTGTAG GGGGAAAGCG GTCGACCGCA TTATCGCTTC TCCGGGCGTG
                                   LacZ
        ~~~~~~~~~~~~~~~~~~~~~~~~~~~~~~~~~~~~~~~~~~~~~~~~~~
2451    CGATCGCCCT TCCCAACAGT TGCGCAGCCT GAATGGCGAA TGGCGCTTTG
        GCTAGCGGGA AGGGTTGTCA ACGCGTCGGA CTTACCGCTT ACCGCGAAAC
                                   LacZ
        ~~~~~~~~~~~~~~~~~~~~~~~~~~~~~~~~~~~~~~~~~~~~~~~~~~
2501    CCTGGTTTCC GGCACCAGAA GCGGTGCCGG AAAGCTGGCT GGAGTGCGAT
        GGACCAAAGG CCGTGGTCTT CGCCACGGCC TTTCGACCGA CCTCACGCTA
                                   LacZ
        ~~~~~~~~~~~~~~~~~~~~~~~~~~~~~~~~~~~~~~~~~~~~~~~~~~
2551    CTTCCTGAGG CCGATACTGT CGTCGTCCCC TCAAACTGGC AGATGCACGG
        GAAGGACTCC GGCTATGACA GCAGCAGGGG AGTTTGACCG TCTACGTGCC
                                   LacZ
        ~~~~~~~~~~~~~~~~~~~~~~~~~~~~~~~~~~~~~~~~~~~~~~~~~~
2601    TTACGATGCG CCCATCTACA CCAACGTGAC CTATCCCATT ACGGTCAATC
        AATGCTACGC GGGTAGATGT GGTTGCACTG GATAGGGTAA TGCCAGTTAG
                                   LacZ
        ~~~~~~~~~~~~~~~~~~~~~~~~~~~~~~~~~~~~~~~~~~~~~~~~~~
2651    CGCCGTTTGT TCCCACGGAG AATCCGACGG GTTGTTACTC GCTCACATTT
        GCGGCAAACA AGGGTGCCTC TTAGGCTGCC CAACAATGAG CGAGTGTAAA
```

FIGURE 3E

```
            LacZ
            ~~~~~~~~~~~~~~~~~~~~~~~~~~~~~~~~~~~~~~~~~~~~~~~~~~
2701   AATGTTGATG AAAGCTGGCT ACAGGAAGGC CAGACGCGAA TTATTTTTGA
       TTACAACTAC TTTCGACCGA TGTCCTTCCG GTCTGCGCTT AATAAAAACT
            LacZ
            ~~~~~~~~~~~~~~~~~~~~~~~~~~~~~~~~~~~~~~~~~~~~~~~~~~
2751   TGGCGTTAAC TCGGCGTTTC ATCTGTGGTG CAACGGGCGC TGGGTCGGTT
       ACCGCAATTG AGCCGCAAAG TAGACACCAC GTTGCCCGCG ACCCAGCCAA
            LacZ
            ~~~~~~~~~~~~~~~~~~~~~~~~~~~~~~~~~~~~~~~~~~~~~~~~~~
2801   ACGGCCAGGA CAGTCGTTTG CCGTCTGAAT TTGACCTGAG CGCATTTTTA
       TGCCGGTCCT GTCAGCAAAC GGCAGACTTA AACTGGACTC GCGTAAAAAT
            LacZ
            ~~~~~~~~~~~~~~~~~~~~~~~~~~~~~~~~~~~~~~~~~~~~~~~~~~
2851   CGCGCCGGAG AAAACCGCCT CGCGGTGATG GTGCTGCGCT GGAGTGACGG
       GCGCGGCCTC TTTTGGCGGA GCGCCACTAC CACGACGCGA CCTCACTGCC
            LacZ
            ~~~~~~~~~~~~~~~~~~~~~~~~~~~~~~~~~~~~~~~~~~~~~~~~~~
2901   CAGTTATCTG GAAGATCAGG ATATGTGGCG GATGAGCGGC ATTTTCCGTG
       GTCAATAGAC CTTCTAGTCC TATACACCGC CTACTCGCCG TAAAAGGCAC
            LacZ
            ~~~~~~~~~~~~~~~~~~~~~~~~~~~~~~~~~~~~~~~~~~~~~~~~~~
2951   ACGTCTCGTT GCTGCATAAA CCGACTACAC AAATCAGCGA TTTCCATGTT
       TGCAGAGCAA CGACGTATTT GGCTGATGTG TTTAGTCGCT AAAGGTACAA
            LacZ
            ~~~~~~~~~~~~~~~~~~~~~~~~~~~~~~~~~~~~~~~~~~~~~~~~~~
3001   GCCACTCGCT TTAATGATGA TTTCAGCCGC GCTGTACTGG AGGCTGAAGT
       CGGTGAGCGA AATTACTACT AAAGTCGGCG CGACATGACC TCCGACTTCA
            LacZ
            ~~~~~~~~~~~~~~~~~~~~~~~~~~~~~~~~~~~~~~~~~~~~~~~~~~
3051   TCAGATGTGC GGCGAGTTGC GTGACTACCT ACGGGTAACA GTTTCTTTAT
       AGTCTACACG CCGCTCAACG CACTGATGGA TGCCCATTGT CAAAGAAATA
            LacZ
            ~~~~~~~~~~~~~~~~~~~~~~~~~~~~~~~~~~~~~~~~~~~~~~~~~~
3101   GGCAGGGTGA AACGCAGGTC GCCAGCGGCA CCGCGCCTTT CGGCGGTGAA
       CCGTCCCACT TTGCGTCCAG CGGTCGCCGT GGCGCGGAAA GCCGCCACTT
            LacZ
            ~~~~~~~~~~~~~~~~~~~~~~~~~~~~~~~~~~~~~~~~~~~~~~~~~~
3151   ATTATCGATG AGCGTGGTGG TTATGCCGAT CGCGTCACAC TACGTCTGAA
       TAATAGCTAC TCGCACCACC AATACGGCTA GCGCAGTGTG ATGCAGACTT
            LacZ
            ~~~~~~~~~~~~~~~~~~~~~~~~~~~~~~~~~~~~~~~~~~~~~~~~~~
3201   CGTCGAAAAC CCGAAACTGT GGAGCGCCGA AATCCCGAAT CTCTATCGTG
       GCAGCTTTTG GGCTTTGACA CCTCGCGGCT TTAGGGCTTA GAGATAGCAC
            LacZ
            ~~~~~~~~~~~~~~~~~~~~~~~~~~~~~~~~~~~~~~~~~~~~~~~~~~
3251   CGGTGGTTGA ACTGCACACC GCCGACGGCA CGCTGATTGA AGCAGAAGCC
       GCCACCAACT TGACGTGTGG CGGCTGCCGT GCGACTAACT TCGTCTTCGG
            LacZ
            ~~~~~~~~~~~~~~~~~~~~~~~~~~~~~~~~~~~~~~~~~~~~~~~~~~
3301   TGCGATGTCG GTTTCCGCGA GGTGCGGATT GAAAATGGTC TGCTGCTGCT
       ACGCTACAGC CAAAGGCGCT CCACGCCTAA CTTTTACCAG ACGACGACGA
            LacZ
            ~~~~~~~~~~~~~~~~~~~~~~~~~~~~~~~~~~~~~~~~~~~~~~~~~~
3351   GAACGGCAAG CCGTTGCTGA TTCGAGGCGT TAACCGTCAC GAGCATCATC
       CTTGCCGTTC GGCAACGACT AAGCTCCGCA ATTGGCAGTG CTCGTAGTAG
```

FIGURE 3F
LacZ

```
3401  CTCTGCATGG TCAGGTCATG GATGAGCAGA CGATGGTGCA GGATATCCTG
      GAGACGTACC AGTCCAGTAC CTACTCGTCT GCTACCACGT CCTATAGGAC
                              LacZ
3451  CTGATGAAGC AGAACAACTT TAACGCCGTG CGCTGTTCGC ATTATCCGAA
      GACTACTTCG TCTTGTTGAA ATTGCGGCAC GCGACAAGCG TAATAGGCTT
                              LacZ
3501  CCATCCGCTG TGGTACACGC TGTGCGACCG CTACGGCCTG TATGTGGTGG
      GGTAGGCGAC ACCATGTGCG ACACGCTGGC GATGCCGGAC ATACACCACC
                              LacZ
3551  ATGAAGCCAA TATTGAAACC CACGGCATGG TGCCAATGAA TCGTCTGACC
      TACTTCGGTT ATAACTTTGG GTGCCGTACC ACGGTTACTT AGCAGACTGG
                              LacZ
3601  GATGATCCGC GCTGGCTACC GGCGATGAGC GAACGCGTAA CGCGAATGGT
      CTACTAGGCG CGACCGATGG CCGCTACTCG CTTGCGCATT GCGCTTACCA
                              LacZ
3651  GCAGCGCGAT CGTAATCACC CGAGTGTGAT CATCTGGTCG CTGGGGAATG
      CGTCGCGCTA GCATTAGTGG GCTCACACTA GTAGACCAGC GACCCCTTAC
                              LacZ
3701  AATCAGGCCA CGGCGCTAAT CACGACGCGC TGTATCGCTG GATCAAATCT
      TTAGTCCGGT GCCGCGATTA GTGCTGCGCG ACATAGCGAC CTAGTTTAGA
                              LacZ
3751  GTCGATCCTT CCCGCCCGGT GCAGTATGAA GGCGGCGGAG CCGACACCAC
      CAGCTAGGAA GGGCGGGCCA CGTCATACTT CCGCCGCCTC GGCTGTGGTG
                              LacZ
3801  GGCCACCGAT ATTATTTGCC CGATGTACGC GCGCGTGGAT GAAGACCAGC
      CCGGTGGCTA TAATAAACGG GCTACATGCG CGCGCACCTA CTTCTGGTCG
                              LacZ
3851  CCTTCCCGGC TGTGCCGAAA TGGTCCATCA AAAAATGGCT TTCGCTACCT
      GGAAGGGCCG ACACGGCTTT ACCAGGTAGT TTTTTACCGA AAGCGATGGA
                              LacZ
3901  GGAGAGACGC GCCCGCTGAT CCTTTGCGAA TACGCCCACG CGATGGGTAA
      CCTCTCTGCG CGGGCGACTA GGAAACGCTT ATGCGGGTGC GCTACCCATT
                              LacZ
3951  CAGTCTTGGC GGTTTCGCTA AATACTGGCA GGCGTTTCGT CAGTATCCCC
      GTCAGAACCG CCAAAGCGAT TTATGACCGT CCGCAAAGCA GTCATAGGGG
                              LacZ
4001  GTTTACAGGG CGGCTTCGTC TGGGACTGGG TGGATCAGTC GCTGATTAAA
      CAAATGTCCC GCCGAAGCAG ACCCTGACCC ACCTAGTCAG CGACTAATTT
                              LacZ
4051  TATGATGAAA ACGGCAACCC GTGGTCGGCT TACGGCGGTG ATTTTGGCGA
      ATACTACTTT TGCCGTTGGG CACCAGCCGA ATGCCGCCAC TAAAACCGCT
```

FIGURE 3G
LacZ

```
4101    TACGCCGAAC GATCGCCAGT TCTGTATGAA CGGTCTGGTC TTTGCCGACC
        ATGCGGCTTG CTAGCGGTCA AGACATACTT GCCAGACCAG AAACGGCTGG
                                   LacZ

4151    GCACGCCGCA TCCAGCGCTG ACGGAAGCAA ACACCAGCA GCAGTTTTTC
        CGTGCGGCGT AGGTCGCGAC TGCCTTCGTT TTGTGGTCGT CGTCAAAAAG
                                   LacZ

4201    CAGTTCCGTT TATCCGGGCA AACCATCGAA GTGACCAGCG AATACCTGTT
        GTCAAGGCAA ATAGGCCCGT TTGGTAGCTT CACTGGTCGC TTATGGACAA
                                   LacZ

4251    CCGTCATAGC GATAACGAGC TCCTGCACTG GATGGTGGCG CTGGATGGTA
        GGCAGTATCG CTATTGCTCG AGGACGTGAC CTACCACCGC GACCTACCAT
                                   LacZ

4301    AGCCGCTGGC AAGCGGTGAA GTGCCTCTGG ATGTCGCTCC ACAAGGTAAA
        TCGGCGACCG TTCGCCACTT CACGGAGACC TACAGCGAGG TGTTCCATTT
                                   LacZ

4351    CAGTTGATTG AACTGCCTGA ACTACCGCAG CCGGAGAGCG CCGGGCAACT
        GTCAACTAAC TTGACGGACT TGATGGCGTC GGCCTCTCGC GGCCCGTTGA
                                   LacZ

4401    CTGGCTCACA GTACGCGTAG TGCAACCGAA CGCGACCGCA TGGTCAGAAG
        GACCGAGTGT CATGCGCATC ACGTTGGCTT GCGCTGGCGT ACCAGTCTTC
                                   LacZ

4451    CCGGGCACAT CAGCGCCTGG CAGCAGTGGC GTCTGGCGGA AAACCTCAGT
        GGCCCGTGTA GTCGCGGACC GTCGTCACCG CAGACCGCCT TTTGGAGTCA
                                   LacZ

4501    GTGACGCTCC CCGCCGCGTC CCACGCCATC CCGCATCTGA CCACCAGCGA
        CACTGCGAGG GGCGGCGCAG GGTGCGGTAG GGCGTAGACT GGTGGTCGCT
                                   LacZ

4551    AATGGATTTT TGCATCGAGC TGGGTAATAA GCGTTGGCAA TTTAACCGCC
        TTACCTAAAA ACGTAGCTCG ACCCATTATT CGCAACCGTT AAATTGGCGG
                                   LacZ

4601    AGTCAGGCTT TCTTTCACAG ATGTGGATTG GCGATAAAAA ACAACTGCTG
        TCAGTCCGAA AGAAAGTGTC TACACCTAAC CGCTATTTTT TGTTGACGAC
                                   LacZ

4651    ACGCCGCTGC GCGATCAGTT CACCCGTGCA CCGCTGGATA ACGACATTGG
        TGCGGCGACG CGCTAGTCAA GTGGGCACGT GGCGACCTAT TGCTGTAACC
                                   LacZ

4701    CGTAAGTGAA GCGACCCGCA TTGACCCTAA CGCCTGGGTC GAACGCTGGA
        GCATTCACTT CGCTGGGCGT AACTGGGATT GCGGACCCAG CTTGCGACCT
                                   LacZ

4751    AGGCGGCGGG CCATTACCAG GCCGAAGCAG CGTTGTTGCA GTGCACGGCA
        TCCGCCGCCC GGTAATGGTC CGGCTTCGTC GCAACAACGT CACGTGCCGT
```

FIGURE 3H

```
               LacZ
      ~~~~~~~~~~~~~~~~~~~~~~~~~~~~~~~~~~~~~~~~~~~~~~~~~
4801  GATACACTTG CTGATGCGGT GCTGATTACG ACCGCTCACG CGTGGCAGCA
      CTATGTGAAC GACTACGCCA CGACTAATGC TGGCGAGTGC GCACCGTCGT
               LacZ
      ~~~~~~~~~~~~~~~~~~~~~~~~~~~~~~~~~~~~~~~~~~~~~~~~~
4851  TCAGGGGAAA ACCTTATTTA TCAGCCGGAA AACCTACCGG ATTGATGGTA
      AGTCCCCTTT TGGAATAAAT AGTCGGCCTT TTGGATGGCC TAACTACCAT
               LacZ
      ~~~~~~~~~~~~~~~~~~~~~~~~~~~~~~~~~~~~~~~~~~~~~~~~~
4901  GTGGTCAAAT GGCGATTACC GTTGATGTTG AAGTGGCGAG CGATACACCG
      CACCAGTTTA CCGCTAATGG CAACTACAAC TTCACCGCTC GCTATGTGGC
               LacZ
      ~~~~~~~~~~~~~~~~~~~~~~~~~~~~~~~~~~~~~~~~~~~~~~~~~
4951  CATCCGGCGC GGATTGGCCT GAACTGCCAG CTGGCGCAGG TAGCAGAGCG
      GTAGGCCGCG CCTAACCGGA CTTGACGGTC GACCGCGTCC ATCGTCTCGC
               LacZ
      ~~~~~~~~~~~~~~~~~~~~~~~~~~~~~~~~~~~~~~~~~~~~~~~~~
5001  GGTAAACTGG CTCGGATTAG GGCCGCAAGA AAACTATCCC GACCGCCTTA
      CCATTTGACC GAGCCTAATC CCGGCGTTCT TTTGATAGGG CTGGCGGAAT
               LacZ
      ~~~~~~~~~~~~~~~~~~~~~~~~~~~~~~~~~~~~~~~~~~~~~~~~~
5051  CTGCCGCCTG TTTTGACCGC TGGGATCTGC CATTGTCAGA CATGTATACC
      GACGGCGGAC AAAACTGGCG ACCCTAGACG GTAACAGTCT GTACATATGG
               LacZ
      ~~~~~~~~~~~~~~~~~~~~~~~~~~~~~~~~~~~~~~~~~~~~~~~~~
5101  CCGTACGTCT TCCCGAGCGA AAACGGTCTG CGCTGCGGGA CGCGCGAATT
      GGCATGCAGA AGGGCTCGCT TTTGCCAGAC GCGACGCCCT GCGCGCTTAA
               LacZ
      ~~~~~~~~~~~~~~~~~~~~~~~~~~~~~~~~~~~~~~~~~~~~~~~~~
5151  GAATTATGGC CCACACCAGT GGCGCGGCGA CTTCCAGTTC AACATCAGCC
      CTTAATACCG GGTGTGGTCA CCGCGCCGCT GAAGGTCAAG TTGTAGTCGG
               LacZ
      ~~~~~~~~~~~~~~~~~~~~~~~~~~~~~~~~~~~~~~~~~~~~~~~~~
5201  GGTACAGTCA ACAGCAATTG ATGGAAACCA GCCATTCGCC ATCTGCTGCA
      CCATGTCAGT TGTCGTTAAC TACCTTTGGT CGGTAAGCGG TAGACGACGT
               LacZ
      ~~~~~~~~~~~~~~~~~~~~~~~~~~~~~~~~~~~~~~~~~~~~~~~~~
5251  CGCGGAAGAG GCACATGGCT GAATATCGAC GGTTTCCATA TGGGGATTGG
      GCGCCTTCTC CGTGTACCGA CTTATAGCTG CCAAAGGTAT ACCCCTAACC
               LacZ
      ~~~~~~~~~~~~~~~~~~~~~~~~~~~~~~~~~~~~~~~~~~~~~~~~~
5301  TGGCGACGAC TCCTGGAGCC CGTCAGTATC GGCGGAATTC CAGCTGAGCG
      ACCGCTGCTG AGGACCTCGG GCAGTCATAG CCGCCTTAAG GTCGACTCGC
                  LacZ
      ~~~~~~~~~~~~~~~~~~~~~~~~~~~~~~~~~~~~~~~~~~~~
5351  CCGGTCGCTA CCATTACCAG TTGGTCTGGT GTCAAAAATA ATAATAACCG
      GGCCAGCGAT GGTAATGGTC AACCAGACCA CAGTTTTTAT TATTATTGGC
5401  GGCAGGGGGG ATCCGGAGCT TATCGCAGAT CAATTCGATA TCAAGCTTAT
      CCGTCCCCCC TAGGCCTCGA ATAGCGTCTA GTTAAGCTAT AGTTCGAATA
                                            H6  Promoter
                                        ~~~~~~~~~~~~~~~~~
5451  CGATACCGTC GACGGTATCG ATAAGCTCTA GTGGAGGGTT CTTTATTCTA
      GCTATGGCAG CTGCCATAGC TATTCGAGAT CACCTCCCAA GAAATAAGAT
                                  H6  Promoter
      ~~~~~~~~~~~~~~~~~~~~~~~~~~~~~~~~~~~~~~~~~~~~~~~~~
```

FIGURE 3I

```
5501    TACTTAAAAA GTGAAAATAA ATACAAAGGT TCTTGAGGGT TGTGTTAAAT
        ATGAATTTTT CACTTTTATT TATGTTTCCA AGAACTCCCA ACACAATTTA
                         H6   Promoter
        ~~~~~~~~~~~~~~~~~~~~~~~~~~~~~~~~~~~~~~~~~~~~~~~~~~~~~
 5551   TGAAAGCGAG AAATAATCAT AAATTATTTC ATTATCGCGA TATCCGTTAA
        ACTTTCGCTC TTTATTAGTA TTTAATAAAG TAATAGCGCT ATAGGCAATT
         H6   Promoter                              NYESO-1
        ~~~~~~~~~~~~~~~~~~                         ~~~~~~~~~~
 5601   GTTTGTATCG TACCCCCCCC GAGCCATGCA GGCCGAAGGC CGGGGCACAG
        CAAACATAGC ATGGGGGGGG CTCGGTACGT CCGGCTTCCG GCCCCGTGTC
                                    NYESO-1
        ~~~~~~~~~~~~~~~~~~~~~~~~~~~~~~~~~~~~~~~~~~~~~~~~~~~~~
 5651   GGGGTTCGAC GGGCGATGCT GATGGCCCAG GAGGCCCTGG CATTCCTGAT
        CCCCAAGCTG CCCGCTACGA CTACCGGGTC CTCCGGGACC GTAAGGACTA
                                    NYESO-1
        ~~~~~~~~~~~~~~~~~~~~~~~~~~~~~~~~~~~~~~~~~~~~~~~~~~~~~
 5701   GGCCCAGGGG GCAATGCTGG CGGCCCAGGA GAGGCGGGTG CCACGGGCGG
        CCGGGTCCCC CGTTACGACC GCCGGGTCCT CTCCGCCCAC GGTGCCCGCC
                                    NYESO-1
        ~~~~~~~~~~~~~~~~~~~~~~~~~~~~~~~~~~~~~~~~~~~~~~~~~~~~~
 5751   CAGAGGTCCC CGGGGCGCAG GGGCAGCAAG GGCCTCGGGG CCGGGAGGAG
        GTCTCCAGGG GCCCCGCGTC CCCGTCGTTC CCGGAGCCCC GGCCCTCCTC
                                    NYESO-1
        ~~~~~~~~~~~~~~~~~~~~~~~~~~~~~~~~~~~~~~~~~~~~~~~~~~~~~
 5801   GCGCCCCGCG GGGTCCGCAT GGCGGCGCGG CTTCAGGGCT GAATGGATGC
        CGCGGGGCGC CCCAGGCGTA CCGCCGCGCC GAAGTCCCGA CTTACCTACG
                                    NYESO-1
        ~~~~~~~~~~~~~~~~~~~~~~~~~~~~~~~~~~~~~~~~~~~~~~~~~~~~~
 5851   TGCAGATGCG GGGCCAGGGG GCCGGAGAGC CGCCTGCTTG AGTTCTACCT
        ACGTCTACGC CCCGGTCCCC CGGCCTCTCG GCGGACGAAC TCAAGATGGA
                                    NYESO-1
        ~~~~~~~~~~~~~~~~~~~~~~~~~~~~~~~~~~~~~~~~~~~~~~~~~~~~~
 5901   CGCCATGCCT TTCGCGACAC CCATGGAAGC AGAGCTGGCC CGCAGGAGCC
        GCGGTACGGA AAGCGCTGTG GGTACCTTCG TCTCGACCGG GCGTCCTCGG
                                    NYESO-1
        ~~~~~~~~~~~~~~~~~~~~~~~~~~~~~~~~~~~~~~~~~~~~~~~~~~~~~
 5951   TGGCCCAGGA TGCCCCACCG CTTCCCGTGC CAGGGGTGCT TCTGAAGGAG
        ACCGGGTCCT ACGGGGTGGC GAAGGGCACG GTCCCCACGA AGACTTCCTC
                                    NYESO-1
        ~~~~~~~~~~~~~~~~~~~~~~~~~~~~~~~~~~~~~~~~~~~~~~~~~~~~~
 6001   TTCACTGTGT CCGGCAACAT ACTGACTATC CGACTGACTG CTGCAGACCA
        AAGTGACACA GGCCGTTGTA TGACTGATAG GCTGACTGAC GACGTCTGGT
                                    NYESO-1
        ~~~~~~~~~~~~~~~~~~~~~~~~~~~~~~~~~~~~~~~~~~~~~~~~~~~~~
 6051   CCGCCAACTG CAGCTCTCCA TCAGCTCCTG TCTCCAGCAG CTTTCCCTGT
        GGCGGTTGAC GTCGAGAGGT AGTCGAGGAC AGAGGTCGTC GAAAGGGACA
                                    NYESO-1
        ~~~~~~~~~~~~~~~~~~~~~~~~~~~~~~~~~~~~~~~~~~~~~~~~~~~~~
 6101   TGATGTGGAT CACGCAGGTG TTTCTGCCCG TGTTTTTGGC TCAGCCTCCC
        ACTACACCTA GTGCGTCCAC AAAGACGGGC ACAAAAACCG AGTCGGAGGG
                   NYESO-1
        ~~~~~~~~~~~~~~~~~~~~~~~~~~~~~~
 6151   TCAGGGCAGA GGCGCTAAGT AATTAATTTT TTTTTGGGCT GCAGGATCGC
        AGTCCCGTCT CCGCGATTCA TTAATTAAAA AAAAACCCGA CGTCCTAGCG
```

FIGURE 3J
sE/L Promoter

```
6201  TAGCAAAAAT TGAAATTTTA TTTTTTTTTT TTGGAATATA AATAAGCTCG
      ATCGTTTTTA ACTTTAAAAT AAAAAAAAAA AACCTTATAT TTATTCGAGC
                               hTRP-2 sE/L Promoter

6251  AAGCTCGAGC CATGAGCCCC CTTTGGTGGG GGTTTCTGCT CAGTTGCTTG
      TTCGAGCTCG GTACTCGGGG GAAACCACCC CCAAAGACGA GTCAACGAAC
                               hTRP-2

6301  GGCTGCAAAA TCCTGCCAGG AGCCCAGGGT CAGTTCCCCC GAGTCTGCAT
      CCGACGTTTT AGGACGGTCC TCGGGTCCCA GTCAAGGGGG CTCAGACGTA
                               hTRP-2

6351  GACGGTGGAC AGCCAGTGA ACAAGGAGTG CTGCCCACGC CTGGGTGCAG
      CTGCCACCTG TCGGATCACT TGTTCCTCAC GACGGGTGCG GACCCACGTC
                               hTRP-2

6401  AGTCGGCCAA TGTCTGTGGC TCTCAGCAAG GCCGGGGGCA GTGCACAGAG
      TCAGCCGGTT ACAGACACCG AGAGTCGTTC CGGCCCCCGT CACGTGTCTC
                               hTRP-2

6451  GTGCGAGCCG ACACAAGGCC CTGGAGTGGT CCCTACATCC TACGAAACCA
      CACGCTCGGC TGTGTTCCGG GACCTCACCA GGGATGTAGG ATGCTTTGGT
                               hTRP-2

6501  GGATGACCGT GAGCTGTGGC CAAGAAAATT CTTCCACCGG ACCTGCAAGT
      CCTACTGGCA CTCGACACCG GTTCTTTTAA GAAGGTGGCC TGGACGTTCA
                               hTRP-2

6551  GCACAGGAAA CTTTGCCGGC TATAATTGTG GAGACTGCAA GTTTGGCTGG
      CGTGTCCTTT GAAACGGCCG ATATTAACAC CTCTGACGTT CAAACCGACC
                               hTRP-2

6601  ACCGGTCCCA ACTGCGAGCG GAAGAAACCA CCAGTGATTC GGCAGAACAT
      TGGCCAGGGT TGACGCTCGC CTTCTTTGGT GGTCACTAAG CCGTCTTGTA
                               hTRP-2

6651  CCATTCCTTG AGTCCTCAGG AAAGAGAGCA GTTCTTGGGC GCCTTAGATC
      GGTAAGGAAC TCAGGAGTCC TTTCTCTCGT CAAGAACCCG CGGAATCTAG
                               hTRP-2

6701  TCGCGAAGAA GAGAGTACAC CCCGACTACG TGATCACCAC ACAACACTGG
      AGCGCTTCTT CTCTCATGTG GGGCTGATGC ACTAGTGGTG TGTTGTGACC
                               hTRP-2

6751  CTGGGCCTGC TTGGGCCCAA TGGAACCCAG CCGCAGTTTG CCAACTGCAG
      GACCCGGACG AACCCGGGTT ACCTTGGGTC GGCGTCAAAC GGTTGACGTC
                               hTRP-2

6801  TGTTTATGAT TCTTCGTGT GGCTCCATTA TTATTCTGTT AGAGATACAT
      ACAAATACTA AGAAGCACA CCGAGGTAAT AATAAGACAA TCTCTATGTA
```

FIGURE 3K
hTRP-2

```
6851  TATTAGGACC AGGACGCCCC TACAGGGCCA TAGATTTCTC ACATCAAGGA
      ATAATCCTGG TCCTGCGGGG ATGTCCCGGT ATCTAAAGAG TGTAGTTCCT
                              hTRP-2

6901  CCTGCATTTG TTACCTGGCA CCGGTACCAT TTGTTGTGTC TGGAAAGAGA
      GGACGTAAAC AATGGACCGT GGCCATGGTA AACAACACAG ACCTTTCTCT
                              hTRP-2

6951  TCTCCAGCGA CTCATTGGCA ATGAGTCTTT TGCTTTGCCC TACTGGAACT
      AGAGGTCGCT GAGTAACCGT TACTCAGAAA ACGAAACGGG ATGACCTTGA
                              hTRP-2

7001  TTGCCACTGG GAGGAACGAG TGTGATGTGT GTACAGACCA GCTGTTTGGG
      AACGGTGACC CTCCTTGCTC ACACTACACA CATGTCTGGT CGACAAACCC
                              hTRP-2

7051  GCAGCGAGAC CAGACGATCC GACTCTGATT AGTCGGAACT CAAGATTCTC
      CGTCGCTCTG GTCTGCTAGG CTGAGACTAA TCAGCCTTGA GTTCTAAGAG
                              hTRP-2

7101  CAGCTGGGAA ACTGTCTGTG ATAGCTTGGA TGACTACAAC CACCTGGTCA
      GTCGACCCTT TGACAGACAC TATCGAACCT ACTGATGTTG GTGGACCAGT
                              hTRP-2

7151  CCTTGTGCAA TGGAACCTAT GAAGGTTTGC TGAGAAGAAA TCAAATGGGA
      GGAACACGTT ACCTTGGATA CTTCCAAACG ACTCTTCTTT AGTTTACCCT
                              hTRP-2

7201  AGAAACAGCA TGAAATTGCC AACCTTAAAA GACATACGAG ATTGCCTGTC
      TCTTTGTCGT ACTTTAACGG TTGGAATTTT CTGTATGCTC TAACGGACAG
                              hTRP-2

7251  TCTCCAGAAG TTTGACAATC CTCCCTTCTT CCAGAACTCT ACCTTCAGTT
      AGAGGTCTTC AAACTGTTAG GAGGGAAGAA GGTCTTGAGA TGGAAGTCAA
                              hTRP-2

7301  TCAGGAATGC TTTGGAAGGG TTTGATAAAG CAGATGGGAC TCTGGATTCT
      AGTCCTTACG AAACCTTCCC AAACTATTTC GTCTACCCTG AGACCTAAGA
                              hTRP-2

7351  CAAGTGATGA GCCTTCATAA TTTGGTTCAT TCCTTCCTGA ACGGGACAAA
      GTTCACTACT CGGAAGTATT AAACCAAGTA AGGAAGGACT TGCCCTGTTT
                              hTRP-2

7401  CGCTTTGCCA CATTCAGCCG CCAATGATCC CATCTTCGTG GTGATTTCTA
      GCGAAACGGT GTAAGTCGGC GGTTACTAGG GTAGAAGCAC CACTAAAGAT
                              hTRP-2

7451  ATCGTTTGCT TTACAATGCT ACAACAAACA TCCTTGAACA TGTAAGAAAA
      TAGCAAACGA AATGTTACGA TGTTGTTTGT AGGAACTTGT ACATTCTTTT
                              hTRP-2

7501  GAGAAAGCGA CCAAGGAACT CCCTTCCCTG CATGTGCTGG TTCTTCATTC
      CTCTTTCGCT GGTTCCTTGA GGGAAGGGAC GTACACGACC AAGAAGTAAG
```

FIGURE 3L

```
                              hTRP-2
      ~~~~~~~~~~~~~~~~~~~~~~~~~~~~~~~~~~~~~~~~~~~~~~~~~~~
7551  CTTTACTGAT GCCATCTTTG ATGAGTGGAT GAAAAGATTT AATCCTCCTG
      GAAATGACTA CGGTAGAAAC TACTCACCTA CTTTTCTAAA TTAGGAGGAC
                              hTRP-2
      ~~~~~~~~~~~~~~~~~~~~~~~~~~~~~~~~~~~~~~~~~~~~~~~~~~~
7601  CAGATGCCTG GCCTCAGGAG CTGGCCCCTA TTGGTCACAA TCGGATGTAC
      GTCTACGGAC CGGAGTCCTC GACCGGGGAT AACCAGTGTT AGCCTACATG
                              hTRP-2
      ~~~~~~~~~~~~~~~~~~~~~~~~~~~~~~~~~~~~~~~~~~~~~~~~~~~
7651  AACATGGTTC CTTTCTTCCC TCCAGTGACT AATGAAGAAC TCTTTTTAAC
      TTGTACCAAG GAAAGAAGGG AGGTCACTGA TTACTTCTTG AGAAAAATTG
                              hTRP-2
      ~~~~~~~~~~~~~~~~~~~~~~~~~~~~~~~~~~~~~~~~~~~~~~~~~~~
7701  CTCAGACCAA CTTGGCTACA GCTATGCCAT CGATCTGCCA GTTTCAGTTG
      GAGTCTGGTT GAACCGATGT CGATACGGTA GCTAGACGGT CAAAGTCAAC
                              hTRP-2
      ~~~~~~~~~~~~~~~~~~~~~~~~~~~~~~~~~~~~~~~~~~~~~~~~~~~
7751  AAGAAACTCC AGGTTGGCCC ACAACTCTCT TAGTAGTCAT GGGAACACTG
      TTCTTTGAGG TCCAACCGGG TGTTGAGAGA ATCATCAGTA CCCTTGTGAC
                              hTRP-2
      ~~~~~~~~~~~~~~~~~~~~~~~~~~~~~~~~~~~~~~~~~~~~~~~~~~~
7801  GTGGCTTTGG TTGGTCTGTT CGTGCTGTTG GCTTTTCTTC AATATAGAAG
      CACCGAAACC AACCAGACAA GCACGACAAC CGAAAAGAAG TTATATCTTC
                              hTRP-2
      ~~~~~~~~~~~~~~~~~~~~~~~~~~~~~~~~~~~~~~~~~~~~~~~~~~~
7851  ACTTCGAAAA GGATATACAC CCCTAATGGA GACACATTTA AGCAGCAAGA
      TGAAGCTTTT CCTATATGTG GGGATTACCT CTGTGTAAAT TCGTCGTTCT
            hTRP-2
      ~~~~~~~~~~~~~~~~~~~~~
7901  GATACACAGA AGAAGCCTAG TTTTTTAATT AAGCATGCTC TAGAATCGAT
      CTATGTGTCT TCTTCGGATC AAAAAATTAA TTCGTACGAG ATCTTAGCTA
                                                C5 Left Arm
                                            ~~~~~~~~~~~~~~~~~~~~
7951  CCCGGGTTTT TATGACTAGT TAATCACGGC CGCTTATAAA GATCTAAAAT
      GGGCCCAAAA ATACTGATCA ATTAGTGCCG GCGAATATTT CTAGATTTTA
                         C5 Left Arm
      ~~~~~~~~~~~~~~~~~~~~~~~~~~~~~~~~~~~~~~~~~~~~~~~~~~~
8001  GCATAATTTC TAAATAATGA AAAAAAAGTA CATCATGAGC AACGCGTTAG
      CGTATTAAAG ATTTATTACT TTTTTTTCAT GTAGTACTCG TTGCGCAATC
                         C5 Left Arm
      ~~~~~~~~~~~~~~~~~~~~~~~~~~~~~~~~~~~~~~~~~~~~~~~~~~~
8051  TATATTTTAC AATGGAGATT AACGCTCTAT ACCGTTCTAT GTTTATTGAT
      ATATAAAATG TTACCTCTAA TTGCGAGATA TGGCAAGATA CAAATAACTA
                         C5 Left Arm
      ~~~~~~~~~~~~~~~~~~~~~~~~~~~~~~~~~~~~~~~~~~~~~~~~~~~
8101  TCAGATGATG TTTTAGAAAA GAAAGTTATT GAATATGAAA ACTTTAATGA
      AGTCTACTAC AAAATCTTTT CTTTCAATAA CTTATACTTT TGAAATTACT
                         C5 Left Arm
      ~~~~~~~~~~~~~~~~~~~~~~~~~~~~~~~~~~~~~~~~~~~~~~~~~~~
8151  AGATGAAGAT GACGACGATG ATTATTGTTG TAAATCTGTT TTAGATGAAG
      TCTACTTCTA CTGCTGCTAC TAATAACAAC ATTTAGACAA AATCTACTTC
                         C5 Left Arm
      ~~~~~~~~~~~~~~~~~~~~~~~~~~~~~~~~~~~~~~~~~~~~~~~~~~~
8201  AAGATGACGC GCTAAAGTAT ACTATGGTTA CAAAGTATAA GTCTATACTA
      TTCTACTGCG CGATTTCATA TGATACCAAT GTTTCATATT CAGATATGAT
```

FIGURE 3M

```
            C5 Left Arm
       ~~~~~~~~~~~~~~~~~~~~~~~~~~~~~~~~~~~~~~~~~~~~~~~~~~~
8251   CTAATGGCGA CTTGTGCAAG AAGGTATAGT ATAGTGAAAA TGTTGTTAGA
       GATTACCGCT GAACACGTTC TTCCATATCA TATCACTTTT ACAACAATCT
                          C5 Left Arm
       ~~~~~~~~~~~~~~~~~~~~~~~~~~~~~~~~~~~~~~~~~~~~~~~~~~~
8301   TTATGATTAT GAAAAACCAA ATAAATCAGA TCCATATCTA AAGGTATCTC
       AATACTAATA CTTTTTGGTT TATTTAGTCT AGGTATAGAT TTCCATAGAG
                          C5 Left Arm
       ~~~~~~~~~~~~~~~~~~~~~~~~~~~~~~~~~~~~~~~~~~~~~~~~~~~
8351   CTTTGCACAT AATTTCATCT ATTCCTAGTT TAGAATACTT TTCATTATAT
       GAAACGTGTA TTAAAGTAGA TAAGGATCAA ATCTTATGAA AAGTAATATA
                          C5 Left Arm
       ~~~~~~~~~~~~~~~~~~~~~~~~~~~~~~~~~~~~~~~~~~~~~~~~~~~
8401   TTGTTTACAG CTGAAGACGA AAAAAATATA TCGATAATAG AAGATTATGT
       AACAAATGTC GACTTCTGCT TTTTTTATAT AGCTATTATC TTCTAATACA
                     C5 Left Arm
       ~~~~~~~~~~~~~~~~~~~~~~~~~~~~~~~~~~~~~~~~~~~~~~~~~
8451   TAACTCTGCT AATAAGATGA AATTGAATGA GTCTGTGACT GCAGCCAAGC
       ATTGAGACGA TTATTCTACT TTAACTTACT CAGACACTGA CGTCGGTTCG
8501   TTGGCACTGG CCGTCGTTTT ACAACGTCGT GACTGGGAAA ACCCTGGCGT
       AACCGTGACC GGCAGCAAAA TGTTGCAGCA CTGACCCTTT TGGGACCGCA
8551   TACCCAACTT AATCGCCTTG CAGCACATCC CCCTTTCGCC AGCTGGCGTA
       ATGGGTTGAA TTAGCGGAAC GTCGTGTAGG GGGAAAGCGG TCGACCGCAT
8601   ATAGCGAAGA GGCCCGCACC GATCGCCCTT CCCAACAGTT GCGCAGCCTG
       TATCGCTTCT CCGGGCGTGG CTAGCGGGAA GGGTTGTCAA CGCGTCGGAC
8651   AATGGCGAAT GGCGCCTGAT GCGGTATTTT CTCCTTACGC ATCTGTGCGG
       TTACCGCTTA CCGCGGACTA CGCCATAAAA GAGGAATGCG TAGACACGCC
8701   TATTTCACAC CGCATATGGT GCACTCTCAG TACAATCTGC TCTGATGCCG
       ATAAAGTGTG GCGTATACCA CGTGAGAGTC ATGTTAGACG AGACTACGGC
8751   CATAGTTAAG CCAGCCCCGA CACCCGCCAA CACCCGCTGA CGCGCCCTGA
       GTATCAATTC GGTCGGGGCT GTGGGCGGTT GTGGGCGACT GCGCGGGACT
8801   CGGGCTTGTC TGCTCCCGGC ATCCGCTTAC AGACAAGCTG TGACCGTCTC
       GCCCGAACAG ACGAGGGCCG TAGGCGAATG TCTGTTCGAC ACTGGCAGAG
8851   CGGGAGCTGC ATGTGTCAGA GGTTTTCACC GTCATCACCG AAACGCGCGA
       GCCCTCGACG TACACAGTCT CCAAAAGTGG CAGTAGTGGC TTTGCGCGCT
8901   GACGAAAGGG CCTCGTGATA CGCCTATTTT TATAGGTTAA TGTCATGATA
       CTGCTTTCCC GGAGCACTAT GCGGATAAAA ATATCCAATT ACAGTACTAT
8951   ATAATGGTTT CTTAGACGTC AGGTGGCACT TTTCGGGGAA ATGTGCGCGG
       TATTACCAAA GAATCTGCAG TCCACCGTGA AAAGCCCCTT TACACGCGCC
9001   AACCCCTATT TGTTTATTTT TCTAAATACA TTCAAATATG TATCCGCTCA
       TTGGGGATAA ACAAATAAAA AGATTTATGT AAGTTTATAC ATAGGCGAGT
9051   TGAGACAATA ACCCTGATAA ATGCTTCAAT AATATTGAAA AAGGAAGAGT
       ACTCTGTTAT TGGGACTATT TACGAAGTTA TTATAACTTT TTCCTTCTCA
                             Amp(R)
       ~~~~~~~~~~~~~~~~~~~~~~~~~~~~~~~~~~~~~~~~~~~~~~~~~~~
9101   ATGAGTATTC AACATTTCCG TGTCGCCCTT ATTCCCTTTT TTGCGGCATT
       TACTCATAAG TTGTAAAGGC ACAGCGGGAA TAAGGGAAAA AACGCCGTAA
                             Amp(R)
       ~~~~~~~~~~~~~~~~~~~~~~~~~~~~~~~~~~~~~~~~~~~~~~~~~~~
9151   TTGCCTTCCT GTTTTTGCTC ACCCAGAAAC GCTGGTGAAA GTAAAAGATG
       AACGGAAGGA CAAAAACGAG TGGGTCTTTG CGACCACTTT CATTTTCTAC
                             Amp(R)
       ~~~~~~~~~~~~~~~~~~~~~~~~~~~~~~~~~~~~~~~~~~~~~~~~~~~
9201   CTGAAGATCA GTTGGGTGCA CGAGTGGGTT ACATCGAACT GGATCTCAAC
       GACTTCTAGT CAACCCACGT GCTCACCCAA TGTAGCTTGA CCTAGAGTTG
```

FIGURE 3N

```
                                  Amp(R)
       ~~~~~~~~~~~~~~~~~~~~~~~~~~~~~~~~~~~~~~~~~~~~~~~~~~~
9251   AGCGGTAAGA TCCTTGAGAG TTTTCGCCCC GAAGAACGTT TTCCAATGAT
       TCGCCATTCT AGGAACTCTC AAAAGCGGGG CTTCTTGCAA AAGGTTACTA
                                  Amp(R)
       ~~~~~~~~~~~~~~~~~~~~~~~~~~~~~~~~~~~~~~~~~~~~~~~~~~~
9301   GAGCACTTTT AAAGTTCTGC TATGTGGCGC GGTATTATCC CGTATTGACG
       CTCGTGAAAA TTTCAAGACG ATACACCGCG CCATAATAGG GCATAACTGC
                                  Amp(R)
       ~~~~~~~~~~~~~~~~~~~~~~~~~~~~~~~~~~~~~~~~~~~~~~~~~~~
9351   CCGGGCAAGA GCAACTCGGT CGCCGCATAC ACTATTCTCA GAATGACTTG
       GGCCCGTTCT CGTTGAGCCA GCGGCGTATG TGATAAGAGT CTTACTGAAC
                                  Amp(R)
       ~~~~~~~~~~~~~~~~~~~~~~~~~~~~~~~~~~~~~~~~~~~~~~~~~~~
9401   GTTGAGTACT CACCAGTCAC AGAAAAGCAT CTTACGGATG GCATGACAGT
       CAACTCATGA GTGGTCAGTG TCTTTTCGTA GAATGCCTAC CGTACTGTCA
                                  Amp(R)
       ~~~~~~~~~~~~~~~~~~~~~~~~~~~~~~~~~~~~~~~~~~~~~~~~~~~
9451   AAGAGAATTA TGCAGTGCTG CCATAACCAT GAGTGATAAC ACTGCGGCCA
       TTCTCTTAAT ACGTCACGAC GGTATTGGTA CTCACTATTG TGACGCCGGT
                                  Amp(R)
       ~~~~~~~~~~~~~~~~~~~~~~~~~~~~~~~~~~~~~~~~~~~~~~~~~~~
9501   ACTTACTTCT GACAACGATC GGAGGACCGA AGGAGCTAAC CGCTTTTTTG
       TGAATGAAGA CTGTTGCTAG CCTCCTGGCT TCCTCGATTG GCGAAAAAAC
                                  Amp(R)
       ~~~~~~~~~~~~~~~~~~~~~~~~~~~~~~~~~~~~~~~~~~~~~~~~~~~
9551   CACAACATGG GGGATCATGT AACTCGCCTT GATCGTTGGG AACCGGAGCT
       GTGTTGTACC CCCTAGTACA TTGAGCGGAA CTAGCAACCC TTGGCCTCGA
                                  Amp(R)
       ~~~~~~~~~~~~~~~~~~~~~~~~~~~~~~~~~~~~~~~~~~~~~~~~~~~
9601   GAATGAAGCC ATACCAAACG ACGAGCGTGA CACCACGATG CCTGTAGCAA
       CTTACTTCGG TATGGTTTGC TGCTCGCACT GTGGTGCTAC GGACATCGTT
                                  Amp(R)
       ~~~~~~~~~~~~~~~~~~~~~~~~~~~~~~~~~~~~~~~~~~~~~~~~~~~
9651   TGGCAACAAC GTTGCGCAAA CTATTAACTG GCGAACTACT TACTCTAGCT
       ACCGTTGTTG CAACGCGTTT GATAATTGAC CGCTTGATGA ATGAGATCGA
                                  Amp(R)
       ~~~~~~~~~~~~~~~~~~~~~~~~~~~~~~~~~~~~~~~~~~~~~~~~~~~
9701   TCCCGGCAAC AATTAATAGA CTGGATGGAG GCGGATAAAG TTGCAGGACC
       AGGGCCGTTG TTAATTATCT GACCTACCTC CGCCTATTTC AACGTCCTGG
                                  Amp(R)
       ~~~~~~~~~~~~~~~~~~~~~~~~~~~~~~~~~~~~~~~~~~~~~~~~~~~
9751   ACTTCTGCGC TCGGCCCTTC CGGCTGGCTG GTTTATTGCT GATAAATCTG
       TGAAGACGCG AGCCGGGAAG GCCGACCGAC CAAATAACGA CTATTTAGAC
                                  Amp(R)
       ~~~~~~~~~~~~~~~~~~~~~~~~~~~~~~~~~~~~~~~~~~~~~~~~~~~
9801   GAGCCGGTGA GCGTGGGTCT CGCGGTATCA TTGCAGCACT GGGGCCAGAT
       CTCGGCCACT CGCACCCAGA GCGCCATAGT AACGTCGTGA CCCCGGTCTA
                                  Amp(R)
       ~~~~~~~~~~~~~~~~~~~~~~~~~~~~~~~~~~~~~~~~~~~~~~~~~~~
9851   GGTAAGCCCT CCCGTATCGT AGTTATCTAC ACGACGGGGA GTCAGGCAAC
       CCATTCGGGA GGGCATAGCA TCAATAGATG TGCTGCCCCT CAGTCCGTTG
                                  Amp(R)
       ~~~~~~~~~~~~~~~~~~~~~~~~~~~~~~~~~~~~~~~~~~~~~~~~~~~
9901   TATGGATGAA CGAAATAGAC AGATCGCTGA GATAGGTGCC TCACTGATTA
       ATACCTACTT GCTTTATCTG TCTAGCGACT CTATCCACGG AGTGACTAAT
```

FIGURE 30

```
      Amp(R)
      ~~~~~~~~~~~~
 9951 AGCATTGGTA ACTGTCAGAC CAAGTTTACT CATATATACT TTAGATTGAT
      TCGTAACCAT TGACAGTCTG GTTCAAATGA GTATATATGA AATCTAACTA
10001 TTAAAACTTC ATTTTTAATT TAAAAGGATC TAGGTGAAGA TCCTTTTTGA
      AATTTTGAAG TAAAAATTAA ATTTTCCTAG ATCCACTTCT AGGAAAAACT
10051 TAATCTCATG ACCAAAATCC CTTAACGTGA GTTTTCGTTC CACTGAGCGT
      ATTAGAGTAC TGGTTTTAGG GAATTGCACT CAAAAGCAAG GTGACTCGCA
10101 CAGACCCCGT AGAAAAGATC AAAGGATCTT CTTGAGATCC TTTTTTTCTG
      GTCTGGGGCA TCTTTTCTAG TTTCCTAGAA GAACTCTAGG AAAAAAAGAC
10151 CGCGTAATCT GCTGCTTGCA AACAAAAAAA CCACCGCTAC CAGCGGTGGT
      GCGCATTAGA CGACGAACGT TTGTTTTTTT GGTGGCGATG GTCGCCACCA
10201 TTGTTTGCCG GATCAAGAGC TACCAACTCT TTTTCCGAAG GTAACTGGCT
      AACAAACGGC CTAGTTCTCG ATGGTTGAGA AAAAGGCTTC CATTGACCGA
10251 TCAGCAGAGC GCAGATACCA AATACTGTCC TTCTAGTGTA GCCGTAGTTA
      AGTCGTCTCG CGTCTATGGT TTATGACAGG AAGATCACAT CGGCATCAAT
10301 GGCCACCACT TCAAGAACTC TGTAGCACCG CCTACATACC TCGCTCTGCT
      CCGGTGGTGA AGTTCTTGAG ACATCGTGGC GGATGTATGG AGCGAGACGA
10351 AATCCTGTTA CCAGTGGCTG CTGCCAGTGG CGATAAGTCG TGTCTTACCG
      TTAGGACAAT GGTCACCGAC GACGGTCACC GCTATTCAGC ACAGAATGGC
10401 GGTTGGACTC AAGACGATAG TTACCGGATA AGGCGCAGCG GTCGGGCTGA
      CCAACCTGAG TTCTGCTATC AATGGCCTAT TCCGCGTCGC CAGCCCGACT
10451 ACGGGGGGTT CGTGCACACA GCCCAGCTTG GAGCGAACGA CCTACACCGA
      TGCCCCCCAA GCACGTGTGT CGGGTCGAAC CTCGCTTGCT GGATGTGGCT
10501 ACTGAGATAC CTACAGCGTG AGCTATGAGA AAGCGCCACG CTTCCCGAAG
      TGACTCTATG GATGTCGCAC TCGATACTCT TTCGCGGTGC GAAGGGCTTC
10551 GGAGAAAGGC GGACAGGTAT CCGGTAAGCG GCAGGGTCGG AACAGGAGAG
      CCTCTTTCCG CCTGTCCATA GGCCATTCGC CGTCCCAGCC TTGTCCTCTC
10601 CGCACGAGGG AGCTTCCAGG GGGAAACGCC TGGTATCTTT ATAGTCCTGT
      GCGTGCTCCC TCGAAGGTCC CCCTTTGCGG ACCATAGAAA TATCAGGACA
10651 CGGGTTTCGC CACCTCTGAC TTGAGCGTCG ATTTTTGTGA TGCTCGTCAG
      GCCCAAAGCG GTGGAGACTG AACTCGCAGC TAAAAACACT ACGAGCAGTC
10701 GGGGGCGGAG CCTATGGAAA AACGCCAGCA ACGCGGCCTT TTTACGGTTC
      CCCCCGCCTC GGATACCTTT TTGCGGTCGT TGCGCCGGAA AAATGCCAAG
10751 CTGGCCTTTT GCTGGCCTTT TGCTCACATG TTCTTTCCTG CGTTATCCCC
      GACCGGAAAA CGACCGGAAA ACGAGTGTAC AAGAAAGGAC GCAATAGGGG
10801 TGATTCTGTG GATAACCGTA TTACCGCCTT TGAGTGAGCT GATACCGCTC
      ACTAAGACAC CTATTGGCAT AATGGCGGAA ACTCACTCGA CTATGGCGAG
10851 GCCGCAGCCG AACGACCGAG CGCAGCGAGT CAGTGAGCGA GGAAGCGGAA
      CGGCGTCGGC TTGCTGGCTC GCGTCGCTCA GTCACTCGCT CCTTCGCCTT
10901 GAGCGCCCAA TACGCAAACC GCCTCTCCCC GCGCGTTGGC CGATTCATTA
      CTCGCGGGTT ATGCGTTTGG CGGAGAGGGG CGCGCAACCG GCTAAGTAAT
10951 ATGCAGCTGG CACGACAGGT TTCCCGACTG GAAAGCGGGC AGTGAGCGCA
      TACGTCGACC GTGCTGTCCA AAGGGCTGAC CTTTCGCCCG TCACTCGCGT
11001 ACGCAATTAA TGTGAGTTAG CTCACTCATT AGGCACCCCA GGCTTTACAC
      TGCGTTAATT ACACTCAATC GAGTGAGTAA TCCGTGGGGT CCGAAATGTG
11051 TTTATGCTTC CGGCTCGTAT GTTGTGTGGA ATTGTGAGCG GATAACAATT
      AAATACGAAG GCCGAGCATA CAACACACCT TAACACTCGC CTATTGTTAA
11101 TCACACAGGA AACAGCTATG ACCATGATTA CGAATTGAAT TGCGGCCGCA
      AGTGTGTCCT TTGTCGATAC TGGTACTAAT GCTTAACTTA ACGCCGGCGT
11151 ATTC
      TAAG
```

FIGURE 5A
DNA Sequence of donor plasmid pT3217

```
                         C5 Right Arm
       ~~~~~~~~~~~~~~~~~~~~~~~~~~~~~~~~~~~~~~~~~~~~~~~~~~~~~~~~~
   1   TGAATGTTAA ATGTTATACT TTGGATGAAG CTATAAATAT GCATTGGAAA
       ACTTACAATT TACAATATGA AACCTACTTC GATATTTATA CGTAACCTTT
                         C5 Right Arm
       ~~~~~~~~~~~~~~~~~~~~~~~~~~~~~~~~~~~~~~~~~~~~~~~~~~~~~~~~~
  51   AATAATCCAT TTAAAGAAAG GATTCAAATA CTACAAAACC TAAGCGATAA
       TTATTAGGTA AATTTCTTTC CTAAGTTTAT GATGTTTTGG ATTCGCTATT
                         C5 Right Arm
       ~~~~~~~~~~~~~~~~~~~~~~~~~~~~~~~~~~~~~~~~~~~~~~~~~~~~~~~~~
 101   TATGTTAACT AAGCTTATTC TTAACGACGC TTTAAATATA CACAAATAAA
       ATACAATTGA TTCGAATAAG AATTGCTGCG AAATTTATAT GTGTTTATTT
                         C5 Right Arm
       ~~~~~~~~~~~~~~~~~~~~~~~~~~~~~~~~~~~~~~~~~~~~~~~~~~~~~~~~~
 151   CATAATTTTT GTATAACCTA ACAAATAACT AAAACATAAA AATAATAAAA
       GTATTAAAAA CATATTGGAT TGTTTATTGA TTTTGTATTT TTATTATTTT
                         C5 Right Arm
       ~~~~~~~~~~~~~~~~~~~~~~~~~~~~~~~~~~~~~~~~~~~~~~~~~~~~~~~~~
 201   GGAAATGTAA TATCGTAATT ATTTTACTCA GGAATGGGGT TAAATATTTA
       CCTTTACATT ATAGCATTAA TAAAATGAGT CCTTACCCCA ATTTATAAAT
                         C5 Right Arm
       ~~~~~~~~~~~~~~~~~~~~~~~~~~~~~~~~~~~~~~~~~~~~~~~~~~~~~~~~~
 251   TATCACGTGT ATATCTATAC TGTTATCGTA TACTCTTTAC AATTACTATT
       ATAGTGCACA TATAGATATG ACAATAGCAT ATGAGAAATG TTAATGATAA
                         C5 Right Arm
       ~~~~~~~~~~~~~~~~~~~~~~~~~~~~~~~~~~~~~~~~~~~~~~~~~~~~~~~~~
 301   ACGAATATGC AAGAGATAAT AAGATTACGT ATTTAAGAGA ATCTTGTCAT
       TGCTTATACG TTCTCTATTA TTCTAATGCA TAAATTCTCT TAGAACAGTA
                         C5 Right Arm
       ~~~~~~~~~~~~~~~~~~~~~~~~~~~~~~~~~~~~~~~~~~~~~~~~~~~~~~~~~
 351   GATAATTGGG TACGACATAG TGATAAATGC TATTTCGCAT CGTTACATAA
       CTATTAACCC ATGCTGTATC ACTATTTACG ATAAAGCGTA GCAATGTATT
                         C5 Right Arm
       ~~~~~~~~~~~~~~~~~~~~~~~~~~~~~~~~~~~~~~~~~~~~~~~~~~~~~~~~~
 401   AGTCAGTTGG AAAGATGGAT TTGACAGATG TAACTTAATA GGTGCAAAAA
       TCAGTCAACC TTTCTACCTA AACTGTCTAC ATTGAATTAT CCACGTTTTT
                         C5 Right Arm
       ~~~~~~~~~~~~~~~~~~~~~~~~~~~~~~~~~~~~~~~~~~~~~~~~~~~~~~~~~
 451   TGTTAAATAA CAGCATTCTA TCGGAAGATA GGATACCAGT TATATTATAC
       ACAATTTATT GTCGTAAGAT AGCCTTCTAT CCTATGGTCA ATATAATATG
                         C5 Right Arm
       ~~~~~~~~~~~~~~~~~~~~~~~~~~~~~~~~~~~~~~~~~~~~~~~~~~~~~~~~~
 501   AAAAATCACT GGTTGGATAA AACAGATTCT GCAATATTCG TAAAGATGA
       TTTTTAGTGA CCAACCTATT TTGTCTAAGA CGTTATAAGC ATTTTCTACT
                         C5 Right Arm
       ~~~~~~~~~~~~~~~~~~~~~~~~~~~~~~~~~~~~~~~~~~~~~~~~~~~~~~~~~
 551   AGATTACTGC GAATTTGTAA ACTATGACAA TAAAAAGCCA TTTATCTCAA
       TCTAATGACG CTTAAACATT TGATACTGTT ATTTTCGGT AAATAGAGTT
```

FIGURE 5B

```
        C5 Right Arm
        ~~~~~~~~~~~~~~~~~~~~~~~~~~~~~~~~~~~~~~~~~~~~~~~~~~
  601   CGACATCGTG TAATTCTTCC ATGTTTTATG TATGTGTTTC AGATATTATG
        GCTGTAGCAC ATTAAGAAGG TACAAAATAC ATACACAAAG TCTATAATAC
                        C5 Right Arm
        ~~~~~~~~~~~~~~~~~~~~~~~~~~~~~~~~~~~~~~~~~~~~~~~~~~
  651   AGATTACTAT AAACTTTTTG TATACTTATA TTCCGTAAAC TATATTAATC
        TCTAATGATA TTTGAAAAAC ATATGAATAT AAGGCATTTG ATATAATTAG
                        C5 Right Arm
        ~~~~~~~~~~~~~~~~~~~~~~~~~~~~~~~~~~~~~~~~~~~~~~~~~~
  701   ATGAAGAAAA TGAAAAAGTA TAGAAGCTGT TCACGAGCGG TTGTTGAAAA
        TACTTCTTTT ACTTTTTCAT ATCTTCGACA AGTGCTCGCC AACAACTTTT
                        C5 Right Arm
        ~~~~~~~~~~~~~~~~~~~~~~~~~~~~~~~~~~~~~~~~~~~~~~~~~~
  751   CAACAAAATT ATACATTCAA GATGGCTTAC ATATACGTCT GTGAGGCTAT
        GTTGTTTTAA TATGTAAGTT CTACCGAATG TATATGCAGA CACTCCGATA
                        C5 Right Arm
        ~~~~~~~~~~~~~~~~~~~~~~~~~~~~~~~~~~~~~~~~~~~~~~~~~~
  801   CATGGATAAT GACAATGCAT CTCTAAATAG GTTTTGGAC AATGGATTCG
        GTACCTATTA CTGTTACGTA GAGATTTATC CAAAAACCTG TTACCTAAGC
                        C5 Right Arm
        ~~~~~~~~~~~~~~~~~~~~~~~~~~~~~~~~~~~~~~~~~~~~~~~~~~
  851   ACCCTAACAC GGAATATGGT ACTCTACAAT CTCCTCTTGA AATGGCTGTA
        TGGGATTGTG CCTTATACCA TGAGATGTTA GAGGAGAACT TTACCGACAT
                        C5 Right Arm
        ~~~~~~~~~~~~~~~~~~~~~~~~~~~~~~~~~~~~~~~~~~~~~~~~~~
  901   ATGTTCAAGA ATACCGAGGC TATAAAAATC TTGATGAGGT ATGGAGCTAA
        TACAAGTTCT TATGGCTCCG ATATTTTTAG AACTACTCCA TACCTCGATT
                        C5 Right Arm
        ~~~~~~~~~~~~~~~~~~~~~~~~~~~~~~~~~~~~~~~~~~~~~~~~~~
  951   ACCTGTAGTT ACTGAATGCA CAACTTCTTG TCTGCATGAT GCGGTGTTGA
        TGGACATCAA TGACTTACGT GTTGAAGAAC AGACGTACTA CGCCACAACT
                        C5 Right Arm
        ~~~~~~~~~~~~~~~~~~~~~~~~~~~~~~~~~~~~~~~~~~~~~~~~~~
 1001   GAGACGACTA CAAAATAGTG AAAGATCTGT TGAAGAATAA CTATGTAAAC
        CTCTGCTGAT GTTTTATCAC TTTCTAGACA ACTTCTTATT GATACATTTG
                        C5 Right Arm
        ~~~~~~~~~~~~~~~~~~~~~~~~~~~~~~~~~~~~~~~~~~~~~~~~~~
 1051   AATGTTCTTT ACAGCGGAGG CTTTACTCCT TTGTGTTTGG CAGCTTACCT
        TTACAAGAAA TGTCGCCTCC GAAATGAGGA AACACAAACC GTCGAATGGA
                        C5 Right Arm
        ~~~~~~~~~~~~~~~~~~~~~~~~~~~~~~~~~~~~~~~~~~~~~~~~~~
 1101   TAACAAAGTT AATTTGGTTA AACTTCTATT GGCTCATTCG GCGGATGTAG
        ATTGTTTCAA TTAAACCAAT TTGAAGATAA CCGAGTAAGC CGCCTACATC
                        C5 Right Arm
        ~~~~~~~~~~~~~~~~~~~~~~~~~~~~~~~~~~~~~~~~~~~~~~~~~~
 1151   ATATTTCAAA CACGGATCGG TTAACTCCTC TACATATAGC CGTATCAAAT
        TATAAAGTTT GTGCCTAGCC AATTGAGGAG ATGTATATCG GCATAGTTTA
                        C5 Right Arm
        ~~~~~~~~~~~~~~~~~~~~~~~~~~~~~~~~~~~~~~~~~~~~~~~~~~
 1201   AAAAATTTAA CAATGGTTAA ACTTCTATTG AACAAGGTG CTGATACTGA
        TTTTTAAATT GTTACCAATT TGAAGATAAC TTGTTTCCAC GACTATGACT
                        C5 Right Arm
        ~~~~~~~~~~~~~~~~~~~~~~~~~~~~~~~~~~~~~~~~~~~~~~~~~~
 1251   CTTGCTGGAT AACATGGGAT GTACTCCTTT AATGATCGCT GTACAATCTG
        GAACGACCTA TTGTACCCTA CATGAGGAAA TTACTAGCGA CATGTTAGAC
```

FIGURE 5C
C5 Right Arm

```
1301    GAAATATTGA AATATGTAGC ACACTACTTA AAAAAAATAA AATGTCCAGA
        CTTTATAACT TTATACATCG TGTGATGAAT TTTTTTTATT TTACAGGTCT
                          C5 Right Arm 1351    ACTGGGAAAA ATTGATCTTG CCAGCTGTAA TTCATGGTAG AAAAGAAGTG
        TGACCCTTTT TAACTAGAAC GGTCGACATT AAGTACCATC TTTTCTTCAC
                          C5 Right Arm 1401    CTCAGGCTAC TTTTCAACAA AGGAGCAGAT GTAAACTACA TCTTTGAAAG
        GAGTCCGATG AAAAGTTGTT TCCTCGTCTA CATTTGATGT AGAAACTTTC
                          C5 Right Arm 1451    AAATGGAAAA TCATATACTG TTTTGGAATT GATTAAAGAA AGTTACTCTG
        TTTACCTTTT AGTATATGAC AAAACCTTAA CTAATTTCTT TCAATGAGAC
                    C5 Right Arm 1501    AGACACAAAA GAGGTAGCTG AAGTGGTACT CTCAAAGGTA CGTGACTAAT
        TCTGTGTTTT CTCCATCGAC TTCACCATGA GAGTTTCCAT GCACTGATTA
                                    Repeat Region 1551    TAGCTATAAA AAGGATCGGG TTCTTTATTC TATACTTAAA AAGTGAAAAT
        ATCGATATTT TTCCTAGCCC AAGAAATAAG ATATGAATTT TTCACTTTTA
                          Repeat Region 1601    AAATACAAAG GTTCTTGAGG GTTGTGTTAA ATTGAAAGCG AGAAATAATC
        TTTATGTTTC CAAGAACTCC CAACACAATT TAACTTTCGC TCTTTATTAG
                          Repeat Region 1651    ATAAATTATT TCATTATCGC GATATCCGTT AAGTTTGTAT CGTAATCTGC
        TATTTAATAA AGTAATAGCG CTATAGGCAA TTCAAACATA GCATTAGACG
                          Repeat Region 1701    AGCCCCCACC ATGGATCTGG TGCTAAAAAG ATGCCTTCTT CATTTGGCTG
        TCGGGGGTGG TACCTAGACC ACGATTTTTC TACGGAAGAA GTAAACCGAC
                          Repeat Region 1751    TGATAGGTGC TTTGCTGGCT GTGGGGGCTA CAAAAGTACC CAGAAACCAG
        ACTATCCACG AAACGACCGA CACCCCCGAT GTTTTCATGG GTCTTTGGTC
                          Repeat Region 1801    GACTGGCTTG GTGTCTCAAG GCAACTCAGA ACCAAAGCCT GGAACAGGCA
        CTGACCGAAC CACAGAGTTC CGTTGAGTCT TGGTTTCGGA CCTTGTCCGT
                          Repeat Region 1851    GCTGTATCCA GAGTGGACAG AAGCCCAGAG ACTTGACTGC TGGAGAGGTG
        CGACATAGGT CTCACCTGTC TTCGGGTCTC TGAACTGACG ACCTCTCCAC
                          Repeat Region 1901    GTCAAGTGTC CCTCAAGGTC AGTAATGATG GGCCTACACT GATTGGTGCA
        CAGTTCACAG GGAGTTCCAG TCATTACTAC CCGGATGTGA CTAACCACGT
                          Repeat Region 1951    AATGCCTCCT TCTCTATTGC CTTGAACTTC CCTGGAAGCC AAAAGGTATT
        TTACGGAGGA AGAGATAACG GAACTTGAAG GGACCTTCGG TTTTCCATAA
```

FIGURE 5D

```
      Repeat Region                    C1B promoter
      ~~~~~~~                  ~~~~~~~~~~~~~~~~~~~~~~~~~~~~~~~
2001  GCCAGATACT AGTTCTAGAG GATCATTATT TAACGTAAAC TAAATGGAAA
      CGGTCTATGA TCAAGATCTC CTAGTAATAA ATTGCATTTG ATTTACCTTT
                          C1B promoter
      ~~~~~~~~~~~~~~~~~~~~~~~~~~~~~~~~~~~~~~~~~~~~~~~~~~
2051  AGCTATTTAC AGGTACATAC GGTGTTTTTC TGGAATCAAA TGATTCTGAT
      TCGATAAATG TCCATGTATG CCACAAAAAG ACCTTAGTTT ACTAAGACTA
                          C1B promoter
      ~~~~~~~~~~~~~~~~~~~~~~~~~~~~~~~~~~~~~~~~~~~~~~~~~~
2101  TTTGAGGATT TTATCAATAC AATAATGACA GTGCTAACTG GTAAAAAGA
      AAACTCCTAA AATAGTTATG TTATTACTGT CACGATTGAC CATTTTTCT
                          C1B promoter
      ~~~~~~~~~~~~~~~~~~~~~~~~~~~~~~~~~~~~~~~~~~~~~~~~~~
2151  AAGCAAACAA TTATCATGGC TAACAATTTT TATTATATTT GTAGTATGCA
      TTCGTTTGTT AATAGTACCG ATTGTTAAAA ATAATATAAA CATCATACGT
                          C1B promoter
      ~~~~~~~~~~~~~~~~~~~~~~~~~~~~~~~~~~~~~~~~~~~~~~~~~~
2201  TAGTGGTCTT TACGTTTCTT TATTTAAAGT TAATGTGTTA AGATTAAATG
      ATCACCAGAA ATGCAAAGAA ATAAATTTCA ATTACACAAT TCTAATTTAC
      C1B promoter                                LacZ
      ~~~~~~~~~~~~~~                   ~~~~~~~~~~~~~~~~~~~~~~~~~
2251  GAGTAATTGG ATCCCCCATC GATGGGGAAT TCACTGGCCG TCGTTTTACA
      CTCATTAACC TAGGGGGTAG CTACCCCTTA AGTGACCGGC AGCAAAATGT
                                LacZ
      ~~~~~~~~~~~~~~~~~~~~~~~~~~~~~~~~~~~~~~~~~~~~~~~~~~
2301  ACGTCGTGAC TGGGAAAACC CTGGCGTTAC CCAACTTAAT CGCCTTGCAG
      TGCAGCACTG ACCCTTTTGG GACCGCAATG GGTTGAATTA GCGGAACGTC
                                LacZ
      ~~~~~~~~~~~~~~~~~~~~~~~~~~~~~~~~~~~~~~~~~~~~~~~~~~
2351  CACATCCCCC TTTCGCCAGC TGGCGTAATA GCGAAGAGGC CCGCACCGAT
      GTGTAGGGGG AAAGCGGTCG ACCGCATTAT CGCTTCTCCG GGCGTGGCTA
                                LacZ
      ~~~~~~~~~~~~~~~~~~~~~~~~~~~~~~~~~~~~~~~~~~~~~~~~~~
2401  CGCCCTTCCC AACAGTTGCG CAGCCTGAAT GGCGAATGGC GCTTTGCCTG
      GCGGGAAGGG TTGTCAACGC GTCGGACTTA CCGCTTACCG CGAAACGGAC
                                LacZ
      ~~~~~~~~~~~~~~~~~~~~~~~~~~~~~~~~~~~~~~~~~~~~~~~~~~
2451  GTTTCCGGCA CCAGAAGCGG TGCCGGAAAG CTGGCTGGAG TGCGATCTTC
      CAAAGGCCGT GGTCTTCGCC ACGGCCTTTC GACCGACCTC ACGCTAGAAG
                                LacZ
      ~~~~~~~~~~~~~~~~~~~~~~~~~~~~~~~~~~~~~~~~~~~~~~~~~~
2501  CTGAGGCCGA TACTGTCGTC GTCCCCTCAA ACTGGCAGAT GCACGGTTAC
      GACTCCGGCT ATGACAGCAG CAGGGGAGTT TGACCGTCTA CGTGCCAATG
                                LacZ
      ~~~~~~~~~~~~~~~~~~~~~~~~~~~~~~~~~~~~~~~~~~~~~~~~~~
2551  GATGCGCCCA TCTACACCAA CGTGACCTAT CCCATTACGG TCAATCCGCC
      CTACGCGGGT AGATGTGGTT GCACTGGATA GGGTAATGCC AGTTAGGCGG
                                LacZ
      ~~~~~~~~~~~~~~~~~~~~~~~~~~~~~~~~~~~~~~~~~~~~~~~~~~
2601  GTTTGTTCCC ACGGAGAATC CGACGGGTTG TTACTCGCTC ACATTTAATG
      CAAACAAGGG TGCCTCTTAG GCTGCCCAAC AATGAGCGAG TGTAAATTAC
                                LacZ
      ~~~~~~~~~~~~~~~~~~~~~~~~~~~~~~~~~~~~~~~~~~~~~~~~~~
2651  TTGATGAAAG CTGGCTACAG GAAGGCCAGA CGCGAATTAT TTTGATGGC
      AACTACTTTC GACCGATGTC CTTCCGGTCT GCGCTTAATA AAAACTACCG
```

FIGURE 5E

```
              LacZ
              ~~~~~~~~~~~~~~~~~~~~~~~~~~~~~~~~~~~~~~~~~~~~~~~~~~
2701    GTTAACTCGG CGTTTCATCT GTGGTGCAAC GGGCGCTGGG TCGGTTACGG
        CAATTGAGCC GCAAAGTAGA CACCACGTTG CCCGCGACCC AGCCAATGCC
              LacZ
              ~~~~~~~~~~~~~~~~~~~~~~~~~~~~~~~~~~~~~~~~~~~~~~~~~~
2751    CCAGGACAGT CGTTTGCCGT CTGAATTTGA CCTGAGCGCA TTTTTACGCG
        GGTCCTGTCA GCAAACGGCA GACTTAAACT GGACTCGCGT AAAAATGCGC
              LacZ
              ~~~~~~~~~~~~~~~~~~~~~~~~~~~~~~~~~~~~~~~~~~~~~~~~~~
2801    CCGGAGAAAA CCGCCTCGCG GTGATGGTGC TGCGCTGGAG TGACGGCAGT
        GGCCTCTTTT GGCGGAGCGC CACTACCACG ACGCGACCTC ACTGCCGTCA
              LacZ
              ~~~~~~~~~~~~~~~~~~~~~~~~~~~~~~~~~~~~~~~~~~~~~~~~~~
2851    TATCTGGAAG ATCAGGATAT GTGGCGGATG AGCGGCATTT TCCGTGACGT
        ATAGACCTTC TAGTCCTATA CACCGCCTAC TCGCCGTAAA AGGCACTGCA
              LacZ
              ~~~~~~~~~~~~~~~~~~~~~~~~~~~~~~~~~~~~~~~~~~~~~~~~~~
2901    CTCGTTGCTG CATAAACCGA CTACACAAAT CAGCGATTTC CATGTTGCCA
        GAGCAACGAC GTATTTGGCT GATGTGTTTA GTCGCTAAAG GTACAACGGT
              LacZ
              ~~~~~~~~~~~~~~~~~~~~~~~~~~~~~~~~~~~~~~~~~~~~~~~~~~
2951    CTCGCTTTAA TGATGATTTC AGCCGCGCTG TACTGGAGGC TGAAGTTCAG
        GAGCGAAATT ACTACTAAAG TCGGCGCGAC ATGACCTCCG ACTTCAAGTC
              LacZ
              ~~~~~~~~~~~~~~~~~~~~~~~~~~~~~~~~~~~~~~~~~~~~~~~~~~
3001    ATGTGCGGCG AGTTGCGTGA CTACCTACGG GTAACAGTTT CTTTATGGCA
        TACACGCCGC TCAACGCACT GATGGATGCC CATTGTCAAA GAAATACCGT
              LacZ
              ~~~~~~~~~~~~~~~~~~~~~~~~~~~~~~~~~~~~~~~~~~~~~~~~~~
3051    GGGTGAAACG CAGGTCGCCA GCGGCACCGC GCCTTTCGGC GGTGAAATTA
        CCCACTTTGC GTCCAGCGGT CGCCGTGGCG CGGAAAGCCG CCACTTTAAT
              LacZ
              ~~~~~~~~~~~~~~~~~~~~~~~~~~~~~~~~~~~~~~~~~~~~~~~~~~
3101    TCGATGAGCG TGGTGGTTAT GCCGATCGCG TCACACTACG TCTGAACGTC
        AGCTACTCGC ACCACCAATA CGGCTAGCGC AGTGTGATGC AGACTTGCAG
              LacZ
              ~~~~~~~~~~~~~~~~~~~~~~~~~~~~~~~~~~~~~~~~~~~~~~~~~~
3151    GAAAACCCGA AACTGTGGAG CGCCGAAATC CCGAATCTCT ATCGTGCGGT
        CTTTTGGGCT TTGACACCTC GCGGCTTTAG GGCTTAGAGA TAGCACGCCA
              LacZ
              ~~~~~~~~~~~~~~~~~~~~~~~~~~~~~~~~~~~~~~~~~~~~~~~~~~
3201    GGTTGAACTG CACACCGCCG ACGGCACGCT GATTGAAGCA GAAGCCTGCG
        CCAACTTGAC GTGTGGCGGC TGCCGTGCGA CTAACTTCGT CTTCGGACGC
              LacZ
              ~~~~~~~~~~~~~~~~~~~~~~~~~~~~~~~~~~~~~~~~~~~~~~~~~~
3251    ATGTCGGTTT CCGCGAGGTG CGGATTGAAA ATGGTCTGCT GCTGCTGAAC
        TACAGCCAAA GGCGCTCCAC GCCTAACTTT TACCAGACGA CGACGACTTG
              LacZ
              ~~~~~~~~~~~~~~~~~~~~~~~~~~~~~~~~~~~~~~~~~~~~~~~~~~
3301    GGCAAGCCGT TGCTGATTCG AGGCGTTAAC CGTCACGAGC ATCATCCTCT
        CCGTTCGGCA ACGACTAAGC TCCGCAATTG GCAGTGCTCG TAGTAGGAGA
              LacZ
              ~~~~~~~~~~~~~~~~~~~~~~~~~~~~~~~~~~~~~~~~~~~~~~~~~~
3351    GCATGGTCAG GTCATGGATG AGCAGACGAT GGTGCAGGAT ATCCTGCTGA
        CGTACCAGTC CAGTACCTAC TCGTCTGCTA CCACGTCCTA TAGGACGACT
```

FIGURE 5F

LacZ

```
3401  TGAAGCAGAA CAACTTTAAC GCCGTGCGCT GTTCGCATTA TCCGAACCAT
      ACTTCGTCTT GTTGAAATTG CGGCACGCGA CAAGCGTAAT AGGCTTGGTA
```
LacZ
```
3451  CCGCTGTGGT ACACGCTGTG CGACCGCTAC GGCCTGTATG TGGTGGATGA
      GGCGACACCA TGTGCGACAC GCTGGCGATG CCGGACATAC ACCACCTACT
```
LacZ
```
3501  AGCCAATATT GAAACCCACG GCATGGTGCC AATGAATCGT CTGACCGATG
      TCGGTTATAA CTTTGGGTGC CGTACCACGG TTACTTAGCA GACTGGCTAC
```
LacZ
```
3551  ATCCGCGCTG GCTACCGGCG ATGAGCGAAC GCGTAACGCG AATGGTGCAG
      TAGGCGCGAC CGATGGCCGC TACTCGCTTG CGCATTGCGC TTACCACGTC
```
LacZ
```
3601  CGCGATCGTA ATCACCCGAG TGTGATCATC TGGTCGCTGG GGAATGAATC
      GCGCTAGCAT TAGTGGGCTC ACACTAGTAG ACCAGCGACC CCTTACTTAG
```
LacZ
```
3651  AGGCCACGGC GCTAATCACG ACGCGCTGTA TCGCTGGATC AAATCTGTCG
      TCCGGTGCCG CGATTAGTGC TGCGCGACAT AGCGACCTAG TTTAGACAGC
```
LacZ
```
3701  ATCCTTCCCG CCCGGTGCAG TATGAAGGCG GCGGAGCCGA CACCACGGCC
      TAGGAAGGGC GGGCCACGTC ATACTTCCGC CGCCTCGGCT GTGGTGCCGG
```
LacZ
```
3751  ACCGATATTA TTTGCCCGAT GTACGCGCGC GTGGATGAAG ACCAGCCCTT
      TGGCTATAAT AAACGGGCTA CATGCGCGCG CACCTACTTC TGGTCGGGAA
```
LacZ
```
3801  CCCGGCTGTG CCGAAATGGT CCATCAAAAA ATGGCTTTCG CTACCTGGAG
      GGGCCGACAC GGCTTTACCA GGTAGTTTTT TACCGAAAGC GATGGACCTC
```
LacZ
```
3851  AGACGCGCCC GCTGATCCTT TGCGAATACG CCCACGCGAT GGGTAACAGT
      TCTGCGCGGG CGACTAGGAA ACGCTTATGC GGGTGCGCTA CCCATTGTCA
```
LacZ
```
3901  CTTGGCGGTT TCGCTAAATA CTGGCAGGCG TTTCGTCAGT ATCCCCGTTT
      GAACCGCCAA AGCGATTTAT GACCGTCCGC AAAGCAGTCA TAGGGGCAAA
```
LacZ
```
3951  ACAGGGCGGC TTCGTCTGGG ACTGGGTGGA TCAGTCGCTG ATTAAATATG
      TGTCCCGCCG AAGCAGACCC TGACCCACCT AGTCAGCGAC TAATTTATAC
```
LacZ
```
4001  ATGAAAACGG CAACCCGTGG TCGGCTTACG GCGGTGATTT TGGCGATACG
      TACTTTTGCC GTTGGGCACC AGCCGAATGC CGCCACTAAA ACCGCTATGC
```
LacZ
```
4051  CCGAACGATC GCCAGTTCTG TATGAACGGT CTGGTCTTTG CCGACCGCAC
      GGCTTGCTAG CGGTCAAGAC ATACTTGCCA GACCAGAAAC GGCTGGCGTG
```

FIGURE 5G

```
                                  LacZ
      ~~~~~~~~~~~~~~~~~~~~~~~~~~~~~~~~~~~~~~~~~~~~~~~~~~
4101  GCCGCATCCA GCGCTGACGG AAGCAAAACA CCAGCAGCAG TTTTTCCAGT
      CGGCGTAGGT CGCGACTGCC TTCGTTTTGT GGTCGTCGTC AAAAAGGTCA
                                  LacZ
      ~~~~~~~~~~~~~~~~~~~~~~~~~~~~~~~~~~~~~~~~~~~~~~~~~~
4151  TCCGTTTATC CGGGCAAACC ATCGAAGTGA CCAGCGAATA CCTGTTCCGT
      AGGCAAATAG GCCCGTTTGG TAGCTTCACT GGTCGCTTAT GGACAAGGCA
                                  LacZ
      ~~~~~~~~~~~~~~~~~~~~~~~~~~~~~~~~~~~~~~~~~~~~~~~~~~
4201  CATAGCGATA ACGAGCTCCT GCACTGGATG GTGGCGCTGG ATGGTAAGCC
      GTATCGCTAT TGCTCGAGGA CGTGACCTAC CACCGCGACC TACCATTCGG
                                  LacZ
      ~~~~~~~~~~~~~~~~~~~~~~~~~~~~~~~~~~~~~~~~~~~~~~~~~~
4251  GCTGGCAAGC GGTGAAGTGC CTCTGGATGT CGCTCCACAA GGTAAACAGT
      CGACCGTTCG CCACTTCACG GAGACCTACA GCGAGGTGTT CCATTTGTCA
                                  LacZ
      ~~~~~~~~~~~~~~~~~~~~~~~~~~~~~~~~~~~~~~~~~~~~~~~~~~
4301  TGATTGAACT GCCTGAACTA CCGCAGCCGG AGAGCGCCGG GCAACTCTGG
      ACTAACTTGA CGGACTTGAT GGCGTCGGCC TCTCGCGGCC CGTTGAGACC
                                  LacZ
      ~~~~~~~~~~~~~~~~~~~~~~~~~~~~~~~~~~~~~~~~~~~~~~~~~~
4351  CTCACAGTAC GCGTAGTGCA ACCGAACGCG ACCGCATGGT CAGAAGCCGG
      GAGTGTCATG CGCATCACGT TGGCTTGCGC TGGCGTACCA GTCTTCGGCC
                                  LacZ
      ~~~~~~~~~~~~~~~~~~~~~~~~~~~~~~~~~~~~~~~~~~~~~~~~~~
4401  GCACATCAGC GCCTGGCAGC AGTGGCGTCT GGCGGAAAAC CTCAGTGTGA
      CGTGTAGTCG CGGACCGTCG TCACCGCAGA CCGCCTTTTG GAGTCACACT
                                  LacZ
      ~~~~~~~~~~~~~~~~~~~~~~~~~~~~~~~~~~~~~~~~~~~~~~~~~~
4451  CGCTCCCCGC CGCGTCCCAC GCCATCCCGC ATCTGACCAC CAGCGAAATG
      GCGAGGGGCG GCGCAGGGTG CGGTAGGGCG TAGACTGGTG GTCGCTTTAC
                                  LacZ
      ~~~~~~~~~~~~~~~~~~~~~~~~~~~~~~~~~~~~~~~~~~~~~~~~~~
4501  GATTTTTGCA TCGAGCTGGG TAATAAGCGT TGGCAATTTA ACCGCCAGTC
      CTAAAAACGT AGCTCGACCC ATTATTCGCA ACCGTTAAAT TGGCGGTCAG
                                  LacZ
      ~~~~~~~~~~~~~~~~~~~~~~~~~~~~~~~~~~~~~~~~~~~~~~~~~~
4551  AGGCTTTCTT TCACAGATGT GGATTGGCGA TAAAAAACAA CTGCTGACGC
      TCCGAAAGAA AGTGTCTACA CCTAACCGCT ATTTTTTGTT GACGACTGCG
                                  LacZ
      ~~~~~~~~~~~~~~~~~~~~~~~~~~~~~~~~~~~~~~~~~~~~~~~~~~
4601  CGCTGCGCGA TCAGTTCACC CGTGCACCGC TGGATAACGA CATTGGCGTA
      GCGACGCGCT AGTCAAGTGG GCACGTGGCG ACCTATTGCT GTAACCGCAT
                                  LacZ
      ~~~~~~~~~~~~~~~~~~~~~~~~~~~~~~~~~~~~~~~~~~~~~~~~~~
4651  AGTGAAGCGA CCCGCATTGA CCCTAACGCC TGGGTCGAAC GCTGGAAGGC
      TCACTTCGCT GGGCGTAACT GGGATTGCGG ACCCAGCTTG CGACCTTCCG
                                  LacZ
      ~~~~~~~~~~~~~~~~~~~~~~~~~~~~~~~~~~~~~~~~~~~~~~~~~~
4701  GGCGGGCCAT TACCAGGCCG AAGCAGCGTT GTTGCAGTGC ACGGCAGATA
      CCGCCCGGTA ATGGTCCGGC TTCGTCGCAA CAACGTCACG TGCCGTCTAT
                                  LacZ
      ~~~~~~~~~~~~~~~~~~~~~~~~~~~~~~~~~~~~~~~~~~~~~~~~~~
4751  CACTTGCTGA TGCGGTGCTG ATTACGACCG CTCACGCGTG GCAGCATCAG
      GTGAACGACT ACGCCACGAC TAATGCTGGC GAGTGCGCAC CGTCGTAGTC
```

FIGURE 5H

```
                          LacZ
      ~~~~~~~~~~~~~~~~~~~~~~~~~~~~~~~~~~~~~~~~~~~~~~~~~~~~~
4801  GGGAAAACCT TATTTATCAG CCGGAAAACC TACCGGATTG ATGGTAGTGG
      CCCTTTTGGA ATAAATAGTC GGCCTTTTGG ATGGCCTAAC TACCATCACC
                          LacZ
      ~~~~~~~~~~~~~~~~~~~~~~~~~~~~~~~~~~~~~~~~~~~~~~~~~~~~
4851  TCAAATGGCG ATTACCGTTG ATGTTGAAGT GGCGAGCGAT ACACCGCATC
      AGTTTACCGC TAATGGCAAC TACAACTTCA CCGCTCGCTA TGTGGCGTAG
                          LacZ
      ~~~~~~~~~~~~~~~~~~~~~~~~~~~~~~~~~~~~~~~~~~~~~~~~~~~~
4901  CGGCGCGGAT TGGCCTGAAC TGCCAGCTGG CGCAGGTAGC AGAGCGGGTA
      GCCGCGCCTA ACCGGACTTG ACGGTCGACC GCGTCCATCG TCTCGCCCAT
                          LacZ
      ~~~~~~~~~~~~~~~~~~~~~~~~~~~~~~~~~~~~~~~~~~~~~~~~~~~~
4951  AACTGGCTCG GATTAGGGCC GCAAGAAAAC TATCCCGACC GCCTTACTGC
      TTGACCGAGC CTAATCCCGG CGTTCTTTTG ATAGGGCTGG CGGAATGACG
                          LacZ
      ~~~~~~~~~~~~~~~~~~~~~~~~~~~~~~~~~~~~~~~~~~~~~~~~~~~~
5001  CGCCTGTTTT GACCGCTGGG ATCTGCCATT GTCAGACATG TATACCCCGT
      GCGGACAAAA CTGGCGACCC TAGACGGTAA CAGTCTGTAC ATATGGGGCA
                          LacZ
      ~~~~~~~~~~~~~~~~~~~~~~~~~~~~~~~~~~~~~~~~~~~~~~~~~~~~
5051  ACGTCTTCCC GAGCGAAAAC GGTCTGCGCT GCGGGACGCG CGAATTGAAT
      TGCAGAAGGG CTCGCTTTTG CCAGACGCGA CGCCCTGCGC GCTTAACTTA
                          LacZ
      ~~~~~~~~~~~~~~~~~~~~~~~~~~~~~~~~~~~~~~~~~~~~~~~~~~~~
5101  TATGGCCCAC ACCAGTGGCG CGGCGACTTC CAGTTCAACA TCAGCCGGTA
      ATACCGGGTG TGGTCACCGC GCCGCTGAAG GTCAAGTTGT AGTCGGCCAT
                          LacZ
      ~~~~~~~~~~~~~~~~~~~~~~~~~~~~~~~~~~~~~~~~~~~~~~~~~~~~
5151  CAGTCAACAG CAATTGATGG AAACCAGCCA TCGCCATCT GCTGCACGCG
      GTCAGTTGTC GTTAACTACC TTTGGTCGGT AAGCGGTAGA CGACGTGCGC
                          LacZ
      ~~~~~~~~~~~~~~~~~~~~~~~~~~~~~~~~~~~~~~~~~~~~~~~~~~~~
5201  GAAGAGGCAC ATGGCTGAAT ATCGACGGTT TCCATATGGG GATTGGTGGC
      CTTCTCCGTG TACCGACTTA TAGCTGCCAA AGGTATACCC CTAACCACCG
                          LacZ
      ~~~~~~~~~~~~~~~~~~~~~~~~~~~~~~~~~~~~~~~~~~~~~~~~~~~~
5251  GACGACTCCT GGAGCCCGTC AGTATCGGCG GAATTCCAGC TGAGCGCCGG
      CTGCTGAGGA CCTCGGGCAG TCATAGCCGC CTTAAGGTCG ACTCGCGGCC
                      LacZ
      ~~~~~~~~~~~~~~~~~~~~~~~~~~~~~~~~~~~~~~~
5301  TCGCTACCAT TACCAGTTGG TCTGGTGTCA AAAATAATAA TAACCGGGCA
      AGCGATGGTA ATGGTCAACC AGACCACAGT TTTTATTATT ATTGGCCCGT
5351  GGGGGGATCC GGAGCTTATC GCAGATCAAT TCGATATCAA GCTTATCGAT
      CCCCCCTAGG CCTCGAATAG CGTCTAGTTA AGCTATAGTT CGAATAGCTA
                                                H6  Promoter
                                          ~~~~~~~~~~~~~~~~~~
5401  ACCGTCGACC TCGAGTCTAG AATCGATCCC GGGTTCTTTA TTCTATACTT
      TGGCAGCTGG AGCTCAGATC TTAGCTAGGG CCCAAGAAAT AAGATATGAA
                        H6  Promoter
      ~~~~~~~~~~~~~~~~~~~~~~~~~~~~~~~~~~~~~~~~~~~~~~~~~~~~
5451  AAAAAGTGAA AATAAATACA AAGGTTCTTG AGGGTTGTGT TAAATTGAAA
      TTTTTCACTT TTATTTATGT TTCCAAGAAC TCCCAACACA ATTTAACTTT
```

FIGURE 5I

```
     H6  Promoter
     ~~~~~~~~~~~~~~~~~~~~~~~~~~~~~~~~~~~~~~~~~~~~~~~~~~
5501 GCGAGAAATA ATCATAAATT ATTTCATTAT CGCGATATCC GTTAAGTTTG
     CGCTCTTTAT TAGTATTTAA TAAAGTAATA GCGCTATAGG CAATTCAAAC
     H6  Promoter                              gp100(M)
     ~~~~~~~                           ~~~~~~~~~~~~~~~~~~~~~~~~~~~~
5551 TATCGTAATC TGCAGCCCCC ACCATGGATC TGGTGCTAAA AGATGCCTT
     ATAGCATTAG ACGTCGGGGG TGGTACCTAG ACCACGATTT TTCTACGGAA
                                     gp100(M)
     ~~~~~~~~~~~~~~~~~~~~~~~~~~~~~~~~~~~~~~~~~~~~~~~~~~
5601 CTTCATTTGG CTGTGATAGG TGCTTTGCTG GCTGTGGGGG CTACAAAAGT
     GAAGTAAACC GACACTATCC ACGAAACGAC CGACACCCCC GATGTTTTCA
                                     gp100(M)
     ~~~~~~~~~~~~~~~~~~~~~~~~~~~~~~~~~~~~~~~~~~~~~~~~~~
5651 ACCCAGAAAC CAGGACTGGC TTGGTGTCTC AAGGCAACTC AGAACCAAAG
     TGGGTCTTTG GTCCTGACCG AACCACAGAG TTCCGTTGAG TCTTGGTTTC
                                     gp100(M)
     ~~~~~~~~~~~~~~~~~~~~~~~~~~~~~~~~~~~~~~~~~~~~~~~~~~
5701 CCTGGAACAG GCAGCTGTAT CCAGAGTGGA CAGAAGCCCA GAGACTTGAC
     GGACCTTGTC CGTCGACATA GGTCTCACCT GTCTTCGGGT CTCTGAACTG
                                     gp100(M)
     ~~~~~~~~~~~~~~~~~~~~~~~~~~~~~~~~~~~~~~~~~~~~~~~~~~
5751 TGCTGGAGAG GTGGTCAAGT GTCCCTCAAG GTCAGTAATG ATGGGCCTAC
     ACGACCTCTC CACCAGTTCA CAGGGAGTTC CAGTCATTAC TACCCGGATG
                                     gp100(M)
     ~~~~~~~~~~~~~~~~~~~~~~~~~~~~~~~~~~~~~~~~~~~~~~~~~~
5801 ACTGATTGGT GCAAATGCCT CCTTCTCTAT TGCCTTGAAC TTCCCTGGAA
     TGACTAACCA CGTTTACGGA GGAAGAGATA ACGGAACTTG AAGGGACCTT
                                     gp100(M)
     ~~~~~~~~~~~~~~~~~~~~~~~~~~~~~~~~~~~~~~~~~~~~~~~~~~
5851 GCCAAAAGGT ATTGCCAGAT GGGCAGGTTA TCTGGGTCAA CAATACCATC
     CGGTTTTCCA TAACGGTCTA CCCGTCCAAT AGACCCAGTT GTTATGGTAG
                                     gp100(M)
     ~~~~~~~~~~~~~~~~~~~~~~~~~~~~~~~~~~~~~~~~~~~~~~~~~~
5901 ATCAATGGGA GCCAGGTGTG GGGAGGACAG CCAGTGTATC CCCAGGAAAC
     TAGTTACCCT CGGTCCACAC CCCTCCTGTC GGTCACATAG GGGTCCTTTG
                                     gp100(M)
     ~~~~~~~~~~~~~~~~~~~~~~~~~~~~~~~~~~~~~~~~~~~~~~~~~~
5951 TGACGATGCC TGCATCTTCC CTGATGGTGG ACCTTGCCCA TCTGGCTCTT
     ACTGCTACGG ACGTAGAAGG GACTACCACC TGGAACGGGT AGACCGAGAA
                                     gp100(M)
     ~~~~~~~~~~~~~~~~~~~~~~~~~~~~~~~~~~~~~~~~~~~~~~~~~~
6001 GGTCTCAGAA GAGAAGCTTT GTTTATGTCT GGAAGACCTG GGGCCAATAC
     CCAGAGTCTT CTCTTCGAAA CAAATACAGA CCTTCTGGAC CCCGGTTATG
                                     gp100(M)
     ~~~~~~~~~~~~~~~~~~~~~~~~~~~~~~~~~~~~~~~~~~~~~~~~~~
6051 TGGCAAGTTC TAGGGGCCCC AGTGTCTGGG CTGAGCATTG GACAGGCAG
     ACCGTTCAAG ATCCCCGGG TCACAGACCC GACTCGTAAC CCTGTCCGTC
                                     gp100(M)
     ~~~~~~~~~~~~~~~~~~~~~~~~~~~~~~~~~~~~~~~~~~~~~~~~~~
6101 GGCAATGCTG GCACACACA CGATGGAAGT GACTGTCTAC CATCGCCGGG
     CCGTTACGAC CCGTGTGTGT GCTACCTTCA CTGACAGATG GTAGCGGCCC
                                     gp100(M)
     ~~~~~~~~~~~~~~~~~~~~~~~~~~~~~~~~~~~~~~~~~~~~~~~~~~
6151 GATCCCGGAG CTATGTGCCT CTTGCTCATT CCAGCTCAGC CTTCACCATT
     CTAGGGCCTC GATACACGGA GAACGAGTAA GGTCGAGTCG GAAGTGGTAA
```

FIGURE 5J gp100(M)

```
6201  ATGGACCAGG TGCCTTTCTC CGTGAGCGTG TCCCAGTTGC GGGCCTTGGA
      TACCTGGTCC ACGGAAAGAG GCACTCGCAC AGGGTCAACG CCCGGAACCT
``` gp100(M)

```
6251  TGGAGGGAAC AAGCACTTCC TGAGAAATCA GCCTCTGACC TTTGCCCTCC
      ACCTCCCTTG TTCGTGAAGG ACTCTTTAGT CGGAGACTGG AAACGGGAGG
``` gp100(M)

```
6301  AGCTCCATGA CCCCAGTGGC TATCTGGCTG AAGCTGACCT CTCCTACACC
      TCGAGGTACT GGGGTCACCG ATAGACCGAC TTCGACTGGA GAGGATGTGG
``` gp100(M)

```
6351  TGGGACTTTG GAGACAGTAG TGGAACCCTG ATCTCTCGGG CACTTGTGGT
      ACCCTGAAAC CTCTGTCATC ACCTTGGGAC TAGAGAGCCC GTGAACACCA
``` gp100(M)

```
6401  CACTCATACT TACCTGGAGC CTGGCCCAGT CACTGTTCAG GTGGTCCTGC
      GTGAGTATGA ATGGACCTCG GACCGGGTCA GTGACAAGTC CACCAGGACG
``` gp100(M)

```
6451  AGGCTGCCAT TCCTCTCACC TCCTGTGGCT CCTCCCCAGT TCCAGGCACC
      TCCGACGGTA AGGAGAGTGG AGGACACCGA GGAGGGGTCA AGGTCCGTGG
``` gp100(M)

```
6501  ACAGATGGGC ACAGGCCAAC TGCAGAGGCC CCTAACACCA CAGCTGGCCA
      TGTCTACCCG TGTCCGGTTG ACGTCTCCGG GGATTGTGGT GTCGACCGGT
``` gp100(M)

```
6551  AGTGCCTACT ACAGAAGTTG TGGGTACTAC ACCTGGTCAG GCGCCAACTG
      TCACGGATGA TGTCTTCAAC ACCCATGATG TGGACCAGTC CGCGGTTGAC
``` gp100(M)

```
6601  CAGAGCCCTC TGGAACCACA TCTGTGCAGG TGCCAACCAC TGAAGTCATA
      GTCTCGGGAG ACCTTGGTGT AGACACGTCC ACGGTTGGTG ACTTCAGTAT
``` gp100(M)

```
6651  AGCACTGCAC CTGTGCAGAT GCCAACTGCA GAGAGCACAG GTATGACACC
      TCGTGACGTG GACACGTCTA CGGTTGACGT CTCTCGTGTC CATACTGTGG
``` gp100(M)

```
6701  TGAGAAGGTG CCAGTTTCAG AGGTCATGGG TACCACACTG GCAGAGATGT
      ACTCTTCCAC GGTCAAAGTC TCCAGTACCC ATGGTGTGAC CGTCTCTACA
``` gp100(M)

```
6751  CAACTCCAGA GGCTACAGGT ATGACACCTG CAGAGGTATC AATTGTGGTG
      GTTGAGGTCT CCGATGTCCA TACTGTGGAC GTCTCCATAG TTAACACCAC
``` gp100(M)

```
6801  CTTTCTGGAA CCACAGCTGC ACAGGTAACA ACTACAGAGT GGGTGGAGAC
      GAAAGACCTT GGTGTCGACG TGTCCATTGT TGATGTCTCA CCCACCTCTG
``` gp100(M)

```
6851  CACAGCTAGA GAGCTACCTA TCCCTGAGCC TGAAGGTCCA GATGCCAGCT
      GTGTCGATCT CTCGATGGAT AGGGACTCGG ACTTCCAGGT CTACGGTCGA
```

FIGURE 5K

```
              gp100(M)
        ~~~~~~~~~~~~~~~~~~~~~~~~~~~~~~~~~~~~~~~~~~~~~~~~~~~
6901    CAATCATGTC TACGGAAAGT ATTACAGGTT CCCTGGGCCC CCTGCTGGAT
        GTTAGTACAG ATGCCTTTCA TAATGTCCAA GGGACCCGGG GGACGACCTA
                                  gp100(M)
        ~~~~~~~~~~~~~~~~~~~~~~~~~~~~~~~~~~~~~~~~~~~~~~~~~~~
6951    GGTACAGCCA CCTTAAGGCT GGTGAAGAGA CAAGTCCCCC TGGATTGTGT
        CCATGTCGGT GGAATTCCGA CCACTTCTCT GTTCAGGGGG ACCTAACACA
                                  gp100(M)
        ~~~~~~~~~~~~~~~~~~~~~~~~~~~~~~~~~~~~~~~~~~~~~~~~~~~
7001    TCTGTATCGA TATGGTTCCT TTTCCGTCAC CCTGGACATT GTCCAGGGTA
        AGACATAGCT ATACCAAGGA AAAGGCAGTG GGACCTGTAA CAGGTCCCAT
                                  gp100(M)
        ~~~~~~~~~~~~~~~~~~~~~~~~~~~~~~~~~~~~~~~~~~~~~~~~~~~
7051    TTGAAAGTGC CGAGATCCTG CAGGCTGTGC CGTCCGGTGA GGGGGATGCA
        AACTTTCACG GCTCTAGGAC GTCCGACACG GCAGGCCACT CCCCCTACGT
                                  gp100(M)
        ~~~~~~~~~~~~~~~~~~~~~~~~~~~~~~~~~~~~~~~~~~~~~~~~~~~
7101    TTTGAGCTGA CTGTGTCCTG CCAAGGCGGG CTGCCCAAGG AAGCCTGCAT
        AAACTCGACT GACACAGGAC GGTTCCGCCC GACGGGTTCC TTCGGACGTA
                                  gp100(M)
        ~~~~~~~~~~~~~~~~~~~~~~~~~~~~~~~~~~~~~~~~~~~~~~~~~~~
7151    GGAGATCTCA TCGCCAGGGT GCCAGCCCCC TGCCCAGCGG CTGTGCCAGC
        CCTCTAGAGT AGCGGTCCCA CGGTCGGGGG ACGGGTCGCC GACACGGTCG
                                  gp100(M)
        ~~~~~~~~~~~~~~~~~~~~~~~~~~~~~~~~~~~~~~~~~~~~~~~~~~~
7201    CTGTGCTACC CAGCCCAGCC TGCCAGCTGG TTCTGCACCA GATACTGAAG
        GACACGATGG GTCGGGTCGG ACGGTCGACC AAGACGTGGT CTATGACTTC
                                  gp100(M)
        ~~~~~~~~~~~~~~~~~~~~~~~~~~~~~~~~~~~~~~~~~~~~~~~~~~~
7251    GGTGGCTCGG GGACATACTG CCTCAATGTG TCTCTGGCTG ATACCAACAG
        CCACCGAGCC CCTGTATGAC GGAGTTACAC AGAGACCGAC TATGGTTGTC
                                  gp100(M)
        ~~~~~~~~~~~~~~~~~~~~~~~~~~~~~~~~~~~~~~~~~~~~~~~~~~~
7301    CCTGGCAGTG GTCAGCACCC AGCTTATCAT GCCTGGTCAA GAAGCAGGCC
        GGACCGTCAC CAGTCGTGGG TCGAATAGTA CGGACCAGTT CTTCGTCCGG
                                  gp100(M)
        ~~~~~~~~~~~~~~~~~~~~~~~~~~~~~~~~~~~~~~~~~~~~~~~~~~~
7351    TTGGGCAGGT TCCGCTGATC GTGGGCATCT TGCTGGTGTT GATGGCTGTG
        AACCCGTCCA AGGCGACTAG CACCCGTAGA ACGACCACAA CTACCGACAC
                                  gp100(M)
        ~~~~~~~~~~~~~~~~~~~~~~~~~~~~~~~~~~~~~~~~~~~~~~~~~~~
7401    GTCCTTGCAT CTCTGATATA TAGGCGCAGA CTTATGAAGC AAGACTTCTC
        CAGGAACGTA GAGACTATAT ATCCGCGTCT GAATACTTCG TTCTGAAGAG
                                  gp100(M)
        ~~~~~~~~~~~~~~~~~~~~~~~~~~~~~~~~~~~~~~~~~~~~~~~~~~~
7451    CGTACCCCAG TTGCCACATA GCAGCAGTCA CTGGCTGCGT CTACCCCGCA
        GCATGGGGTC AACGGTGTAT CGTCGTCAGT GACCGACGCA GATGGGGCGT
                                  gp100(M)
        ~~~~~~~~~~~~~~~~~~~~~~~~~~~~~~~~~~~~~~~~~~~~~~~~~~~
7501    TCTTCTGCTC TTGTCCCATT GGTGAGAACA GCCCCCTCCT CAGTGGGCAG
        AGAAGACGAG AACAGGGTAA CCACTCTTGT CGGGGGAGGA GTCACCCGTC
        gp100(M)                                42K promoter
        ~~~~~~~~~                     ~~~~~~~~~~~~~~~~~~~~~~~
7551    CAGGTCTGAT TTTTATTCTA GTTCAAAAAA ATATAAATGA TTCACCATCT
        GTCCAGACTA AAAATAAGAT CAAGTTTTTT TATATTTACT AAGTGGTAGA
```

FIGURE 5L
42K promoter

```
       42K promoter
      ~~~~~~~~~~~~~~~~~~~~~~~~~~~~~~~~~~~~~~~~~~~~~~~~~~~~~~~~
7601  GATAGAAAAA AAATTTATTG GGAGAATATG ATAATATTTT GGGATTTCAA
      CTATCTTTTT TTTAAATAAC CCTCTTATAC TATTATAAAA CCCTAAAGTT
             42K promoter                              Mart-1
      ~~~~~~~~~~~~~~~~~~~~~~~~~~~~~~                ~~~~~~~~~~~
7651  AATTGAAAAT ATATAATTAC AATATAAATC TAGACCACCA TGCCAAGAGA
      TTAACTTTTA TATATTAATG TTATATTTAG ATCTGGTGGT ACGGTTCTCT
                              Mart-1
      ~~~~~~~~~~~~~~~~~~~~~~~~~~~~~~~~~~~~~~~~~~~~~~~~~~~~~~~~
7701  AGATGCTCAC TTCATCTATG GTTACCCCAA GAAGGGGCAC GGCCACTCTT
      TCTACGAGTG AAGTAGATAC CAATGGGGTT CTTCCCCGTG CCGGTGAGAA
                              Mart-1
      ~~~~~~~~~~~~~~~~~~~~~~~~~~~~~~~~~~~~~~~~~~~~~~~~~~~~~~~~
7751  ACACCACGGC TGAAGAGGCC GCTGGGATCG GCATCCTGAC AGTGATCCTG
      TGTGGTGCCG ACTTCTCCGG CGACCCTAGC CGTAGGACTG TCACTAGGAC
                              Mart-1
      ~~~~~~~~~~~~~~~~~~~~~~~~~~~~~~~~~~~~~~~~~~~~~~~~~~~~~~~~
7801  GGAGTCTTAC TGCTCATCGG CTGTTGGTAT TGTAGAAGAC GAAATGGATA
      CCTCAGAATG ACGAGTAGCC GACAACCATA ACATCTTCTG CTTTACCTAT
                              Mart-1
      ~~~~~~~~~~~~~~~~~~~~~~~~~~~~~~~~~~~~~~~~~~~~~~~~~~~~~~~~
7851  CAGAGCCTTG ATGGATAAAA GTCTTCATGT TGGCACTCAA TGTGCCTTAA
      GTCTCGGAAC TACCTATTTT CAGAAGTACA ACCGTGAGTT ACACGGAATT
                              Mart-1
      ~~~~~~~~~~~~~~~~~~~~~~~~~~~~~~~~~~~~~~~~~~~~~~~~~~~~~~~~
7901  CAAGAAGATG CCCACAAGAA GGGTTTGATC ATCGGGACAG CAAAGTGTCT
      GTTCTTCTAC GGGTGTTCTT CCCAAACTAG TAGCCCTGTC GTTTCACAGA
                              Mart-1
      ~~~~~~~~~~~~~~~~~~~~~~~~~~~~~~~~~~~~~~~~~~~~~~~~~~~~~~~~
7951  CTTCAAGAGA AAAACTGTGA ACCTGTGGTT CCCAATGCTC CACCTGCTTA
      GAAGTTCTCT TTTTGACACT TGGACACCAA GGGTTACGAG GTGGACGAAT
                              Mart-1
      ~~~~~~~~~~~~~~~~~~~~~~~~~~~~~~~~~~~~~~~~~~~~~~~~~~~~~~~~
8001  TGAGAAACTC TCTGCAGAAC AGTCACCACC ACCTTATTCA CCTTAATCTA
      ACTCTTTGAG AGACGTCTTG TCAGTGGTGG TGGAATAAGT GGAATTAGAT
                                              sE/L Promoter
                                           ~~~~~~~~~~~~~~~~~~~~
8051  GAGTCGACCT GCAGGCATGC AAAAATTGAA ATTTTATTTT TTTTTTTTGG
      CTCAGCTGGA CGTCCGTACG TTTTTAACTT TAAATAAAA AAAAAAACC
      sE/L Promoter
      ~~~~~~~~~~~
                       Mage 1-3 minigene
                    ~~~~~~~~~~~~~~~~~~~~~~~~~~~~~~~~~~~~~~~~~~~
8101  AATATAAATA ATGGAGTCCT TGCAGCTGGT CTTTGGCATT GACGTGAAGG
      TTATATTTAT TACCTCAGGA ACGTCGACCA GAAACCGTAA CTGCACTTCC
                       Mage 1-3 minigene
      ~~~~~~~~~~~~~~~~~~~~~~~~~~~~~~~~~~~~~~~~~~~~~~~~~~~~~~~~
8151  AAGCAGACCC CACCGGCCAC TCCTATGTCC TTGTCACCTG CCTAGGTCTC
      TTCGTCTGGG GTGGCCGGTG AGGATACAGG AACAGTGGAC GGATCCAGAG
                       Mage 1-3 minigene
      ~~~~~~~~~~~~~~~~~~~~~~~~~~~~~~~~~~~~~~~~~~~~~~~~~~~~~~~~
8201  TCCTATGATG GCAATAAGCG TAAAGAAGTG GACCCCATCG GCCACTTGTA
      AGGATACTAC CGTTATTCGC ATTTCTTCAC CTGGGGTAGC CGGTGAACAT
```

FIGURE 5M

```
                Mage 1-3 minigene                              C5 Left Arm
                ~~~~                                           ~~~~~~~
         8251   CTAGTTTTTA TCCCGGGTTT TTATGACTAG TTAATCACGG CCGCTTATAA
                GATCAAAAAT AGGGCCCAAA AATACTGATC AATTAGTGCC GGCGAATATT
                                    C5 Left Arm
                ~~~~~~~~~~~~~~~~~~~~~~~~~~~~~~~~~~~~~~~~~~~~~~~~~~~~
         8301   AGATCTAAAA TGCATAATTT CTAAATAATG AAAAAAAAGT ACATCATGAG
                TCTAGATTTT ACGTATTAAA GATTATTAC TTTTTTTTCA TGTAGTACTC
                                    C5 Left Arm
                ~~~~~~~~~~~~~~~~~~~~~~~~~~~~~~~~~~~~~~~~~~~~~~~~~~~~
         8351   CAACGCGTTA GTATATTTTA CAATGGAGAT TAACGCTCTA TACCGTTCTA
                GTTGCGCAAT CATATAAAAT GTTACCTCTA ATTGCGAGAT ATGGCAAGAT
                                    C5 Left Arm
                ~~~~~~~~~~~~~~~~~~~~~~~~~~~~~~~~~~~~~~~~~~~~~~~~~~~~
         8401   TGTTTATTGA TTCAGATGAT GTTTTAGAAA AGAAAGTTAT TGAATATGAA
                ACAAATAACT AAGTCTACTA CAAAATCTTT TCTTTCAATA ACTTATACTT
                                    C5 Left Arm
                ~~~~~~~~~~~~~~~~~~~~~~~~~~~~~~~~~~~~~~~~~~~~~~~~~~~~
         8451   AACTTTAATG AAGATGAAGA TGACGACGAT GATTATTGTT GTAAATCTGT
                TTGAAATTAC TTCTACTTCT ACTGCTGCTA CTAATAACAA CATTTAGACA
                                    C5 Left Arm
                ~~~~~~~~~~~~~~~~~~~~~~~~~~~~~~~~~~~~~~~~~~~~~~~~~~~~
         8501   TTTAGATGAA GAAGATGACG CGCTAAAGTA TACTATGGTT ACAAAGTATA
                AAATCTACTT CTTCTACTGC GCGATTTCAT ATGATACCAA TGTTTCATAT
                                    C5 Left Arm
                ~~~~~~~~~~~~~~~~~~~~~~~~~~~~~~~~~~~~~~~~~~~~~~~~~~~~
         8551   AGTCTATACT ACTAATGGCG ACTTGTGCAA GAAGGTATAG TATAGTGAAA
                TCAGATATGA TGATTACCGC TGAACACGTT CTTCCATATC ATATCACTTT
                                    C5 Left Arm
                ~~~~~~~~~~~~~~~~~~~~~~~~~~~~~~~~~~~~~~~~~~~~~~~~~~~~
         8601   ATGTTGTTAG ATTATGATTA TGAAAAACCA AATAAATCAG ATCCATATCT
                TACAACAATC TAATACTAAT ACTTTTTGGT TTATTTAGTC TAGGTATAGA
                                    C5 Left Arm
                ~~~~~~~~~~~~~~~~~~~~~~~~~~~~~~~~~~~~~~~~~~~~~~~~~~~~
         8651   AAAGGTATCT CCTTTGCACA TAATTTCATC TATTCCTAGT TTAGAATACT
                TTTCCATAGA GGAAACGTGT ATTAAAGTAG ATAAGGATCA AATCTTATGA
                                    C5 Left Arm
                ~~~~~~~~~~~~~~~~~~~~~~~~~~~~~~~~~~~~~~~~~~~~~~~~~~~~
         8701   TTTCATTATA TTTGTTTACA GCTGAAGACG AAAAAAATAT ATCGATAATA
                AAAGTAATAT AAACAAATGT CGACTTCTGC TTTTTTTATA TAGCTATTAT
                                    C5 Left Arm
                ~~~~~~~~~~~~~~~~~~~~~~~~~~~~~~~~~~~~~~~~~~~~~~~~~~~~
         8751   GAAGATTATG TTAACTCTGC TAATAAGATG AAATTGAATG AGTCTGTGAC
                CTTCTAATAC AATTGAGACG ATTATTCTAC TTTAACTTAC TCAGACACTG
                C5 Left Arm
                ~~~~~~
         8801   TGCAGCCAAG CTTGGCACTG GCCGTCGTTT TACAACGTCG TGACTGGGAA
                ACGTCGGTTC GAACCGTGAC CGGCAGCAAA ATGTTGCAGC ACTGACCCTT
         8851   AACCCTGGCG TTACCCAACT TAATCGCCTT GCAGCACATC CCCCTTTCGC
                TTGGGACCGC AATGGGTTGA ATTAGCGGAA CGTCGTGTAG GGGGAAAGCG
         8901   CAGCTGGCGT AATAGCGAAG AGGCCCGCAC CGATCGCCCT TCCCAACAGT
                GTCGACCGCA TTATCGCTTC TCCGGGCGTG GCTAGCGGGA AGGGTTGTCA
         8951   TGCGCAGCCT GAATGGCGAA TGGCGCCTGA TGCGGTATTT TCTCCTTACG
                ACGCGTCGGA CTTACCGCTT ACCGCGGACT ACGCCATAAA AGAGGAATGC
         9001   CATCTGTGCG GTATTTCACA CCGCATATGG TGCACTCTCA GTACAATCTG
                GTAGACACGC CATAAAGTGT GGCGTATACC ACGTGAGAGT CATGTTAGAC
```

FIGURE 5N

```
9051   CTCTGATGCC GCATAGTTAA GCCAGCCCCG ACACCCGCCA ACACCCGCTG
       GAGACTACGG CGTATCAATT CGGTCGGGGC TGTGGGCGGT TGTGGGCGAC
9101   ACGCGCCCTG ACGGGCTTGT CTGCTCCCGG CATCCGCTTA CAGACAAGCT
       TGCGCGGGAC TGCCCGAACA GACGAGGGCC GTAGGCGAAT GTCTGTTCGA
9151   GTGACCGTCT CCGGGAGCTG CATGTGTCAG AGGTTTTCAC CGTCATCACC
       CACTGGCAGA GGCCCTCGAC GTACACAGTC TCCAAAAGTG GCAGTAGTGG
9201   GAAACGCGCG AGACGAAAGG GCCTCGTGAT ACGCCTATTT TTATAGGTTA
       CTTTGCGCGC TCTGCTTTCC CGGAGCACTA TGCGGATAAA AATATCCAAT
9251   ATGTCATGAT AATAATGGTT TCTTAGACGT CAGGTGGCAC TTTTCGGGGA
       TACAGTACTA TTATTACCAA AGAATCTGCA GTCCACCGTG AAAAGCCCCT
9301   AATGTGCGCG GAACCCCTAT TTGTTTATTT TTCTAAATAC ATTCAAATAT
       TTACACGCGC CTTGGGGATA AACAAATAAA AAGATTTATG TAAGTTTATA
9351   GTATCCGCTC ATGAGACAAT AACCCTGATA AATGCTTCAA TAATATTGAA
       CATAGGCGAG TACTCTGTTA TTGGGACTAT TTACGAAGTT ATTATAACTT
                                    Amp(R)
       ~~~~~~~~~~~~~~~~~~~~~~~~~~~~~~~~~~~~~~~~~~~~~~~~~~
9401   AAAGGAAGAG TATGAGTATT CAACATTTCC GTGTCGCCCT TATTCCCTTT
       TTTCCTTCTC ATACTCATAA GTTGTAAAGG CACAGCGGGA ATAAGGGAAA
                                    Amp(R)
       ~~~~~~~~~~~~~~~~~~~~~~~~~~~~~~~~~~~~~~~~~~~~~~~~~~
9451   TTTGCGGCAT TTTGCCTTCC TGTTTTTGCT CACCCAGAAA CGCTGGTGAA
       AAACGCCGTA AAACGGAAGG ACAAAAACGA GTGGGTCTTT GCGACCACTT
                                    Amp(R)
       ~~~~~~~~~~~~~~~~~~~~~~~~~~~~~~~~~~~~~~~~~~~~~~~~~~
9501   AGTAAAAGAT GCTGAAGATC AGTTGGGTGC ACGAGTGGGT TACATCGAAC
       TCATTTTCTA CGACTTCTAG TCAACCCACG TGCTCACCCA ATGTAGCTTG
                                    Amp(R)
       ~~~~~~~~~~~~~~~~~~~~~~~~~~~~~~~~~~~~~~~~~~~~~~~~~~
9551   TGGATCTCAA CAGCGGTAAG ATCCTTGAGA GTTTTCGCCC CGAAGAACGT
       ACCTAGAGTT GTCGCCATTC TAGGAACTCT CAAAAGCGGG GCTTCTTGCA
                                    Amp(R)
       ~~~~~~~~~~~~~~~~~~~~~~~~~~~~~~~~~~~~~~~~~~~~~~~~~~
9601   TTTCCAATGA TGAGCACTTT TAAAGTTCTG CTATGTGGCG CGGTATTATC
       AAAGGTTACT ACTCGTGAAA ATTTCAAGAC GATACACCGC GCCATAATAG
                                    Amp(R)
       ~~~~~~~~~~~~~~~~~~~~~~~~~~~~~~~~~~~~~~~~~~~~~~~~~~
9651   CCGTATTGAC GCCGGGCAAG AGCAACTCGG TCGCCGCATA CACTATTCTC
       GGCATAACTG CGGCCCGTTC TCGTTGAGCC AGCGGCGTAT GTGATAAGAG
                                    Amp(R)
       ~~~~~~~~~~~~~~~~~~~~~~~~~~~~~~~~~~~~~~~~~~~~~~~~~~
9701   AGAATGACTT GGTTGAGTAC TCACCAGTCA CAGAAAAGCA TCTTACGGAT
       TCTTACTGAA CCAACTCATG AGTGGTCAGT GTCTTTTCGT AGAATGCCTA
                                    Amp(R)
       ~~~~~~~~~~~~~~~~~~~~~~~~~~~~~~~~~~~~~~~~~~~~~~~~~~
9751   GGCATGACAG TAAGAGAATT ATGCAGTGCT GCCATAACCA TGAGTGATAA
       CCGTACTGTC ATTCTCTTAA TACGTCACGA CGGTATTGGT ACTCACTATT
                                    Amp(R)
       ~~~~~~~~~~~~~~~~~~~~~~~~~~~~~~~~~~~~~~~~~~~~~~~~~~
9801   CACTGCGGCC AACTTACTTC TGACAACGAT CGGAGGACCG AAGGAGCTAA
       GTGACGCCGG TTGAATGAAG ACTGTTGCTA GCCTCCTGGC TTCCTCGATT
                                    Amp(R)
       ~~~~~~~~~~~~~~~~~~~~~~~~~~~~~~~~~~~~~~~~~~~~~~~~~~
9851   CCGCTTTTTT GCACAACATG GGGGATCATG TAACTCGCCT TGATCGTTGG
       GGCGAAAAAA CGTGTTGTAC CCCCTAGTAC ATTGAGCGGA ACTAGCAACC
```

FIGURE 50

```
             Amp(R)
       ~~~~~~~~~~~~~~~~~~~~~~~~~~~~~~~~~~~~~~~~~~~~~~~~~~
 9901  GAACCGGAGC TGAATGAAGC CATACCAAAC GACGAGCGTG ACACCACGAT
       CTTGGCCTCG ACTTACTTCG GTATGGTTTG CTGCTCGCAC TGTGGTGCTA
             Amp(R)
       ~~~~~~~~~~~~~~~~~~~~~~~~~~~~~~~~~~~~~~~~~~~~~~~~~~
 9951  GCCTGTAGCA ATGGCAACAA CGTTGCGCAA ACTATTAACT GGCGAACTAC
       CGGACATCGT TACCGTTGTT GCAACGCGTT TGATAATTGA CCGCTTGATG
             Amp(R)
       ~~~~~~~~~~~~~~~~~~~~~~~~~~~~~~~~~~~~~~~~~~~~~~~~~~
10001  TTACTCTAGC TTCCCGGCAA CAATTAATAG ACTGGATGGA GGCGGATAAA
       AATGAGATCG AAGGGCCGTT GTTAATTATC TGACCTACCT CCGCCTATTT
             Amp(R)
       ~~~~~~~~~~~~~~~~~~~~~~~~~~~~~~~~~~~~~~~~~~~~~~~~~~
10051  GTTGCAGGAC CACTTCTGCG CTCGGCCCTT CCGGCTGGCT GGTTTATTGC
       CAACGTCCTG GTGAAGACGC GAGCCGGGAA GGCCGACCGA CCAAATAACG
             Amp(R)
       ~~~~~~~~~~~~~~~~~~~~~~~~~~~~~~~~~~~~~~~~~~~~~~~~~~
10101  TGATAAATCT GGAGCCGGTG AGCGTGGGTC TCGCGGTATC ATTGCAGCAC
       ACTATTTAGA CCTCGGCCAC TCGCACCCAG AGCGCCATAG TAACGTCGTG
             Amp(R)
       ~~~~~~~~~~~~~~~~~~~~~~~~~~~~~~~~~~~~~~~~~~~~~~~~~~
10151  TGGGGCCAGA TGGTAAGCCC TCCCGTATCG TAGTTATCTA CACGACGGGG
       ACCCCGGTCT ACCATTCGGG AGGGCATAGC ATCAATAGAT GTGCTGCCCC
             Amp(R)
       ~~~~~~~~~~~~~~~~~~~~~~~~~~~~~~~~~~~~~~~~~~~~~~~~~~
10201  AGTCAGGCAA CTATGGATGA ACGAAATAGA CAGATCGCTG AGATAGGTGC
       TCAGTCCGTT GATACCTACT TGCTTTATCT GTCTAGCGAC TCTATCCACG
             Amp(R)
       ~~~~~~~~~~~~~~~~~~~~~~~
10251  CTCACTGATT AAGCATTGGT AACTGTCAGA CCAAGTTTAC TCATATATAC
       GAGTGACTAA TTCGTAACCA TTGACAGTCT GGTTCAAATG AGTATATATG
10301  TTTAGATTGA TTTAAAACTT CATTTTTAAT TTAAAAGGAT CTAGGTGAAG
       AAATCTAACT AAATTTTGAA GTAAAAATTA AATTTTCCTA GATCCACTTC
10351  ATCCTTTTTG ATAATCTCAT GACCAAAATC CCTTAACGTG AGTTTTCGTT
       TAGGAAAAAC TATTAGAGTA CTGGTTTTAG GGAATTGCAC TCAAAAGCAA
10401  CCACTGAGCG TCAGACCCCG TAGAAAAGAT CAAAGGATCT TCTTGAGATC
       GGTGACTCGC AGTCTGGGGC ATCTTTTCTA GTTTCCTAGA AGAACTCTAG
10451  CTTTTTTTCT GCGCGTAATC TGCTGCTTGC AAACAAAAAA ACCACCGCTA
       GAAAAAAAGA CGCGCATTAG ACGACGAACG TTTGTTTTTT TGGTGGCGAT
10501  CCAGCGGTGG TTTGTTTGCC GGATCAAGAG CTACCAACTC TTTTTCCGAA
       GGTCGCCACC AAACAAACGG CCTAGTTCTC GATGGTTGAG AAAAAGGCTT
10551  GGTAACTGGC TTCAGCAGAG CGCAGATACC AAATACTGTC CTTCTAGTGT
       CCATTGACCG AAGTCGTCTC GCGTCTATGG TTTATGACAG GAAGATCACA
10601  AGCCGTAGTT AGGCCACCAC TTCAAGAACT CTGTAGCACC GCCTACATAC
       TCGGCATCAA TCCGGTGGTG AAGTTCTTGA GACATCGTGG CGGATGTATG
10651  CTCGCTCTGC TAATCCTGTT ACCAGTGGCT GCTGCCAGTG GCGATAAGTC
       GAGCGAGACG ATTAGGACAA TGGTCACCGA CGACGGTCAC CGCTATTCAG
10701  GTGTCTTACC GGGTTGGACT CAAGACGATA GTTACCGGAT AAGGCGCAGC
       CACAGAATGG CCCAACCTGA GTTCTGCTAT CAATGGCCTA TTCCGCGTCG
10751  GGTCGGGCTG AACGGGGGGT TCGTGCACAC AGCCCAGCTT GGAGCGAACG
       CCAGCCCGAC TTGCCCCCCA AGCACGTGTG TCGGGTCGAA CCTCGCTTGC
10801  ACCTACACCG AACTGAGATA CCTACAGCGT GAGCTATGAG AAAGCGCCAC
       TGGATGTGGC TTGACTCTAT GGATGTCGCA CTCGATACTC TTTCGCGGTG
10851  GCTTCCCGAA GGGAGAAAGG CGGACAGGTA TCCGGTAAGC GGCAGGGTCG
       CGAAGGGCTT CCCTCTTTCC GCCTGTCCAT AGGCCATTCG CCGTCCCAGC
```

FIGURE 5P

```
10901   GAACAGGAGA GCGCACGAGG GAGCTTCCAG GGGGAAACGC CTGGTATCTT
        CTTGTCCTCT CGCGTGCTCC CTCGAAGGTC CCCCTTTGCG GACCATAGAA
10951   TATAGTCCTG TCGGGTTTCG CCACCTCTGA CTTGAGCGTC GATTTTGTG
        ATATCAGGAC AGCCCAAAGC GGTGGAGACT GAACTCGCAG CTAAAAACAC
11001   ATGCTCGTCA GGGGGGCGGA GCCTATGGAA AAACGCCAGC AACGCGGCCT
        TACGAGCAGT CCCCCCGCCT CGGATACCTT TTTGCGGTCG TTGCGCCGGA
11051   TTTTACGGTT CCTGGCCTTT TGCTGGCCTT TTGCTCACAT GTTCTTTCCT
        AAAATGCCAA GGACCGGAAA ACGACCGGAA AACGAGTGTA CAAGAAAGGA
11101   GCGTTATCCC CTGATTCTGT GGATAACCGT ATTACCGCCT TTGAGTGAGC
        CGCAATAGGG GACTAAGACA CCTATTGGCA TAATGGCGGA AACTCACTCG
11151   TGATACCGCT CGCCGCAGCC GAACGACCGA GCGCAGCGAG TCAGTGAGCG
        ACTATGGCGA GCGGCGTCGG CTTGCTGGCT CGCGTCGCTC AGTCACTCGC
11201   AGGAAGCGGA AGAGCGCCCA ATACGCAAAC CGCCTCTCCC CGCGCGTTGG
        TCCTTCGCCT TCTCGCGGGT TATGCGTTTG GCGGAGAGGG GCGCGCAACC
11251   CCGATTCATT AATGCAGCTG GCACGACAGG TTTCCCGACT GGAAAGCGGG
        GGCTAAGTAA TTACGTCGAC CGTGCTGTCC AAAGGGCTGA CCTTTCGCCC
11301   CAGTGAGCGC AACGCAATTA ATGTGAGTTA GCTCACTCAT TAGGCACCCC
        GTCACTCGCG TTGCGTTAAT TACACTCAAT CGAGTGAGTA ATCCGTGGGG
11351   AGGCTTTACA CTTTATGCTT CCGGCTCGTA TGTTGTGTGG AATTGTGAGC
        TCCGAAATGT GAAATACGAA GGCCGAGCAT ACAACACACC TTAACACTCG
11401   GGATAACAAT TCACACAGG  AAACAGCTAT GACCATGATT ACGAATTGAA
        CCTATTGTTA AAGTGTGTCC TTTGTCGATA CTGGTACTAA TGCTTAACTT
11451   TTGCGGCCGC AATTC
        AACGCCGGCG TTAAG
```

FIGURE 6A

NY-ESO-1

Met Gln Ala Glu Gly Arg Gly Thr Gly Gly Ser Thr Gly Asp Ala Asp
Gly Pro Gly Gly Pro Gly Ile Pro Asp Gly Pro Gly Gly Asn Ala Gly
Gly Pro Gly Glu Ala Gly Ala Thr Gly Gly Arg Gly Pro Arg Gly Ala
Gly Ala Ala Arg Ala Ser Gly Pro Gly Gly Gly Ala Pro Arg Gly Pro
His Gly Gly Ala Ala Ser Gly Leu Asn Gly Cys Cys Arg Cys Gly Ala
Arg Gly Pro Glu Ser Arg Leu Leu Glu Phe Tyr Leu Ala Met Pro Phe
Ala Thr Pro Met Glu Ala Glu Leu Ala Arg Arg Ser Leu Ala Gln Asp
Ala Pro Pro Leu Pro Val Pro Gly Val Leu Leu Lys Glu Phe Thr Val
Ser Gly Asn Ile Leu Thr Ile Arg Leu Thr Ala Ala Asp His Arg Gln
Leu Gln Leu Ser Ile Ser Ser Cys Leu Gln Gln Leu Ser Leu Leu Met
Trp Ile Thr Gln Cys Phe Leu Pro Val Phe Leu Ala Gln Pro Pro Ser
Gly Gln Arg Arg

FIGURE 6B

TRP-2

Met Ser Pro Leu Trp Trp Gly Phe Leu Leu Ser Cys Leu Gly Cys Lys Ile
Leu Pro Gly Ala Gln Gly Gln Phe Pro Arg Val Cys Met Thr Val Asp Ser
Leu Val Asn Lys Glu Cys Cys Pro Arg Leu Gly Ala Glu Ser Ala Asn Val
Cys Gly Ser Gln Gln Gly Arg Gly Gln Cys Thr Glu Val Arg Ala Asp Thr
Arg Pro Trp Ser Gly Pro Tyr Ile Leu Arg Asn Gln Asp Asp Arg Glu Leu
Trp Pro Arg Lys Phe Phe His Arg Thr Cys Lys Cys Thr Gly Asn Phe Ala
Gly Tyr Asn Cys Gly Asp Cys Lys Phe Gly Trp Thr Gly Pro Asn Cys Glu
Arg Lys Lys Pro Pro Val Ile Arg Gln Asn Ile His Ser Leu Ser Pro Gln
Glu Arg Glu Gln Phe Leu Gly Ala Leu Asp Leu Ala Lys Lys Arg Val His
Pro Asp Tyr Val Ile Thr Thr Gln His Trp Leu Gly Leu Leu Gly Pro Asn
Gly Thr Gln Pro Gln Phe Ala Asn Cys Ser Val Tyr Asp Phe Phe Val Trp
Leu His Tyr Tyr Ser Val Arg Asp Thr Leu Leu Gly Pro Gly Arg Pro Tyr
Arg Ala Ile Asp Phe Ser His Gln Gly Pro Ala Phe Val Thr Trp His Arg
Tyr His Leu Leu Cys Leu Glu Arg Asp Leu Gln Arg Leu Ile Gly Asn Glu
Ser Phe Ala Leu Pro Tyr Trp Asn Phe Ala Thr Gly Arg Asn Glu Cys Asp
Val Cys Thr Asp Gln Leu Phe Gly Ala Ala Arg Pro Asp Asp Pro Thr Leu
Ile Ser Arg Asn Ser Arg Phe Ser Ser Trp Glu Thr Val Cys Asp Ser Leu
Asp Asp Tyr Asn His Leu Val Thr Leu Cys Asn Gly Thr Tyr Glu Gly Leu
Leu Arg Arg Asn Gln Met Gly Arg Asn Ser Met Lys Leu Pro Thr Leu Lys
Asp Ile Arg Asp Cys Leu Ser Leu Gln Lys Phe Asp Asn Pro Pro Phe Phe
Gln Asn Ser Thr Phe Ser Phe Arg Asn Ala Leu Glu Gly Phe Asp Lys Ala
Asp Gly Thr Leu Asp Ser Gln Val Met Ser Leu His Asn Leu Val His Ser
Phe Leu Asn Gly Thr Asn Ala Leu Pro His Ser Ala Ala Asn Asp Pro Ile
Phe Val Val Leu His Ser Phe Thr Asp Ala Ile Phe Asp Glu Trp Met Lys
Arg Phe Asn Pro Pro Ala Asp Ala Trp Pro Gln Glu Leu Ala Pro Ile Gly
His Asn Arg Met Tyr Asn Met Val Pro Phe Phe Pro Pro Val Thr Asn Glu
Glu Leu Phe Leu Thr Ser Asp Gln Leu Gly Tyr Ser Tyr Ala Ile Asp Leu
Pro Val Ser Val Glu Glu Thr Pro Gly Trp Pro Thr Thr Leu Leu Val Val
Met Gly Thr Leu Val Ala Leu Val Gly Leu Phe Val Leu Leu Ala Phe Leu
Gln Tyr Arg Arg Leu Arg Lys Gly Tyr Thr Pro Leu Met Glu Thr His Leu
Ser Ser Lys Arg Tyr Thr Glu Glu Ala

FIGURE 6C gp100 and gp100M

```
1         MDL VLKRCLLHLA VIGALLAVGA TKVPRNQDWL GVSRQLRTKA WNRQLYPEWT
2         *** ********** ********** ********** ********** **********

1 EAQRLDCWRG GQVSLKVSND GPTLIGANAS FSIALNFPGS QKVLPDGQVI WVNNTIINGS
2 ********** ********** ********** ********** ********** **********

1 QVWGGQPVYP QETDDACIFP DGGPCPSGSW SQKRSFVYVW KTWGQYWQFL GGPVSGLSIG
2 ********** ********** ********** ********** ********V* **********

1 TGRAMLGTHT MEVTVYHRRG SRSYVPLAHS SSAFTITDQV PFSVSVSQLR ALDGGNKHFL
2 ********** ********** ********** ******M*** ********** **********

1 RNQPLTFALQ LHDPSGYLAE ADLSYTWDFG DSSGTLISRA LVVTHTYLEP GPVTAQVVLQ
2 ********** ********** ********** ********** ********** ****V*****

1 AAIPLTSCGS SPVPGTTDGH RPTAEAPNTT AGQVPTTEVV GTTPGQAPTA EPSGTTSVQV
2 ********** ********** ********** ********** ********** **********

1 PTTEVISTAP VQMPTAESTG MTPEKVPVSE VMGTTLAEMS TPEATGMTPA EVSIVVLSGT
2 ********** ********** ********** ********** ********** **********

1 TAAQVTTTEW VETTARELPI PEPEGPDASS IMSTESITGS LGPLLDGTAT LRLVKRQVPL
2 ********** ********** ********** ********** ********** **********

1 DCVLYRYGSF SVTLDIVQGI ESAEILQAVP SGEGDAFELT VSCQGGLPKE ACMEISSPGC
2 ********** ********** ********** ********** ********** **********

1 QPPAQRLCQP VLPSPACQLV LHQILKGGSG TYCLNVSLAD TNSLAVVSTQ LIMPGQEAGL
2 ********** ********** ********** ********** ********** **********

1 GQVPLIVGIL LVLMAVVLAS LIYRRRLMKQ DFSVPQLPHS SSHWLRLPRI FCSCPIGENS
2 ********** ********** ********** ********** ********** **********

1 PLLSGQQV
2 ********
```

Key
*=identical amino acid residue
1=gp100
2=gp100M

FIGURE 6D

MART-1

```
Met Pro Arg Glu Asp Ala His Phe Ile Tyr Gly Tyr Pro
Lys Lys Gly His Gly His Ser Tyr Thr Thr Ala Glu Glu
Ala Ala Gly Ile Gly Ile Leu Thr Val Ile Leu Gly Val
Leu Leu Leu Ile Gly Cys Trp Tyr Cys Arg Arg Arg Asn
Gly Tyr Arg Ala Leu Met Asp Lys Ser Leu His Val Gly
Thr Gln Cys Ala Leu Thr Arg Arg Cys Pro Gln Glu Gly
Phe Asp His Arg Asp Ser Lys Val Ser Leu Gln Glu Lys
Asn Cys Glu Pro Val Val Pro Asn Ala Pro Pro Ala Tyr
Glu Lys Leu Ser Ala Glu Gln Ser Pro Pro Pro Tyr Ser
Pro
```

FIGURE 6E

MAGE-1

Met Ser Asp Asn Lys Lys Pro Asp Lys Ala His Ser Gly Ser Gly Gly
Asp Gly Asp Gly Asn Arg Cys Asn Leu Leu His Arg Tyr Ser Leu Glu
Glu Ile Leu Pro Tyr Leu Gly Trp Leu Val Phe Ala Val Val Thr Thr
Ser Phe Leu Ala Leu Gln Met Phe Ile Asp Ala Leu Tyr Glu Glu Gln
Tyr Glu Arg Asp Val Ala Trp Ile Ala Arg Gln Ser Lys Arg Met Ser
Ser Val Asp Glu Asp Glu Asp Asp Glu Asp Asp Glu Asp Asp Tyr Tyr
Asp Asp Glu Asp Asp Asp Asp Ala Phe Tyr Asp Asp Glu Asp Asp
Glu Glu Glu Glu Leu Glu Asn Leu Met Asp Asp Glu Ser Glu Asp Glu
Ala Glu Glu Glu Met Ser Val Glu Met Gly Ala Gly Ala Glu Glu Met
Gly Ala Gly Ala Asn Cys Ala Cys Val Pro Gly His His Leu Arg Lys
Asn Glu Val Lys Cys Arg Met Ile Tyr Phe Phe His Asp Pro Asn Phe
Leu Val Ser Ile Pro Val Asn Pro Lys Glu Gln Met Glu Cys Arg Cys
Glu Asn Ala Asp Glu Glu Val Ala Met Glu Glu Glu Glu Glu Glu Glu
Glu Glu Glu Glu Glu Glu Glu Met Gly Asn Pro Asp Gly Phe Ser Pro

FIGURE 6F

MAGE-3

```
mpleqrsqhc kpeeglearg ealglvgaqa pateeqeaas ssstlvevtl gevpaaespd
ppqspqgass lpttmnyplw sqsyedssnq eeegpstfpd lesefqaals rkvaelvhfl
llkyrarepv tkaemlgsvv gnwqyffpvi fskassslql vfgielmevd pighlyifat
clglsydgll gdnqimpkag lliivlaiia regdcapeek iweelsvlev fegredsilg
dpkklltqhf vqenyleyrq vpgsdpacye flwgpralve tsyvkvlhhm vkisggphis
ypplhewvlr egee
```

FIGURE 6G
B7.1 mghtrrqgts pskcpylnff qllvlaglsh fcsgvihvtk evkevatlsc ghnvsveela
qtriywqkek kmvltmmsgd mniwpeyknr tifditnnls ivilalrpsd egtyecvvlk
yekdafkreh laevtlsvka dfptpsisdf eiptsnirri icstsggfpe phlswlenge
elnainttvs qdpetelyav sskldfnmtt nhsfmcliky ghlrvnqtfn wnttkqehfp
dnllpswait lisvngifvi ccltycfapr crerrrnerl rresvrpv

FIGURE 6H
LFA-3 mvagsdagra lgvlsvvcll hcfgfiscfs qqiygvvygn vtfhvpsnvp lkevlwkkqk
dkvaelense frafssfknr vyldtvsgsl tiynltssde deyemespni tdtmkfflyv
leslpsptlt caltngsiev qcmipehyns hrglimyswd cpmeqckrns tsiyfkmend
lpqkiqctls nplfnttssi ilttcipssg hsrhryalip iplavittci vlymngilkc
drkpdrtnsn

FIGURE 6I
ICAM-1* mapssprpal pallvllgal fpgpgnaqts vspskvilpr ggsvlvtcst scdqpkllgi
etplpkkell lpgnnrkvye lsnvqedsqp mcysncpdgq staktfltvy wtpervelap
lpswqpvgkn ltlrcqvegg apranltvvl lrgekelkre pavgepaevt ttvlvrrdhh
ganfscrtel dlrpqglelf entsapyqlq tfvlpatppq lvsprvlevd tqgtvvcsld
glfpvseaqv hlalgdqrln ptvtygndsf sakasvsvta edegtqrltc avilgnqsqe
tlqtvtiysf papnviltkp evsegtevtv kceahprakv tlngvpaqpl gpraqlllka
tpedngrsfs csatlevagq lihknqtrel rvlygprlde rdcpgnwtwp ensqqtpmcq
awgnplpelk clkdgtfplp igesvtvtrd legtylcrar stqgevtrev tvnvlsprye
iviitvvaaa vimgtaglst ylynrqrkik kyrlqqaqkg tpmkpntqat pp

*mature sequence begins at residue 28 (q)

MULTI-ANTIGEN VECTORS OF MELANOMA

RELATED APPLICATIONS

This application claims priority to U.S. Ser. No. 60/500,572 filed Sep. 5, 2003 and U.S. Ser. No. 60/504,007 filed Sep. 18, 2003.

FIELD OF THE INVENTION

The present invention relates to multi-antigen vectors for use in preventing and/or treating cancer. In particular, the invention relates to multi-antigen vectors for use in treating and/or preventing melanoma.

BACKGROUND OF THE INVENTION

There has been tremendous increase in last few years in the development of cancer vaccines with tumour-associated antigens (TAAs) due to the great advances in identification of molecules based on the expression profiling on primary tumours and normal cells with the help of several techniques such as high density microarray, SEREX, immunohistochemistry (IHC), RT-PCR, in-situ hybridization (ISH) and laser capture microscopy (Rosenberg, Immunity, 1999; Sgroi et al, 1999, Schena et al, 1995, Offringa et al, 2000). The TAAs are antigens expressed or over-expressed by tumour cells and could be specific to one or several tumours for example CEA antigen is expressed in colorectal, breast and lung cancers. Sgroi et al (1999) identified several genes differentially expressed in invasive and metastatic carcinoma cells with combined use of laser capture microdissection and cDNA microarrays. Several delivery systems like DNA or viruses could be used for therapeutic vaccination against human cancers (Bonnet et al, 2000) and can elicit immune responses and also break immune tolerance against TAAs. Tumour cells can be rendered more immunogenic by inserting transgenes encoding T cell co-stimulatory molecules such as B7.1 or cytokines such as IFN-γ, IL2, or GM-CSF, among others. Co-expression of a TAA and a cytokine or a co-stimulatory molecule can develop effective therapeutic vaccine (Hodge et al, 95, Bronte et al, 1995, Chamberlain et al, 1996).

There is a need in the art for reagents and methodologies useful in stimulating an immune response to prevent or treat cancers. The present invention provides such reagents and methodologies that overcome many of the difficulties encountered by others in attempting to treat cancer.

SUMMARY OF THE INVENTION

The present invention provides multi-antigen vectors for administration to a patient to prevent and/or treat cancer. In particular, the multi-antigen vector encodes one or more tumor antigens ("TA"). The multi-antigen vector may also encode an immune stimulator such as a co-stimulatory molecule and/or be administered with an adjuvant.

BRIEF DESCRIPTION OF THE DRAWINGS

FIG. 2A-N. DNA sequence of plasmid pALVAC.Tricom (#33) (SEQ ID NOS. 1 and 2).

FIG. 3A-O. DNA sequence of plasmid pT1132 (SEQ ID NOS.: 3 and 4).

FIG. 3. DNA sequence of plasmid pT1132.

FIG. 5A-P. DNA sequence of plasmid pT3217 (SEQ ID NOS. 5 and 6).

FIG. 6. Amino acid sequences of exemplary NY-ESO-1 (SEO ID NO.: 7), TRP-2 (SEQ ID NO.: 8) gp100 (SEQ ID NO.: 9) gp100M (SEQ ID NO.: 10), MART-1 (SEO ID NO.: 11), MAGE-1 (SEO ID NO.: 12), MAGE-3 (SEQ ID NO.: 13), B7.1 (SEO ID NO.: 14), LFA-3 (SEQ, ID NO.: 15), and ICAM-1 (SEQ ID NO: 16) proteins.

DETAILED DESCRIPTION

Figure 1:
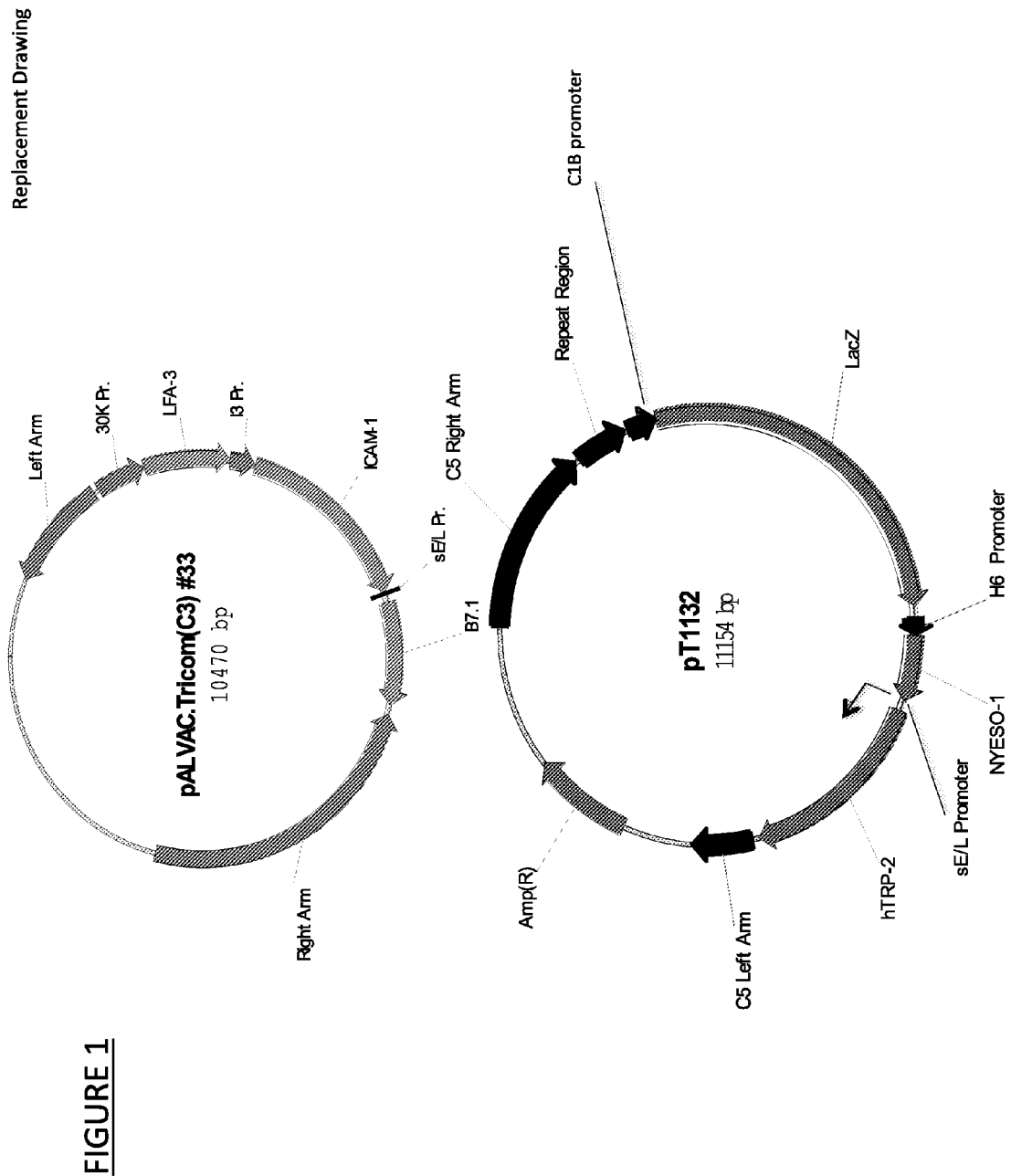

The present invention provides reagents and methodologies useful for treating and/or preventing cancer. All references cited within this application are incorporated by reference.

In one embodiment, the present invention relates to the induction or enhancement of an immune response against one or more tumor antigens ("TA") to prevent and/or treat cancer. In certain embodiments, one or more TAs may be combined. In preferred embodiments, the immune response results from expression of a TA in a host cell following administration of a nucleic acid vector encoding the tumor antigen or the tumor antigen itself in the form of a peptide or polypeptide, for example.

As used herein, an "antigen" is a molecule (such as a polypeptide) or a portion thereof that produces an immune response in a host to whom the antigen has been administered. The immune response may include the production of antibodies that bind to at least one epitope of the antigen and/or the generation of a cellular immune response against cells expressing an epitope of the antigen. The response may be an enhancement of a current immune response by, for example, causing increased antibody production, production of antibodies with increased affinity for the antigen, or an increase in the cellular immune response (i.e., increased number or activity of immunoreactive T cells). An antigen that produces an immune response may alternatively be referred to as being immunogenic or as an immunogen. In describing the present invention, a TA may be referred to as an "immunogenic target". The present invention provide expression vectors for expressing in a host one or more immunogenic targets.

The term TA includes both tumor-associated antigens (TAAs) and tumor-specific antigens (TSAs), where a cancerous cell is the source of the antigen. A TAA is an antigen that is expressed on the surface of a tumor cell in higher amounts than is observed on normal cells or an antigen that is expressed on normal cells during fetal development. A TSA is an antigen that is unique to tumor cells and is not expressed on normal cells. TA further includes TAAs or TSAs, antigenic fragments thereof, and modified versions that retain their antigenicity.

TAs are typically classified into five categories according to their expression pattern, function, or genetic origin: cancer-testis (CT) antigens (i.e., MAGE, NY-ESO-1); melanocyte differentiation antigens (i.e., Melan A/MART-1, tyrosinase, gp100); mutational antigens (i.e., MUM-1, p53, CDK-4); overexpressed 'self' antigens (i.e., HER-2/neu, p53); and, viral antigens (i.e., HPV, EBV). For the purposes of practicing the present invention, a suitable TA is any TA that induces or enhances an anti-tumor immune response in a host to whom the TA has been administered. Suitable TAs include, for example, species of gp100 (Cox et al., *Science*, 264:716-719 (1994); U.S. Pat. No. 6,500,919 B1 and WO 01/30847 with Val at residue 162, also referred to as "gp100M"; U.S. Pat. No. 6,537,560 B1 with Phe at residue 162), MART-1/MelanA (Kawakami et al., *J. Exp. Med.*, 180:347-352 (1994); U.S. Pat. No. 5,874,560), gp75 (TRP-1) (Wang et al., *J. Exp.*

Med., 186:1131-1140 (1996)), TRP-2 (Wang et al. 1996 J. Exp. Med. 184:2207; U.S. Pat. Nos. 5,831,016 and 6,083, 783), tyrosinase (Wolfel et al., *Eur. J. Immunol.*, 24:759-764 (1994); WO 200175117; WO 200175016; WO 200175007), NY-ESO-1 (WO 98/14464; WO 99/18206; GenBank Accession No. P78358; U.S. Pat. No. 5,804,381), melanoma proteoglycan (Hellstrom et al., *J. Immunol.*, 130:1467-1472 (1983)), MAGE family antigens (i.e., MAGE-1, 2, 3, 4, 6, 12, 51; Van der Bruggen et al., *Science*, 254:1643-1647 (1991); U.S. Pat. No. 6,235,525; CN 1319611), BAGE family antigens (Boel et al., *Immunity*, 2:167-175 (1995)), GAGE family antigens (i.e., GAGE-1,2; Van den Eynde et al., *J. Exp. Med.*, 182:689-698 (1995); U.S. Pat. No. 6,013,765), RAGE family antigens (i.e., RAGE-1; Gaugler et at., *Immunogenetics*, 44:323-330 (1996); U.S. Pat. No. 5,939,526), N-acetylglucosaminyltransferase-V (Guilloux et at., *J. Exp. Med.*, 183: 1173-1183 (1996)), p15 (Robbins et al., *J. Immunol.* 154: 5944-5950 (1995)), β-catenin (Robbins et al., *J. Exp. Med.*, 183:1185-1192 (1996)), MUM-1 (Coulie et al., *Proc. Natl. Acad. Sci. USA*, 92:7976-7980 (1995)), cyclin dependent kinase-4 (CDK4) (Wolfel et al., *Science*, 269:1281-1284 (1995)), p21-ras (Fossum et at., *Int. J. Cancer*, 56:40-45 (1994)), BCR-abl (Bocchia et al., *Blood*, 85:2680-2684 (1995)), p53 (Theobald et al., *Proc. Natl. Acad. Sci. USA*, 92:11993-11997 (1995)), p185 HER2/neu (erb-B1; Fisk et al., *J. Exp. Med.*, 181:2109-2117 (1995)), epidermal growth factor receptor (EGFR) (Harris et al., Breast Cancer Res. Treat, 29:1-2 (1994)), carcinoembryonic antigens (CEA) (Kwong et al., *J. Natl. Cancer Inst.* 85:982-990 (1995) U.S. Pat. Nos. 5,756,103; 5,274,087; 5,571,710; 6,071,716; 5,698, 530; 6,045,802; EP 263933; EP 346710; and, EP 784483); carcinoma-associated mutated mucins (i.e., MUC-1 gene products; Jerome et al., *J. Immunol.*, 151:1654-1662 (1993)); EBNA gene products of EBV (i.e., EBNA-1; Rickinson et al., *Cancer Surveys*, 13:53-80 (1992)); E7, E6 proteins of human papillomavirus (Ressing et al., *J. Immunol*, 154:5934-5943 (1995)); prostate specific antigen (PSA; Xue et al., *The Prostate*, 30:73-78 (1997)); prostate specific membrane antigen (PSMA; Israeli, et al., *Cancer Res.*, 54:1807-1811 (1994)); idiotypic epitopes or antigens, for example, immunoglobulin idiotypes or T cell receptor idiotypes (Chen et al., *J. Immunol.*, 153:4775-4787 (1994)); KSA (U.S. Pat. No. 5,348,887), kinesin 2 (Dietz, et al. Biochem Biophys Res Commun 2000 Sep. 7; 275(3):731-8), HIP-55, TGFβ-1 anti-apoptotic factor (Toomey, et al. Br J Biomed Sci 2001; 58(3):177-83), tumor protein D52 (Bryne J. A., et al., Genomics, 35:523-532 (1996)), H1FT, -BR-1 (WO 01/47959), NY-BR-62, NY-BR-75, NY-BR-85, NY-BR-87, NY-BR-96 (Scanlan, M. Serologic and Bioinformatic Approaches to the Identification of Human Tumor Antigens, in *Cancer Vaccines* 2000, Cancer Research Institute, New York, N.Y.), including "wild-type" (i.e., normally encoded by the genome, naturally-occurring), modified, and mutated versions as well as other fragments and derivatives thereof. Any of these TAs may be utilized alone or in combination with one another in a co-immunization protocol.

Preferred TAs are useful for inducing an immune response against melanoma cells. The term "melanoma" includes but is not limited to melanomas, metastatic melanomas, melanomas derived from either melanocytes or melanocyte related nevus cells, melanocarcinomas, melanoepitheliomas, melanosarcomas, melanoma in situ, superficial spreading melanoma, nodular melanoma, lentigo maligna melanoma, acral lentiginous melanoma, invasive melanoma and familial atypical mole and melanoma (FAM-M) syndrome, for example. In general, melanomas result from chromosomal abnormalities, degenerative growth and development disorders, mitogenic agents, ultraviolet radiation (UV), viral infections, inappropriate tissue expression of a gene, alterations in expression of a gene or carcinogenic agents, for example.

In certain cases, it may be beneficial to co-immunize patients with both TA and other antigens, such as angiogenesis-associated antigens ("AA"). An AA is an immunogenic molecule (i.e., peptide, polypeptide) associated with cells involved in the induction and/or continued development of blood vessels. For example, an AA may be expressed on an endothelial cell ("EC"), which is a primary structural component of blood vessels. Where the cancer is cancer, it is preferred that that the AA be found within or near blood vessels that supply a tumor. Immunization of a patient against an AA preferably results in an anti-AA immune response whereby angiogenic processes that occur near or within tumors are prevented and/or inhibited. Exemplary AAs include, for example, vascular endothelial growth factor (i.e., VEGF; Bernardini, et al. *J. Urol.*, 2001, 166(4): 1275-9; Starnes, et al. *J. Thorac. Cardiovasc. Surg.*, 2001, 122(3): 518-23; Dias, et al. *Blood*, 2002, 99: 2179-2184), the VEGF receptor (i.e., VEGF-R, flk-1/KDR; Starnes, et al. *J. Thorac. Cardiovasc. Surg.*, 2001, 122(3): 518-23), EPH receptors (i.e., EPHA2; Gerety, et al. 1999, *Cell*, 4: 403-414), epidermal growth factor receptor (i.e., EGFR; Ciardeillo, et al. Clin. Cancer Res., 2001, 7(10): 2958-70), basic fibroblast growth factor (i.e., bFGF; Davidson, et al. Clin. Exp. Metastasis 2000, 18(6): 501-7; Poon, et al. Am J. Surg., 2001, 182(3): 298-304), platelet-derived cell growth factor (i.e., PDGF-B), platelet-derived endothelial cell growth factor (PD-ECGF; Hong, et al. J. Mol. Med., 2001, 8(2):141-8), transforming growth factors (i.e., TGF-α; Hong, et al. J. Mol. Med., 2001, 8(2):141-8), endoglin (Balza, et al. *Int. J. Cancer*, 2001, 94: 579-585), Id proteins (Benezra, R. Trends Cardiovasc. Med., 2001, 11(6):237-41), proteases such as uPA, uPAR, and matrix metalloproteinases (MMP-2, MMP-9; Djonov, et al. J. Pathol., 2001, 195(2):147-55), nitric oxide synthase (Am. J. Ophthalmol., 2001, 132(4):551-6), aminopeptidase (Rouslhati, E. Nature Cancer, 2: 84-90, 2002), thrombospondins (i.e., TSP-1, TSP-2; Alvarez, et al. Gynecol. Oncol., 2001, 82(2):273-8; Seki, et al. Int. J. Oncol., 2001, 19(2):305-10), k-ras (Zhang, et al. Cancer Res., 2001, 61(16):6050-4), Wnt (Zhang, et al. Cancer Res., 2001, 61(16):6050-4), cyclin-dependent kinases (CDKs; Drug Resist. Updat. 2000, 3(2): 83-88), microtubules (Timar, et al. 2001. *Path. Oncol. Res.*, 7(2): 85-94), heat shock proteins (i.e., HSP90 (Timar, supra)), heparin-binding factors (i.e., heparinase; Gohji, et al. Int. J. Cancer, 2001, 95(5):295-301), synthases (i.e., ATP synthase, thymidilate synthase), collagen receptors, integrins (i.e., αvβ3, αvβ5, α1β1, α2β1, α5β1), the surface proteolglycan NG2, AAC2-1, or AAC2-2, among others, including "wild-type" (i.e., normally encoded by the genome, naturally-occurring), modified, mutated versions as well as other fragments and derivatives thereof. Any of these targets may be suitable in practicing the present invention, either alone or in combination with one another or with other agents.

The nucleic acid molecule may comprise or consist of a nucleotide sequence encoding one or more immunogenic targets, or fragments or derivatives thereof, such as that contained in a DNA insert in an ATCC Deposit. The term "nucleic acid sequence" or "nucleic acid molecule" refers to a DNA or RNA sequence. The term encompasses molecules formed from any of the known base analogs of DNA and RNA such as, but not limited to 4-acetylcytosine, 8-hydroxy-N6-methyladenosine, aziridinyl-cytosine, pseudoisocytosine, 5-(carboxyhydroxylmethyl) uracil, 5-fluorouracil, 5-bromouracil, 5-carboxymethylaminomethyl-2-thiouracil, 5-carboxymethylaminomethyluracil, dihydrouracil, inosine, N6-iso-pentenyladenine, 1-methyladenine, 1-methylpseudouracil, 1-methylguanine, 1-methylinosine, 2,2-dimethyl-guanine, 2-methyladenine, 2-methylguanine, 3-methylcytosine, 5-methylcytosine, N6-methyladenine, 7-methylguanine, 5-methylaminomethyluracil, 5-methoxyamino-methyl-2-thiouracil, beta-D-mannosylqueosine, 5'-methoxycarbonyl-methyluracil, 5-methoxyuracil, 2-methylthio-N-6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine, among others.

An isolated nucleic acid molecule is one that: (1) is separated from at least about 50 percent of proteins, lipids, carbohydrates, or other materials with which it is naturally found when total nucleic acid is isolated from the source cells; (2) is not be linked to all or a portion of a polynucleotide to which the nucleic acid molecule is linked in nature; (3) is operably linked to a polynucleotide which it is not linked to in nature; and/or, (4) does not occur in nature as part of a larger polynucleotide sequence. Preferably, the isolated nucleic acid molecule of the present invention is substantially free from any other contaminating nucleic acid molecule(s) or other contaminants that are found in its natural environment that would interfere with its use in polypeptide production or its therapeutic, diagnostic, prophylactic or research use. As used herein, the term "naturally occurring" or "native" or "naturally found" when used in connection with biological materials such as nucleic acid molecules, polypeptides, host cells, and the like, refers to materials which are found in nature and are not manipulated by man. Similarly, "non-naturally occurring" or "non-native" as used herein refers to a material that is not found in nature or that has been structurally modified or synthesized by man.

The identity of two or more nucleic acid or amino acid sequences is determined by comparing the sequences. As known in the art, "identity" means the degree of sequence relatedness between nucleic acid or amino acid sequences as determined by the match between the units making up the molecules (i.e., nucleotides or amino acid residues). Identity measures the percent of identical matches between the smaller of two or more sequences with gap alignments (if any) addressed by a particular mathematical model or computer program (i.e., an algorithm). Identity between nucleic acid sequences may also be determined by the ability of the nucleic acid sequences to hybridize to one another. In defining the process of hybridization, the term "highly stringent conditions" and "moderately stringent conditions" refer to conditions that permit hybridization of nucleic acid strands whose sequences are complementary, and to exclude hybridization of significantly mismatched nucleic acids. Examples of "highly stringent conditions" for hybridization and washing are 0.015 M sodium chloride, 0.0015 M sodium citrate at 65-68° C. or 0.015 M sodium chloride, 0.0015 M sodium citrate, and 50% formamide at 42° C. (see, for example, Sambrook, Fritsch & Maniatis, *Molecular Cloning: A Laboratory Manual* (2nd ed., Cold Spring Harbor Laboratory, 1989); Anderson et al., *Nucleic Acid Hybridisation: A Practical Approach* Ch. 4 (IRL Press Limited)). The term "moderately stringent conditions" refers to conditions under which a DNA duplex with a greater degree of base pair mismatching than could occur under "highly stringent conditions" is able to form. Exemplary moderately stringent conditions are 0.015 M sodium chloride, 0.0015 M sodium citrate at 50-65° C. or 0.015 M sodium chloride, 0.0015 M sodium citrate, and 20% formamide at 37-50° C. By way of example, moderately stringent conditions of 50° C. in 0.015 M sodium ion will allow about a 21% mismatch. During hybridization, other agents may be included in the hybridization and washing buffers for the purpose of reducing non-specific and/or background hybridization. Examples are 0.1% bovine serum albumin, 0.1% polyvinyl-pyrrolidone, 0.1% sodium pyrophosphate, 0.1% sodium dodecylsulfate, NaDodSO$_4$, (SDS), ficoll, Denhardt's solution, sonicated salmon sperm DNA (or another non-complementary DNA), and dextran sulfate, although other suitable agents can also be used. The concentration and types of these additives can be changed without substantially affecting the stringency of the hybridization conditions. Hybridization experiments are usually carried out at pH 6.8-7.4; however, at typical ionic strength conditions, the rate of hybridization is nearly independent of pH.

In preferred embodiments of the present invention, vectors are used to transfer a nucleic acid sequence encoding an immunogenic target to a cell. A vector is any molecule used to transfer a nucleic acid sequence to a host cell. In certain cases, an expression vector is utilized. An expression vector is a nucleic acid molecule that is suitable for transformation of a host cell and contains nucleic acid sequences that direct and/or control the expression of the transferred nucleic acid sequences. Expression includes, but is not limited to, processes such as transcription, translation, and splicing, if introns are present. Expression vectors typically comprise one or more flanking sequences operably linked to a heterologous nucleic acid sequence encoding a polypeptide. Flanking sequences may be homologous (i.e., from the same species and/or strain as the host cell), heterologous (i.e., from a species other than the host cell species or strain), hybrid (i.e., a combination of flanking sequences from more than one source), or synthetic, for example.

A flanking sequence is preferably capable of effecting the replication, transcription and/or translation of the coding sequence and is operably linked to a coding sequence. As used herein, the term operably linked refers to a linkage of polynucleotide elements in a functional relationship. For instance, a promoter or enhancer is operably linked to a coding sequence if it affects the transcription of the coding sequence. However, a flanking sequence need not necessarily be contiguous with the coding sequence, so long as it functions correctly. Thus, for example, intervening untranslated yet transcribed sequences can be present between a promoter sequence and the coding sequence and the promoter sequence may still be considered operably linked to the coding sequence. Similarly, an enhancer sequence may be located upstream or downstream from the coding sequence and affect transcription of the sequence.

In certain embodiments, it is preferred that the flanking sequence is a transcriptional regulatory region that drives high-level gene expression in the target cell. The transcriptional regulatory region may comprise, for example, a promoter, enhancer, silencer, repressor element, or combinations thereof. The transcriptional regulatory region may be either constitutive, tissue-specific, cell-type specific (i.e., the region is drives higher levels of transcription in a one type of tissue or cell as compared to another), or regulatable (i.e., responsive to interaction with a compound such as tetracycline). The source of a transcriptional regulatory region may be any prokaryotic or eukaryotic organism, any vertebrate or invertebrate organism, or any plant, provided that the flanking sequence functions in a cell by causing transcription of a nucleic acid within that cell. A wide variety of transcriptional regulatory regions may be utilized in practicing the present invention.

Suitable transcriptional regulatory regions include the CMV promoter (i.e., the CMV-immediate early promoter); promoters from eukaryotic genes (i.e., the estrogen-inducible chicken ovalbumin gene, the interferon genes, the glucocorticoid-inducible tyrosine aminotransferase gene, and the thymidine kinase gene); and the major early and late adenovirus gene promoters; the SV40 early promoter region (Bernoist and Chambon, 1981, *Nature* 290:304-10); the promoter contained in the 3' long terminal repeat (LTR) of Rous sarcoma virus (RSV) (Yamamoto, et al., 1980, *Cell* 22:787-97); the herpes simplex virus thymidine kinase (HSV-TK) promoter (Wagner et al., 1981, *Proc. Natl. Acad. Sci. U.S.A.* 78:1444-45); the regulatory sequences of the metallothionine gene (Brinster et al., 1982, *Nature* 296:39-42); prokaryotic expression vectors such as the beta-lactamase promoter (Villa-Kamaroff et al., 1978, *Proc. Natl. Acad. Sci. U.S.A.*, 75:3727-31); or the tac promoter (DeBoer et al., 1983, *Proc. Natl. Acad. Sci. U.S.A.*, 80:21-25). Tissue- and/or cell-type specific transcriptional control regions include, for example, the elastase I gene control region which is active in pancreatic acinar cells (Swift et al., 1984, *Cell* 38:639-46; Ornitz et al., 1986, *Cold Spring Harbor Symp. Quant. Biol.* 50:399-409 (1986); MacDonald, 1987, *Hepatology* 7:425-515); the insulin gene control region which is active in pancreatic beta cells (Hanahan, 1985, *Nature* 315:115-22); the immunoglobulin gene control region which is active in lymphoid cells (Grosschedl et al., 1984, *Cell* 38:647-58; Adames et al., 1985, *Nature* 318:533-38; Alexander et al., 1987, *Mol. Cell. Biol.*, 7:1436-44); the mouse mammary tumor virus control region in testicular, breast, lymphoid and mast cells (Leder et al., 1986, *Cell* 45:485-95); the albumin gene control region in liver (Pinkert et al., 1987, *Genes and Devel.* 1:268-76); the alpha-feto-protein gene control region in liver (Krumlauf et al., 1985, *Mol. Cell. Biol.*, 5:1639-48; Hammer et al., 1987, *Science* 235:53-58); the alpha 1-antitrypsin gene control region in liver (Kelsey et al., 1987, *Genes and Devel.* 1:161-71); the beta-globin gene control region in myeloid cells (Mogram et al., 1985, *Nature* 315:338-40; Kollias et al., 1986, *Cell* 46:89-94); the myelin basic protein gene control region in oligodendrocyte cells in the brain (Readhead et al., 1987, *Cell* 48:703-12); the myosin light chain-2 gene control region in skeletal muscle (Sani, 1985, *Nature* 314:283-86); the gonadotropic releasing hormone gene control region in the hypothalamus (Mason et al., 1986, *Science* 234:1372-78), and the tyrosinase promoter in melanoma cells (Hart, I. Semin Oncol 1996 February; 23(1):154-8; Siders, et al. Cancer Gene Ther 1998 September-October; 5(5):281-91), among others. Inducible promoters that are activated in the presence of a certain compound or condition such as light, heat, radiation, tetracycline, or heat shock proteins, for example, may also be utilized (see, for example, WO 00/10612). Other suitable promoters are known in the art.

As described above, enhancers may also be suitable flanking sequences. Enhancers are cis-acting elements of DNA, usually about 10-300 bp in length, that act on the promoter to increase transcription. Enhancers are typically orientation- and position-independent, having been identified both 5' and 3' to controlled coding sequences. Several enhancer sequences available from mammalian genes are known (i.e., globin, elastase, albumin, alpha-feto-protein and insulin). Similarly, the SV40 enhancer, the cytomegalovirus early promoter enhancer, the polyoma enhancer, and adenovirus enhancers are useful with eukaryotic promoter sequences. While an enhancer may be spliced into the vector at a position 5' or 3' to nucleic acid coding sequence, it is typically located at a site 5' from the promoter. Other suitable enhancers are known in the art, and would be applicable to the present invention.

While preparing reagents of the present invention, cells may need to be transfected or transformed. Transfection refers to the uptake of foreign or exogenous DNA by a cell, and a cell has been transfected when the exogenous DNA has been introduced inside the cell membrane. A number of transfection techniques are well known in the art (i.e., Graham et al., 1973, *Virology* 52:456; Sambrook et al., *Molecular Cloning, A Laboratory Manual* (Cold Spring Harbor Laboratories, 1989); Davis et al., *Basic Methods in Molecular Biology* (Elsevier, 1986); and Chu et al., 1981, *Gene* 13:197). Such techniques can be used to introduce one or more exogenous DNA moieties into suitable host cells.

In certain embodiments, it is preferred that transfection of a cell results in transformation of that cell. A cell is transformed when there is a change in a characteristic of the cell, being transformed when it has been modified to contain a new nucleic acid. Following transfection, the transfected nucleic acid may recombine with that of the cell by physically integrating into a chromosome of the cell, may be maintained transiently as an episomal element without being replicated, or may replicate independently as a plasmid. A cell is stably transformed when the nucleic acid is replicated with the division of the cell.

The expression vectors of the present invention also provide for expression of fragments of immunogenic targets. Fragments may include sequences truncated at the amino terminus (with or without a leader sequence) and/or the carboxy terminus. Fragments may also include variants (i.e., allelic, splice), orthologs, homologues, and other variants having one or more amino acid additions or substitutions or internal deletions as compared to the parental sequence. In preferred embodiments, truncations and/or deletions comprise about 1-5 amino acids, 5-10 amino acids, 10-20 amino acids, 20-30 amino acids, 30-40 amino acids, 40-50 amino acids, or more. Such polypeptide fragments may optionally comprise an amino terminal methionine residue. It will be appreciated that such fragments can be used, for example, to generate antibodies or cellular immune responses to immunogenic targets.

A variant is a sequence having one or more sequence substitutions, deletions, and/or additions as compared to the subject sequence. Variants may be naturally occurring or artificially constructed. Such variants may be prepared from the corresponding nucleic acid molecules. In preferred embodiments, the variants have from 1 to 3, or from 1 to 5, or from 1 to 10, or from 1 to 15, or from 1 to 20, or from 1 to 25, or from 1 to 30, or from 1 to 40, or from 1 to 50, or more than 50 amino acid substitutions, insertions, additions and/or deletions.

An allelic variant is one of several possible naturally-occurring alternate forms of a sequence occupying a given locus on a chromosome of an organism or a population of organisms. A splice variant is a polypeptide generated from one of several RNA transcript resulting from splicing of a primary transcript. An ortholog is a similar nucleic acid or polypeptide sequence from another species. For example, the mouse and human versions of an immunogenic target may be considered orthologs of each other. A derivative of a sequence is one that is derived from a parental sequence those sequences having substitutions, additions, deletions, or chemically modified variants. Variants may also include fusion proteins, which refers to the fusion of one or more first sequences (such as a peptide) at the amino or carboxy terminus of at least one other sequence (such as a heterologous peptide).

"Similarity" is a concept related to identity, except that similarity refers to a measure of relatedness which includes both identical matches and conservative substitution matches. If two polypeptide sequences have, for example, 10/20 identical amino acids, and the remainder are all non-conservative substitutions, then the percent identity and similarity would both be 50%. If in the same example, there are five more positions where there are conservative substitutions, then the percent identity remains 50%, but the percent similarity would be 75% (15/20). Therefore, in cases where there are conservative substitutions, the percent similarity between two polypeptides will be higher than the percent identity between those two polypeptides.

Substitutions may be conservative, or non-conservative, or any combination thereof. Conservative amino acid modifications to the sequence of a polypeptide (and the corresponding modifications to the encoding nucleotides) may produce polypeptides having functional and chemical characteristics similar to those of a parental polypeptide. For example, a "conservative amino acid substitution" may involve a substitution of a native amino acid residue with a non-native residue such that there is little or no effect on the size, polarity, charge, hydrophobicity, or hydrophilicity of the amino acid residue at that position and, in particlar, does not result in decreased immunogenicity. Suitable conservative amino acid substitutions are shown in Table I.

TABLE I

| Original Residues | Exemplary Substitutions | Preferred Substitutions |
| --- | --- | --- |
| Ala | Val, Leu, Ile | Val |
| Arg | Lys, Gln, Asn | Lys |
| Asn | Gln | Gln |
| Asp | Glu | Glu |
| Cys | Ser, Ala | Ser |
| Gln | Asn | Asn |
| Glu | Asp | Asp |
| Gly | Pro, Ala | Ala |
| His | Asn, Gln, Lys, Arg | Arg |
| Ile | Leu, Val, Met, Ala, Phe, Norleucine | Leu |
| Leu | Norleucine, Ile, Val, Met, Ala, Phe | Ile |
| Lys | Arg, 1,4 Diamino-butyric Acid, Gln, Asn | Arg |
| Met | Leu, Phe, Ile | Leu |
| Phe | Leu, Val, Ile, Ala, Tyr | Leu |
| Pro | Ala | Gly |
| Ser | Thr, Ala, Cys | Thr |
| Thr | Ser | Ser |
| Trp | Tyr, Phe | Tyr |
| Tyr | Trp, Phe, Thr, Ser | Phe |
| Val | Ile, Met, Leu, Phe, Ala, Norleucine | Leu |

A skilled artisan will be able to determine suitable variants of an immunogenic target using well-known techniques. For identifying suitable areas of the molecule that may be changed without destroying biological activity (i.e., MHC binding, immunogenicity), one skilled in the art may target areas not believed to be important for that activity. For example, when immunogenic targets with similar activities from the same species or from other species are known, one skilled in the art may compare the amino acid sequence of a polypeptide to such similar polypeptides. By performing such analyses, one can identify residues and portions of the molecules that are conserved. It will be appreciated that changes in areas of the molecule that are not conserved relative to such similar immunogenic targets would be less likely to adversely affect the biological activity and/or structure of a polypeptide. Similarly, the residues required for binding to MHC are known, and may be modified to improve binding. However, modifications resulting in decreased binding to MHC will not be appropriate in most situations. One skilled in the art would also know that, even in relatively conserved regions, one may substitute chemically similar amino acids for the naturally occurring residues while retaining activity. Therefore, even areas that may be important for biological activity or for structure may be subject to conservative amino acid substitutions without destroying the biological activity or without adversely affecting the structure of the immunogenic target.

Other preferred polypeptide variants include glycosylation variants wherein the number and/or type of glycosylation sites have been altered compared to the subject amino acid sequence. In one embodiment, polypeptide variants comprise a greater or a lesser number of N-linked glycosylation sites than the subject amino acid sequence. An N-linked glycosylation site is characterized by the sequence Asn-X-Ser or Asn-X-Thr, wherein the amino acid residue designated as X may be any amino acid residue except proline. The substitution of amino acid residues to create this sequence provides a potential new site for the addition of an N-linked carbohydrate chain. Alternatively, substitutions that eliminate this sequence will remove an existing N-linked carbohydrate chain. Also provided is a rearrangement of N-linked carbohydrate chains wherein one or more N-linked glycosylation sites (typically those that are naturally occurring) are eliminated and one or more new N-linked sites are created. To affect O-linked glycosylation of a polypeptide, one would modify serine and/or threonine residues.

Additional preferred variants include cysteine variants, wherein one or more cysteine residues are deleted or substituted with another amino acid (e.g., serine) as compared to the subject amino acid sequence set. Cysteine variants are useful when peptides or polypeptides must be refolded into a biologically active conformation such as after the isolation of insoluble inclusion bodies. Cysteine variants generally have fewer cysteine residues than the native protein, and typically have an even number to minimize interactions resulting from unpaired cysteines.

In other embodiments, the peptides or polypeptides may be attached to one or more fusion segments that assist in purification of the polypeptides. Fusions can be made either at the amino terminus or at the carboxy terminus of the subject polypeptide variant thereof. Fusions may be direct with no linker or adapter molecule or may be through a linker or adapter molecule. A linker or adapter molecule may be one or more amino acid residues, typically from about 20 to about 50 amino acid residues. A linker or adapter molecule may also be designed with a cleavage site for a DNA restriction endonuclease or for a protease to allow for the separation of the fused moieties. It will be appreciated that once constructed, the fusion polypeptides can be derivatized according to the methods described herein. Suitable fusion segments include, among others, metal binding domains (e.g., a poly-histidine segment), immunoglobulin binding domains (i.e., Protein A, Protein G, T cell, B cell, Fc receptor, or complement protein antibody-binding domains), sugar binding domains (e.g., a maltose binding domain), and/or a "tag" domain (i.e., at least a portion of α-galactosidase, a strep tag peptide, a T7 tag peptide, a FLAG peptide, or other domains that can be purified using compounds that bind to the domain, such as monoclonal antibodies). This tag is typically fused to the peptide or polypeptide and upon expression may serve as a means for affinity purification of the sequence of interest polypeptide from the host cell. Affinity purification can be accomplished, for example, by column chromatography using antibodies against the tag as an affinity matrix. Optionally, the tag can subsequently be removed from the purified sequence of interest polypeptide by various means such as using certain peptidases for cleavage. As described below, fusions may also be made between a TA and a co-stimulatory components such as the chemokines CXC10 (IP-10), CCL7 (MCP-3), or CCL5 (RANTES), for example.

A fusion motif may enhance transport of an immunogenic target to an MHC processing compartment, such as the endoplasmic reticulum. The sequences, referred to as transduction or transcytosis sequences, include sequences derived from HIV tat (sec Kim et al. 1997 J. Immunol. 159:1666), Drosophila antennapedia (see Schutze-Redelmeier et al. 1996 J. Immunol. 157:650), or human period-1 protein (hPER1; in particular, SRRHHCRSKAKRSRHH) (SEQ ID NO.: 17).

In addition, the polypeptide or variant thereof may be fused to a homologous peptide or polypeptide to form a homodimer or to a heterologous peptide or polypeptide to form a heterodimer. Heterologous peptides and polypeptides include, but are not limited to an epitope to allow for the detection and/or isolation of a fusion polypeptide; a transmembrane receptor protein or a portion thereof, such as an extracellular domain or a transmembrane and intracellular domain; a ligand or a portion thereof which binds to a transmembrane receptor protein; an enzyme or portion thereof which is catalytically active; a polypeptide or peptide which promotes oligomerization, such as a leucine zipper domain; a polypeptide or peptide which increases stability, such as an immunoglobulin constant region; a peptide or polypeptide which has a therapeutic activity different from the peptide or polypeptide; and/or variants thereof.

In certain embodiments, it may be advantageous to combine a nucleic acid sequence encoding an immunogenic target with one or more co-stimulatory component(s) such as cell surface proteins, cytokines or chemokines in a composition of the present invention. The co-stimulatory component may be included in the composition as a polypeptide or as a nucleic acid encoding the polypeptide, for example. Suitable co-stimulatory molecules include, for instance, polypeptides that bind members of the CD28 family (i.e., CD28, ICOS; Hutloff, et al. *Nature* 1999, 397: 263-265; Peach, et al. *J Exp Med* 1994, 180: 2049-2058) such as the CD28 binding polypeptides B7.1 (CD80; Schwartz, 1992; Chen et al, 1992; Ellis, et al. *J. Immunol.*, 156(8): 2700-9), B7.2 (CD86; Ellis, et al. *J. Immunol.*, 156(8): 2700-9), and mutants/variants thereof (WO 00/66162); polypeptides which bind members of the integrin family (i.e., LFA-1 (CD11a/CD18); Sedwick, et al. *J Immunol* 1999, 162: 1367-1375; Wülfing, et al. *Science* 1998, 282: 2266-2269; Lub, et al. *Immunol Today* 1995, 16: 479-483) including members of the ICAM family (i.e., ICAM-1, -2 or -3); polypeptides which bind CD2 family members (i.e., CD2, signalling lymphocyte activation molecule (CDw150 or "SLAM"; Aversa, et al. *J Immunol* 1997, 158: 4036-4044)) such as CD58 (LFA-3; CD2 ligand; Davis, et al. *Immunol Today* 1996, 17: 177-187) or SLAM ligands (Sayos, et al. *Nature* 1998, 395: 462-469); polypeptides which bind heat stable antigen (HSA or CD24; Zhou, et al. *Eur J Immunol* 1997, 27: 2524-2528); polypeptides which bind to members of the TNF receptor (TNFR) family (i.e., 4-1BB (CD137; Vinay, et al. *Semin Immunol* 1998, 10: 481-489), OX40 (CD134; Weinberg, et al. *Semin Immunol* 1998, 10: 471-480; Higgins, et al. *J Immunol* 1999, 162: 486-493), and CD27 (Lens, et al. *Semin Immunol* 1998, 10: 491-499)) such as 4-1BBL (4-1BB ligand; Vinay, et al. *Semin Immunol* 1998, 10: 481-48; DeBenedette, et al. *J Immunol* 1997, 158: 551-559), TNFR associated factor-1 (TRAF-1; 4-1BB ligand; Saoulli, et al. *J Exp Med* 1998, 187: 1849-1862, Arch, et al. *Mol Cell Biol* 1998, 18: 558-565), TRAF-2 (4-1BB and OX40 ligand; Saoulli, et al. *J Exp Med* 1998, 187: 1849-1862; Oshima, et al. *Int Immunol* 1998, 10: 517-526, Kawamata, et al. *J Biol Chem* 1998, 273: 5808-5814), TRAF-3 (4-1BB and OX40 ligand; Arch, et al. *Mol Cell Biol* 1998, 18: 558-565; Jang, et al. *Biochem Biophys Res Commun* 1998, 242: 613-620; Kawamata S, et al. *J Biol Chem* 1998, 273: 5808-5814), OX40L (OX40 ligand; Gramaglia, et al. *J Immunol* 1998, 161: 6510-6517), TRAF-5 (OX40 ligand; Arch, et al. *Mol Cell Biol* 1998, 18: 558-565; Kawamata, et al. *J Biol Chem* 1998, 273: 5808-5814), and CD70 (CD27 ligand; Couderc, et al. *Cancer Gene Ther.*, 5(3): 163-75). CD154 (CD40 ligand or "CD40L"; Gurunathan, et al. *J. Immunol.*, 1998, 161: 4563-4571; Sine, et al. *Hum. Gene Ther.*, 2001, 12: 1091-1102) may also be suitable.

One or more cytokines may also be suitable co-stimulatory components or "adjuvants", either as polypeptides or being encoded by nucleic acids contained within the compositions of the present invention (Parmiani, et al. Immunol Lett 2000 Sep. 15; 74(1): 41-4; Berzofsky, et al. Nature Immunol. 1: 209-219). Suitable cytokines include, for example, interleukin-2 (IL-2) (Rosenberg, et al. *Nature Med.* 4: 321-327 (1998)), IL-4, IL-7, IL-12 (reviewed by Pardoll, 1992; Harries, et al. J. Gene Med. 2000 July-August; 2(4):243-9; Rao, et al. *J. Immunol.* 156: 3357-3365 (1996)), IL-15 (Xin, et al. *Vaccine*, 17:858-866, 1999), IL-16 (Cruikshank, et al. J. Leuk Biol. 67(6): 757-66, 2000), IL-18 (*J. Cancer Res. Clin. Oncol.* 2001. 127(12): 718-726), GM-CSF (CSF (Disis, et al. *Blood*, 88: 202-210 (1996)), tumor necrosis factor-alpha (TNF-α), or interferons such as IFN-α or INF-γ. Other cytokines may also be suitable for practicing the present invention, as is known in the art.

Chemokines may also be utilized, in either polypeptide or nucleic acid form. Fusion proteins comprising CXCL10 (IP-10) and CCL7 (MCP-3) fused to a tumor self-antigen have been shown to induce anti-tumor immunity (Biragyn, et al. *Nature Biotech.* 1999, 17: 253-258). The chemokines CCL3 (MIP-1α) and CCL5 (RANTES) (Boyer, et al. *Vaccine*, 1999, 17 (Supp. 2): S53-S64) may also be of use in practicing the present invention. Other suitable chemokines are known in the art.

It is also known in the art that suppressive or negative regulatory immune mechanisms may be blocked, resulting in enhanced immune responses. For instance, treatment with anti-CTLA-4 (Shrikant, et al. *Immunity*, 1996, 14: 145-155; Sutmuller, et al. *J. Exp. Med.*, 2001, 194: 823-832), anti-CD25 (Sutmuller, supra), anti-CD4 (Matsui, et al. *J. Immunol.*, 1999, 163: 184-193), the fusion protein IL13Ra2-Fc (Terabe, et al. *Nature Immunol.*, 2000, 1: 515-520), and combinations thereof (i.e., anti-CTLA-4 and anti-CD25, Sutmuller, supra) have been shown to upregulate anti-tumor immune responses and would be suitable in practicing the present invention. Such treatments, among others, may also be combined with the one or more immunogenic targets of the present invention.

Any of these components may be used alone or in combination with other agents. For instance, it has been shown that a combination of CD80, ICAM-1 and LFA-3 ("TRICOM") may potentiate anti-cancer immune responses (Hodge, et al. *Cancer Res.* 59: 5800-5807 (1999). Other effective combinations include, for example, IL-12+GM-CSF (Ahlers, et al. *J. Immunol.*, 158: 3947-3958 (1997); Iwasaki, et al. *J. Immunol.* 158: 4591-4601 (1997)), IL-12+GM-CSF+TNF-α (Ahlers, et al. *Int. Immunol.* 13: 897-908 (2001)), CD80+IL-12 (Fruend, et al. *Int. J. Cancer,* 85: 508-517 (2000); Rao, et al. supra), and CD86+GM-CSF+IL-12 (Iwasaki, supra). One of skill in the art would be aware of additional combinations useful in carrying out the present invention. In addition, the skilled artisan would be aware of additional reagents or methods that may be used to modulate such mechanisms. These reagents and methods, as well as others known by those of skill in the art, may be utilized in practicing the present invention.

Additional strategies for improving the efficiency of nucleic acid-based immunization may also be used including, for example, the use of self-replicating viral replicons (Caley, et al. 1999. *Vaccine,* 17: 3124-2135; Dubensky, et al. 2000. *Mol. Med.* 6: 723-732; Leitner, et al. 2000. *Cancer Res.* 60: 51-55), codon optimization (Liu, et al. 2000. *Mol. Ther.,* 1: 497-500; Dubensky, supra; Huang, et al. 2001. *J. Virol.* 75: 4947-4951), in vivo electroporation (Widera, et al. 2000. *J. Immunol.* 164: 4635-3640), incorporation of CpG stimulatory motifs (Gurunathan, et al. *Ann. Rev. Immunol.,* 2000, 18: 927-974; Leitner, supra; Cho, et al. J. Immunol. 168(10): 4907-13), sequences for targeting of the endocytic or ubiquitin-processing pathways (Thomson, et al. 1998. *J. Virol.* 72: 2246-2252; Velders, et al. 2001. *J. Immunol.* 166: 5366-5373), Marek's disease virus type 1 VP22 sequences (J. Virol. 76(6):2676-82, 2002), prime-boost regimens (Gurunathan, supra; Sullivan, et al. 2000. *Nature,* 408: 605-609; Hanke, et al. 1998. *Vaccine,* 16: 439-445; Amara, et al. 2001. *Science,* 292: 69-74), and the use of mucosal delivery vectors such as *Salmonella* (Darji, et al. 1997. *Cell,* 91: 765-775; Woo, et al. 2001. *Vaccine,* 19: 2945-2954). Other methods are known in the art, some of which are described below.

Chemotherapeutic agents, radiation, anti-angiogenic compounds, or other agents may also be utilized in treating and/or preventing cancer using immunogenic targets (Sebti, et al. Oncogene 2000 Dec. 27; 19(56):6566-73). For example, in treating metastatic melanoma, suitable chemotherapeutic regimens may include BELD (bleomycin, vindesine, lomustine, and deacarbazine; Young, et al. 1985. Cancer, 55: 1879-81), BOLD (bleomycin, vincristine, lomustine, dacarbazine; Seigler, et al. 1980. Cancer, 46: 2346-8); DD (dacarbazine, actinomycin; Hochster, et al. Cancer Treatment Reports, 69: 39-42), or POC (procarbazine, vincristine, lomustine; Carmo-Pereira, et al. 1984. Cancer Treatment Reports, 68: 1211-4) among others. Other suitable chemotherapeutic regimens may also be utilized.

Many anti-angiogenic agents are known in the art and would be suitable for co-administration with the immunogenic target vaccines and/or chemotherapeutic regimens (see, for example, Timar, et al. 2001. *Pathology Oncol. Res.,* 7(2): 85-94). Such agents include, for example, physiological agents such as growth factors (i.e., ANG-2, NK1,2,4 (HGF), transforming growth factor beta (TGF-β)), cytokines (i.e., interferons such as IFN-α, -β, -γ, platelet factor 4 (PF-4), PR-39), proteases (i.e., cleaved AT-III, collagen XVIII fragment (Endostatin)), HmwKallikrein-d5 plasmin fragment (Angiostatin), prothrombin-F1-2, TSP-1), protease inhibitors (i.e., tissue inhibitor of metalloproteases such as TIMP-1, -2, or -3; maspin; plasminogen activator-inhibitors such as PAI-1; pigment epithelium derived factor (PEDF)), Tumstatin (available through ILEX, Inc.), antibody products (i.e., the collagen-binding antibodies HUIV26, HUI77, XL313; anti-VEGF; anti-integrin (i.e., Vitaxin, (Lxsys))), and glycosidases (i.e., heparinase-I, -III). "Chemical" or modified physiological agents known or believed to have anti-angiogenic potential include, for example, vinblastine, taxol, ketoconazole, thalidomide, dolestatin, combrestatin A, rapamycin (Guba, et al. 2002, *Nature Med.,* 8: 128-135), CEP-7055 (available from Cephalon, Inc.), flavone acetic acid, Bay 12-9566 (Bayer Corp.), AG3340 (Agouron, Inc.), CGS 27023A (Novartis), tetracylcine derivatives (i.e., COL-3 (Collagenix, Inc.)), Neovastat (Aetema), BMS-275291 (Bristol-Myers Squibb), low dose 5-FU, low dose methotrexate (MTX), irsofladine, radicicol, cyclosporine, captopril, celecoxib, D45152-sulphated polysaccharide, cationic protein (Protamine), cationic peptide-VEGF, Suramin (polysulphonated napthyl urea), compounds that interfere with the function or production of VEGF (i.e., SU5416 or SU6668 (Sugen), PTK787/ZK22584 (Novartis)), Distamycin A, Angiozyme (ribozyme), isoflavinoids, staurosporine derivatives, genistein, EMD121974 (Merck KcgaA), tyrphostins, isoquinolones, retinoic acid, carboxyamidotriazole, TNP-470, octreotide, 2-methoxyestradiol, aminosterols (i.e., squalamine), glutathione analogues (i.e., N-acteyl-L-cysteine), combretastatin A-4 (Oxigene), Eph receptor blocking agents (*Nature,* 414:933-938, 2001), Rh-Angiostatin, Rh-Endostatin (WO 01/93897), cyclic-RGD peptide, accutin-disintegrin, benzodiazepenes, humanized anti-avb3 Ab, Rh-PAI-2, amiloride, p-amidobenzamidine, anti-uPA ab, anti-uPAR Ab, L-phanylalanin-N-methylamides (i.e., Batimistat, Marimastat), AG3340, and minocycline. Many other suitable agents are known in the art and would suffice in practicing the present invention.

The present invention may also be utilized in combination with "non-traditional" methods of treating cancer. For example, it has recently been demonstrated that administration of certain anaerobic bacteria may assist in slowing tumor growth. In one study, *Clostridium novyi* was modified to eliminate a toxin gene carried on a phage episome and administered to mice with colorectal tumors (Dang, et al. *P.N.A.S. USA,* 98(26): 15155-15160, 2001). In combination with chemotherapy, the treatment was shown to cause tumor necrosis in the animals. The reagents and methodologies described in this application may be combined with such treatment methodologies.

Nucleic acids encoding immunogenic targets may be administered to patients by any of several available techniques. Various viral vectors that have been successfully utilized for introducing a nucleic acid to a host include retrovirus, adenovirus, adeno-associated virus (AAV), herpes virus, and poxvirus, among others. It is understood in the art that many such viral vectors are available in the art. The vectors of the present invention may be constructed using standard recombinant techniques widely available to one skilled in the art. Such techniques may be found in common molecular biology references such as *Molecular Cloning: A Laboratory Manual* (Sambrook, et al., 1989, Cold Spring Harbor Laboratory Press), *Gene Expression Technology* (Methods in Enzymology, Vol. 185, edited by D. Goeddel, 1991. Academic Press, San Diego, Calif.), and *PCR Protocols: A Guide to Methods and Applications* (Innis, et al. 1990. Academic Press, San Diego, Calif.).

Preferred retroviral vectors are derivatives of lentivirus as well as derivatives of murine or avian retroviruses. Examples of suitable retroviral vectors include, for example, Moloney murine leukemia virus (MoMuLV), Harvey murine sarcoma virus (HaMuSV), murine mammary tumor virus (MuMTV), SIV, BIV, HIV and Rous Sarcoma Virus (RSV). A number of retroviral vectors can incorporate multiple exogenous nucleic acid sequences. As recombinant retroviruses are defective, they require assistance in order to produce infectious vector particles. This assistance can be provided by, for example, helper cell lines encoding retrovirus structural genes. Suitable helper cell lines include Ψ2, PA317 and PA12, among others. The vector virions produced using such cell lines may then be used to infect a tissue cell line, such as NIH 3T3 cells, to produce large quantities of chimeric retroviral virions. Retroviral vectors may be administered by traditional methods (i.e., injection) or by implantation of a "producer cell line" in proximity to the target cell population (Culver, K., et al., 1994, *Hum. Gene Ther.*, 5 (3): 343-79; Culver, K., et al., *Cold Spring Harb. Symp. Quant. Biol.*, 59: 685-90); Oldfield, E., 1993, *Hum. Gene Ther.*, 4 (1): 39-69). The producer cell line is engineered to produce a viral vector and releases viral particles in the vicinity of the target cell. A portion of the released viral particles contact the target cells and infect those cells, thus delivering a nucleic acid of the present invention to the target cell. Following infection of the target cell, expression of the nucleic acid of the vector occurs.

Adenoviral vectors have proven especially useful for gene transfer into eukaryotic cells (Rosenfeld, M., et al., 1991, *Science*, 252 (5004): 431-4; Crystal, R., et al., 1994, *Nat. Genet.*, 8 (1): 42-51), the study eukaryotic gene expression (Levrero, M., et al., 1991, *Gene*, 101 (2): 195-202), vaccine development (Graham, F. and Prevec, L., 1992, *Biotechnology*, 20: 363-90), and in animal models (Stratford-Perricaudet, L., et al., 1992, *Bone Marrow Transplant.*, 9 (Suppl. 1): 151-2; Rich, D., et al., 1993, *Hum. Gene Ther.*, 4 (4): 461-76). Experimental routes for administrating recombinant Ad to different tissues in vivo have included intratracheal instillation (Rosenfeld, M., et al., 1992, *Cell*, 68 (1): 143-55) injection into muscle (Quantin, B., et al., 1992, *Proc. Natl. Acad. Sci. U.S.A.*, 89 (7): 2581-4), peripheral intravenous injection (Herz, J., and Gerard, R., 1993, *Proc. Natl. Acad. Sci. U.S.A.*, 90 (7): 2812-6) and stereotactic inoculation to brain (Le Gal La Salle, G., et al., 1993, *Science*, 259 (5097): 988-90), among others.

Adeno-associated virus (AAV) demonstrates high-level infectivity, broad host range and specificity in integrating into the host cell genome (Hermonat, P., et al., 1984, *Proc. Natl. Acad. Sci. U.S.A.*, 81 (20): 6466-70). And Herpes Simplex Virus type-1 (HSV-1) is yet another attractive vector system, especially for use in the nervous system because of its neurotropic property (Geller, A., et al., 1991, *Trends Neurosci.*, 14 (10): 428-32; Glorioso, et al., 1995, *Mol. Biotechnol.*, 4 (1): 87-99; Glorioso, et al., 1995, *Annu. Rev. Microbiol.*, 49: 675-710).

Poxvirus is another useful expression vector (Smith, et al. 1983, *Gene*, 25 (1): 21-8; Moss, et al, 1992, *Biotechnology*, 20: 345-62; Moss, et al, 1992, *Curr. Top. Microbiol. Immunol.*, 158: 25-38; Moss, et al. 1991. *Science*, 252: 1662-1667). Poxviruses shown to be useful include vaccinia, NYVAC, avipox, fowlpox, canarypox, ALVAC, and ALVAC(2), among others.

NYVAC (vP866) was derived from the Copenhagen vaccine strain of vaccinia virus by deleting six nonessential regions of the genome encoding known or potential virulence factors (see, for example, U.S. Pat. Nos. 5,364,773 and 5,494, 807). The deletion loci were also engineered as recipient loci for the insertion of foreign genes. The deleted regions are: hymidine kinase gene (TK; J2R); hemorrhagic region (u; B13R+B14R); A type inclusion body region (ATI; A26L); hemagglutinin gene (HA; A56R); host range gene region (C7L-K1L); and, large subunit, ribonucleotide reductase (14L). NYVAC is a genetically engineered vaccinia virus strain that was generated by the specific deletion of eighteen open reading frames encoding gene products associated with virulence and host range. NYVAC has been show to be useful for expressing TAs (see, for example, U.S. Pat. No. 6,265, 189). NYVAC (vP866), vP994, vCP205, vCP1433, placZH6H4Lreverse, pMPC6H6K3E3 and pC3H6FHVB were also deposited with the ATCC under the terms of the Budapest Treaty, accession numbers VR-2559, VR-2558, VR-2557, VR-2556, ATCC-97913, ATCC-97912, and ATCC-97914, respectively.

ALVAC-based recombinant viruses (i.e., ALVAC-1 and ALVAC-2) are also suitable for use in practicing the present invention (see, for example, U.S. Pat. No. 5,756,103). ALVAC(2) is identical to ALVAC(1) except that ALVAC(2) genome comprises the vaccinia E3L and K3L genes under the control of vaccinia promoters (U.S. Pat. No. 6,130,066; Beattie et al., 1995a, 1995b, 1991; Chang et al., 1992; Davies et al., 1993). Both ALVAC(1) and ALVAC(2) have been demonstrated to be useful in expressing foreign DNA sequences, such as TAs (Tartaglia et al., 1993 a,b; U.S. Pat. No. 5,833, 975). ALVAC was deposited under the terms of the Budapest Treaty with the American Type Culture Collection (ATCC), 10801 University Boulevard, Manassas, Va. 20110-2209, USA, ATCC accession number VR-2547.

Another useful poxvirus vector is TROVAC. TROVAC refers to an attenuated fowlpox that was a plaque-cloned isolate derived from the FP-1 vaccine strain of fowlpoxvirus which is licensed for vaccination of 1 day old chicks. TROVAC was likewise deposited under the terms of the Budapest Treaty with the ATCC, accession number 2553.

"Non-viral" plasmid vectors may also be suitable in practicing the present invention. Preferred plasmid vectors are compatible with bacterial, insect, and/or mammalian host cells. Such vectors include, for example, PCR-II, pCR3, and pcDNA3.1 (Invitrogen, San Diego, Calif.), pBSII (Stratagene, La Jolla, Calif.), pET15 (Novagen, Madison, Wis.), pGEX (Pharmacia Biotech, Piscataway, N.J.), pEGFP-N2 (Clontech, Palo Alto, Calif.), pETL (BlueBacII, Invitrogen), pDSR-alpha (PCT pub. No. WO 90/14363) and pFast-BacDual (Gibco-BRL, Grand Island, N.Y.) as well as Bluescript® plasmid derivatives (a high copy number COLE1-based phagemid, Stratagene Cloning Systems, La Jolla, Calif.), PCR cloning plasmids designed for cloning Taq-amplified PCR products (e.g., TOPO™ TA Cloning® kit, PCR2.1® plasmid derivatives, Invitrogen, Carlsbad, CA). Bacterial vectors may also be used with the current invention. These vectors include, for example, *Shigella, Salmonella, Vibrio cholerae, Lactobacillus, Bacille calmette guerin* (BCG), and *Streptococcus* (see for example, WO 88/6626; WO 90/0594; WO 91/13157; WO 92/1796; and WO 92/21376). Many other non-viral plasmid expression vectors and systems are known in the art and could be used with the current invention.

Suitable nucleic acid delivery techniques include DNA-ligand complexes, adenovirus-ligand-DNA complexes, direct injection of DNA, $CaPO_4$ precipitation, gene gun techniques, electroporation, and colloidal dispersion systems, among others. Colloidal dispersion systems include macromolecule complexes, nanocapsules, microspheres, beads, and lipid-based systems including oil-in-water emulsions, micelles, mixed micelles, and liposomes. The preferred colloidal system of this invention is a liposome, which are artificial membrane vesicles useful as delivery vehicles in vitro and in vivo. RNA, DNA and intact virions can be encapsulated within the aqueous interior and be delivered to cells in a biologically active form (Fraley, R., et al., 1981, *Trends Biochem. Sci.*, 6: 77). The composition of the liposome is usually a combination of phospholipids, particularly high-phase-transition-temperature phospholipids, usually in combination with steroids, especially cholesterol. Other phospholipids or other lipids may also be used. The physical characteristics of liposomes depend on pH, ionic strength, and the presence of divalent cations. Examples of lipids useful in liposome production include phosphatidyl compounds, such as phosphatidylglycerol, phosphatidylcholine, phosphatidylserine, phosphatidylethanolamine, sphingolipids, cerebrosides, and gangliosides. Particularly useful are diacylphosphatidylglycerols, where the lipid moiety contains from 14-18 carbon atoms, particularly from 16-18 carbon atoms, and is saturated. Illustrative phospholipids include egg phosphatidylcholine, dipalmitoylphosphatidylcholine and distearoylphosphatidylcholine.

An immunogenic target may also be administered in combination with one or more adjuvants to boost the immune response. Exemplary adjuvants are shown in Table II below:

TABLE II

Types of Immunologic Adjuvants

| Type of Adjuvant | General Examples | Specific Examples/References |
|---|---|---|
| Gel-type | Aluminum hydroxide/phosphate ("alum adjuvants") | (Aggerbeck and Heron, 1995) |
|  | Calcium phosphate | (Relyveld, 1986) |
| Microbial | Muramyl dipeptide (MDP) | (Chedid et al., 1986) |
|  | Bacterial exotoxins | Cholera toxin (CT), *E. coli* labile toxin (LT)(Freytag and Clements, 1999) |
|  | Endotoxin-based adjuvants | Monophosphoryl lipid A (MPL) (Ulrich and Myers, 1995) |
|  | Other bacterial | CpG oligonucleotides (Corral and Petray, 2000), BCG sequences (Krieg, et al. Nature, 374: 576), tetanus toxoid (Rice, et al. J. Immunol., 2001, 167: 1558–1565) |
| Particulate | Biodegradable Polymer microspheres | (Gupta et al., 1998) |
|  | Immunostimulatory complexes (ISCOMs) | (Morein and Bengtsson, 1999) |
|  | Liposomes | (Wassef et al., 1994) |
| Oil-emulsion and surfactant-based adjuvants | Freund's incomplete adjuvant | (Jensen et al., 1998) |
|  | Microfluidized emulsions | MF59 (Ott et al., 1995) SAF (Allison and Byars, 1992) (Allison, 1999) |
|  | Saponins | QS-21 (Kensil, 1996) |
| Synthetic | Muramyl peptide derivatives | Murabutide (Lederer, 1986) Threony-MDP (Allison, 1997) |
|  | Nonionic block copolymers | L121 (Allison, 1999) |
|  | Polyphosphazene (PCPP) | (Payne et al., 1995) |
|  | Synthetic polynucleotides | Poly A:U, Poly I:C (Johnson, 1994) |
|  | Thalidomide derivatives | CC-4047/ACTIMID (J. Immunol., 168(10): 4914–9) |

Administration of a composition of the present invention to a host may be accomplished using any of a variety of techniques known to those of skill in the art. The composition(s) may be processed in accordance with conventional methods of pharmacy to produce medicinal agents for administration to patients, including humans and other mammals (i.e., a "pharmaceutical composition"). The pharmaceutical composition is preferably made in the form of a dosage unit containing a given amount of DNA, viral vector particles, polypeptide or peptide, for example. A suitable daily dose for a human or other mammal may vary widely depending on the condition of the patient and other factors, but, once again, can be determined using routine methods.

The pharmaceutical composition may be administered orally, parentally, by inhalation spray, rectally, intranodally, or topically in dosage unit formulations containing conventional pharmaceutically acceptable carriers, adjuvants, and vehicles. The term "pharmaceutically acceptable carrier" or "physiologically acceptable carrier" as used herein refers to one or more formulation materials suitable for accomplishing or enhancing the delivery of a nucleic acid, polypeptide, or peptide as a pharmaceutical composition. A "pharmaceutical composition" is a composition comprising a therapeutically effective amount of a nucleic acid or polypeptide. The terms "effective amount" and "therapeutically effective amount" each refer to the amount of a nucleic acid or polypeptide used to induce or enhance an effective immune response. It is preferred that compositions of the present invention provide for the induction or enhancement of an anti-tumor immune response in a host which protects the host from the development of a tumor and/or allows the host to eliminate an existing tumor from the body.

For oral administration, the pharmaceutical composition may be of any of several forms including, for example, a capsule, a tablet, a suspension, or liquid, among others. Liquids may be administered by injection as a composition with suitable carriers including saline, dextrose, or water. The term parenteral as used herein includes subcutaneous, intravenous, intramuscular, intrasternal, infusion, or intraperitoneal administration. Suppositories for rectal administration of the drug can be prepared by mixing the drug with a suitable non-irritating excipient such as cocoa butter and polyethylene glycols that are solid at ordinary temperatures but liquid at the rectal temperature.

The dosage regimen for immunizing a host or otherwise treating a disorder or a disease with a composition of this invention is based on a variety of factors, including the type of disease, the age, weight, sex, medical condition of the patient, the severity of the condition, the route of administration, and the particular compound employed. For example, a poxviral vector may be administered as a composition comprising $1 \times 10^6$ infectious particles per dose. Thus, the dosage regimen may vary widely, but can be determined routinely using standard methods.

A prime-boost regimen may also be utilized (WO 01/30382 A1) in which the targeted immunogen is initially administered in a priming step in one form followed by a boosting step in which the targeted immunogen is administered in another form. The form of the targeted immunogen in the priming and boosting steps are different. For instance, if the priming step utilized a nucleic acid, the boost may be administered as a peptide. Similarly, where a priming step utilized one type of recombinant virus (i.e., ALVAC), the boost step may utilize another type of virus (i.e., NYVAC). This prime-boost method of administration has been shown to induce strong immunological responses. Various combinations of forms are suitable in practicing the present invention.

While the compositions of the invention can be administered as the sole active pharmaceutical agent, they can also be used in combination with one or more other compositions or agents (i.e., other immunogenic targets, co-stimulatory molecules, adjuvants). When administered as a combination, the individual components can be formulated as separate compositions administered at the same time or different times, or the components can be combined as a single composition.

Injectable preparations, such as sterile injectable aqueous or oleaginous suspensions, may be formulated according to known methods using suitable dispersing or wetting agents and suspending agents. The injectable preparation may also be a sterile injectable solution or suspension in a non-toxic parenterally acceptable diluent or solvent. Suitable vehicles and solvents that may be employed are water, Ringer's solution, and isotonic sodium chloride solution, among others. For instance, a viral vector such as a poxvirus may be prepared in 0.4% NaCl. In addition, sterile, fixed oils are conventionally employed as a solvent or suspending medium. For this purpose, any bland fixed oil may be employed, including synthetic mono- or diglycerides. In addition, fatty acids such as oleic acid find use in the preparation of injectables.

For topical administration, a suitable topical dose of a composition may be administered one to four, and preferably two or three times daily. The dose may also be administered with intervening days during which no does is applied. Suitable compositions may comprise from 0.001% to 10% w/w, for example, from 1% to 2% by weight of the formulation, although it may comprise as much as 10% w/w, but preferably not more than 5% w/w, and more preferably from 0.1% to 1% of the formulation. Formulations suitable for topical administration include liquid or semi-liquid preparations suitable for penetration through the skin (e.g., liniments, lotions, ointments, creams, or pastes) and drops suitable for administration to the eye, ear, or nose.

The pharmaceutical compositions may also be prepared in a solid form (including granules, powders or suppositories). The pharmaceutical compositions may be subjected to conventional pharmaceutical operations such as sterilization and/or may contain conventional adjuvants, such as preservatives, stabilizers, wetting agents, emulsifiers, buffers etc. Solid dosage forms for oral administration may include capsules, tablets, pills, powders, and granules. In such solid dosage forms, the active compound may be admixed with at least one inert diluent such as sucrose, lactose, or starch. Such dosage forms may also comprise, as in normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings. Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting sweetening, flavoring, and perfuming agents.

Pharmaceutical compositions comprising a nucleic acid or polypeptide of the present invention may take any of several forms and may be administered by any of several routes. In preferred embodiments, the compositions are administered via a parenteral route (intradermal, intramuscular or subcutaneous) to induce an immune response in the host. Alternatively, the composition may be administered directly into a lymph node (intranodal) or tumor mass (i.e., intratumoral administration). For example, the dose could be administered subcutaneously at days 0, 7, and 14. Suitable methods for immunization using compositions comprising TAs are known in the art, as shown for p53 (Hollstein et al., 1991), p21-ras (Almoguera et al., 1988), HER-2 (Fendly et al., 1990), the melanoma-associated antigens (MAGE-1; MAGE-2) (van der Bruggen et al., 1991), p97 (Hu et al., 1988), melanoma-associated antigen E (WO 99/30737) and carcinoembryonic antigen (CEA) (Kantor et al., 1993; Fishbein et al., 1992; Kaufman et al., 1991), among others.

Preferred embodiments of administratable compositions include, for example, nucleic acids or polypeptides in liquid preparations such as suspensions, syrups, or elixirs. Preferred injectable preparations include, for example, nucleic acids or polypeptides suitable for parental, subcutaneous, intradermal, intramuscular or intravenous administration such as sterile suspensions or emulsions. For example, a recombinant poxvirus may be in admixture with a suitable carrier, diluent, or excipient such as sterile water, physiological saline, glucose or the like. The composition may also be provided in lyophilized form for reconstituting, for instance, in isotonic aqueous, saline buffer. In addition, the compositions can be co-administered or sequentially administered with other antineoplastic, anti-tumor or anti-cancer agents and/or with agents which reduce or alleviate ill effects of antineoplastic, anti-tumor or anti-cancer agents.

A kit comprising a composition of the present invention is also provided. The kit can include a separate container containing a suitable carrier, diluent or excipient. The kit can also include an additional anti-cancer, anti-tumor or antineoplastic agent and/or an agent that reduces or alleviates ill effects of antineoplastic, anti-tumor or anti-cancer agents for co- or sequential-administration. Additionally, the kit can include instructions for mixing or combining ingredients and/or administration.

A better understanding of the present invention and of its many advantages will be had from the following examples, given by way of illustration.

EXAMPLES

Example 1

Construction of the Multi-Antigen Construct vT416

The expression vector vT416 (ALVAC-NY-ESO-1/Trp-2-LFA-3/ICAM-1/B7.1-E3L/K3L) was constructed in the ALVAC vector using standard techniques. DNA sequences encoding NY-ESO-1, Trp-2, LFA-3, ICAM-1, B7.1, vvE3L and vvK3L were inserted into various loci within the ALVAC genome. DNA sequences encoding NY-ESO-1 (Chen et al. 1997 PNAS 94:1914) and TRP-2 (Wang et al. 1996 J. Exp. Med. 184:2207) were inserted into the C5 locus. DNA sequences encoding LFA-3 (Wallner, et al. (1987) J. Exp. Med. 166:923-932), ICAM-1 (Staunton, et al. (1988) Cell 52:925-933) and B7.1 (Chen, et al. (1992). Cell 71:1093-1102) were inserted into the C3 locus. LFA-3, ICAM-1 and B7.1 form an expression cassette known as TRICOM. DNA sequences encoding vvE3L (Chang, et al. 1992. Proc. Natl. Acad. Sci. U.S. A 89:4825-4829) and vvK3L (Beattie, et al. 1991. Virology 183:419-422) were inserted into the C6 locus. Promoters were utilized as follows:

TABLE III

| DNA sequence | Promoter |
| --- | --- |
| E3L | vaccinia E3L |
| K3L | vaccinia H6 |
| LFA-3 | vaccinia 30K |
| ICAM-1 | vaccinia I3 |
| B7.1 | sE/L |
| NY-ESO-1 | vaccinia H6 |
| TRP-2 | sE/L |

Promoter sE/L is described by Chakrabarti, et al. (BioTechniques 23: 1094-1097, 1997). The donor plasmids utilized are shown below:

TABLE IV

| Plasmid | Size (bp) | Vector | Antibiotic Resitance Gene |
| --- | --- | --- | --- |
| pMPC6H6K3E3 | — | pBS-SK | Amp |
| pALVAC.Tricom(C3) #33 | 10,470 | pBS-SK | Amp |
| pT1132 | 11,154 | pBS-SK | Amp |

NY-ESO-1 and TRP-2 DNA sequences were inserted into the ALVAC donor plasmid pT1132. This donor plasmid was then used with pALVAC.Tricom(C3) #33 to generate the ALVAC-TRICOM recombinant expressing these genes using standard techniques. The plasmids pALVAC.Tricom(C3) #33 and pT1132 are shown in FIG. 1. The DNA sequences of pALVAC.Tricom(C3) #33 and pT1132 are shown in FIGS. 2 and 3, respectively.

Example 2

Construction of the Multi-Antigen Construct vT419

The expression vector vT419 (ALVAC-gp100M/Mart-1/Mage-1,3 minigene-LFA-3/ICAM-1/B7.1-E3L/K3L) was constructed in the ALVAC vector using standard techniques. DNA sequences encoding the gp100M/MART-1/MAGE-1,3 minigene, LFA-3, ICAM-1, B7.1, vvE3L and vvK3L were inserted into various loci within the ALVAC genome. The gp100M/MART-1/MAGE-1,3 minigene was inserted into the C5 locus. DNA sequences encoding LFA-3 (Wallner, et al. (1987) J. Exp. Med. 166:923-932), ICAM-1 (Staunton, et al. (1988) Cell 52:925-933) and B7.1 (Chen, et al. (1992) Cell 71:1093-1102) were inserted into the C3 locus. LFA-3, ICAM-1 and B7.1 form an expression cassette known as TRICOM. DNA sequences encoding vvE3L (Chang, et al. 1992. Proc. Natl. Acad. Sci. U.S. A 89:4825-4829) and vvK3L (Beattie, et al. 1991. Virology 183:419-422) were inserted into the C6 locus. Promoters were utilized as follows:

TABLE V

| Gene | Promoter |
| --- | --- |
| E3L | vaccinia E3L |
| K3L | vaccinia H6 |
| LFA-3 | vaccinia 30K |
| ICAM-1 | vaccinia I3 |
| B7.1 | sE/L |
| gp100(M) | vaccinia H6 |
| Mart-1 | vaccinia 42K |

Promoter sE/L is described by Chakrabarti, et al. (BioTechniques 23: 1094-1097, 1997). The donor plasmids utilized are shown below:

TABLE VI

Figure 4:
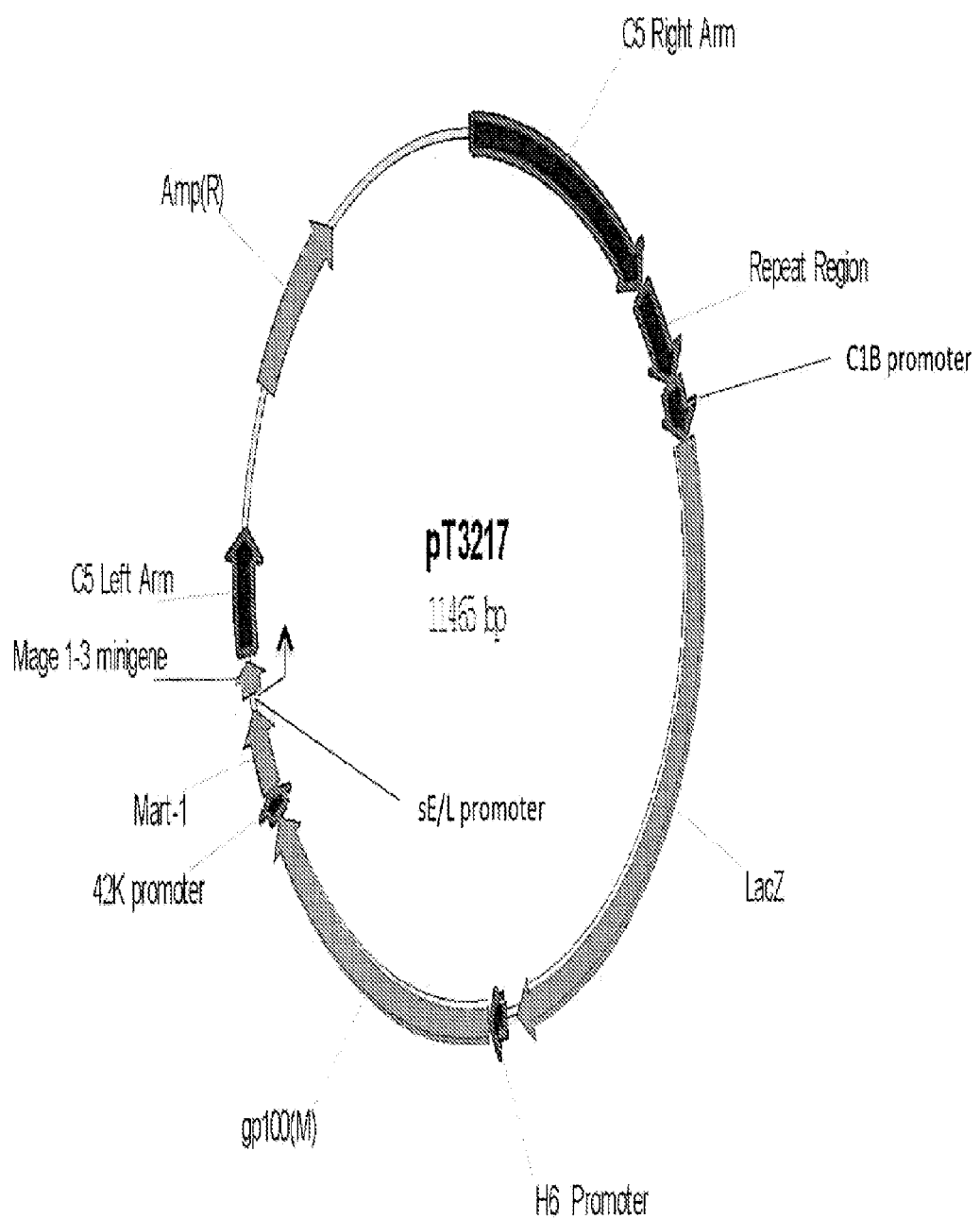
FIG. 4. Schematic of plasmid pT3217.

| Plasmid | Size (bp) | Vector | Antibiotic Resitance Gene |
| --- | --- | --- | --- |
| pMPC6H6K3E3 | — | pBS-SK | Amp |
| pALVAC.Tricom(C3) #33 | 10,470 | pBS-SK | Amp |
| pT3217 | 11,465 | pBS-SK | Amp | gp100(M), Mart-1 and Mage-1,3 minigene were inserted into the ALVAC C5 donor plasmid pT3217. This donor plasmid was then used with pALVAC.Tricom(C3) #33 to generate the ALVAC-TRICOM recombinant expressing these genes using standard techniques. This donor plasmid inserts into the C5 site. pALVAC.Tricom(C3) #33 is shown in FIGS. 1 and 2. The pT3217 plasmid is shown in FIG. 4. The DNA sequence of pT3217 is shown in FIG. 5.

Example 3

Immunological Assessment of Multi-Antigen Vectors

The results of the first animal experiment indicated a trend toward higher immunological responses to three (Mart 1, NY-ESO-1 and gp100) of the four antigens when the vaccine was given as two separate injections. However, these differences were not statistically significant. In detail, HLA-A2/K$^b$ transgenic mice (5/group) were immunized subcutaneously with vT419 (ALVAC(2)-gp100M/MART-1/MAGE-1/3 minigene/TRICOM) and vT416 (ALVAC(2)-TRP-2/NY-ESO-1/TRICOM) either combined at one site or given as separate injections. Control mice were immunized with parental ALVAC(2). Mice were vaccinated three times (at three week intervals), and three weeks after the last boost T cell responses in individual mice were analyzed by IFN-g ELISPOT and CTL assays following in vitro restimulation with peptide. Compared to control animals, mice vaccinated with the multi-antigen vectors (at 2 sites) exhibited statistically significant ELISPOT responses against MART-1. The IFN-gamma response to gp100M and NY-ESO-1 were also detectable, although these responses were not statistically significant due to response variability and the small number of cultures tested. ELISPOT responses against the TRP-2 antigen were elevated in all groups tested (including control animals), presumably due to the fact that the dominant A2-restricted TRP-2 peptide (180-188) cross-reacts with H-2K$^b$ and can induce low avidity T cell responses in naïve mice following in vitro culture, and were therefore not statistically significant. Interestingly, ELISPOT responses in mice injected with an admixture of vT416 and vT419 were generally lower than in mice receiving each virus separately, although these differences did not achieve statistical significance. The CTL data were largely negative, except for one strong anti-gp100 response and one marginal anti-MART-1 response, both of which occurred in mice vaccinated with vT416 and vT419 (two sites). Overall, these results provided encouraging data that establish that the multi-antigen vectors can generate responses against MART-1, and suggest that anti-gp100 and anti-NY-ESO-1 responses can also be induced.

Two additional pre-clinical animal studies have been completed using the melanoma multi-antigen ALVAC recombinants. In these experiments, HLA-A2/K$^b$ transgenic mice (5/group) were immunized subcutaneously with vT419 (ALVAC(2)-gp100M/MART-1/MAGE-1/3 minigene/TRICOM) and vT416 (ALVAC(2)-TRP-2/NY-ESO-1/TRICOM) either combined at one site or given as separate injections. Control mice were immunized with parental ALVAC(2). After vaccination, the T cell responses in individual mice were assessed by IFN-gamma ELISPOT assay following in vitro restimulation with peptide. Unlike the previous multi-antigen experiment, which provided encouraging immunogenicity data, the two most recent studies generated inconclusive data, due to high background responses in control immunized animals. Therefore, overall the results were deemed as inconclusive.

To confirm the immunogenicity of the multi-antigen constructs, and to repeat results from the first study, another pre-clinical animal study has been completed. HLA-A2/K$^b$ transgenic mice (10/group) were immunized subcutaneously with vT419 (ALVAC(2)-gp100M/MART-1/MAGE-1/3 minigene/TRICOM) and vT416 (ALVAC(2)-TRP-2/NY-ESO-1/TRICOM) given as separate injections. Control mice were immunized with parental ALVAC(2). Statistically significant ELISPOT responses were detectable against gp100, Mart-1 and TRP-2, and some responses were detected against NY-ESO-1, which were at the border of being statistically significant.

While the present invention has been described in terms of the preferred embodiments, it is understood that variations and modifications will occur to those skilled in the art. Therefore, it is intended that the appended claims cover all such equivalent variations that come within the scope of the invention as claimed.

---

What is claimed is:

1. A dosage unit comprising at least first and second separate compositions, the first composition containing an ALVAC(2) expression vector encoding CD80 (SEQ ID NO: 14), ICAM-1 (SEQ ID NO: 16), LFA-3 (SEQ ID NO: 15), gp100M (SEQ ID NO: 10), MART-1 (SEQ ID NO: 11), and the MAGE1/3 minigene (nucleotides 8111-8254 of SEQ ID NO.:5), and the second composition comprising an ALVAC (2) expression vector encoding CD80 (SEQ ID NO: 14), ICAM-1 (SEQ ID NO: 16), LFA-3 (SEQ ID NO: 15), TRP-2 (SEQ ID NO: 8), and NY-ESO-1 (SEQ ID NO: 7), wherein administration of the compositions to a host results in an immune response in the host against gp100, MART-1 and NY-ESO-1.

* * * * *

SEQUENCE LISTING

<160> NUMBER OF SEQ ID NOS: 17

<210> SEQ ID NO 1
<211> LENGTH: 10470
<212> TYPE: DNA
<213> ORGANISM: Artificial Sequence
<220> FEATURE:
<223> OTHER INFORMATION: Canarypox virus (ALVAC) and Homo sapiens

<400> SEQUENCE: 1

```
ggaaattgta aacgttaata ttttgttaaa attcgcgtta aattttttgtt aaatcagctc      60 atttttttaac caataggccg aaatcggcaa aatcccttat aaatcaaaag aatagaccga     120 gataggttg agtgttgttc cagtttggaa caagagtcca ctattaaaga acgtggactc      180
caacgtcaaa gggcgaaaaa ccgtctatca gggcgatggc ccactacgtg aaccatcacc      240
ctaatcaagt tttttgggggt cgaggtgccg taaagcacta aatcggaacc ctaaagggag      300
cccccgattt agagcttgac ggggaaagcc ggcgaacgtg gcgagaaagg aagggaagaa      360
agcgaaagga gcgggcgcta gggcgctggc aagtgtagcg gtcacgctgc gcgtaaccac      420
cacacccgcc gcgcttaatg cgccgctaca gggcgcgtcg cgccattcgc cattcaggct      480
gcgcaactgt tgggaagggc gatcggtgcg ggcctcttcg ctattacgcc agctggcgaa      540 aggggggatgt gctgcaaggc gattaagttg ggtaacgcca gggttttccc agtcacgacg      600
ttgtaaaacg acgccagtg aattgtaata cgactcacta tagggcgaat tgggtaccgc      660
ggccgcgtcg acatgcattg ttagttctgt agatcagtaa cgtatagcat acgagtataa      720
ttatcgtagg tagtaggtat cctaaaataa atctgataca gataataact ttgtaaatca      780
attcagcaat ttctctatta tcatgataat gattaataca cagcgtgtcg ttatttttg      840 ttacgatagt atttctaaag taaagagcag gaatccctag tataatagaa ataatccata      900
tgaaaaatat agtaatgtac atatttctaa tgttaacata tttataggta aatccaggaa      960
gggtaatttt tacatatcta tatacgctta ttacagttat taaaaatata cttgcaaaca     1020
tgttagaagt aaaaaagaaa gaactaattt tacaaagtgc tttaccaaaa tgccaatgga     1080
aattacttag tatgtatata atgtataaag gtatgaatat cacaaacagc aaatcggcta     1140
ttcccaagtt gagaaacggt ataatagata tatttctaga taccattaat aaccttataa     1200
gcttgacgtt tcctataatg cctactaaga aaactagaag atacatacat actaacgcca     1260
tacgagagta actactcatc gtataactac tgttgctaac agtgacactg atgttataac     1320
tcatctttga tgtggtataa atgtataata actatattac actggtattt tatttcagtt     1380
atatactata tagtattaaa aattatattt gtataattat attattatat tcagtgtaga     1440
aagtaaaata ctataaatat gtatctctta tttataactt attagtaaag tatgtactat     1500
```

```
tcagttatat tgttttataa aagctaaatg ctactagatt gatataaatg aatatgtaat   1560
aaattagtaa tgtagtatac taatattaac tcacatttga ctaattagct ataaaaaccc   1620
taaggtaggc ggccgcacta gaggattcga caaacaccaa taattcccttctcttcattc   1680 cggacattaa attggctata gataataaag acattgagat gttacaggct ctgttcaaat   1740
acgacattaa tatctattct gctaatctgg aaaatgtact attggatgat gccgaaatag   1800
ctaaaatgat tatagaaaag catgttgaat acaagtctga ctcctataca aaagatctcg   1860
atatagtcaa gaataataaa ttggatgaaa taattagcaa aaacaaggaa ctcagactca   1920
tgtacgtcaa ttgtgtaaag aaaaactaat tagattctcc cacattttg ttaacattac    1980 actaactaat tggtaaaatt gatagaataa ttatgtgtat ataagataga tttcctattg   2040
tcttactcat tgcatcgtgg gaattcagat cagcttccgc ggcatggttg ctgggagcga   2100
cgcggggcgg gccctggggg tcctcagcgt ggtctgcctg ctgcactgct ttggtttcat   2160
cagctgtttt tcccaacaaa tatatggtgt tgtgtatggg aatgtaactt tccatgtacc   2220
aagcaatgtg cctttaaaag aggtcctatg gaaaaaacaa aaggataaag ttgcagaact   2280
ggaaaattct gaattcagag cttctctcatc ttttaaaaat agggtttatt tagacactgt   2340
gtcaggtagc ctcactatct acaacttaac atcatcagat gaagatgagt atgaaatgga   2400
atcgccaaat attactgata ccatgaagtt cttctcttat gtgcttgagt ctcttccatc   2460
tcccacacta acttgtgcat tgactaatgg aagcattgaa gtccaatgca tgataccaga   2520
gcattacaac agccatcgag gacttataat gtactcatgg gattgtccta tggagcaatg   2580
taaacgtaac tcaaccagta tatttttaaa gatggaaaat gatcttccac aaaaaataca   2640
gtgtactctt agcaatccat tatttaatac aacatcatca atcattttga caacctgtat   2700
cccaagcagc ggtcattcaa gacacagata tgcacttata cccataccat tagcagtaat   2760
tacaacatgt attgtgctgt atatgaatgg tattctgaaa tgtgacagaa accagacag   2820 aaccaactcc aattgattgg ctcgaccggg aatgtactat ctacgtacga aacccgcatc   2880
cgctcccatt caattcacat tggacaagga taaaataaaa ccactggtgg tttgcgattc   2940
cgaaatctgt acatcatgca gtggttaaac aaaaacattt ttattctcaa atgagataaa   3000
gtgaaaatat atatcattat attacaaagt acaattattt aggtttaatc aatcccgcgg   3060
gctatggctc ccagcagccc ccggcccgcg ctgcccgcac tcctggtcct gctcggggct   3120
ctgttcccag gacctggcaa tgcccagaca tctgtgtccc cctcaaaagt catcctgccc   3180
cggggaggct ccgtgctggt gacatgcagc acctcctgtg accagcccaa gttgttgggc   3240
atagagaccc cgttgcctaa aaaggagttg ctcctgcctg gaacaaccg gaaggtgtat    3300 gaactgagca atgtgcaaga agatagccaa ccaatgtgct attcaaactg ccctgatggg   3360
cagtcaacag ctaaaacctt cctcaccgtg tactggactc cagaacgggt ggaactggca   3420 cccctccccct cttggcagcc agtgggcaag aaccttaccc tacgctgcca ggtggagggt   3480
ggggcacccc gggccaacct caccgtggtg ctgctccgtg gggagaagga gctgaaacgg   3540
gagccagctg tggggagcc cgctgaggtc acgaccacgg tgctggtgag gagagatcac   3600
catggagcca atttctcgtg ccgcactgaa ctggacctgc ggcccaagg gctggagctg   3660 tttgagaaca cctcggcccc ctaccagctc cagaccctttg tcctgccagc gactccccca   3720
caacttgtca gccccccggg tcctagaggtg gacacgcagg ggaccgtggt ctgttccctg   3780
gacgggctgt tccagtctct ggaggcccag gtccacctgg cactggggga ccagaggttg   3840
aaccccacag tcacctatgg caacgactcc ttctcggcca aggcctcagt cagtgtgacc   3900
```

```
gcagaggacg agggcaccca gcggctgacg tgtgcagtaa tactgggaaa ccagagccag   3960
gagacactgc agacagtgac catctacagc tttccggcgc ccaacgtgat tctgacgaag   4020
ccagaggtct cagaagggac cgaggtgaca gtgaagtgtg aggcccaccc tagagccaag   4080
gtgacgctga atggggttcc agcccagcca ctgggcccga gggcccagct cctgctgaag   4140
gccaccccag aggacaacgg gcgcagcttc tcctgctctg caaccctgga ggtggccggc   4200
cagcttatac acaagaacca gacccgggag cttcgtgtcc tgtatggccc ccgactggac   4260
gagagggatt gtccgggaaa ctggacgtgg ccagaaaatt cccagcagac tccaatgtgc   4320
caggcttggg ggaacccatt gcccgagctc aagtgtctaa aggatggcac tttcccactg   4380
cccatcgggg aatcagtgac tgtcactcga gatcttgagg gcacctacct ctgtcgggcc   4440
aggagcactc aaggggaggt cacccgcgag gtgaccgtga atgtgctctc cccccggtat   4500
gagattgtca tcatcactgt ggtagcagcc gcagtcataa tgggcactgc aggcctcagc   4560
acgtacctct ataaccgcca gcggaagatc aagaaataca gactacaaca gcccaaaaa   4620 gggaccccca tgaaaccgaa cacacaagcc acgcctccct gagcatgcat gtagcttaaa   4680
aattgaaatt ttatttttt ttttggaat ataaataagc tcgaagtcga aattcctgca   4740
gcccggggcc atgggccaca cacggaggca gggaacatca ccatccaagt gtccatacct   4800
caatttcttt cagctcttgg tgctggctgg tctttctcac ttctgttcag gtgttatcca   4860
cgtgaccaag gaagtgaaag aagtggcaac gctgtcctgt ggtcacaatg tttctgttga   4920
agagctggca caaactcgca tctactggca aaggagaag aaaatggtgc tgactatgat   4980
gtctggagac atgaatatat ggcccgagta caagaaccgg accatctttg atatcactaa   5040
taacctctcc attgtgatcc tggctctgcg cccatctgac gagggcacat acgagtgtgt   5100
tgttctgaag tatgaaaaag acgctttcaa gcgggaacac ctggctgaag tgacgttatc   5160
agtcaaagct gacttcccta cacctagtat atctgacttt gaaattccaa cttctaatat   5220
tagaaggata atttgctcaa cctctggagg ttttccagag cctcacctct cctggttgga   5280
aaatggagaa gaattaaatg ccatcaacac aacagtttcc caagatcctg aaactgagct   5340
ctatgctgtt agcagcaaac tggatttcaa tatgacaacc aaccacagct tcatgtgtct   5400
catcaagtat ggacatttaa gagtgaatca gaccttcaac tggaatacaa ccaagcaaga   5460
gcattttcct gataacctgc tcccatcctg ggccattacc ttaatctcag taaatggaat   5520
tttcgtgata tgctgcctga cctactgctt tgccccacgc tgcagagaga aaggaggaa   5580 tgagagattg agaagggaaa gtgtacgccc tgtataaaag ctttctaggt ttttgtttag   5640
ggctgcagga attcctcgag ggatcccgat ttttatgact agttaatcaa ataaaaagca   5700
tacaagctat tgcttcgcta tcgttacaaa atggcaggaa ttttgtgtaa actaagccac   5760
atacttgcca atgaaaaaa tagtagaaag gatactattt taatgggatt agatgttaag   5820
gttccttggg attatagtaa ctgggcatct gttaactttt acgacgttag gttagatact   5880
gatgttacag attataataa tgttacaata aaatacatga caggatgtga tatttttcct   5940
catataactc ttggaatagc aaatatggat caatgtgata gatttgaaaa tttcaaaaag   6000
caaataactg atcaagattt acagactatt tctatagtct gtaaagaaga gatgtgtttt   6060
cctcagagta acgcctctaa acagttggga gcgaaaggat gcgctgtagt tatgaaactg   6120
gaggtatctg atgaacttag agccctaaga aatgttctgc tgaatgcggt accctgttcg   6180
aaggacgtgt ttggtgatat cacagtagat aatccgtgga atcctcacat aacagtagga   6240
```

```
tatgttaagg aggacgatgt cgaaaacaag aaacgcctaa tggagtgcat gtccaagttt    6300
aggggggcaag aaatacaagt tctaggatgg tattaataag tatctaagta tttggtataa   6360
tttattaaat agtataatta taacaaataa taaataacat gataacggtt tttattagaa    6420
taaaatagag ataatatcat aatgatatat aatacttcat taccagaaat gagtaatgga    6480
agacttataa atgaactgca taaagctata aggtatagag atataaattt agtaaggtat    6540
atacttaaaa aatgcaaata caataacgta aatatactat caacgtcttt gtatttagcc    6600
gtaagtattt ctgatataga aatggtaaaa ttattactag aacacggtgc cgatatttta    6660
aaatgtaaaa atcctcctct tcataaagct gctagtttag ataatacaga aattgctaaa    6720
ctactaatag attctggcgc tgacatagaa cagatacatt ctggaaatag tccgttatat    6780
atttctgtat atagaaacaa taagtcatta actagatatt tattaaaaaa aggtgttaat    6840
tgtaatagat tctttctaaa ttattacgat gtactgtatg ataagatatc tgatgatatg    6900
tataaaatat ttatagattt taatattgat cttaatatac aaactagaaa ttttgaaact    6960
ccgttacatt acgctataaa gtataagaat atagatttaa ttaggatatt gttagataat    7020
agtattaaaa tagataaaag tttattttttg cataaacagt atctcataaa ggcacttaaa   7080
aataattgta gttacgatat aatagcgtta cttataaatc acggagtgcc tataaacgaa    7140
caagatgatt taggtaaaac cccattacat cattcggtaa ttaatagaag aaaagatgta    7200
acagcacttc tgttaaatct aggagctgat ataaacgtaa tagatgactg tatgggcagt    7260
cccttacatt acgctgtttc acgtaacgat atcgaaacaa caaagacact tttagaaaga    7320
ggatctaatg ttaatgtggt taataatcat atagataccg ttctaaatat agctgttgca    7380
tctaaaaaca aaactatagt aaacttatta ctgaagtacg gtactgatac aaagttggta    7440
ggattagata aacatgttat tcacatagct atagaaatga aagatattaa tatactgaat    7500
gcgatcttat tatatggttg ctatgtaaac gtctataatc ataaaggttt cactcctcta    7560
tacatggcag ttagttctat gaaaacagaa tttgttaaac tcttacttga ccacggtgct    7620
tacgtaaatg ctaaagctaa gttatctgga aatactcctt tacataaagc tatgttatct    7680
aatagtttta ataatataaa attacttttta tcttataacg ccgactataa ttctctaaat   7740
aatcacggta atacgcctct aacttgtgtt agcttttttag atgacaagat agctattatg    7800
ataatatcta aaatgatgtt agaaatatct aaaaatcctg aaatagctaa ttcagaaggt    7860
tttatagtaa acatggaaca tataaacagt aataaaagac tactatctat aaaagaatca    7920
tgcgaaaaag aactagatgt tataacacat ataaagttaa attctatata ttcttttaat    7980
atctttcttg acaataacat agatcttatg gtaaagttcg taactaatcc tagagttaat    8040
aagatacctg catgtatacg tatatatagg gaattaatac ggaaaaataa atcattagct    8100
tttcatagac atcagctaat agttaaagct gtaaaagaga gtaagaatct aggaataata    8160
ggtaggttac ctatagatat caaacatata ataatgaac tattaagtaa taatgattta     8220
cattctgtta tcaccagctg ttgtaaccca gtagtataaa gagctccagc ttttgttccc    8280
tttagtgagg gttaattccg agcttggcgt aatcatggtc atagctgttt cctgtgtgaa    8340
attgttatcc gctcacaatt ccacacaaca tacgagccgg aagcataaag tgtaaagcct    8400
ggggtgccta atgagtgagc taactcacat taattgcgtt gcgctcactg cccgctttcc    8460
agtcgggaaa cctgtcgtgc cagctgcatt aatgaatcgg ccaacgcgcg gggagaggcg    8520
gtttgcgtat tgggcgctct tccgcttcct cgctcactga ctcgctgcgc tcggtcgttc    8580
ggctgcggcg agcggtatca gctcactcaa aggcggtaat acggttatcc acagaatcag    8640
```

```
gggataacgc aggaaagaac atgtgagcaa aaggccagca aaaggccagg aaccgtaaaa    8700
aggccgcgtt gctggcgttt ttccataggc tccgcccccc tgacgagcat cacaaaaatc    8760
gacgctcaag tcagaggtgg cgaaacccga caggactata agataccag gcgtttcccc     8820 ctggaagctc cctcgtgcgc tctcctgttc cgacctgcc gcttaccgga tacctgtccg     8880
cctttctccc ttcgggaagc gtggcgcttt ctcatagctc acgctgtagg tatctcagtt    8940
cggtgtaggt cgttcgctcc aagctgggct gtgtgcacga accccccgtt cagcccgacc    9000
gctgcgcctt atccggtaac tatcgtcttg agtccaaccc ggtaagacac gacttatcgc    9060
cactggcagc agccactggt aacaggatta gcagagcgag gtatgtaggc ggtgctacag    9120
agttcttgaa gtggtggcct aactacggct acactagaag gacagtattt ggtatctgcg    9180
ctctgctgaa gccagttacc ttcggaaaaa gagttggtag ctcttgatcc ggcaaacaaa    9240
ccaccgctgg tagcggtggt ttttttgttt gcaagcagca gattacgcgc agaaaaaaag    9300
gatctcaaga gatcctttg atcttttcta cggggtctga cgctcagtgg aacgaaaact     9360
cacgttaagg gattttggtc atgagattat caaaaaggat cttcacctag atccttttaa    9420
attaaaaatg aagttttaaa tcaatctaaa gtatatatga gtaaacttgg tctgacagtt    9480
accaatgctt aatcagtgag gcacctatct cagcgatctg tctatttcgt tcatccatag    9540
ttgcctgact ccccgtcgtg tagataacta cgatacggga gggcttacca tctgccccca    9600
gtgctgcaat gataccgcga gacccacgct caccggctcc agatttatca gcaataaacc    9660
agccagccgg aagggccgag cgcagaagtg gtcctgcaac tttatccgcc tccatccagt    9720
ctattaattg ttgccgggaa gctagagtaa gtagttcgcc agttaatagt ttgcgcaacg    9780
ttgttgccat tgctacaggc atcgtggtgt cacgctcgtc gtttggtatg gcttcattca    9840
gctccggttc ccaacgatca aggcgagtta catgatcccc catgttgtgc aaaaaagcgg    9900
ttagctcctt cggtcctccg atcgttgtca gaagtaagtt ggccgcagtg ttatcactca    9960
tggttatggc agcactgcat aattctctta ctgtcatgcc atccgtaaga tgcttttctg   10020
tgactggtga gtactcaacc aagtcattct gagaatagtg tatgcggcga ccgagttgct   10080
cttgcccggc gtcaatacgg gataataccg cgccacatag cagaacttta aaagtgctca   10140
tcattggaaa acgttcttcg gggcgaaaac tctcaaggat cttaccgctg ttgagatcca   10200
gttcgatgta acccactcgt gcacccaact gatcttcagc atcttttact ttcaccagcg   10260
tttctgggtg agcaaaaaca ggaaggcaaa atgccgcaaa aaagggaata agggcgacac   10320
ggaaatgttg aatactcata ctcttccttt ttcaatatta ttgaagcatt tatcagggtt   10380
attgtctcat gagcggatac atatttgaat gtatttagaa aaataaacaa ataggggttc   10440
cgcgcacatt tccccgaaaa gtgccacctg                                    10470
```

<210> SEQ ID NO 2
<211> LENGTH: 10470
<212> TYPE: DNA
<213> ORGANISM: Artificial Sequence
<220> FEATURE:
<223> OTHER INFORMATION: Canarypox virus (ALVAC) and Homo sapiens

<400> SEQUENCE: 2

```
cctttaacat ttgcaattat aaaacaattt taagcgcaat ttaaaaacaa tttagtcgag      60
taaaaaattg gttatccggc tttagccgtt ttagggaata tttagttttc ttatctggct     120
ctatcccaac tcacaacaag gtcaaacctt gttctcaggt gataatttct tgcacctgag    180
```

```
gttgcagttt cccgcttttt ggcagatagt cccgctaccg ggtgatgcac ttggtagtgg    240
gattagttca aaaaccccca gctccacggc atttcgtgat ttagccttgg gatttccctc    300
gggggctaaa tctcgaactg cccctttcgg ccgcttgcac cgctctttcc ttcccttctt    360
tcgctttcct cgcccgcgat cccgcgaccg ttcacatcgc cagtgcgacg cgcattggtg    420
gtgtgggcgg cgcgaattac gcggcgatgt cccgcgcagc gcggtaagcg gtaagtccga    480
cgcgttgaca acccttcccg ctagccacgc cggagaagc gataatgcgg tcgaccgctt     540 tcccctaca cgacgttccg ctaattcaac ccattgcggt cccaaaaggg tcagtgctgc     600
aacattttgc tgccggtcac ttaacattat gctgagtgat atcccgctta acccatggcg    660
ccggcgcagc tgtacgtaac aatcaagaca tctagtcatt gcatatcgta tgctcatatt    720
aatagcatcc atcatccata ggattttatt tagactatgt ctattattga aacatttagt    780
taagtcgtta aagagataat agtactatta ctaattatgt gtcgcacagc aataaaaaac    840
aatgctatca taaagatttc atttctcgtc cttagggatc atattatctt tattaggtat    900 acttttata tcattacatg tataaagatt acaattgtat aaatatccat ttaggtcctt     960
cccattaaaa atgtatagat atatgcgaat aatgtcaata atttttatat gaacgtttgt   1020
acaatcttca ttttttcttt cttgattaaa atgtttcacg aaatggtttt acggttacct   1080
ttaatgaatc atacatatat tacatatttc catacttata gtgtttgtcg tttagccgat   1140
aagggttcaa ctctttgcca tattatctat ataaagatct atggtaatta ttggaatatt   1200
cgaactgcaa aggatattac ggatgattct tttgatcttc tatgtatgta tgattgcggt   1260
atgctctcat tgatgagtag catattgatg acaacgattg tcactgtgac tacaatattg   1320
agtagaaact acaccatatt tacatattat tgatataatg tgaccataaa ataaagtcaa   1380
tatatgatat atcataattt ttaatataaa catattaata taataatata agtcacatct   1440
ttcattttat gatatttata catagagaat aaatattgaa taatcatttc atacatgata   1500
agtcaatata acaaaatatt ttcgatttac gatgatctaa ctatatttac ttatacatta   1560
tttaatcatt acatcatatg attataattg agtgtaaact gattaatcga tattttttggg  1620 attccatccg ccggcgtgat ctcctaagct gtttgtggtt attaagggaa gagaagtaag   1680
gcctgtaatt taaccgatat ctattatttc tgtaactcta caatgtccga gacaagttta   1740
tgctgtaatt atagataaga cgattagacc ttttacatga taacctacta cggctttatc   1800
gattttacta atatcttttc gtacaactta tgttcagact gaggatatgt tttctagagc   1860
tatatcagtt cttattattt aacctacttt attaatcgtt tttgttcctt gagtctgagt   1920
acatgcagtt aacacatttc ttttttgatta atctaagagg gtgtaaaaac aattgtaatg   1980
tgattgatta accattttaa ctatcttatt aatacacata tattctatct aaaggataac   2040
agaatgagta acgtagcacc cttaagtcta gtcgaaggcg ccgtaccaac gaccctcgct   2100
gcgccccgcc cgggacccc aggagtcgca ccagacggac gacgtgacga aaccaaagta    2160
gtcgacaaaa agggttgttt atataccaca acacataccc ttacattgaa aggtacatgg   2220
ttcgttacac ggaaattttc tccaggatac ctttttttgtt ttcctatttc aacgtcttga   2280
ccttttaaga cttaagtctc gaaagagtag aaaattttta tcccaaataa atctgtgaca   2340
cagtccatcg gagtgataga tgttgaattg tagtagtcta cttctactca tactttacct   2400
tagcggttta taatgactat ggtacttcaa gaaagaaata cacgaactca gagaaggtag   2460
agggtgtgat tgaacacgta actgattacc ttcgtaactt caggttacgt actatggtct   2520
cgtaatgttg tcggtagctc ctgaatatta catgagtacc ctaacaggat acctcgttac   2580
```

```
atttgcattg agttggtcat atataaaatt ctacctttta ctagaaggtg ttttttatgt    2640
cacatgagaa tcgttaggta ataaattatg ttgtagtagt tagtaaaact gttggacata    2700
gggttcgtcg ccagtaagtt ctgtgtctat acgtgaatat gggtatggta atcgtcatta    2760
atgttgtaca taacacgaca tatacttacc ataagacttt acactgtctt ttggtctgtc    2820
ttggttgagg ttaactaacc gagctggccc ttacatgata gatgcatgct ttgggcgtag    2880
gcgagggtaa gttaagtgta acctgttcct attttatttt ggtgaccacc aaacgctaag    2940
gctttagaca tgtagtacgt caccaatttg ttttttgtaaa aataagagtt tactctatttt   3000 cactttata tatagtaata taatgtttca tgttaataaa tccaaattag ttagggcgcc    3060
cgataccgag ggtcgtcggg ggccgggcgc gacgggcgtg aggaccagga cgagccccga    3120
gacaagggtc ctggaccgtt acgggtctgt agacacaggg ggagttttca gtaggacggg    3180
gcccctccga ggcacgacca ctgtacgtcg tggaggacac tggtcgggtt caacaacccg    3240
tatctctggg gcaacggatt tttcctcaac gaggacggaa ccttgttggc cttccacata    3300
cttgactcgt tacacgttct tctatcggtt ggttacacga taagtttgac gggactaccc    3360
gtcagttgtc gattttggaa ggagtggcac atgacctgag gtcttgccca ccttgaccgt    3420
ggggagggga gaaccgtcgg tcacccgttc ttggaatggg atgcgacggt ccacctccca    3480
ccccgtgggg cccggttgga gtggcaccac gacgaggcac ccctcttcct cgactttgcc    3540
ctcggtcgac accccctcgg gcgactccag tgctggtgcc acgaccactc ctctctagtg    3600
gtacctcggt taaagagcac ggcgtgactt gacctgacg ccggggttcc cgacctcgac     3660
aaactcttgt ggagccgggg gatggtcgag gtctggaaac aggacggtcg ctgaggggt     3720 gttgaacagt cgggggccca ggatctccac ctgtgcgtcc cctggcacca gacaagggac    3780
ctgcccgaca agggtcagag cctccgggtc caggtggacc gtgaccccct ggtctccaac    3840
ttggggtgtc agtggatacc gttgctgagg aagagccggt tccggagtca gtcacactgg    3900
cgtctcctgc tcccgtgggt cgccgactgc acacgtcatt atgacccctt ggtctcggtc    3960
ctctgtgacg tctgtcactg gtagatgtcg aaaggccgcg ggttgcacta agactgcttc    4020
ggtctccaga gtcttccctg gctccactgt cacttcacac tccgggtggg atctcggttc    4080
cactgcgact taccccaagg tcgggtcggt gacccgggct cccgggtcga ggacgacttc    4140 cggtgggtc tcctgttgcc cgcgtcgaag aggacgagac gttgggacct ccaccggccg    4200
gtcgaatatg tgttcttggt ctgggccctc gaagcacagg acataccggg ggctgacctg    4260
ctctccctaa caggcccttt gacctgcacc ggtcttttaa gggtcgtctg aggttacacg    4320
gtccgaaccc ccttgggtaa cgggctcgag ttcacagatt tcctaccgtg aaagggtgac    4380
gggtagcccc ttagtcactg acagtgagct ctagaactcc cgtggatgga gacagcccgg    4440
tcctcgtgag ttcccctcca gtgggcgctc cactggcact tacacgagag gggggccata    4500
ctctaacagt agtagtgaca ccatcgtcgg cgtcagtatt acccgtgacg tccggagtcg    4560
tgcatggaga tattggcggt cgccttctag ttctttatgt ctgatgttgt ccgggttttt    4620
ccctgggggt actttggctt gtgtgttcgg tgcggaggga ctcgtacgta catcgaattt    4680
ttaactttaa aataaaaaaa aaaacctta tatttattcg agcttcagct ttaaggacgt    4740
cgggccccgg taccggtgt gtgcctccgt cccttgtagt ggtaggttca caggtatgga    4800
gttaaagaaa gtcgagaacc acgaccgacc agaaagagtg aagacaagtc cacaataggt    4860
gcactggttc cttcacttc ttcaccgttg cgacaggaca ccagtgttac aaagacaact    4920
```

```
tctcgaccgt gtttgagcgt agatgaccgt tttcctcttc ttttaccacg actgatacta    4980
cagacctctg tacttatata ccgggctcat gttcttggcc tggtagaaac tatagtgatt    5040
attggagagg taacactagg accgagacgc gggtagactg ctcccgtgta tgctcacaca    5100
acaagacttc atacttttc tgcgaaagtt cgcccttgtg gaccgacttc actgcaatag    5160
tcagtttcga ctgaagggat gtggatcata tagactgaaa ctttaaggtt gaagattata    5220
atcttcctat taaacgagtt ggagacctcc aaaaggtctc ggagtggaga ggaccaacct    5280
tttacctctt cttaatttac ggtagttgtg ttgtcaaagg gttctaggac tttgactcga    5340
gatacgacaa tcgtcgtttg acctaaagtt atactgttgg ttggtgtcga agtacacaga    5400
gtagttcata cctgtaaatt ctcacttagt ctggaagttg accttatgtt ggttcgttct    5460
cgtaaaagga ctattggacg agggtaggac ccggtaatgg aattagagtc atttacctta    5520
aaagcactat acgacggact ggatgacgaa acggggtgcg acgtctctct cttcctcctt    5580
actctctaac tcttcccttt cacatgcggg acatattttc gaaagatcca aaaacaaatc    5640
ccgacgtcct taaggagctc cctagggcta aaaatactga tcaattagtt tattttttcgt    5700
atgttcgata acgaagcgat agcaatgttt taccgtcctt aaaacacatt tgattcggtg    5760
tatgaacggt tacttttttt atcatctttc ctatgataaa attaccctaa tctacaattc    5820
caaggaaccc taatatcatt gacccgtaga caattgaaaa tgctgcaatc caatctatga    5880
ctacaatgtc taatattatt acaatgttat tttatgtact gtcctacact ataaaaagga    5940
gtatattgag aaccttatcg tttataccta gttacactat ctaaactttt aaagttttc     6000
gtttattgac tagttctaaa tgtctgataa agatatcaga catttcttct ctacacaaaa    6060
ggagtctcat tgcggagatt tgtcaaccct cgctttccta cgcgacatca atactttgac    6120
ctccatagac tacttgaatc tcgggattct ttacaagacg acttacgcca tgggacaagc    6180
ttcctgcaca aaccactata gtgtcatcta ttaggcacct taggagtgta ttgtcatcct    6240
atacaattcc tcctgctaca gcttttgttc tttgcggatt acctcacgta caggttcaaa    6300
tccccgttc tttatgttca agatcctacc ataattattc atagattcat aaaccatatt    6360
aaataattta tcatattaat attgtttatt atttattgta ctattgccaa aaataatctt    6420
attttatctc tattatagta ttactatata ttatgaagta atggtcttta ctcattacct    6480
tctgaatatt tacttgacgt atttcgatat tccatatctc tatatttaaa tcattccata    6540
tatgaatttt ttacgtttat gttattgcat ttatatgata gttgcagaaa cataaatcgg    6600
cattcataaa gactatatct ttaccatttt aataatgatc ttgtgccacg gctataaaat    6660
tttacatttt taggaggaga agtatttcga cgatcaaatc tattatgtct ttaacgattt    6720
gatgattatc taagaccgcg actgtatctt gtctatgtaa gacctttatc aggcaatata    6780
taaagacata tatctttgtt attcagtaat tgatctataa ataattttt tccacaatta    6840
acattatcta agaaagattt aataatgcta catgacatac tattctatag actactatac    6900
atattttata aatatctaaa attataacta gaattatatg tttgatcttt aaaactttga    6960
ggcaatgtaa tgcgatattt catattctta tatctaaatt aatcctataa caatctatta    7020
tcataatttt atctatttc aaataaaaac gtatttgtca tagagtattt ccgtgaattt    7080
ttattaacat caatgctata ttatcgcaat gaatatttag tgcctcacgg atatttgctt    7140
gttctactaa atccattttg gggtaatgta gtaagccatt aattatcttc ttttctacat    7200
tgtcgtgaag acaatttaga tcctcgacta tatttgcatt atctactgac atacccgtca    7260
gggaatgtaa tgcgacaaag tgcattgcta tagctttgtt gtttctgtga aaatctttct    7320
```

```
cctagattac aattacacca attattagta tatctatggc aagatttata tcgacaacgt    7380
agatttttgt tttgatatca tttgaataat gacttcatgc catgactatg tttcaaccat    7440
cctaatctat ttgtacaata agtgtatcga tatctttact ttctataatt atatgactta    7500
cgctagaata atataccaac gatacatttg cagatattag tatttccaaa gtgaggagat    7560
atgtaccgtc aatcaagata cttttgtctt aaacaatttg agaatgaact ggtgccacga    7620
atgcatttac gatttcgatt caatagacct ttatgaggaa atgtatttcg atacaataga    7680
ttatcaaaat tattatattt taatgaaaat agaatattgc ggctgatatt aagagattta    7740
ttagtgccat tatgcggaga ttgaacacaa tcgaaaaatc tactgttcta tcgataatac    7800
tattatagat tttactacaa tctttataga ttttaggac tttatcgatt aagtcttcca    7860
aaatatcatt tgtaccttgt atatttgtca ttattttctg atgatagata ttttcttagt    7920 acgcttttc ttgatctaca atattgtgta tatttcaatt taagatatat aagaaaatta    7980
tagaaagaac tgttattgta tctagaatac catttcaagc attgattagg atctcaatta    8040
ttctatggac gtacatatgc atatatatcc cttaattatg cctttttatt tagtaatcga    8100
aaagtatctg tagtcgatta tcaatttcga cattttctct cattcttaga tccttattat    8160
ccatccaatg gatatctata gtttgtatat tattaccttg ataattcatt attactaaat    8220
gtaagacaat agtggtcgac aacattgggt catcatattt ctcgaggtcg aaaacaaggg    8280
aaatcactcc caattaaggc tcgaaccgca ttagtaccag tatcgacaaa ggacacactt    8340
taacaatagg cgagtgttaa ggtgtgttgt atgctcggcc ttcgtatttc acatttcgga    8400
ccccacggat tactcactcg attgagtgta attaacgcaa cgcgagtgac gggcgaaagg    8460
tcagcccttt ggacagcacg gtcgacgtaa ttacttagcc ggttgcgcgc ccctctccgc    8520
caaacgcata acccgcgaga aggcgaagga gcgagtgact gagcgacgcg agccagcaag    8580
ccgacgccgc tcgccatagt cgagtgagtt tccgccatta tgccaatagg tgtcttagtc    8640
ccctattgcg tccttttcttg tacactcgtt ttccggtcgt tttccggtcc ttggcatttt    8700
tccggcgcaa cgaccgcaaa aaggtatccg aggcggggg actgctcgta gtgtttttag    8760
ctgcgagttc agtctccacc gctttgggct gtcctgatat ttctatggtc cgcaaagggg    8820
gaccttcgag ggagcacgcg agaggacaag gctgggacgg cgaatggcct atggacaggc    8880
ggaaagaggg aagcccttcg caccgcgaaa gagtatcgag tgcgacatcc atagagtcaa    8940
gccacatcca gcaagcgagg ttcgacccga cacacgtgct tgggggcaa gtcgggctgg    9000 cgacgcggaa taggccattg atagcagaac tcaggttggg ccattctgtg ctgaatagcg    9060
gtgaccgtcg tcggtgacca ttgtcctaat cgtctcgctc catacatccg ccacgatgtc    9120
tcaagaactt caccaccgga ttgatgccga tgtgatcttc ctgtcataaa ccatagacgc    9180
gagacgactt cggtcaatgg aagccttttt ctcaaccatc gagaactagg ccgtttgttt    9240
ggtggcgacc atcgccacca aaaaacaaa cgttcgtcgt ctaatgcgcg tcttttttc    9300 ctagagttct tctaggaaac tagaaagat gccccagact gcgagtcacc ttgctttttga    9360 gtgcaattcc ctaaaaccag tactctaata gttttctta gaagtggatc taggaaaatt    9420 taattttac ttcaaaattt agttagattt catatatact catttgaacc agactgtcaa    9480
tggttacgaa ttagtcactc cgtggataga gtcgctagac agataaagca agtaggtatc    9540
aacggactga ggggcagcac atctattgat gctatgccct cccgaatggt agaccggggt    9600
cacgacgtta ctatggcgct ctgggtgcga gtggccgagg tctaaatagt cgttatttgg    9660
```

```
tcggtcggcc ttcccggctc gcgtcttcac caggacgttg aaataggcgg aggtaggtca   9720
gataattaac aacggcccttt cgatctcatt catcaagcgg tcaattatca aacgcgttgc   9780
aacaacggta acgatgtccg tagcaccaca gtgcgagcag caaaccatac cgaagtaagt   9840
cgaggccaag ggttgctagt tccgctcaat gtactagggg gtacaacacg tttttttcgcc  9900 aatcgaggaa gccaggaggc tagcaacagt cttcattcaa ccggcgtcac aatagtgagt  9960
accaataccg tcgtgacgta ttaagagaat gacagtacgg taggcattct acgaaaagac  10020
actgaccact catgagttgg ttcagtaaga ctcttatcac atacgccgct ggctcaacga  10080
gaacgggccg cagttatgcc ctattatggc gcggtgtatc gtcttgaaat tttcacgagt  10140
agtaaccttt tgcaagaagc cccgcttttg agagttccta gaatggcgac aactctaggt  10200
caagctacat tgggtgagca cgtgggttga ctagaagtcg tagaaaatga aagtggtcgc  10260
aaagacccac tcgttttttgt ccttccgttt tacggcgttt tttcccttat tcccgctgtg  10320
cctttacaac ttatgagtat gagaaggaaa aagttataat aacttcgtaa atagtcccaa  10380
taacagagta ctcgcctatg tataaactta cataaatctt tttatttgtt tatccccaag  10440
gcgcgtgtaa aggggctttt cacggtggac                                   10470
```

<210> SEQ ID NO 3
<211> LENGTH: 11154
<212> TYPE: DNA
<213> ORGANISM: Artificial Sequence
<220> FEATURE:
<223> OTHER INFORMATION: Canarypox virus (ALVAC) and Homo sapiens

<400> SEQUENCE: 3

```
tgaatgttaa atgttatact ttggatgaag ctataaatat gcattggaaa aataatccat     60
ttaaagaaag gattcaaata ctacaaaacc taagcgataa tatgttaact aagcttattc    120
ttaacgacgc tttaaatata cacaaataaa cataattttt gtataaccta acaaataact    180
aaaacataaa aataataaaa ggaaatgtaa tatcgtaatt attttactca ggaatggggt    240
taaatattta tatcacgtgt atatctatac tgttatcgta tactctttac aattactatt    300
acgaatatgc aagagataat aagattacgt atttaagaga atcttgtcat gataattggg    360
tacgacatag tgataaatgc tatttcgcat cgttacataa agtcagttgg aaagatggat    420
ttgacagatg taacttaata ggtgcaaaaa tgttaaataa cagcattcta tcggaagata    480
ggataccagt tatattatac aaaaatcact ggttggataa aacagattct gcaatattcg    540
taaaagatga agattactgc gaatttgtaa actatgacaa taaaaagcca tttatctcaa    600
cgacatcgtg taattcttcc atgtttttatg tatgtgtttc agatattatg agattactat    660
aaactttttg tatacttata ttccgtaaac tatattaatc atgaagaaaa tgaaaaagta    720
tagaagctgt tcacgagcgg ttgttgaaaa caacaaaatt atacattcaa gatggcttac    780
atatacgtct gtgaggctat catggataat gacaatgcat ctctaaatag gttttttggac    840 aatggattcg accctaacac ggaatatggt actctacaat ctcctcttga aatggctgta    900
atgttcaaga ataccgaggc tataaaaatc ttgatgaggt atggagctaa acctgtagtt    960
actgaatgca caacttcttg tctgcatgat gcggtgttga gagacgacta caaaatagtg   1020
aaagatctgt tgaagaataa ctatgtaaac aatgttcttt acagcggagg ctttactcct   1080
ttgtgtttgg cagcttacct taacaaagtt aatttggtta aacttctatt ggctcattcg   1140
gcggatgtag atatttcaaa cacgatcgg ttaactcctc tacatatagc cgtatcaaat   1200
aaaaatttaa caatggttaa acttctattg aacaaaggtg ctgatactga cttgctggat   1260
```

```
aacatgggat gtactccttt aatgatcgct gtacaatctg gaaatattga aatatgtagc    1320
acactactta aaaaaaataa aatgtccaga actgggaaaa attgatcttg ccagctgtaa    1380
ttcatggtag aaaagaagtg ctcaggctac ttttcaacaa aggagcagat gtaaactaca    1440
tctttgaaag aaatggaaaa tcatatactg ttttggaatt gattaaagaa agttactctg    1500
agacacaaaa gaggtagctg aagtggtact ctcaaaggta cgtgactaat tagctataaa    1560
aaggatcggc cgctctagaa ctagtggatc gggttcttta ttctatactt aaaaagtgaa    1620
aataaataca aaggttcttg agggttgtgt taaattgaaa gcgagaaata atcataaatt    1680
atttcattat cgcgatatcc gttaagtttg tatcgtaccc cgatccccg agccatgcag     1740 gccgaaggcc ggggcacagg gggttcgacg ggcgatgctg atgcccagg aggccctggc     1800 attcctgatg gcccaggggg caatgctggc ggcccaggag aggcgggtgc cacgggcggc    1860
agaggtcccc ggggcgcagg ggcagcaagg gcctcggggc cgggaggagg cgcccgcgg    1920 ggtccgcatg gcgcgcggc ttcagggctg aatggatgct gcagatgcgg ggccagggg    1980 ccggagagcc gcctgcttga gttctacctc gccatgcctt tcgcgacacc catagcttga    2040
tatcgaattc taggggatc cactagttct agaggatcat tatttaacgt aaactaaatg    2100
gaaaagctat ttacaggtac atacggtgtt tttctggaat caaatgattc tgattttgag    2160
gattttatca atacaataat gacagtgcta actggtaaaa aagaaagcaa acaattatca    2220
tggctaacaa ttttttattat atttgtagta tgcatagtgg tctttacgtt tctttattta    2280
aagttaatgt gttaagatta aatggagtaa ttggatcccc catcgatggg gaattcactg    2340
gccgtcgttt tacaacgtcg tgactgggaa accctggcg ttacccaact taatcgcctt     2400
gcagcacatc ccccttttcgc cagctggcgt aatagcgaag aggcccgcac cgatcgccct    2460
tcccaacagt tgcgcagcct gaatggcgaa tggcgctttg cctggttttcc ggcaccagaa    2520 gcggtgccgg aaagctggct ggagtgcgat cttcctgagg ccgatactgt cgtcgtcccc    2580
tcaaactggc agatgcacgg ttacgatgcg cccatctaca ccaacgtgac ctatcccatt    2640
acggtcaatc cgccgtttgt tcccacgag aatccgacgg ttgttactc gctcacatt       2700 aatgttgatg aaagctggct acaggaaggc cagacgcgaa ttattttga tggcgttaac    2760 tcggcgtttc atctgtggtg caacgggcgc tgggtcggtt acggccagga cagtcgtttg    2820
ccgtctgaat ttgacctgag cgcattttta cgcgccggag aaaaccgcct cgcggtgatg    2880
gtgctgcgct ggagtgacgg cagttatctg gaagatcagg atatgtggcg gatgagcggc    2940
attttccgtg acgtctcgtt gctgcataaa ccgactacac aaatcagcga tttccatgtt    3000
gccactcgct ttaatgatga tttcagccgc gctgtactgg aggctgaagt tcagatgtgc    3060
ggcgagttgc gtgactacct acgggtaaca gtttctttat ggcagggtga acgcaggtc     3120 gccagcggca ccgcgccttt cggcggtgaa attatcgatg agcgtggtgg ttatgccgat    3180
cgcgtcacac tacgtctgaa cgtcgaaaac ccgaaactgt ggagcgccga atcccgaat    3240 ctctatcgtg cggtggttga actgcacacc gccgacggca cgctgattga agcagaagcc    3300
tgcgatgtcg gtttccgcga ggtgcggatt gaaaatggtc tgctgctgct gaacggcaag    3360
ccgttgctga ttcgaggcgt taaccgtcac gagcatcatc tctgcatgg tcaggtcatg     3420 gatgagcaga cgatggtgca ggatatcctg ctgatgaagc agaacaactt taacgccgtg    3480
cgctgttcgc attatccgaa ccatccgctg tggtacacgc tgtgcgaccg ctacggcctg    3540
tatgtggtgg atgaagccaa tattgaaacc cacggcatgg tgccaatgaa tcgtctgacc    3600
```

```
gatgatccgc gctggctacc ggcgatgagc gaacgcgtaa cgcgaatggt gcagcgcgat    3660
cgtaatcacc cgagtgtgat catctggtcg ctggggaatg aatcaggcca cggcgctaat    3720
cacgacgcgc tgtatcgctg gatcaaatct gtcgatcctt cccgcccggt gcagtatgaa    3780
ggcggcggag ccgacaccac ggccaccgat attatttgcc cgatgtacgc gcgcgtggat    3840
gaagaccagc ccttcccggc tgtgccgaaa tggtccatca aaaaatggct ttcgctacct    3900
ggagagacgc gcccgctgat cctttgcgaa tacgcccacg cgatgggtaa cagtcttggc    3960
ggtttcgcta atactggca ggcgtttcgt cagtatcccc gtttacaggg cggcttcgtc    4020
tgggactggg tggatcagtc gctgattaaa tatgatgaaa acggcaaccc gtggtcggct    4080
tacggcggtg attttggcga tacgccgaac gatcgccagt tctgtatgaa cggtctggtc    4140
tttgccgacc gcacgccgca tccagcgctg acggaagcaa acaccagca gcagtttttc    4200
cagttccgtt tatccgggca aaccatcgaa gtgaccagcg aatacctgtt ccgtcatagc    4260
gataacgagc tcctgcactg gatggtggcg ctggatggta agccgctggc aagcggtgaa    4320
gtgcctctgg atgtcgctcc acaaggtaaa cagttgattg aactgcctga actaccgcag    4380
ccggagagcg ccgggcaact ctggctcaca gtacgcgtag tgcaaccgaa cgcgaccgca    4440
tggtcagaag ccgggcacat cagcgcctgg cagcagtggc gtctggcgga aaacctcagt    4500
gtgacgctcc ccgccgcgtc ccacgccatc ccgcatctga ccaccagcga aatggatttt    4560
tgcatcgagc tgggtaataa gcgttggcaa tttaaccgcc agtcaggctt tctttcacag    4620
atgtggattg gcgataaaaa acaactgctg acgccgctgc gcgatcagtt cacccgtgca    4680
ccgctggata cgacattggg cgtaagtgaa gcgacccgca ttgaccctaa cgcctgggtc    4740
gaacgctgga aggcggcggg ccattaccag gccgaagcag cgttgttgca gtgcacggca    4800
gatacacttg ctgatgcggt gctgattacg accgctcacg cgtggcagca tcaggggaaa    4860
accttattta tcagccggaa aacctaccgg attgatggta gtggtcaaat ggcgattacc    4920
gttgatgttg aagtgcgag cgatacaccg catccgcgc ggattggcct gaactgccag    4980
ctggcgcagg tagcagagcg ggtaaactgg ctcggattag gccgcaaga aaactatccc    5040
gaccgcctta ctgccgcctg ttttgaccgc tgggatctgc cattgtcaga catgtatacc    5100
ccgtacgtct tcccgagcga aaacggtctg cgctgcggga cgcgcgaatt gaattatggc    5160
ccacaccagt ggcgcggcga cttccagttc aacatcagcc ggtacagtca acagcaattg    5220
atggaaacca gccattcgcc atctgctgca cgcggaagag gcacatggct gaatatcgac    5280
ggtttccata tggggattgg tggcgacgac tcctggagcc cgtcagtatc ggcggaattc    5340
cagctgagcg ccggtcgcta ccattaccag ttggtctggt gtcaaaaata ataataaccg    5400
ggcaggggg atccggagct tatcgcagat caattcgata tcaagcttat cgataccgtc    5460
gacggtatcg ataagctcta gtggagggtt ctttattcta tacttaaaaa gtgaaaataa    5520
atacaaaggt tcttgagggt tgtgttaaat tgaaagcgag aaataatcat aaattatttc    5580
attatcgcga tatccgttaa gtttgtatcg tacccccccc gagccatgca ggccgaaggc    5640
cggggcacag ggggttcgac gggcgatgct gatgcccag gaggccctgg cattcctgat    5700
ggcccagggg gcaatgctgg cggcccagga gaggcgggtg ccacgggcgg cagaggtccc    5760
cggggcgcag gggcagcaag ggcctcgggg ccgggaggag gcgccccgcg gggtccgcat    5820
ggcggcgcg cttcagggct gaatggatgc tgcagatgcg gggccagggg gccggagagc    5880
cgcctgcttg agttctacct cgccatgcct ttcgcgacac ccatggaagc agagctggcc    5940
cgcaggagcc tggcccagga tgccccaccg cttcccgtgc caggggtgct tctgaaggag    6000
```

```
ttcactgtgt ccggcaacat actgactatc cgactgactg ctgcagacca ccgccaactg    6060
cagctctcca tcagctcctg tctccagcag cttteectgt tgatgtggat cacgcaggtg    6120
tttctgcccg tgttttttggc tcagcctccc tcagggcaga ggcgctaagt aattaattt     6180 tttttgggct gcaggatcgc tagcaaaaat tgaaattta ttttttttt ttggaatata     6240 aataagctcg aagctcgagc catgagcccc ctttggtggg ggtttctgct cagttgcttg    6300
ggctgcaaaa tcctgccagg agcccagggt cagttccccc gagtctgcat gacggtggac    6360
agcctagtga caaggagtg ctgcccacgc ctgggtgcag agtcggccaa tgtctgtggc     6420
tctcagcaag gccgggggca gtgcacagag gtgcgagccg acacaaggcc ctggagtggt    6480
ccctacatcc tacgaaacca ggatgaccgt gagctgtggc caagaaaatt cttccaccgg    6540
acctgcaagt gcacaggaaa cttgccggc tataattgtg gagactgcaa gtttggctgg     6600
accggtccca actgcgagcg aagaaaacca ccagtgattc ggcagaacat ccattccttg    6660
agtcctcagg aaagagagca gttcttgggc gccttagatc tcgcgaagaa gagagtacac    6720
cccgactacg tgatcaccac acaacactgg ctgggcctgc ttgggcccaa tggaacccag    6780
ccgcagtttg ccaactgcag tgtttatgat ttcttcgtgt ggctccatta ttattctgtt    6840
agagatacat tattaggacc aggacgcccc tacagggcca tagatttctc acatcaagga    6900
cctgcatttg ttacctggca ccggtaccat tgttgtgtc tggaaagaga tctccagcga     6960
ctcattggca atgagtcttt tgcttgccc tactggaact ttgccactgg gaggaacgag     7020
tgtgatgtgt gtacagacca gctgtttggg gcagcgagac cagacgatcc gactctgatt    7080
agtcggaact caagattctc cagctgggaa actgtctgtg atagcttgga tgactacaac    7140
cacctggtca ccttgtgcaa tggaacctat gaaggtttgc tgagaagaaa tcaaatggga    7200
agaaacagca tgaaattgcc aaccttaaaa gacatacgag attgcctgtc tctccagaag    7260
tttgacaatc ctcccttctt ccagaactct acctcagtt tcaggaatgc tttggaaggg    7320
tttgataaag cagatgggac tctggattct caagtgatga gccttcataa tttggttcat    7380
tccttcctga acgggacaaa cgctttgcca cattcagccg ccaatgatcc catcttcgtg    7440
gtgatttcta atcgtttgct ttacaatgct acaacaaaca tccttgaaca tgtaagaaaa    7500
gagaaagcga ccaaggaact cccttccctg catgtgctgg ttcttcattc ctttactgat    7560 gccatcttg atgagtggat gaaaagattt aatcctctg cagatgcctg gcctcaggag     7620 ctggcccca ttggtcacaa tcggatgtac aacatggttc ctttcttccc tccagtgact     7680
aatgaagaac tctttttaac ctcagaccaa cttggctaca gctatgccat cgatctgcca    7740
gtttcagttg aagaaactcc aggttggccc acaactctct tagtagtcat gggaacactg    7800
gtggctttgg ttggtctgtt cgtgctgttg gcttttcttc aatatagaag acttcgaaaa    7860
ggatatacac ccctaatgga gacacattta agcagcaaga gatacacaga agaagcctag    7920 tttttaatt aagcatgctc tagaatcgat cccgggtttt tatgactagt taatcacggc     7980
cgcttataaa gatctaaaat gcataatttc taaataatga aaaaaagta catcatgagc     8040 aacgcgttag tatattttac aatggagatt aacgctctat accgttctat gtttatgat    8100 tcagatgatg ttttagaaaa gaagttatt gaatatgaaa actttaatga agatgaagat    8160
gacgacgatg attattgttg taaatctgtt ttagatgaag aagatgacgc gctaaagtat    8220
actatggtta caagtataa gtctatacta ctaatggcga cttgtgcaag aaggtatagt    8280
atagtgaaaa tgttgttaga ttatgattat gaaaaaccaa ataaatcaga tccatatcta    8340
```

```
aaggtatctc ctttgcacat aatttcatct attcctagtt tagaatactt ttcattatat    8400
ttgtttacag ctgaagacga aaaaaatata tcgataatag aagattatgt taactctgct    8460
aataagatga aattgaatga gtctgtgact gcagccaagc ttggcactgg ccgtcgtttt    8520
acaacgtcgt gactgggaaa accctggcgt tacccaactt aatcgccttg cagcacatcc    8580
cccttccgcc agctggcgta atagcgaaga ggcccgcacc gatcgccctt cccaacagtt    8640
gcgcagcctg aatggcgaat ggcgcctgat gcggtatttt ctccttacgc atctgtgcgg    8700
tatttcacac cgcatatggt gcactctcag tacaatctgc tctgatgccg catagttaag    8760
ccagccccga cacccgccaa cacccgctga cgcgccctga cgggcttgtc tgctcccggc    8820
atccgcttac agacaagctg tgaccgtctc cgggagctgc atgtgtcaga ggttttcacc    8880
gtcatcaccg aaacgcgcga gacgaaaggg cctcgtgata cgcctatttt tataggttaa    8940
tgtcatgata ataatggttt cttagacgtc aggtggcact tttcgggaa atgtgcgcgg    9000 aaccctatt tgtttatttt tctaaataca ttcaaatatg tatccgctca tgagacaata    9060
accctgataa atgcttcaat aatattgaaa aaggaagagt atgagtattc aacatttccg    9120
tgtcgccctt attccctttt ttgcggcatt ttgccttcct gttttgctc acccagaaac    9180 gctggtgaaa gtaaaagatg ctgaagatca gttgggtgca cgagtgggtt acatcgaact    9240
ggatctcaac agcggtaaga tccttgagag ttttcgcccc gaagaacgtt ttccaatgat    9300
gagcactttt aaagttctgc tatgtggcgc ggtattatcc cgtattgacg ccgggcaaga    9360
gcaactcggt cgccgcatac actattctca gaatgacttg gttgagtact caccagtcac    9420
agaaaagcat cttacggatg gcatgacagt aagagaatta tgcagtgctg ccataaccat    9480
gagtgataac actgcggcca acttacttct gacaacgatc ggaggaccga aggagctaac    9540
cgcttttttg cacaacatgg gggatcatgt aactcgcctt gatcgttggg aaccggagct    9600
gaatgaagcc ataccaaacg acgagcgtga ccacacgatg cctgtagcaa tggcaacaac    9660
gttgcgcaaa ctattaactg gcgaactact tactctagct tcccggcaac aattaataga    9720
ctggatggag gcggataaag ttgcaggacc acttctgcgc tcggcccttc cggctggctg    9780
gtttattgct gataaatctg gagccggtga gcgtgggtct cgcggtatca ttgcagcact    9840
ggggccagat ggtaagccct cccgtatcgt agttatctac acgacgggga gtcaggcaac    9900
tatggatgaa cgaaatagac agatcgctga gataggtgcc tcactgatta agcattggta    9960
actgtcagac caagtttact catatatact ttagattgat ttaaaacttc atttttaatt   10020
taaaaggatc taggtgaaga tcctttttga atctcatg accaaaatcc cttaacgtga   10080
gttttcgttc cactgagcgt cagacccgt agaaaagatc aaaggatctt cttgagatcc   10140 ttttttctg cgcgtaatct gctgcttgca acaaaaaaa ccaccgctac cagcggtggt   10200
ttgtttgccg gatcaagagc taccaactct ttttccgaag gtaactggct tcagcagagc   10260
gcagatacca aatactgtcc ttctagtgta gccgtagtta ggccaccact tcaagaactc   10320
tgtagcaccg cctacatacc tcgctctgct aatcctgtta ccagtggctg ctgccagtgg   10380
cgataagtcg tgtcttaccg ggttggactc aagacgatag ttaccggata aggcgcagcg   10440
gtcgggctga acgggggtt cgtgcacaca gcccagcttg gagcgaacga cctacaccga   10500
actgagatac ctacagcgtg agctatgaga aagcgccacg cttcccgaag ggagaaaggc   10560
ggacaggtat ccggtaagcg gcagggtcgg aacaggagag cgcacgaggg agcttccagg   10620
gggaaacgcc tggtatcttt atagtcctgt cgggtttcgc cacctctgac ttgagcgtcg   10680
atttttgtga tgctcgtcag gggggcggag cctatggaaa aacgccagca acgcggcctt   10740
```

| | | | | |
|---|---|---|---|---|
| tttacggttc | ctggccttttt | gctggccttt | tgctcacatg | ttctttcctg cgttatcccc | 10800 |
| tgattctgtg | gataaccgta | ttaccgcctt | tgagtgagct | gataccgctc gccgcagccg | 10860 |
| aacgaccgag | cgcagcgagt | cagtgagcga | ggaagcggaa | gagcgcccaa tacgcaaacc | 10920 |
| gcctctcccc | gcgcgttggc | cgattcatta | atgcagctgg | cacgacaggt ttcccgactg | 10980 |
| gaaagcgggc | agtgagcgca | acgcaattaa | tgtgagttag | ctcactcatt aggcacccca | 11040 |
| ggctttacac | tttatgcttc | cggctcgtat | gttgtgtgga | attgtgagcg ataacaatt | 11100 |
| tcacacagga | aacagctatg | accatgatta | cgaattgaat | tgcggccgca attc | 11154 |

<210> SEQ ID NO 4
<211> LENGTH: 11154
<212> TYPE: DNA
<213> ORGANISM: Artificial Sequence
<220> FEATURE:
<223> OTHER INFORMATION: Canarypox virus (ALVAC) and Homo sapiens

<400> SEQUENCE: 4

| | | | | | |
|---|---|---|---|---|---|
| acttacaatt | tacaatatga | aacctacttc | gatatttata | cgtaaccttt ttattaggta | 60 |
| aatttctttc | ctaagtttat | gatgttttgg | attcgctatt | atacaattga ttcgaataag | 120 |
| aattgctgcg | aaatttatat | gtgtttattt | gtattaaaaa | catattggat tgtttattga | 180 |
| ttttgtattt | ttattatttt | cctttacatt | atagcattaa | taaaatgagt ccttacccca | 240 |
| atttataaat | atagtgcaca | tatagatatg | acaatagcat | atgagaaatg ttaatgataa | 300 |
| tgcttatacg | ttctctatta | ttctaatgca | taaattctct | tagaacagta ctattaaccc | 360 |
| atgctgtatc | actatttacg | ataaagcgta | gcaatgtatt | tcagtcaacc tttctaccta | 420 |
| aactgtctac | attgaattat | ccacgttttt | acaatttatt | gtcgtaagat agccttctat | 480 |
| cctatggtca | atataatatg | ttttagtga | ccaacctatt | ttgtctaaga cgttataagc | 540 |
| attttctact | tctaatgacg | cttaaacatt | tgatactgtt | atttttcggt aaatagagtt | 600 |
| gctgtagcac | attaagaagg | tacaaaatac | atacacaaag | tctataatac tctaatgata | 660 |
| tttgaaaaac | atatgaatat | aaggcatttg | atataattag | tacttctttt actttttcat | 720 |
| atcttcgaca | agtgctcgcc | aacaactttt | gttgttttaa | tatgtaagtt ctaccgaatg | 780 |
| tatatgcaga | cactccgata | gtacctatta | ctgttacgta | gagatttatc caaaaacctg | 840 |
| ttacctaagc | tgggattgtg | ccttatacca | tgagatgtta | gaggagaact ttaccgacat | 900 |
| tacaagttct | tatggctccg | atatttttag | aactactcca | tacctcgatt tggacatcaa | 960 |
| tgacttacgt | gttgaagaac | agacgtacta | cgccacaact | ctctgctgat gttttatcac | 1020 |
| tttctagaca | acttcttatt | gatacatttg | ttacaagaaa | tgtcgcctcc gaaatgagga | 1080 |
| aacacaaacc | gtcgaatgga | attgtttcaa | ttaaccaat | ttgaagataa ccgagtaagc | 1140 |
| cgcctacatc | tataaagttt | gtgcctagcc | aattgaggag | atgtatatcg gcatagttta | 1200 |
| ttttaaattt | gttaccaatt | tgaagataac | ttgtttccac | gactatgact gaacgaccta | 1260 |
| ttgtacccta | catgaggaaa | ttactagcga | catgttagac | ctttataact ttatacatcg | 1320 |
| tgtgatgaat | ttttttatt | ttacaggtct | tgacccttt | taactagaac ggtcgacatt | 1380 |
| aagtaccatc | ttttcttcac | gagtccgatg | aaaagttgtt | tcctcgtcta catttgatgt | 1440 |
| agaaactttc | tttaccttt | agtatatgac | aaaaccttaa | ctaatttctt tcaatgagac | 1500 |
| tctgtgttt | ctccatcgac | ttcaccatga | gagtttccat | gcactgatta atcgatattt | 1560 |
| ttcctagccg | gcgagatctt | gatcacctag | cccaagaaat | aagatatgaa tttttcactt | 1620 |

```
ttatttatgt tttccaagaac tcccaacaca atttaacttt cgctctttat tagtatttaa   1680
taaagtaata gcgctatagg caattcaaac atagcatggg gctagggggc tcggtacgtc   1740
cggcttccgg ccccgtgtcc cccaagctgc ccgctacgac taccgggtcc tccgggaccg   1800
taaggactac cgggtccccc gttacgaccg ccgggtcctc tccgcccacg gtgcccgccg   1860
tctccagggg ccccgcgtcc ccgtcgttcc cggagccccg gccctcctcc gcggggcgcc   1920
ccaggcgtac cgccgcgccg aagtcccgac ttacctacga cgtctacgcc ccggtccccc   1980
ggcctctcgg cggacgaact caagatggag cggtacggaa agcgctgtgg gtatcgaact   2040
atagcttaag atcccctag gtgatcaaga tctcctagta ataaattgca tttgatttac   2100
cttttcgata aatgtccatg tatgccacaa aaagaccttaa gtttactaag actaaaactc   2160
ctaaaatagt tatgttatta ctgtcacgat tgaccatttt ttctttcgtt tgttaatagt   2220
accgattgtt aaaaataata taaacatcat acgtatcacc agaaatgcaa agaaataaat   2280
ttcaattaca caattctaat ttacctcatt aacctagggg gtagctaccc cttaagtgac   2340
cggcagcaaa atgttgcagc actgacccctt ttgggaccgc aatgggttga attagcggaa   2400
cgtcgtgtag ggggaaagcg gtcgaccgca ttatcgcttc tccgggcgtg gctagcggga   2460
agggttgtca acgcgtcgga cttaccgctt accgcgaaac ggaccaaagg ccgtggtctt   2520
cgccacggcc tttcgaccga cctcacgcta aaggactcc ggctatgaca gcagcagggg   2580
agtttgaccg tctacgtgcc aatgctacgc gggtagatgt ggttgcactg gatagggtaa   2640
tgccagttag gcggcaaaca agggtgcctc ttaggctgcc caacaatgag cgagtgtaaa   2700
ttacaactac tttcgaccga tgtccttccg gtctgcgctt aataaaaact accgcaattg   2760
agccgcaaag tagacaccac gttgcccgcg acccagccaa tgccggtcct gtcagcaaac   2820
ggcagactta aactggactc gcgtaaaaat gcgcggcctc ttttggcgga gcgccactac   2880
cacgacgcga cctcactgcc gtcaatagac cttctagtcc tatacaccgc ctactcgccg   2940
taaaaggcac tgcagagcaa cgacgtattt ggctgatgtg tttagtcgct aaaggtacaa   3000
cggtgagcga aattactact aaagtcggcg cgacatgacc tccgacttca agtctacacg   3060
ccgctcaacg cactgatgga tgcccattgt caaagaaata ccgtcccact ttgcgtccag   3120
cggtcgccgt ggcgcggaaa gccgccactt taatagctac tcgcaccacc aatacggcta   3180
gcgcagtgtg atgcagactt gcagcttttg ggctttgaca cctcgcggct ttagggctta   3240
gagatagcac gccaccaact tgacgtgtgg cggctgccgt gcgactaact tcgtcttcgg   3300
acgctacagc caaaggcgct ccacgcctaa ctttttaccag acgacgacga cttgccgttc   3360
ggcaacgact aagctccgca attggcagtg ctcgtagtag gagacgtacc agtccagtac   3420
ctactcgtct gctaccacgt cctataggac gactacttcg tcttgttgaa attgcggcac   3480
gcgacaagcg taataggctt ggtaggcgac accatgtgcg acacgctggc gatgccggac   3540
atacaccacc tacttcggtt ataactttgg gtgccgtacc acggttactt agcagactgg   3600
ctactaggcg cgaccgatgg ccgctactcg cttgcgcatt gcgcttacca cgtcgcgcta   3660
gcattagtgg gctcacacta gtagaccagc gaccccttac ttagtccggt gccgcgatta   3720
gtgctgcgcg acatagcgac ctagtttaga cagctaggaa gggcgggcca cgtcatactt   3780
ccgccgcctc ggctgtggtg ccggtggcta ataaaacgg gctacatgcg cgcgcaccta   3840
cttctggtcg ggaagggccg acacggcttt accaggtagt ttttaccgaa aagcgatgga   3900
cctctctgcg cgggcgacta ggaaacgctt atgcgggtgc gctacccatt gtcagaaccg   3960
ccaaagcgat ttatgaccgt ccgcaaagca gtcataggg caaatgtccc gccgaagcag   4020
```

```
accctgaccc acctagtcag cgactaattt atactacttt tgccgttggg caccagccga    4080
atgccgccac taaaaccgct atgcggcttg ctagcggtca agacatactt gccagaccag    4140
aaacggctgg cgtgcggcgt aggtcgcgac tgccttcgtt ttgtggtcgt cgtcaaaaag    4200
gtcaaggcaa ataggcccgt ttggtagctt cactggtcgc ttatggacaa ggcagtatcg    4260
ctattgctcg aggacgtgac ctaccaccgc gacctaccat tcggcgaccg ttcgccactt    4320 cacgagacc tacagcgagg tgttccattt gtcaactaac ttgacggact tgatggcgtc     4380
ggcctctcgc ggcccgttga gaccgagtgt catgcgcatc acgttggctt gcgctggcgt    4440
accagtcttc ggcccgtgta gtcgcggacc gtcgtcaccg cagaccgcct tttggagtca    4500
cactgcgagg ggcggcgcag ggtgcggtag ggcgtagact ggtggtcgct ttacctaaaa    4560
acgtagctcg acccattatt cgcaaccgtt aaattggcgg tcagtccgaa agaaagtgtc    4620
tacacctaac cgctattttt tgttgacgac tgcggcgacg cgctagtcaa gtgggcacgt    4680
ggcgacctat tgctgtaacc gcattcactt cgctgggcgt aactgggatt gcggacccag    4740
cttgcgacct tccgccgccc ggtaatggtc cggcttcgtc gcaacaacgt cacgtgccgt    4800
ctatgtgaac gactacgcca cgactaatgc tggcgagtgc gcaccgtcgt agtccccttt    4860
tggaataaat agtcggcctt ttggatggcc taactaccat caccagttta ccgctaatgg    4920
caactacaac ttcaccgctc gctatgtggc gtaggccgcg cctaaccgga cttgacggtc    4980
gaccgcgtcc atcgtctcgc ccatttgacc gagcctaatc ccggcgttct tttgataggg    5040
ctggcggaat gacggcggac aaaactggcg accctagacg gtaacagtct gtacatatgg    5100
ggcatgcaga agggctcgct tttgccagac gcgacgccct gcgcgcttaa cttaataccg    5160
ggtgtggtca ccgcgccgct gaaggtcaag ttgtagtcgg ccatgtcagt tgtcgttaac    5220 taccttggt cggtaagcgg tagacgacgt gcgccttctc cgtgtaccga cttatagctg     5280
ccaaaggtat acccctaacc accgctgctg aggacctcgg gcagtcatag ccgccttaag    5340
gtcgactcgc ggccagcgat ggtaatggtc aaccagacca cagttttat tattattggc     5400 ccgtccccc taggcctcga atagcgtcta gttaagctat agttcgaata gctatggcag     5460
ctgccatagc tattcgagat caccctcccaa gaaataagat atgaattttt cacttttatt    5520
tatgtttcca agaactccca acacaattta actttcgctc tttattagta tttaataaag    5580
taatagcgct ataggcaatt caaacatagc atggggggg ctcggtacgt ccggcttccg     5640
gccccgtgtc cccaagctg cccgctacga ctaccgggtc ctccgggacc gtaaggacta     5700
ccgggtcccc cgttacgacc gccgggtcct ctccgcccac ggtgcccgcc gtctccaggg    5760
gccccgcgtc cccgtcgttc ccggagcccc ggccctcctc cgcggggcgc cccaggcgta    5820
ccgccgcgcc gaagtcccga cttacctacg acgtctacgc cccggtcccc cggcctctcg    5880
gcggacgaac tcaagatgga gcggtacgga aagcgctgtg ggtaccttcg tctcgaccgg    5940
gcgtcctcgg accgggtcct acggggtggc gaagggcacg gtcccacga agacttcctc     6000 aagtgacaca ggccgttgta tgactgatag gctgactgac gacgtctggt ggcggttgac    6060
gtcgagaggt agtcgaggac agaggtcgtc gaaagggaca actacaccta gtgcgtccac    6120
aaagacgggc acaaaaaccg agtcggaggg agtcccgtct ccgcgattca ttaattaaaa    6180
aaaaacccga cgtcctagcg atcgtttta actttaaaat aaaaaaaaa aaccttatat      6240 ttattcgagc ttcgagctcg gtactcgggg gaaaccaccc ccaaagacga gtcaacgaac    6300
ccgacgtttt aggacggtcc tcgggtccca gtcaagggg ctcagacgta ctgccacctg     6360
```

```
tcggatcact tgttcctcac gacgggtgcg gacccacgtc tcagccggtt acagacaccg    6420
agagtcgttc cggcccccgt cacgtgtctc cacgctcggc tgtgttccgg gacctcacca    6480
gggatgtagg atgctttggt cctactggca ctcgacaccg gttcttttaa gaaggtggcc    6540
tggacgttca cgtgtccttt gaaacggccg atattaacac ctctgacgtt caaaccgacc    6600
tggccagggt tgacgctcgc cttctttggt ggtcactaag ccgtcttgta ggtaaggaac    6660
tcaggagtcc tttctctcgt caagaacccg cggaatctag agcgcttctt ctctcatgtg    6720
gggctgatgc actagtggtg tgttgtgacc gacccggacg aacccggggtt accttgggtc    6780 ggcgtcaaac ggttgacgtc acaaatacta agaagcaca ccgaggtaat aataagacaa    6840
tctctatgta ataatcctgg tcctgcgggg atgtcccggt atctaaagag tgtagttcct    6900
ggacgtaaac aatggaccgt ggccatggta acaacacag acctttctct agaggtcgct    6960
gagtaaccgt tactcagaaa acgaacggg atgaccttga aacggtgacc ctccttgctc    7020
acactacaca catgtctggt cgacaaaccc cgtcgctctg gtctgctagg ctgagactaa    7080
tcagccttga gttctaagag gtcgacccttt tgacagacac tatcgaacct actgatgttg    7140
gtggaccagt ggaacacgtt accttggata cttccaaacg actcttcttt agtttaccct    7200 tcttttgtcgt actttaacgg ttggaatttt ctgtatgctc taacggacag agaggtcttc    7260
aaactgttag gagggaagaa ggtcttgaga tggaagtcaa agtccttacg aaaccttccc    7320
aaactatttc gtctaccctg agacctaaga gttcactact cggaagtatt aaaccaagta    7380
aggaaggact tgccctgttt gcgaaacggt gtaagtcggc ggttactagg gtagaagcac    7440
cactaaagat tagcaaacga aatgttacga tgttgtttgt aggaacttgt acattctttt    7500
ctctttcgct ggttccttga gggaagggac gtacacgacc aagaagtaag gaaatgacta    7560
cggtagaaac tactccaccta cttttctaaa ttaggaggac gtctacggac cggagtcctc    7620
gaccggggat aaccagtgtt agcctacatg ttgtaccaag gaaagaaggg aggtcactga    7680
ttacttcttg agaaaaattg gagtctggtt gaaccgatgt cgatacggta gctagacggt    7740
caaagtcaac ttctttgagg tccaaccggg tgttgagaga atcatcagta cccttgtgac    7800
caccgaaacc aaccagacaa gcacgacaac cgaaaagaag ttatatcttc tgaagctttt    7860
cctatatgtg gggattacct ctgtgtaaat tcgtcgttct ctatgtgtct tcttcggatc    7920
aaaaaattaa ttcgtacgag atcttagcta gggcccaaaa atactgatca attagtgccg    7980
gcgaatattt ctagattta cgtattaaag atttattact ttttttttcat gtagtactcg    8040 ttgcgcaatc atataaaatg ttacctctaa ttgcgagata tggcaagata caaataacta    8100
agtctactac aaaatctttt ctttcaataa cttatacttt tgaaattact tctacttcta    8160
ctgctgctac taataacaac atttagacaa aatctacttc ttctactgcg cgatttcata    8220
tgataccaat gtttcatatt cagatatgat gattaccgct gaacacgttc ttccatatca    8280
tatcactttt acaacaatct aatactaata cttttttggtt tatttagtct aggtatagat    8340
ttccatagag gaaacgtgta ttaaagtaga taaggatcaa atcttatgaa aagtaatata    8400
aacaaatgtc gacttctgct ttttttatat agctattatc ttctaataca attgagacga    8460
ttattctact ttaacttact cagacactga cgtcggttcg aaccgtgacc ggcagcaaaa    8520
tgttgcagca ctgacccttt tgggaccgca atgggttgaa ttagcggaac gtcgtgtagg    8580
gggaaagcgg tcgaccgcat tatcgcttct ccgggcgtgg ctagcgggaa gggttgtcaa    8640
cgcgtcggac ttaccgctta ccgcggacta cgccataaaa gaggaatgcg tagacacgcc    8700
ataaagtgtg gcgtatacca cgtgagagtc atgttagacg agactacggc gtatcaattc    8760
```

```
ggtcggggct gtgggcggtt gtgggcgact gcgcgggact gcccgaacag acgagggccg    8820
taggcgaatg tctgttcgac actggcagag gccctcgacg tacacagtct ccaaaagtgg    8880
cagtagtggc tttgcgcgct ctgctttccc ggagcactat gcggataaaa atatccaatt    8940
acagtactat tattaccaaa gaatctgcag tccaccgtga aaagccccct tacacgcgcc    9000
ttggggataa acaaataaaa agatttatgt aagtttatac ataggcgagt actctgttat    9060
tgggactatt tacgaagtta ttataacttt ttccttctca tactcataag ttgtaaaggc    9120
acagcgggaa taagggaaaa aacgccgtaa aacggaagga caaaaacgag tgggtctttg    9180
cgaccacttt cattttctac gacttctagt caacccacgt gctcacccaa tgtagcttga    9240
cctagagttg tcgccattct aggaactctc aaaagcgggg cttcttgcaa aaggttacta    9300
ctcgtgaaaa tttcaagacg atacaccgcg ccataatagg gcataactgc ggcccgttct    9360
cgttgagcca gcggcgtatg tgataagagt cttactgaac caactcatga gtggtcagtg    9420
tcttttcgta gaatgcctac cgtactgtca ttctcttaat acgtcacgac ggtattggta    9480
ctcactattg tgacgccggt tgaatgaaga ctgttgctag cctcctggct tcctcgattg    9540
gcgaaaaaac gtgttgtacc ccctagtaca ttgagcggaa ctagcaaccc ttggcctcga    9600
cttacttcgg tatggtttgc tgctcgcact gtggtgctac ggacatcgtt accgttgttg    9660
caacgcgttt gataattgac cgcttgatga atgagatcga agggccgttg ttaattatct    9720
gacctacctc cgcctatttc aacgtcctgg tgaagacgcg agccgggaag gccgaccgac    9780
caaataacga ctatttagac ctcggccact cgcacccaga gcgccatagt aacgtcgtga    9840
ccccggtcta ccattcggga gggcatagca tcaatagatg tgctgcccct cagtccgttg    9900
atacctactt gctttatctg tctagcgact ctatccacgg agtgactaat tcgtaaccat    9960
tgacagtctg gttcaaatga gtatatatga aatctaacta aattttgaag taaaaattaa    10020
attttcctag atccacttct aggaaaaact attagagtac tggttttagg gaattgcact    10080
caaaagcaag gtgactcgca gtctggggca tctttctag tttcctagaa gaactctagg    10140
aaaaaaagac gcgcattaga cgacgaacgt ttgttttttt ggtggcgatg gtcgccacca    10200
aacaaacggc ctagttctcg atggttgaga aaaaggcttc cattgaccga agtcgtctcg    10260
cgtctatggt ttatgacagg aagatcacat cggcatcaat ccggtggtga agttcttgag    10320
acatcgtggc ggatgtatgg agcgagacga ttaggacaat ggtcaccgac gacggtcacc    10380
gctattcagc acagaatggc ccaacctgag ttctgctatc aatggcctat tccgcgtcgc    10440
cagcccgact tgcccccccaa gcacgtgtgt cgggtcgaac ctcgcttgct ggatgtggct    10500
tgactctatg gatgtcgcac tcgatactct ttcgcggtgc gaagggcttc cctctttccg    10560
cctgtccata ggccattcgc cgtcccagcc ttgtcctctc gcgtgctccc tcgaaggtcc    10620 cccttttgcgg accatagaaa tatcaggaca gcccaaagcg gtggagactg aactcgcagc    10680
taaaaacact acgagcagtc cccccgcctc ggatacctt ttgcggtcgt tgcgccggaa    10740
aaatgccaag gaccggaaaa cgaccggaaa acgagtgtac aagaaaggac gcaatagggg    10800
actaagacac ctattggcat aatggcggaa actcactcga ctatggcgag cggcgtcggc    10860
ttgctggctc gcgtcgctca gtcactcgct ccttcgcctt tcgcgggtt atgcgtttgg    10920 cggagagggg cgcgcaaccg gctaagtaat tacgtcgacc gtgctgtcca aagggctgac    10980 cttttcgcccg tcactcgcgt tgcgttaatt acactcaatc gagtgagtaa tccgtggggt    11040
ccgaaatgtg aaatacgaag gccgagcata caacacacct taacactcgc ctattgttaa    11100
```

```
agtgtgtcct tgtcgatac tggtactaat gcttaactta acgccggcgt taag      11154

<210> SEQ ID NO 5
<211> LENGTH: 11480
<212> TYPE: DNA
<213> ORGANISM: Artificial Sequence
<220> FEATURE:
<223> OTHER INFORMATION: Canarypox virus (ALVAC) and Homo sapiens

<400> SEQUENCE: 5
tgaatgttaa atgttatact ttggatgaag ctataaatat gcattggaaa aataatccat    60
ttaaagaaag gattcaaata ctacaaaacc taagcgataa tatgttaact aagcttattc   120
ttaacgacgc tttaaatata cacaaataaa cataattttt gtataaccta acaaataact   180
aaaacataaa aataataaaa ggaaatgtaa tatcgtaatt attttactca ggaatggggt   240
taaatattta tatcacgtgt atatctatac tgttatcgta tactctttac aattactatt   300
acgaatatgc aagagataat aagattacgt atttaagaga atcttgtcat gataattggg   360
tacgacatag tgataaatgc tatttcgcat cgttacataa agtcagttgg aaagatggat   420
ttgacagatg taacttaata ggtgcaaaaa tgttaaataa cagcattcta tcggaagata   480
ggataccagt tatattatac aaaaatcact ggttggataa aacagattct gcaatattcg   540
taaaagatga agattactgc gaatttgtaa actatgacaa taaaaagcca tttatctcaa   600
cgacatcgtg taattcttcc atgttttatg tatgtgtttc agatattatg agattactat   660
aaacttttg tatacttata ttccgtaaac tatattaatc atgaagaaaa tgaaaaagta   720
tagaagctgt tcacgagcgg ttgttgaaaa caacaaaatt atacattcaa gatggcttac   780
atatacgtct gtgaggctat catggataat gacaatgcat ctctaaatag gttttttggac   840
aatggattcg accctaacac ggaatatggt actctacaat ctcctcttga aatggctgta   900
atgttcaaga ataccgaggc tataaaaatc ttgatgaggt atggagctaa acctgtagtt   960
actgaatgca caacttcttg tctgcatgat gcggtgttga gagacgacta caaaatagtg  1020
aaagatctgt tgaagaataa ctatgtaaac aatgttcttt acagcggagg ctttactcct  1080
ttgtgtttgg cagcttacct taacaaagtt aatttggtta aacttctatt ggctcattcg  1140
gcggatgtag atatttcaaa cacggatcgg ttaactcctc tacatatagc cgtatcaaat  1200
aaaaatttaa caatggttaa acttctattg aacaaaggtg ctgatactga cttgctggat  1260
aacatgggat gtactccttt aatgatcgct gtacaatctg gaaatattga aatatgtagc  1320
acactactta aaaaaaataa aatgtccaga actgggaaaa attgatcttg ccagctgtaa  1380
ttcatggtag aaaagaagtg ctcaggctac ttttcaacaa aggagcagat gtaaactaca  1440
tctttgaaag aaatggaaaa tcatatactg ttttggaatt gattaaagaa agttactctg  1500
agacacaaaa gaggtagctg aagtggtact ctcaaaggta cgtgactaat tagctataaa  1560
aaggatcggg ttctttattc tatacttaaa aagtgaaaat aaatacaaag gttcttgagg  1620
gttgtgttaa attgaaagcg agaaataatc ataaattatt tcattatcgc gatatccgtt  1680
aagtttgtat cgtaatctgc agcccccacc atggatctgg tgctaaaaag atgccttctt  1740
catttggctg tgataggtgc tttgctggct gtggggcta caaaagtacc cagaaaccag  1800
gactggcttg gtgtctcaag gcaactcaga accaaagcct ggaacaggca gctgtatcca  1860
gagtggacag aagcccagag acttgactgc tggagaggtg gtcaagtgtc cctcaaggtc  1920
agtaatgatg ggcctacact gattggtgca aatgcctcct tctctattgc cttgaacttc  1980
cctggaagcc aaaaggtatt gccagatact agttctagag gatcattatt taacgtaaac  2040
```

```
taaatggaaa agctatttac aggtacatac ggtgttttc tggaatcaaa tgattctgat    2100
tttgaggatt ttatcaatac aataatgaca gtgctaactg gtaaaaaaga aagcaaacaa    2160
ttatcatggc taacaatttt tattatattt gtagtatgca tagtggtctt tacgtttctt    2220
tatttaaagt taatgtgtta agattaaatg gagtaattgg atccccatc gatggggaat    2280 tcactggccg tcgttttaca acgtcgtgac tgggaaaacc ctggcgttac ccaacttaat    2340
cgccttgcag cacatccccc tttcgccagc tggcgtaata gcgaagaggc ccgcaccgat    2400
cgcccttccc aacagttgcg cagcctgaat ggcgaatggc gctttgcctg gtttccggca    2460
ccagaagcgg tgccggaaag ctggctggag tgcgatcttc ctgaggccga tactgtcgtc    2520
gtcccctcaa actggcagat gcacggttac gatgcgccca tctacaccaa cgtgacctat    2580
cccattacgg tcaatccgcc gtttgttccc acggagaatc cgacggttg ttactcgctc    2640 acatttaatg ttgatgaaag ctggctacag gaaggccaga cgcgaattat ttttgatggc    2700
gttaactcgg cgtttcatct gtggtgcaac gggcgctggg tcggttacgg ccaggacagt    2760
cgtttgccgt ctgaatttga cctgagcgca ttttacgcg ccggagaaaa ccgcctcgcg    2820
gtgatggtgc tgcgctggag tgacggcagt tatctggaag atcaggatat gtggcggatg    2880
agcggcattt tccgtgacgt ctcgttgctg cataaaccga ctacacaaat cagcgatttc    2940
catgttgcca ctcgctttaa tgatgatttc agccgcgctg tactggaggc tgaagttcag    3000
atgtgcggcg agttgcgtga ctacctacgg gtaacagttt ctttatggca gggtgaaacg    3060
caggtcgcca gcggcaccgc gcctttcggc ggtgaaatta tcgatgagcg tggtggttat    3120
gccgatcgcg tcacactacg tctgaacgtc gaaaacccga actgtggag cgccgaaatc    3180 ccgaatctct atcgtgcggt ggttgaactg cacaccgccg acggcacgct gattgaagca    3240
gaagcctgcg atgtcggttt ccgcgaggtg cggattgaaa atggtctgct gctgctgaac    3300
ggcaagccgt tgctgattcg aggcgttaac cgtcacgagc atcatcctct gcatggtcag    3360
gtcatggatg agcagacgat ggtgcaggat atcctgctga tgaagcagaa caactttaac    3420
gccgtgcgct gttcgcatta tccgaaccat ccgctgtggt acacgctgtg cgaccgctac    3480
ggcctgtatg tggtggatga agccaatatt gaaacccacg gcatggtgcc aatgaatcgt    3540
ctgaccgatg atccgcgctg gctaccggcg atgagcgaac gcgtaacgcg aatggtgcag    3600
cgcgatcgta atcacccgag tgtgatcatc tggtcgctgg ggaatgaatc aggccacggc    3660
gctaatcacg acgcgctgta tcgctggatc aaatctgtcg atccttcccg cccggtgcag    3720
tatgaaggcg gcggagccga caccacggcc accgatatta tttgcccgat gtacgcgcgc    3780
gtggatgaag accagccctt cccggctgtg ccgaaatggt ccatcaaaaa atggctttcg    3840
ctacctggag agacgcgccc gctgatcctt tgcgaatacg cccacgcgat gggtaacagt    3900
cttggcggtt tcgctaaata ctggcaggcg tttcgtcagt atccccgttt acagggcggc    3960
ttcgtctggg actgggtgga tcagtcgctg attaaatatg atgaaaacgg caacccgtgg    4020
tcggcttacg gcggtgattt tggcgatacg ccgaacgatc gccagttctg tatgaacggt    4080
ctggtctttg ccgaccgcac gccgcatcca gcgctgacgg aagcaaaaca ccagcagcag    4140 ttttccagt tccgtttatc cgggcaaacc atcgaagtga ccagcgaata cctgttccgt    4200
catagcgata acgagctcct gcactggatg gtggcgctgg atggtaagcc gctggcaagc    4260
ggtgaagtgc ctctggatgt cgctccacaa ggtaaacagt tgattgaact gcctgaacta    4320
ccgcagccgg agagcgccgg gcaactctgg ctcacagtac gcgtagtgca accgaacgcg    4380
```

```
accgcatggt cagaagccgg gcacatcagc gcctggcagc agtggcgtct ggcggaaaac    4440
ctcagtgtga cgctcccgc cgcgtcccac gccatcccgc atctgaccac cagcgaaatg    4500 gattttgca tcgagctggg taataagcgt tggcaattta accgccagtc aggctttctt    4560
tcacagatgt ggattggcga taaaaaacaa ctgctgacgc cgctgcgcga tcagttcacc    4620
cgtgcaccgc tggataacga cattggcgta agtgaagcga cccgcattga ccctaacgcc    4680
tgggtcgaac gctggaaggc ggcgggccat taccaggccg aagcagcgtt gttgcagtgc    4740
acggcagata cacttgctga tgcggtgctg attacgaccg ctcacgcgtg gcagcatcag    4800
gggaaaacct tatttatcag ccggaaaacc taccggattg atggtagtgg tcaaatggcg    4860
attaccgttg atgttgaagt ggcgagcgat acaccgcatc cggcgcggat tggcctgaac    4920
tgccagctgg cgcaggtagc agagcgggta aactggctcg gattagggcc gcaagaaaac    4980
tatcccgacc gccttactgc cgcctgtttt gaccgctggg atctgccatt gtcagacatg    5040 taccccgt acgtcttccc gagcgaaaac ggtctgcgct gcgggacgcg cgaattgaat    5100 tatgcccac accagtggcg cggcgacttc cagttcaaca tcagccggta cagtcaacag    5160
caattgatgg aaaccagcca ttcgccatct gctgcacgcg gaagaggcac atggctgaat    5220
atcgacggtt ccatatgggg gattggtggc gacgactcct ggagcccgtc agtatcggcg    5280
gaattccagc tgagcgccgg tcgctaccat taccagttgg tctggtgtca aaataataa    5340 taaccgggca gggggggatcc ggagcttatc gcagatcaat tcgatatcaa gcttatcgat    5400
accgtcgacc tcgagtctag aatcgatccc gggttctta ttctatactt aaaaagtgaa    5460
aataaataca aaggttcttg aggtttgtgt taaattgaaa gcgagaaata atcataaatt    5520
atttcattat cgcgatatcc gttaagtttg tatcgtaatc tgcagccccc accatggatc    5580
tggtgctaaa aagatgcctt cttcatttgg ctgtgatagg tgctttgctg gctgtggggg    5640
ctacaaaagt acccagaaac caggactggc ttggtgtctc aaggcaactc agaaccaaag    5700 cctgaacag gcagctgtat ccagagtgga cagaagccca gagacttgac tgctggagag    5760
gtggtcaagt gtccctcaag gtcagtaatg atgggcctac actgattggt gcaaatgcct    5820
ccttctctat tgccttgaac ttccctggaa gccaaaaggt attgccagat gggcaggtta    5880
tctgggtcaa caataccatc atcaatggga gccaggtgtg gggaggacag ccagtgtatc    5940
cccaggaaac tgacgatgcc tgcatcttcc ctgatggtgg accttgccca tctggctctt    6000
ggtctcagaa gagaagcttt gtttatgtct ggaagacctg gggccaatac tggcaagttc    6060 taggggccc agtgtctggg ctgagcattg ggacaggcag ggcaatgctg ggcacacaca    6120
cgatggaagt gactgtctac catcgccggg gatcccggag ctatgtgcct cttgctcatt    6180
ccagctcagc cttcaccatt atggaccagg tgcctttctc cgtgagcgtg tcccagttgc    6240
gggccttgga tgggggaac aagcacttcc tgagaaatca gcctctgacc tttgccctcc    6300
agctccatga ccccagtggc tatctggctg aagctgacct ctcctacacc tgggactttg    6360
gagacagtag tggaacccctg atctctcggg cacttgtggt cactcatact tacctggagc    6420
ctggcccagt cactgttcag gtggtcctgc aggctgccat tcctctcacc tcctgtggct    6480
cctccccagt tccaggcacc acagatgggc acaggccaac tgcagaggcc ctaacacca    6540 cagctggcca agtgcctact acagaagttg tgggtactac acctggtcag gcgccaactg    6600
cagagccctc tggaaccaca tctgtgcagg tgccaaccac tgaagtcata agcactgcac    6660
ctgtgcagat gccaactgca gagagcacag gtatgacacc tgagaaggtg ccagtttcag    6720
aggtcatggg taccacactg gcagagatgt caactccaga ggctacaggt atgacacctg    6780
```

```
cagaggtatc aattgtggtg ctttctggaa ccacagctgc acaggtaaca actacagagt    6840
gggtggagac cacagctaga gagctaccta tccctgagcc tgaaggtcca gatgccagct    6900
caatcatgtc tacggaaagt attacaggtt ccctgggccc cctgctggat ggtacagcca    6960
ccttaaggct ggtgaagaga caagtccccc tggattgtgt tctgtatcga tatggttcct    7020
tttccgtcac cctggacatt gtccagggta ttgaaagtgc cgagatcctg caggctgtgc    7080
cgtccggtga gggggatgca tttgagctga ctgtgtcctg ccaaggcggg ctgcccaagg    7140
aagcctgcat ggagatctca tcgccagggt gccagccccc tgcccagcgg ctgtgccagc    7200
ctgtgctacc cagcccagcc tgccagctgg ttctgcacca gatactgaag ggtggctcgg    7260
ggacatactg cctcaatgtg tctctggctg ataccaacag cctggcagtg gtcagcaccc    7320
agcttatcat gcctggtcaa gaagcaggcc ttgggcaggt tccgctgatc gtgggcatct    7380
tgctggtgtt gatggctgtg gtccttgcat ctctgatata taggcgcaga cttatgaagc    7440
aagacttctc cgtaccccag ttgccacata gcagcagtca ctggctgcgt ctaccccgca    7500
tcttctgctc ttgtcccatt ggtgagaaca gccccctcct cagtgggcag caggtctgat    7560
ttttattcta gttcaaaaaa atataaatga ttcaccatct gatagaaaaa aaatttattg    7620
ggagaatatg ataatatttt gggatttcaa aattgaaaat atataattac aatataaatc    7680
tagaccacca tgccaagaga agatgctcac ttcatctatg gttacccccaa gaaggggcac    7740
ggccactctt acaccacggc tgaagaggcc gctgggatcg gcatcctgac agtgatcctg    7800
ggagtcttac tgctcatcgg ctgttggtat tgtagaagac gaaatggata cagagccttg    7860
atggataaaa gtcttcatgt tggcactcaa tgtgccttaa caagaagatg cccacaagaa    7920
gggtttgatc atcgggacag caaagtgtct cttcaagaga aaaactgtga acctgtggtt    7980
cccaatgctc cacctgctta tgagaaactc tctgcagaac agtcaccacc accttattca    8040
ccttaatcta gagtcgacct gcaggcatgc aaaaattgaa attttatttt ttttttttgg    8100
aatataaata atggagtcct tgcagctggt ctttggcatt gacgtgaagg aagcagaccc    8160
caccggccac tcctatgtcc ttgtcacctg cctaggtctc tcctatgatg caataagcg    8220
taaagaagtg gaccccatcg gccacttgta ctagttttta tcccgggttt ttatgactag    8280
ttaatcacgg ccgcttataa agatctaaaa tgcataattt ctaaataatg aaaaaaaagt    8340
acatcatgag caacgcgtta gtatatttta caatggagat taacgctcta taccgttcta    8400
tgtttattga ttcagatgat gttttagaaa agaaagttat tgaatatgaa aactttaatg    8460
aagatgaaga tgacgacgat gattattgtt gtaaatctgt tttagatgaa gagatgacg    8520
cgctaaagta tactatggtt acaaagtata agtctatact actaatggcg acttgtgcaa    8580
gaaggtatag tatagtgaaa atgttgttag attatgatta tgaaaaccaa aataaatcag    8640
atccatatct aaaggtatct cctttgcaca taatttcatc tattcctagt ttagaatact    8700
tttcattata tttgtttaca gctgaagacg aaaaaaatat atcgataata gaagattatg    8760
ttaactctgc taataagatg aaattgaatg agtctgtgac tgcagccaag cttggcactg    8820
gccgtcgttt tacaacgtcg tgactgggaa accctggcg ttacccaact taatcgcctt    8880
gcagcacatc cccctttcgc cagctggcgt aatagcgaag aggcccgcac cgatcgccct    8940
tcccaacagt tgcgcagcct gaatggcgaa tggcgcctga tgcggtattt tctccttacg    9000
catctgtgcg gtatttcaca ccgcatatgg tgcactctca gtacaatctg ctctgatgcc    9060
gcatagttaa gccagccccg acaccgcca acacccgctg acgcgccctg acgggcttgt    9120
```

```
ctgctcccgg catccgctta cagacaagct gtgaccgtct ccgggagctg catgtgtcag    9180
aggttttcac cgtcatcacc gaaacgcgcg agacgaaagg gcctcgtgat acgcctattt    9240
ttataggtta atgtcatgat aataatggtt tcttagacgt caggtggcac ttttcgggga    9300
aatgtgcgcg gaaccctat ttgtttattt ttctaaatac attcaaatat gtatccgctc     9360
atgagacaat aaccctgata aatgcttcaa taatattgaa aaggaagag tatgagtatt     9420
caacatttcc gtgtcgccct tattcccttt tttgcggcat tttgccttcc tgttttgct     9480
cacccagaaa cgctggtgaa agtaaaagat gctgaagatc agttgggtgc acgagtgggt    9540
tacatcgaac tggatctcaa cagcggtaag atccttgaga gttttcgccc cgaagaacgt    9600
tttccaatga tgagcacttt taaagttctg ctatgtggcg cggtattatc ccgtattgac    9660
gccgggcaag agcaactcgg tcgccgcata cactattctc agaatgactt ggttgagtac    9720
tcaccagtca cagaaaagca tcttacggat ggcatgacag taagagaatt atgcagtgct    9780
gccataacca tgagtgataa cactgcggcc aacttacttc tgacaacgat cggaggaccg    9840
aaggagctaa ccgcttttt gcacaacatg ggggatcatg taactcgcct tgatcgttgg     9900
gaaccggagc tgaatgaagc cataccaaac gacgagcgtg acaccacgat gcctgtagca    9960
atggcaacaa cgttgcgcaa actattaact ggcgaactac ttactctagc ttcccggcaa   10020
caattaatag actggatgga ggcggataaa gttgcaggac cacttctgcg ctcggccctt   10080
ccggctggct ggtttattgc tgataaatct ggagccggtg agcgtgggtc tcgcggtatc   10140
attgcagcac tggggccaga tggtaagccc tcccgtatcg tagttatcta cacgacgggg   10200
agtcaggcaa ctatggatga acgaaataga cagatcgctg agataggtgc ctcactgatt   10260
aagcattggt aactgtcaga ccaagtttac tcatatatac tttagattga tttaaaactt   10320
catttttaat ttaaaaggat ctaggtgaag atcctttttg ataatctcat gaccaaaatc   10380
ccttaacgtg agttttcgtt ccactgagcg tcagacccog tagaaaagat caaaggatct   10440
tcttgagatc cttttttct gcgcgtaatc tgctgcttgc aaacaaaaaa accaccgcta    10500
ccagcggtgg tttgtttgcc ggatcaagag ctaccaactc tttttccgaa ggtaactggc   10560
ttcagcagag cgcagatacc aaatactgtc cttctagtgt agccgtagtt aggccaccac   10620
ttcaagaact ctgtagcacc gcctacatac ctcgctctgc taatcctgtt accagtggct   10680
gctgccagtg gcgataagtc gtgtcttacc gggttggact caagacgata gttaccggat   10740
aaggcgcagc ggtcgggctg aacggggggt tcgtgcacac agcccagctt ggagcgaacg   10800
acctacaccg aactgagata cctacagcgt gagctatgag aaagcgccac gcttcccgaa   10860
gggagaaagg cggacaggta tccggtaagc ggcagggtcg aacaggaga gcgcacgagg    10920
gagcttccag ggggaaacgc ctggtatctt tatagtcctg tcgggtttcg ccacctctga   10980
cttgagcgtc gatttttgtg atgctcgtca gggggggcgga gcctatggaa aaacgccagc  11040
aacgcggcct ttttacggtt cctggccttt tgctggcctt tgctcacat gttctttcct    11100
gcgttatccc ctgattctgt ggataaccgt attaccgcct tgagtgagc tgataccgct    11160
cgccgcagcc gaacgaccga gcgcagcgag tcagtgagcg aggaagcgga agagcgccca   11220
atacgcaaac cgcctctccc cgcgcgttgg ccgattcatt aatgcagctg gcacgacagg   11280
tttcccgact ggaaagcggg cagtgagcgc aacgcaatta atgtgagtta gctcactcat   11340
taggcacccc aggctttaca ctttatgctt ccggctcgta tgttgtgtgg aattgtgagc   11400
ggataacaat ttcacacagg aaacagctat gaccatgatt acgaattgaa ttgcggccgc   11460
aattcaacgc cggcgttaag                                                11480
```

<210> SEQ ID NO 6
<211> LENGTH: 11450
<212> TYPE: DNA
<213> ORGANISM: Artificial Sequence
<220> FEATURE:
<223> OTHER INFORMATION: Canarypox virus (ALVAC) and Homo sapiens

<400> SEQUENCE: 6

| | | | | | |
|---|---|---|---|---|---|
| acttacaatt | tacaatatga | aacctacttc | gatatttata | cgtaacctttt | ttattaggta | 60 |
| aatttctttc | ctaagtttat | gatgttttgg | attcgctatt | atacaattga | ttcgaataag | 120 |
| aattgctgcg | aaatttatat | gtgtttattt | gtattaaaaa | catattggat | tgtttattga | 180 |
| ttttgtattt | ttattatttt | cctttacatt | atagcattaa | taaaatgagt | ccttacccca | 240 |
| atttataaat | atagtgcaca | tatagatatg | acaatagcat | atgagaaatg | ttaatgataa | 300 |
| tgcttatacg | ttctctatta | ttctaatgca | taaattctct | tagaacagta | ctattaaccc | 360 |
| atgctgtatc | actatttacg | ataaagcgta | gcaatgtatt | tcagtcaacc | tttctaccta | 420 |
| aactgtctac | attgaattat | ccacgttttt | acaatttatt | gtcgtaagat | agccttctat | 480 |
| cctatggtca | atataaatg | ttttagtga | ccaacctatt | ttgtctaaga | cgttataagc | 540 |
| attttctact | tctaatgacg | cttaaacatt | tgatactgtt | attttttcggt | aaatagagtt | 600 |
| gctgtagcac | attaagaagg | tacaaaatac | atacacaaag | tctataatac | tctaatgata | 660 |
| tttgaaaaac | atatgaatat | aaggcatttg | atataattag | tacttctttt | acttttttcat | 720 |
| atcttcgaca | agtgctcgcc | aacaactttt | gttgttttaa | tatgtaagtt | ctaccgaatg | 780 |
| tatatgcaga | cactccgata | gtacctatta | ctgttacgta | gagatttatc | caaaaacctg | 840 |
| ttacctaagc | tgggattgtg | ccttatacca | tgagatgtta | gaggagaact | ttaccgacat | 900 |
| tacaagttct | tatggctccg | atattttag | aactactcca | tacctcgatt | tggacatcaa | 960 |
| tgacttacgt | gttgaagaac | agacgtacta | cgccacaact | ctctgctgat | gttttatcac | 1020 |
| tttctagaca | acttcttatt | gatacatttg | ttacaagaaa | tgtcgcctcc | gaaatgagga | 1080 |
| aacacaaacc | gtcgaatgga | attgtttcaa | ttaaaccaat | ttgaagataa | ccgagtaagc | 1140 |
| cgcctacatc | tataaagttt | gtgcctagcc | aattgaggag | atgtatatcg | gcatagttta | 1200 |
| tttttaaatt | gttaccaatt | tgaagataac | ttgtttccac | gactatgact | gaacgaccta | 1260 |
| tgtacccta | catgaggaaa | ttactagcga | catgttagac | ctttataact | ttatacatcg | 1320 |
| tgtgatgaat | tttttttatt | ttacaggtct | tgaccctttt | taactagaac | ggtcgacatt | 1380 |
| aagtaccatc | ttttcttcac | gagtccgatg | aaaagttgtt | tcctcgtcta | catttgatgt | 1440 |
| agaaactttc | tttaccttttt | agtatatgac | aaaaccttaa | ctaatttctt | tcaatgagac | 1500 |
| tctgtgttt | ctccatcgac | ttcaccatga | gagtttccat | gcactgatta | atcgatattt | 1560 |
| ttcctagccc | aagaaataag | atatgaattt | ttcacttta | tttatgtttc | caagaactcc | 1620 |
| caacacaatt | taactttcgc | tctttattag | tatttaataa | agtaatagcg | ctataggcaa | 1680 |
| ttcaaacata | gcattagacg | tcgggggtgg | tacctagacc | acgatttttc | tacggaagaa | 1740 |
| gtaaaccgac | actatccacg | aaacgaccga | cacccccgat | gttttcatgg | gtctttggtc | 1800 |
| ctgaccgaac | cacagagttc | cgttgagtct | tggtttcgga | ccttgtccgt | cgacataggt | 1860 |
| ctcacctgtc | ttcgggtctc | tgaactgacg | acctctccac | cagttcacag | ggagttccag | 1920 |
| tcattactac | ccggatgtga | ctaaccacgt | ttacggagga | agagataacg | gaacttgaag | 1980 |
| ggaccttcgg | ttttccataa | cggtctatga | tcaagatctc | ctagtaataa | attgcatttg | 2040 |

```
atttaccttt tcgataaatg tccatgtatg ccacaaaaag accttagttt actaagacta    2100
aaactcctaa aatagttatg ttattactgt cacgattgac cattttttct ttcgtttgtt    2160
aatagtaccg attgttaaaa ataatataaa catcatacgt atcaccagaa atgcaaagaa    2220
ataaatttca attacacaat tctaatttac ctcattaacc taggggtag ctacccctta    2280 agtgaccggc agcaaaatgt tgcagcactg acccttttgg gaccgcaatg ggttgaatta    2340
gcggaacgtc gtgtagggggg aaagcggtcg accgcattat cgcttctccg ggcgtggcta    2400
gcgggaaggg ttgtcaacgc gtcggactta ccgcttaccg cgaaacggac caaaggccgt    2460
ggtcttcgcc acggcctttc gaccgacctc acgctagaag gactccggct atgacagcag    2520
caggggagtt tgaccgtcta cgtgccaatg ctacgcgggt agatgtggtt gcactggata    2580
gggtaatgcc agttaggcgg caaacaaggg tgcctcttag gctgcccaac aatgagcgag    2640
tgtaaattac aactactttc gaccgatgtc cttccggtct gcgcttaata aaaactaccg    2700
caattgagcc gcaaagtaga caccacgttg cccgcgaccc agccaatgcc ggtcctgtca    2760
gcaaacggca gacttaaact ggactcgcgt aaaaatgcgc ggcctctttt ggcggagcgc    2820
cactaccacg acgcgacctc actgccgtca atagaccttc tagtcctata caccgcctac    2880
tcgccgtaaa aggcactgca gagcaacgac gtatttggct gatgtgttta gtcgctaaag    2940
gtacaacggt gagcgaaatt actactaaag tcggcgcgac atgacctccg acttcaagtc    3000
tacacgccgc tcaacgcact gatggatgcc cattgtcaaa gaataccgt cccactttgc    3060 gtccagcggt cgccgtggcg cggaaagccg ccactttaat agctactcgc accaccaata    3120
cggctagcgc agtgtgatgc agacttcag cttttgggct ttgacacctc gcggctttag    3180
ggcttagaga tagcacgcca ccaacttgac gtgtggcggc tgccgtgcga ctaacttcgt    3240
cttcggacgc tacagccaaa ggcgctccac gcctaacttt taccgacga cgacgacttg    3300 ccgttcggca acgactaagc tccgcaattg gcagtgctcg tagtaggaga cgtaccagtc    3360
cagtacctac tcgtctgcta ccacgtccta taggacgact acttcgtctt gttgaaattg    3420
cggcacgcga caagcgtaat aggcttggta ggcgacacca tgtgcgacac gctggcgatg    3480
ccggacatac accacctact tcggttataa ctttgggtgc cgtaccacgg ttacttagca    3540
gactggctac taggcgcgac cgatggccgc tactcgcttg cgcattgcgc ttaccacgtc    3600
gcgctagcat tagtgggctc acactagtag accagcgacc ccttacttag tccggtgccg    3660
cgattagtgc tgcgcgacat agcgacctag tttagacagc taggaagggc gggccacgtc    3720
atacttccgc cgcctcggct gtggtgccgg tggctataat aaacgggcta catgcgcgcg    3780
cacctacttc tggtcgggaa gggccgacac ggctttacca ggtagttttt taccgaaagc    3840
gatggacctc tctgcgcggg cgactaggaa acgcttatgc gggtgcgcta cccattgtca    3900
gaaccgccaa agcgatttat gaccgtccgc aaagcagtca taggggcaaa tgtcccgccg    3960
aagcagaccc tgacccacct agtcagcgac taatttatac tacttttgcc gttgggcacc    4020
agccgaatgc cgccactaaa accgctatgc ggcttgctag cggtcaagac atacttgcca    4080
gaccagaaac ggctggcgtg cggcgtaggt cgcgactgcc ttcgttttgt ggtcgtcgtc    4140
aaaaaggtca aggcaaatag gcccgttggg tagcttcact ggtcgcttat ggacaaggca    4200
gtatcgctat tgctcgagga cgtgacctac caccgcgacc taccattcgg cgaccgttcg    4260
ccacttcacg gagacctaca gcgaggtgtt ccatttgtca actaacttga cggacttgat    4320
ggcgtcggcc tctcgcggcc cgttgagacc gagtgtcatg cgcatcacgt tggcttgcgc    4380
tggcgtacca gtcttcggcc cgtgtagtcg cggaccgtcg tcaccgcaga ccgccttttg    4440
```

```
gagtcacact gcgagggcg gcgcagggtg cggtagggcg tagactggtg gtcgctttac    4500
ctaaaaacgt agctcgaccc attattcgca accgttaaat tggcggtcag tccgaaagaa    4560
agtgtctaca cctaaccgct attttttgtt gacgactgcg gcgacgcgct agtcaagtgg    4620
gcacgtggcg acctattgct gtaaccgcat tcacttcgct gggcgtaact gggattgcgg    4680
acccagcttg cgaccttccg ccgcccggta atggtccggc ttcgtcgcaa caacgtcacg    4740
tgccgtctat gtgaacgact acgccacgac taatgctggc gagtgcgcac cgtcgtagtc    4800 ccctttttgga ataaatagtc ggccttttgg atggcctaac taccatcacc agtttaccgc    4860
taatggcaac tacaacttca ccgctcgcta tgtggcgtag gccgcgccta accggacttg    4920
acggtcgacc gcgtccatcg tctcgcccat ttgaccgagc ctaatcccgg cgttcttttg    4980
atagggctgg cggaatgacg gcggacaaaa ctggcgaccc tagacggtaa cagtctgtac    5040
atatggggca tgcagaaggg ctcgcttttg ccagacgcga cgccctgcgc gcttaactta    5100
ataccgggtg tggtcaccgc gccgctgaag gtcaagttgt agtcggccat gtcagttgtc    5160
gttaactacc tttggtcggt aagcggtaga cgacgtgcgc cttctccgtg taccgactta    5220
tagctgccaa aggtataccc ctaaccaccg ctgctgagga cctcgggcag tcatagccgc    5280
cttaaggtcg actcgcggcc agcgatggta atggtcaacc agaccacagt ttttattatt    5340 attgcccgt ccccctagg cctcgaatag cgtctagtta agctatagtt cgaatagcta    5400
tggcagctgg agctcagatc ttagctaggg cccaagaaat aagatatgaa ttttcactt    5460 ttatttatgt ttccaagaac tcccaacaca atttaacttt cgctctttat tagtatttaa    5520
taaagtaata gcgctatagg caattcaaac atagcattag acgtcggggg tggtacctag    5580
accacgattt ttctacggaa gaagtaaacc gacactatcc acgaaacgac cgacaccccc    5640
gatgttttca tgggtctttg gtcctgaccg aaccacagag ttccgttgag tcttggtttc    5700
ggaccttgtc cgtcgacata ggtctcacct gtcttcgggt ctctgaactg acgacctctc    5760
caccagttca cagggagttc cagtcattac tacccggatg tgactaacca cgtttacgga    5820
ggaagagata acgaacttg aagggaccttt cggttttcca taacggtcta cccgtccaat    5880
agacccagtt gttatggtag tagttaccct cggtccacac ccctcctgtc ggtcacatag    5940
gggtcctttg actgctacgg acgtagaagg gactaccacc tggaacgggt agaccgagaa    6000
ccagagtctt ctcttcgaaa caaatacaga ccttctggac cccggttatg accgttcaag    6060
atcccccggg tcacagaccc gactcgtaac cctgtccgtc ccgttacgac ccgtgtgtgt    6120
gctaccttca ctgacagatg gtagcggccc ctagggcctc gatacacgga gaacgagtaa    6180
ggtcgagtcg gaagtggtaa tacctggtcc acggaaagag gcactcgcac agggtcaacg    6240
cccggaacct acctcccttg ttcgtgaagg actctttagt cggagactgg aaacgggagg    6300
tcgaggtact ggggtcaccg atagaccgac ttcgactgga gaggatgtgg accctgaaac    6360
ctctgtcatc accttgggac tagagagccc gtgaacacca gtgagtatga atggacctcg    6420
gaccgggtca gtgacaagtc caccaggacg tccgacggta aggagagtgg aggacaccga    6480
ggaggggtca aggtccgtgg tgtctacccg tgtccggttg acgtctccgg ggattgtggt    6540
gtcgaccggt tcacggatga tgtcttcaac acccatgatg tggaccagtc cgcggttgac    6600
gtctcgggag accttggtgt agacacgtcc acggttggtg acttcagtat tcgtgacgtg    6660
gacacgtcta cggttgacgt ctctcgtgtc catactgtgg actcttccac ggtcaaagtc    6720
tccagtaccc atggtgtgac cgtctctaca gttgaggtct ccgatgtcca tactgtggac    6780
```

```
gtctccatag ttaacaccac gaaagacctt ggtgtcgacg tgtccattgt tgatgtctca    6840
cccacctctg gtgtcgatct ctcgatggat agggactcgg acttccaggt ctacggtcga    6900
gttagtacag atgcctttca taatgtccaa gggacccggg ggacgaccta ccatgtcggt    6960
ggaattccga ccacttctct gttcaggggg acctaacaca agacatagct ataccaagga    7020
aaaggcagtg ggacctgtaa caggtcccat aactttcacg gctctaggac gtccgacacg    7080
gcaggccact cccctacgt aaactcgact gacacaggac ggttccgccc gacgggttcc    7140
ttcggacgta cctctagagt agcggtccca cggtcggggg acgggtcgcc gacacggtcg    7200
gacacgatgg gtcgggtcgg acggtcgacc aagacgtggt ctatgacttc ccaccgagcc    7260
cctgtatgac ggagttacac agagaccgac tatggttgtc ggaccgtcac cagtcgtggg    7320
tcgaatagta cggaccagtt cttcgtccgg aacccgtcca aggcgactag cacccgtaga    7380
acgaccacaa ctaccgacac caggaacgta gagactatat atccgcgtct gaatacttcg    7440
ttctgaagag gcatgggtc aacggtgtat cgtcgtcagt gaccgacgca gatgggcgt    7500 agaagacgag aacagggtaa ccactcttgt cgggggagga gtcacccgtc gtccagacta    7560
aaaataagat caagtttttt tatatttact aagtggtaga ctatctttt tttaaataac    7620 cctcttatac tattataaaa ccctaaagtt ttaactttta tatattaatg ttatatttag    7680
atctggtggt acggttctct tctacgagtg aagtagatac caatgggggtt cttccccgtg    7740 ccggtgagaa tgtggtgccg acttctccgg cgacccctagc cgtaggactg tcactaggac    7800
cctcagaatg acgagtagcc gacaaccata acatcttctg ctttacctat gtctcggaac    7860 taccttatttt cagaagtaca accgtgagtt acacggaatt gttcttctac gggtgttctt    7920
cccaaactag tagccctgtc gtttcacaga gaagttctct ttttgacact tggacaccaa    7980
gggttacgag gtgggacgaat actctttgag agacgtcttg tcagtggtgg tggaataagt    8040
ggaattagat ctcagctgga cgtccgtacg tttttaactt taaaataaaa aaaaaaaacc    8100
ttatatttat tacctcagga acgtcgacca gaaaccgtaa ctgcacttcc ttcgtctggg    8160
gtggccggtg aggatacagg aacagtggac ggatccagag aggatactac cgttattcgc    8220
atttcttcac ctggggtagc cggtgaacat gatcaaaaat agggcccaaa atactgatc    8280 aattagtgcc ggcgaatatt tctagatttt acgtattaaa gatttattac ttttttttca    8340
tgtagtactc gttgcgcaat catataaaat gttacctcta attgcgagat atggcaagat    8400
acaaataact aagtctacta caaaatcttt tctttcaata acttatactt ttgaaattac    8460
ttctacttct actgctgcta ctaataacaa catttagaca aaatctactt cttctactgc    8520
gcgatttcat atgataccaa tgtttcatat tcagatatga tgattaccgc tgaacacgtt    8580
cttccatatc atatcacttt tacaacaatc taatactaat acttttttggt ttatttagtc    8640 taggtataga tttccataga ggaaacgtgt attaaagtag ataaggatca aatcttatga    8700 aaagtaaatat aaacaaatgt cgacttctgc tttttttata tagctattat cttctaaatac   8760 aattgagacg attattctac tttaacttac tcagacactg acgtcggttc gaaccgtgac    8820
cggcagcaaa atgttgcagc actgacccctt ttgggaccgc aatgggttga attagcggaa    8880
cgtcgtgtag ggggaaagcg gtcgaccgca ttatcgcttc tccggcgtg gctagcggaa    8940 agggttgtca acgcgtcgga cttaccgctt accgcggact acgccataaa agaggaatgc    9000
gtagacacgc cataaagtgt ggcgtatacc acgtgagagt catgttagac gagactacgg    9060
cgtatcaatt cggtcgggc tgtgggcggt tgtgggcgac tgcgcgggac tgcccgaaca    9120
gacgagggcc gtaggcgaat gtctgttcga cactggcaga ggccctcgac gtacacagtc    9180
```

```
tccaaaagtg gcagtagtgg ctttgcgcgc tctgctttcc cggagcacta tgcggataaa    9240
aatatccaat tacagtacta ttattaccaa agaatctgca gtccaccgtg aaaagcccct    9300
ttacacgcgc cttggggata aacaaataaa aagatttatg taagtttata cataggcgag    9360
tactctgtta ttgggactat ttacgaagtt attataactt tttccttctc atactcataa    9420
gttgtaaagg cacagcggga ataagggaaa aaacgccgta aaacggaagg acaaaaacga    9480
gtgggtcttt gcgaccactt tcattttcta cgacttctag tcaacccacg tgctcaccca    9540
atgtagcttg acctagagtt gtcgccattc taggaactct caaaagcggg gcttcttgca    9600
aaaggttact actcgtgaaa atttcaagac gatacaccgc gccataatag gcataactg     9660
cggcccgttc tcgttgagcc agcggcgtat gtgataagag tcttactgaa ccaactcatg    9720
agtggtcagt gtcttttcgt agaatgccta ccgtactgtc attctcttaa tacgtcacga    9780
cggtattggt actcactatt gtgacgccgg ttgaatgaag actgttgcta gcctcctggc    9840
ttcctcgatt ggcgaaaaaa cgtgttgtac ccctagtac attgagcgga actagcaacc     9900
cttggcctcg acttacttcg gtatggtttg ctgctcgcac tgtggtgcta cggacatcgt    9960
taccgttgtt gcaacgcgtt tgataattga ccgcttgatg aatgagatcg aagggccgtt   10020
gttaattatc tgacctacct ccgcctattt caacgtcctg gtgaagacgc gagccgggaa   10080
ggccgaccga ccaaataacg actatttaga cctcggccac tcgcacccag agcgccatag   10140
taacgtcgtg accccggtct accattcggg agggcatagc atcaatagat gtgctgcccc   10200
tcagtccgtt gataccctact tgctttatct gtctagcgac tctatccacg gagtgactaa  10260
ttcgtaacca ttgacagtct ggttcaaatg agtatatatg aaatctaact aaattttgaa   10320
gtaaaaatta aattttccta gatccacttc taggaaaaac tattagagta ctggttttag   10380
ggaattgcac tcaaaagcaa ggtgactcgc agtctggggc atcttttcta gtttcctaga   10440
agaactctag gaaaaaaaga cgcgcattag acgacgaacg tttgtttttt tggtggcgat   10500
ggtcgccacc aaacaaacgg cctagttctc gatggttgag aaaaaggctt ccattgaccg   10560
aagtcgtctc gcgtctatgg tttatgacag gaagatcaca tcggcatcaa tccggtggtg   10620
aagttcttga gacatcgtgg cggatgtatg gagcgagacg attaggacaa tggtcaccga   10680
cgacggtcac cgctattcag cacagaatgg cccaacctga gttctgctat caatggccta   10740
ttccgcgtcg ccagcccgac ttgccccca agcacgtgtg tcgggtcgaa cctcgcttgc    10800
tggatgtggc ttgactctat ggatgtcgca ctcgatactc tttcgcggtg cgaagggctt   10860
ccctctttcc gcctgtccat aggccattcg ccgtcccagc cttgtcctct cgcgtgctcc   10920
ctcgaaggtc ccccttgcg gaccatagaa atatcaggac agcccaaagc ggtggagact    10980
gaactcgcag ctaaaacac tacgagcagt cccccgcct cggataccttt tttgcggtcg   11040
ttgcgccgga aaatgccaa ggaccggaaa acgaccggaa aacgagtgta caagaaagga    11100
cgcaataggg gactaagaca cctattggca taatggcgga aactcactcg actatgcga    11160
gcggcgtcgg cttgctggct cgcgtcgctc agtcactcgc tccttcgcct tctcgcgggt   11220
tatgcgtttg gcggagaggg gcgcgcaacc ggctaagtaa ttacgtcgac cgtgctgtcc   11280
aaagggctga cctttcgccc gtcactcgcg ttgcgttaat tacactcaat cgagtgagta   11340
atccgtgggg tccgaaatgt gaaatacgaa ggccgagcat acaacacacc ttaacactcg   11400
cctattgtta aagtgtgtcc tttgtcgata ctggtactaa tgcttaactt                11450
```

<210> SEQ ID NO 7

-continued

```
<211> LENGTH: 180
<212> TYPE: PRT
<213> ORGANISM: Homo sapiens

<400> SEQUENCE: 7

Met Gln Ala Glu Gly Arg Gly Thr Gly Gly Ser Thr Gly Asp Ala Asp
1               5                   10                  15

Gly Pro Gly Gly Pro Gly Ile Pro Asp Gly Pro Gly Gly Asn Ala Gly
            20                  25                  30

Gly Pro Gly Glu Ala Gly Ala Thr Gly Gly Arg Gly Pro Arg Gly Ala
        35                  40                  45

Gly Ala Ala Arg Ala Ser Gly Pro Gly Gly Ala Pro Arg Gly Pro
    50                  55                  60

His Gly Gly Ala Ala Ser Gly Leu Asn Gly Cys Cys Arg Cys Gly Ala
65                  70                  75                  80

Arg Gly Pro Glu Ser Arg Leu Leu Glu Phe Tyr Leu Ala Met Pro Phe
                85                  90                  95

Ala Thr Pro Met Glu Ala Glu Leu Ala Arg Arg Ser Leu Ala Gln Asp
            100                 105                 110

Ala Pro Pro Leu Pro Val Pro Gly Val Leu Leu Lys Glu Phe Thr Val
        115                 120                 125

Ser Gly Asn Ile Leu Thr Ile Arg Leu Thr Ala Ala Asp His Arg Gln
    130                 135                 140

Leu Gln Leu Ser Ile Ser Ser Cys Leu Gln Gln Leu Ser Leu Leu Met
145                 150                 155                 160

Trp Ile Thr Gln Val Phe Leu Pro Val Phe Leu Ala Gln Pro Pro Ser
                165                 170                 175

Gly Gln Arg Arg
            180

<210> SEQ ID NO 8
<211> LENGTH: 552
<212> TYPE: PRT
<213> ORGANISM: Homo sapiens

<400> SEQUENCE: 8

Met Ser Pro Leu Trp Trp Gly Phe Leu Leu Ser Cys Leu Gly Cys Lys
1               5                   10                  15

Ile Leu Pro Gly Ala Gln Gly Gln Phe Pro Arg Val Cys Met Thr Val
            20                  25                  30

Asp Ser Leu Val Asn Lys Glu Cys Cys Pro Arg Leu Gly Ala Glu Ser
        35                  40                  45

Ala Asn Val Cys Gly Ser Gln Gln Gly Arg Gly Gln Cys Thr Glu Val
    50                  55                  60

Arg Ala Asp Thr Arg Pro Trp Ser Gly Pro Tyr Ile Leu Arg Asn Gln
65                  70                  75                  80

Asp Asp Arg Glu Leu Trp Pro Arg Lys Phe Phe His Arg Thr Cys Lys
                85                  90                  95

Cys Thr Gly Asn Phe Ala Gly Tyr Asn Cys Gly Asp Cys Lys Phe Gly
            100                 105                 110

Trp Thr Gly Pro Asn Cys Glu Arg Lys Lys Pro Pro Val Ile Arg Gln
        115                 120                 125

Asn Ile His Ser Leu Ser Pro Gln Glu Arg Glu Gln Phe Leu Gly Ala
    130                 135                 140

Leu Asp Leu Ala Lys Lys Arg Val His Pro Asp Tyr Val Ile Thr Thr
145                 150                 155                 160
```

Gln His Trp Leu Gly Leu Leu Gly Pro Asn Gly Thr Gln Pro Gln Phe
                165                 170                 175

Ala Asn Cys Ser Val Tyr Asp Phe Phe Val Trp Leu His Tyr Tyr Ser
            180                 185                 190

Val Arg Asp Thr Leu Leu Gly Pro Gly Arg Pro Tyr Arg Ala Ile Asp
        195                 200                 205

Phe Ser His Gln Gly Pro Ala Phe Val Thr Trp His Arg Tyr His Leu
    210                 215                 220

Leu Cys Leu Glu Arg Asp Leu Gln Arg Leu Ile Gly Asn Glu Ser Phe
225                 230                 235                 240

Ala Leu Pro Tyr Trp Asn Phe Ala Thr Gly Arg Asn Glu Cys Asp Val
                245                 250                 255

Cys Thr Asp Gln Leu Phe Gly Ala Ala Arg Pro Asp Asp Pro Thr Leu
            260                 265                 270

Ile Ser Arg Asn Ser Arg Phe Ser Ser Trp Glu Thr Val Cys Asp Ser
        275                 280                 285

Leu Asp Asp Tyr Asn His Leu Val Thr Leu Cys Asn Gly Thr Tyr Glu
    290                 295                 300

Gly Leu Leu Arg Arg Asn Gln Met Gly Arg Asn Ser Met Lys Leu Pro
305                 310                 315                 320

Thr Leu Lys Asp Ile Arg Asp Cys Leu Ser Leu Gln Lys Phe Asp Asn
                325                 330                 335

Pro Pro Phe Phe Gln Asn Ser Thr Phe Ser Phe Arg Asn Ala Leu Glu
            340                 345                 350

Gly Phe Asp Lys Ala Asp Gly Thr Leu Asp Ser Gln Val Met Ser Leu
        355                 360                 365

His Asn Leu Val His Ser Phe Leu Asn Gly Thr Asn Ala Leu Pro His
    370                 375                 380

Ser Ala Ala Asn Asp Pro Ile Phe Val Val Ile Ser Asn Arg Leu Leu
385                 390                 395                 400

Tyr Asn Ala Thr Thr Asn Ile Leu Glu His Val Arg Lys Glu Lys Ala
                405                 410                 415

Thr Lys Glu Leu Pro Ser Leu His Val Leu Val Leu His Ser Phe Thr
            420                 425                 430

Asp Ala Ile Phe Asp Glu Trp Met Lys Arg Phe Asn Pro Pro Ala Asp
        435                 440                 445

Ala Trp Pro Gln Glu Leu Ala Pro Ile Gly His Asn Arg Met Tyr Asn
    450                 455                 460

Met Val Pro Phe Phe Pro Val Thr Asn Glu Leu Phe Leu Thr
465                 470                 475                 480

Ser Asp Gln Leu Gly Tyr Ser Tyr Ala Ile Asp Leu Pro Val Ser Val
                485                 490                 495

Glu Glu Thr Pro Gly Trp Pro Thr Thr Leu Leu Val Val Met Gly Thr
            500                 505                 510

Leu Val Ala Leu Val Gly Leu Phe Val Leu Leu Ala Phe Leu Gln Tyr
        515                 520                 525

Arg Arg Leu Arg Lys Gly Tyr Thr Pro Leu Met Glu Thr His Leu Ser
    530                 535                 540

Ser Lys Arg Tyr Thr Glu Glu Ala
545                 550

<210> SEQ ID NO 9
<211> LENGTH: 661

<212> TYPE: PRT
<213> ORGANISM: Homo sapiens

<400> SEQUENCE: 9

```
Met Asp Leu Val Leu Lys Arg Cys Leu Leu His Leu Ala Val Ile Gly
1               5                   10                  15

Ala Leu Leu Ala Val Gly Ala Thr Lys Val Pro Arg Asn Gln Asp Trp
            20                  25                  30

Leu Gly Val Ser Arg Gln Leu Arg Thr Lys Ala Trp Asn Arg Gln Leu
        35                  40                  45

Tyr Pro Glu Trp Thr Glu Ala Gln Arg Leu Asp Cys Trp Arg Gly Gly
    50                  55                  60

Gln Val Ser Leu Lys Val Ser Asn Asp Gly Pro Thr Leu Ile Gly Ala
65                  70                  75                  80

Asn Ala Ser Phe Ser Ile Ala Leu Asn Phe Pro Gly Ser Gln Lys Val
                85                  90                  95

Leu Pro Asp Gly Gln Val Ile Trp Val Asn Asn Thr Ile Ile Asn Gly
            100                 105                 110

Ser Gln Val Trp Gly Gly Gln Pro Val Tyr Pro Gln Glu Thr Asp Asp
        115                 120                 125

Ala Cys Ile Phe Pro Asp Gly Gly Pro Cys Pro Ser Gly Ser Trp Ser
    130                 135                 140

Gln Lys Arg Ser Phe Val Tyr Val Trp Lys Thr Trp Gly Gln Tyr Trp
145                 150                 155                 160

Gln Phe Leu Gly Gly Pro Val Ser Gly Leu Ser Ile Gly Thr Gly Arg
                165                 170                 175

Ala Met Leu Gly Thr His Thr Met Glu Val Thr Val Tyr His Arg Arg
            180                 185                 190

Gly Ser Arg Ser Tyr Val Pro Leu Ala His Ser Ser Ser Ala Phe Thr
        195                 200                 205

Ile Thr Asp Gln Val Pro Phe Ser Val Ser Val Ser Gln Leu Arg Ala
    210                 215                 220

Leu Asp Gly Gly Asn Lys His Phe Leu Arg Asn Gln Pro Leu Thr Phe
225                 230                 235                 240

Ala Leu Gln Leu His Asp Pro Ser Gly Tyr Leu Ala Glu Ala Asp Leu
                245                 250                 255

Ser Tyr Thr Trp Asp Phe Gly Asp Ser Ser Gly Thr Leu Ile Ser Arg
            260                 265                 270

Ala Leu Val Val Thr His Thr Tyr Leu Glu Pro Gly Pro Val Thr Ala
        275                 280                 285

Gln Val Val Leu Gln Ala Ala Ile Pro Leu Thr Ser Cys Gly Ser Ser
    290                 295                 300

Pro Val Pro Gly Thr Thr Asp Gly His Arg Pro Thr Ala Glu Ala Pro
305                 310                 315                 320

Asn Thr Thr Ala Gly Gln Val Pro Thr Thr Glu Val Val Gly Thr Thr
                325                 330                 335

Pro Gly Gln Ala Pro Thr Ala Glu Pro Ser Gly Thr Thr Ser Val Gln
            340                 345                 350

Val Pro Thr Thr Glu Val Ile Ser Thr Ala Pro Val Gln Met Pro Thr
        355                 360                 365

Ala Glu Ser Thr Gly Met Thr Pro Glu Lys Val Pro Val Ser Glu Val
    370                 375                 380

Met Gly Thr Thr Leu Ala Glu Met Ser Thr Pro Glu Ala Thr Gly Met
385                 390                 395                 400
```

```
Thr Pro Ala Glu Val Ser Ile Val Leu Ser Gly Thr Ala Ala
            405                 410                 415

Gln Val Thr Thr Thr Glu Trp Val Glu Thr Thr Ala Arg Glu Leu Pro
        420                 425                 430

Ile Pro Glu Pro Glu Gly Pro Asp Ala Ser Ser Ile Met Ser Thr Glu
        435                 440                 445

Ser Ile Thr Gly Ser Leu Gly Pro Leu Leu Asp Gly Thr Ala Thr Leu
    450                 455                 460

Arg Leu Val Lys Arg Gln Val Pro Leu Asp Cys Val Leu Tyr Arg Tyr
465                 470                 475                 480

Gly Ser Phe Ser Val Thr Leu Asp Ile Val Gln Gly Ile Glu Ser Ala
                485                 490                 495

Glu Ile Leu Gln Ala Val Pro Ser Gly Glu Gly Asp Ala Phe Glu Leu
            500                 505                 510

Thr Val Ser Cys Gln Gly Gly Leu Pro Lys Glu Ala Cys Met Glu Ile
        515                 520                 525

Ser Ser Pro Gly Cys Gln Pro Pro Ala Gln Arg Leu Cys Gln Pro Val
    530                 535                 540

Leu Pro Ser Pro Ala Cys Gln Leu Val Leu His Gln Ile Leu Lys Gly
545                 550                 555                 560

Gly Ser Gly Thr Tyr Cys Leu Asn Val Ser Leu Ala Asp Thr Asn Ser
                565                 570                 575

Leu Ala Val Val Ser Thr Gln Leu Ile Met Pro Gly Gln Glu Ala Gly
            580                 585                 590

Leu Gly Gln Val Pro Leu Ile Val Gly Ile Leu Leu Val Leu Met Ala
        595                 600                 605

Val Val Leu Ala Ser Leu Ile Tyr Arg Arg Arg Leu Met Lys Gln Asp
    610                 615                 620

Phe Ser Val Pro Gln Leu Pro His Ser Ser His Trp Leu Arg Leu
625                 630                 635                 640

Pro Arg Ile Phe Cys Ser Cys Pro Ile Gly Glu Asn Ser Pro Leu Leu
                645                 650                 655

Ser Gly Gln Gln Val
            660

<210> SEQ ID NO 10
<211> LENGTH: 661
<212> TYPE: PRT
<213> ORGANISM: Artificial sequence
<220> FEATURE:
<223> OTHER INFORMATION: Homo sapiens

<400> SEQUENCE: 10

Met Asp Leu Val Leu Lys Arg Cys Leu Leu His Leu Ala Val Ile Gly
1               5                   10                  15

Ala Leu Leu Ala Val Gly Ala Thr Lys Val Pro Arg Asn Gln Asp Trp
            20                  25                  30

Leu Gly Val Ser Arg Gln Leu Arg Thr Lys Ala Trp Asn Arg Gln Leu
        35                  40                  45

Tyr Pro Glu Trp Thr Glu Ala Gln Arg Leu Asp Cys Trp Arg Gly Gly
    50                  55                  60

Gln Val Ser Leu Lys Val Ser Asn Asp Gly Pro Thr Leu Ile Gly Ala
65                  70                  75                  80

Asn Ala Ser Phe Ser Ile Ala Leu Asn Phe Pro Gly Ser Gln Lys Val
                85                  90                  95
```

Leu Pro Asp Gly Gln Val Ile Trp Val Asn Asn Thr Ile Ile Asn Gly
            100                 105                 110

Ser Gln Val Trp Gly Gly Gln Pro Val Tyr Pro Gln Glu Thr Asp Asp
            115                 120                 125

Ala Cys Ile Phe Pro Asp Gly Gly Pro Cys Pro Ser Gly Ser Trp Ser
            130                 135                 140

Gln Lys Arg Ser Phe Val Tyr Val Trp Lys Thr Trp Gly Gln Tyr Trp
145                 150                 155                 160

Gln Val Leu Gly Gly Pro Val Ser Gly Leu Ser Ile Gly Thr Gly Arg
                165                 170                 175

Ala Met Leu Gly Thr His Thr Met Glu Val Thr Val Tyr His Arg Arg
            180                 185                 190

Gly Ser Arg Ser Tyr Val Pro Leu Ala His Ser Ser Ala Phe Thr
            195                 200                 205

Ile Met Asp Gln Val Pro Phe Ser Val Ser Val Ser Gln Leu Arg Ala
            210                 215                 220

Leu Asp Gly Gly Asn Lys His Phe Leu Arg Asn Gln Pro Leu Thr Phe
225                 230                 235                 240

Ala Leu Gln Leu His Asp Pro Ser Gly Tyr Leu Ala Glu Ala Asp Leu
                245                 250                 255

Ser Tyr Thr Trp Asp Phe Gly Asp Ser Ser Gly Thr Leu Ile Ser Arg
            260                 265                 270

Ala Leu Val Val Thr His Thr Tyr Leu Glu Pro Gly Pro Val Thr Val
            275                 280                 285

Gln Val Val Leu Gln Ala Ala Ile Pro Leu Thr Ser Cys Gly Ser Ser
            290                 295                 300

Pro Val Pro Gly Thr Thr Asp Gly His Arg Pro Thr Ala Glu Ala Pro
305                 310                 315                 320

Asn Thr Thr Ala Gly Gln Val Pro Thr Thr Glu Val Val Gly Thr Thr
                325                 330                 335

Pro Gly Gln Ala Pro Thr Ala Glu Pro Ser Gly Thr Thr Ser Val Gln
            340                 345                 350

Val Pro Thr Thr Glu Val Ile Ser Thr Ala Pro Val Gln Met Pro Thr
            355                 360                 365

Ala Glu Ser Thr Gly Met Thr Pro Glu Lys Val Pro Val Ser Glu Val
            370                 375                 380

Met Gly Thr Thr Leu Ala Glu Met Ser Thr Pro Glu Ala Thr Gly Met
385                 390                 395                 400

Thr Pro Ala Glu Val Ser Ile Val Val Leu Ser Gly Thr Thr Ala Ala
                405                 410                 415

Gln Val Thr Thr Thr Glu Trp Val Glu Thr Thr Ala Arg Glu Leu Pro
            420                 425                 430

Ile Pro Glu Pro Glu Gly Pro Asp Ala Ser Ser Ile Met Ser Thr Glu
            435                 440                 445

Ser Ile Thr Gly Ser Leu Gly Pro Leu Leu Asp Gly Thr Ala Thr Leu
            450                 455                 460

Arg Leu Val Lys Arg Gln Val Pro Leu Asp Cys Val Leu Tyr Arg Tyr
465                 470                 475                 480

Gly Ser Phe Ser Val Thr Leu Asp Ile Val Gln Gly Ile Glu Ser Ala
                485                 490                 495

Glu Ile Leu Gln Ala Val Pro Ser Gly Glu Gly Asp Ala Phe Glu Leu
            500                 505                 510

```
Thr Val Ser Cys Gln Gly Gly Leu Pro Lys Glu Ala Cys Met Glu Ile
            515                 520                 525

Ser Ser Pro Gly Cys Gln Pro Ala Gln Arg Leu Cys Gln Pro Val
530                 535                 540

Leu Pro Ser Pro Ala Cys Gln Leu Val Leu His Gln Ile Leu Lys Gly
545                 550                 555                 560

Gly Ser Gly Thr Tyr Cys Leu Asn Val Ser Leu Ala Asp Thr Asn Ser
                565                 570                 575

Leu Ala Val Val Ser Thr Gln Leu Ile Met Pro Gly Gln Glu Ala Gly
            580                 585                 590

Leu Gly Gln Val Pro Leu Ile Val Gly Ile Leu Leu Val Leu Met Ala
            595                 600                 605

Val Val Leu Ala Ser Leu Ile Tyr Arg Arg Arg Leu Met Lys Gln Asp
610                 615                 620

Phe Ser Val Pro Gln Leu Pro His Ser Ser His Trp Leu Arg Leu
625                 630                 635                 640

Pro Arg Ile Phe Cys Ser Cys Pro Ile Gly Glu Asn Ser Pro Leu Leu
                645                 650                 655

Ser Gly Gln Gln Val
            660

<210> SEQ ID NO 11
<211> LENGTH: 118
<212> TYPE: PRT
<213> ORGANISM: Homo sapiens

<400> SEQUENCE: 11

Met Pro Arg Glu Asp Ala His Phe Ile Tyr Gly Tyr Pro Lys Lys Gly
1                   5                   10                  15

His Gly His Ser Tyr Thr Thr Ala Glu Glu Ala Ala Gly Ile Gly Ile
                20                  25                  30

Leu Thr Val Ile Leu Gly Val Leu Leu Leu Ile Gly Cys Trp Tyr Cys
            35                  40                  45

Arg Arg Arg Asn Gly Tyr Arg Ala Leu Met Asp Lys Ser Leu His Val
50                  55                  60

Gly Thr Gln Cys Ala Leu Thr Arg Arg Cys Pro Gln Glu Gly Phe Asp
65                  70                  75                  80

His Arg Asp Ser Lys Val Ser Leu Gln Glu Lys Asn Cys Glu Pro Val
                85                  90                  95

Val Pro Asn Ala Pro Pro Ala Tyr Glu Lys Leu Ser Ala Glu Gln Ser
            100                 105                 110

Pro Pro Pro Tyr Ser Pro
            115

<210> SEQ ID NO 12
<211> LENGTH: 208
<212> TYPE: PRT
<213> ORGANISM: Homo sapiens

<400> SEQUENCE: 12

Met Ser Asp Asn Lys Lys Pro Asp Leu Ala His Ser Gly Ser Gly Gly
1                   5                   10                  15

Asp Gly Asp Gly Asn Arg Cys Asn Leu Leu His Arg Tyr Ser Leu Gln
                20                  25                  30

Gly Ile Leu Pro Tyr Leu Gly Trp Leu Val Phe Ala Val Val Thr Thr
            35                  40                  45
```

```
Ser Phe Leu Ala Leu Glu Met Phe Ile Asp Ala Leu Tyr Gln Gln Glu
 50                  55                  60

Tyr Gln Arg Asp Val Ala Trp Ile Ala Arg Gln Ser Lys Arg Met Ser
 65                  70                  75                  80

Ser Val Asp Gln Asp Gln Asp Gln Asp Gln Asp Asp Tyr Tyr
                 85                  90                  95

Gln Gln Gln Gln Leu Gln Asn Leu Met Asp Asp Gln Ser Gln Asp Gln
            100                 105                 110

Ala Gln Gln Met Ser Val Gln Met Gly Ala Gly Ala Gln Gln Met
            115                 120                 125

Gly Ala Gly Ala Asn Cys Ala Cys Val Pro Gly His His Leu Arg Lys
130                 135                 140

Asn Gln Val Lys Cys Arg Met Ile Tyr Phe Phe His Asp Pro Asn Phe
145                 150                 155                 160

Leu Val Ser Ile Pro Val Asn Pro Lys Gln Glu Met Gln Cys Arg Cys
                165                 170                 175

Gln Asn Ala Asp Gln Gln Val Ala Met Gln Gln Gln Gln Gln Gln
                180                 185                 190

Gln Gln Gln Gln Gln Gln Met Gly Asn Pro Asp Gly Phe Ser Pro
            195                 200                 205
```

<210> SEQ ID NO 13
<211> LENGTH: 314
<212> TYPE: PRT
<213> ORGANISM: Homo sapiens

<400> SEQUENCE: 13

```
Met Pro Leu Glu Gln Arg Ser Gln His Cys Lys Pro Glu Glu Ala Leu
 1               5                  10                  15

Glu Ala Arg Gly Glu Ala Leu Gly Leu Val Gly Ala Gln Ala Pro Ala
                 20                  25                  30

Thr Glu Glu Gln Glu Ala Ala Ser Ser Ser Thr Leu Val Glu Val
             35                  40                  45

Thr Leu Gly Glu Val Pro Ala Ala Glu Ser Pro Asp Pro Pro Gln Ser
 50                  55                  60

Pro Gln Gly Ala Ser Ser Leu Pro Thr Thr Met Asn Tyr Pro Leu Trp
 65                  70                  75                  80

Ser Gln Ser Tyr Glu Asp Ser Ser Asn Gln Glu Glu Glu Gly Pro Ser
                 85                  90                  95

Thr Phe Pro Asp Leu Glu Ser Glu Phe Gln Ala Ala Leu Ser Arg Lys
             100                 105                 110

Val Ala Glu Leu Val His Phe Leu Leu Leu Lys Tyr Arg Ala Arg Glu
            115                 120                 125

Pro Val Thr Lys Ala Glu Met Leu Gly Ser Val Val Gly Asn Trp Gln
            130                 135                 140

Tyr Phe Phe Pro Val Ile Phe Ser Lys Ala Ser Ser Ser Leu Gln Leu
145                 150                 155                 160

Val Phe Gly Ile Glu Leu Met Glu Val Asp Pro Ile Gly His Leu Tyr
                165                 170                 175

Ile Phe Ala Thr Cys Leu Gly Leu Ser Tyr Asp Gly Leu Leu Gly Asp
            180                 185                 190

Asn Gln Ile Met Pro Lys Ala Gly Leu Leu Ile Ile Val Leu Ala Ile
            195                 200                 205

Ile Ala Arg Glu Gly Asp Cys Ala Pro Glu Glu Lys Ile Trp Glu Glu
210                 215                 220
```

Leu Ser Val Leu Glu Val Phe Glu Gly Arg Glu Asp Ser Ile Leu Gly
225                 230                 235                 240

Asp Pro Lys Lys Leu Leu Thr Gln His Phe Val Gln Glu Asn Tyr Leu
            245                 250                 255

Glu Tyr Arg Gln Val Pro Gly Ser Asp Pro Ala Cys Tyr Glu Phe Leu
        260                 265                 270

Trp Gly Pro Arg Ala Leu Val Glu Thr Ser Tyr Val Lys Val Leu His
            275                 280                 285

His Met Val Lys Ile Ser Gly Gly Pro His Ile Ser Tyr Pro Pro Leu
290                 295                 300

His Glu Trp Val Leu Arg Glu Gly Glu Glu
305                 310

<210> SEQ ID NO 14
<211> LENGTH: 288
<212> TYPE: PRT
<213> ORGANISM: Homo sapiens

<400> SEQUENCE: 14

Met Gly His Thr Arg Arg Gln Gly Thr Ser Pro Ser Lys Cys Pro Tyr
1               5                   10                  15

Leu Asn Phe Phe Gln Leu Leu Val Leu Ala Gly Leu Ser His Phe Cys
            20                  25                  30

Ser Gly Val Ile His Val Thr Lys Glu Val Lys Glu Val Ala Thr Leu
        35                  40                  45

Ser Cys Gly His Asn Val Ser Val Glu Glu Leu Ala Gln Thr Arg Ile
50                  55                  60

Tyr Trp Gln Lys Glu Lys Lys Met Val Leu Thr Met Met Ser Gly Asp
65                  70                  75                  80

Met Asn Ile Trp Pro Glu Tyr Lys Asn Arg Thr Ile Phe Asp Ile Thr
                85                  90                  95

Asn Asn Leu Ser Ile Val Ile Leu Ala Leu Arg Pro Ser Asp Glu Gly
            100                 105                 110

Thr Tyr Glu Cys Val Val Leu Lys Tyr Glu Lys Asp Ala Phe Lys Arg
        115                 120                 125

Glu His Leu Ala Glu Val Thr Leu Ser Val Lys Ala Asp Phe Pro Thr
130                 135                 140

Pro Ser Ile Ser Asp Phe Glu Ile Pro Thr Ser Asn Ile Arg Arg Ile
145                 150                 155                 160

Ile Cys Ser Thr Ser Gly Gly Phe Pro Glu Pro His Leu Ser Trp Leu
                165                 170                 175

Glu Asn Gly Glu Glu Leu Asn Ala Ile Asn Thr Thr Val Ser Gln Asp
            180                 185                 190

Pro Glu Thr Glu Leu Tyr Ala Val Ser Ser Lys Leu Asp Phe Asn Met
        195                 200                 205

Thr Thr Asn His Ser Phe Met Cys Leu Ile Lys Tyr Gly His Leu Arg
210                 215                 220

Val Asn Gln Thr Phe Asn Trp Asn Thr Thr Lys Gln Glu His Phe Pro
225                 230                 235                 240

Asp Asn Leu Leu Pro Ser Trp Ala Ile Thr Leu Ile Ser Val Asn Gly
                245                 250                 255

Ile Phe Val Ile Cys Cys Leu Thr Tyr Cys Phe Ala Pro Arg Cys Arg
            260                 265                 270

Glu Arg Arg Arg Asn Glu Arg Leu Arg Arg Glu Ser Val Arg Pro Val

```
              275                 280                 285
```

<210> SEQ ID NO 15
<211> LENGTH: 250
<212> TYPE: PRT
<213> ORGANISM: Homo sapiens

<400> SEQUENCE: 15

```
Met Val Ala Gly Ser Asp Ala Gly Arg Ala Leu Gly Val Leu Ser Val
1               5                   10                  15

Val Cys Leu Leu His Cys Phe Gly Phe Ile Ser Cys Phe Ser Gln Gln
            20                  25                  30

Ile Tyr Gly Val Val Tyr Gly Asn Val Thr Phe His Val Pro Ser Asn
        35                  40                  45

Val Pro Leu Lys Glu Val Leu Trp Lys Lys Gln Lys Asp Lys Val Ala
    50                  55                  60

Glu Leu Glu Asn Ser Glu Phe Arg Ala Phe Ser Ser Phe Lys Asn Arg
65                  70                  75                  80

Val Tyr Leu Asp Thr Val Ser Gly Ser Leu Thr Ile Tyr Asn Leu Thr
                85                  90                  95

Ser Ser Asp Glu Asp Glu Tyr Glu Met Glu Ser Pro Asn Ile Thr Asp
            100                 105                 110

Thr Met Lys Phe Phe Leu Tyr Val Leu Glu Ser Leu Pro Ser Pro Thr
        115                 120                 125

Leu Thr Cys Ala Leu Thr Asn Gly Ser Ile Glu Val Gln Cys Met Ile
130                 135                 140

Pro Glu His Tyr Asn Ser His Arg Gly Leu Ile Met Tyr Ser Trp Asp
145                 150                 155                 160

Cys Pro Met Glu Gln Cys Lys Arg Asn Ser Thr Ser Ile Tyr Phe Lys
                165                 170                 175

Met Glu Asn Asp Leu Pro Gln Lys Ile Gln Cys Thr Leu Ser Asn Pro
            180                 185                 190

Leu Phe Asn Thr Thr Ser Ser Ile Ile Leu Thr Thr Cys Ile Pro Ser
        195                 200                 205

Ser Gly His Ser Arg His Arg Tyr Ala Leu Ile Pro Ile Pro Leu Ala
    210                 215                 220

Val Ile Thr Thr Cys Ile Val Leu Tyr Met Asn Gly Ile Leu Lys Cys
225                 230                 235                 240

Asp Arg Lys Pro Asp Arg Thr Asn Ser Asn
                245                 250
```

<210> SEQ ID NO 16
<211> LENGTH: 532
<212> TYPE: PRT
<213> ORGANISM: Homo sapiens

<400> SEQUENCE: 16

```
Met Ala Pro Ser Ser Pro Arg Pro Ala Leu Pro Ala Leu Leu Val Leu
1               5                   10                  15

Leu Gly Ala Leu Phe Pro Gly Pro Gly Asn Ala Gln Thr Ser Val Ser
            20                  25                  30

Pro Ser Lys Val Ile Leu Pro Arg Gly Gly Ser Val Leu Val Thr Cys
        35                  40                  45

Ser Thr Ser Cys Asp Gln Pro Lys Leu Leu Gly Ile Glu Thr Pro Leu
    50                  55                  60

Pro Lys Lys Glu Leu Leu Leu Pro Gly Asn Asn Arg Lys Val Tyr Glu
```

-continued

```
            65                  70                  75                  80
Leu Ser Asn Val Gln Glu Asp Ser Gln Pro Met Cys Tyr Ser Asn Cys
                    85                  90                  95

Pro Asp Gly Gln Ser Thr Ala Lys Thr Phe Leu Thr Val Tyr Trp Thr
                100                 105                 110

Pro Glu Arg Val Glu Leu Ala Pro Leu Pro Ser Trp Gln Pro Val Gly
                115                 120                 125

Lys Asn Leu Thr Leu Arg Cys Gln Val Glu Gly Gly Ala Pro Arg Ala
130                 135                 140

Asn Leu Thr Val Val Leu Leu Arg Gly Glu Lys Glu Leu Lys Arg Glu
145                 150                 155                 160

Pro Ala Val Gly Glu Pro Ala Glu Val Thr Thr Thr Val Leu Val Arg
                165                 170                 175

Arg Asp His His Gly Ala Asn Phe Ser Cys Arg Thr Glu Leu Asp Leu
                180                 185                 190

Arg Pro Gln Gly Leu Glu Leu Phe Glu Asn Thr Ser Ala Pro Tyr Gln
                195                 200                 205

Leu Gln Thr Phe Val Leu Pro Ala Thr Pro Pro Gln Leu Val Ser Pro
210                 215                 220

Arg Val Leu Glu Val Asp Thr Gln Gly Thr Val Val Cys Ser Leu Asp
225                 230                 235                 240

Gly Leu Phe Pro Val Ser Glu Ala Gln Val His Leu Ala Leu Gly Asp
                245                 250                 255

Gln Arg Leu Asn Pro Thr Val Thr Tyr Gly Asn Asp Ser Phe Ser Ala
                260                 265                 270

Lys Ala Ser Val Ser Val Thr Ala Glu Asp Glu Gly Thr Gln Arg Leu
                275                 280                 285

Thr Cys Ala Val Ile Leu Gly Asn Gln Ser Gln Glu Thr Leu Gln Thr
                290                 295                 300

Val Thr Ile Tyr Ser Phe Pro Ala Pro Asn Val Ile Leu Thr Lys Pro
305                 310                 315                 320

Glu Val Ser Glu Gly Thr Glu Val Thr Val Lys Cys Glu Ala His Pro
                325                 330                 335

Arg Ala Lys Val Thr Leu Asn Gly Val Pro Ala Gln Pro Leu Gly Pro
                340                 345                 350

Arg Ala Gln Leu Leu Leu Lys Ala Thr Pro Glu Asp Asn Gly Arg Ser
                355                 360                 365

Phe Ser Cys Ser Ala Thr Leu Glu Val Ala Gly Gln Leu Ile His Lys
370                 375                 380

Asn Gln Thr Arg Glu Leu Arg Val Leu Tyr Gly Pro Arg Leu Asp Glu
385                 390                 395                 400

Arg Asp Cys Pro Gly Asn Trp Thr Trp Pro Glu Asn Ser Gln Gln Thr
                405                 410                 415

Pro Met Cys Gln Ala Trp Gly Asn Pro Leu Pro Glu Leu Lys Cys Leu
                420                 425                 430

Lys Asp Gly Thr Phe Pro Leu Pro Ile Gly Glu Ser Val Thr Val Thr
                435                 440                 445

Arg Asp Leu Glu Gly Thr Tyr Leu Cys Arg Ala Arg Ser Thr Gln Gly
                450                 455                 460

Glu Val Thr Arg Glu Val Thr Val Asn Val Leu Ser Pro Arg Tyr Glu
465                 470                 475                 480

Ile Val Ile Ile Thr Val Val Ala Ala Ala Val Ile Met Gly Thr Ala
                485                 490                 495
```

```
Gly Leu Ser Thr Tyr Leu Tyr Asn Arg Gln Arg Lys Ile Lys Lys Tyr
            500                 505                 510

Arg Leu Gln Gln Ala Gln Lys Gly Thr Pro Met Lys Pro Asn Thr Gln
        515                 520                 525

Ala Thr Pro Pro
    530

<210> SEQ ID NO 17
<211> LENGTH: 16
<212> TYPE: PRT
<213> ORGANISM: Homo sapiens

<400> SEQUENCE: 17

Ser Arg Arg His His Cys Arg Ser Lys Ala Lys Arg Ser Arg His His
1               5                   10                  15
```